(12) United States Patent
Miller et al.

(10) Patent No.: US 12,338,240 B2
(45) Date of Patent: *Jun. 24, 2025

(54) NONMUSCLE MYOSIN II INHIBITORS

(71) Applicant: The University of Florida Research Foundation, Inc., Gainesville, FL (US)

(72) Inventors: Courtney Anne Miller, Jupiter, FL (US); Patrick Robert Griffin, Jupiter, FL (US); Theodore Mark Kamenecka, Palm Beach Gardens, FL (US); Gavin Rumbaugh, Jupiter, FL (US); Matthew Surman, Albany, NY (US); Steve Young, Lansdale, PA (US); Steven Duddy, Ann Arbor, MI (US); Laszlo Radnai, East Palm Beach Gardens, FL (US)

(73) Assignee: THE UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 113 days.

This patent is subject to a terminal disclaimer.

(21) Appl. No.: 18/169,660

(22) Filed: Feb. 15, 2023

(65) Prior Publication Data

US 2023/0227452 A1    Jul. 20, 2023

Related U.S. Application Data

(63) Continuation of application No. 17/250,203, filed as application No. PCT/US2019/036897 on Jun. 13, 2019, now Pat. No. 11,649,234.

(60) Provisional application No. 62/685,158, filed on Jun. 14, 2018.

(51) Int. Cl.
  *C07D 471/04*  (2006.01)
  *C07D 471/14*  (2006.01)
  *C07D 495/14*  (2006.01)
  *C07D 519/00*  (2006.01)

(52) U.S. Cl.
  CPC ......... *C07D 471/04* (2013.01); *C07D 471/14* (2013.01); *C07D 495/14* (2013.01); *C07D 519/00* (2013.01)

(58) Field of Classification Search
  CPC ............................ C07D 471/04; C07D 495/14
  USPC ...................................................... 546/84, 83
  See application file for complete search history.

(56) References Cited

U.S. PATENT DOCUMENTS

| | | | |
|---|---|---|---|
| 11,649,234 B2 | 5/2023 | Miller et al. | |
| 2017/0020861 A1 | 1/2017 | DiSanto | |
| 2017/0129886 A1 | 5/2017 | DiSanto | |
| 2021/0317117 A1 | 10/2021 | Miller et al. | |

FOREIGN PATENT DOCUMENTS

| | | |
|---|---|---|
| AU | 2019285034 | 1/2023 |
| CA | 3103144 | 9/2023 |
| CN | 112584832 A | 3/2021 |
| JP | 2004509895 A | 4/2004 |
| JP | 2008528349 A | 7/2008 |
| JP | 2021527089 A | 10/2021 |
| JP | 7273454 | 5/2023 |
| KR | 102559394 | 7/2023 |
| TW | 201722958 | 7/2017 |
| WO | WO-2017129782 A1 | 8/2017 |
| WO | WO-2019202346 A2 | 10/2019 |
| WO | WO-2019241469 A1 | 12/2019 |

OTHER PUBLICATIONS

"U.S. Appl. No. 17/250,203, Corrected Notice of Allowability mailed Feb. 1, 2023", 2 pgs.
"U.S. Appl. No. 17/250,203, Final Office Action mailed Jun. 27, 2022", 9 pgs.

(Continued)

*Primary Examiner* — Charanjit Aulakh
(74) *Attorney, Agent, or Firm* — SCHWEGMAN LUNDBERG & WOESSNER, P.A.

(57) ABSTRACT

The invention can provide compounds, analogs of blebbistatin, effective and selective inhibitors of nonmuscle myosin II relative to cardiac myosin II. Compounds can be used in the method of treating a disease, disorder, or medical condition in a patient, comprising modulating myosin II ATPase, such as treatment of substance abuse relapse disorder, or of renal disease, cancer and metastasis, benign prostate hyperplasia, hemostasis or thrombosis, nerve injury including retinal damage, lung fibrosis, liver fibrosis, arthrofibrosis, wound healing, spinal cord injury, periodontitis, glaucoma and immune-related diseases including multiple sclerosis; or wherein the disease, disorder, or medical condition comprises addiction including abuse of or addiction to anything classified as a Substance-Related or Addictive Disorder in the Diagnostic and Statistical Manual of Mental Disorders (DSM), such as, but not limited to, cocaine, opioids, amphetamines, ethanol, *cannabis*/marijuana, nicotine, and activities including gambling.

Compounds are of general formula

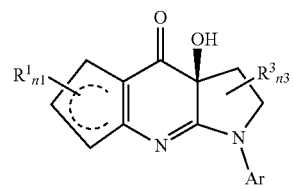

with substituents as defined herein.

5 Claims, 7 Drawing Sheets

(56) References Cited

OTHER PUBLICATIONS

"U.S. Appl. No. 17/250,203, Non Final Office Action mailed Jan. 24, 2022", 9 pgs.
"U.S. Appl. No. 17/250,203, Notice of Allowance mailed Nov. 17, 2022", 8 pgs.
"U.S. Appl. No. 17/250,203, PTO Response to Rule 312 Communication mailed Jan. 12, 2023", 2 pgs.
"U.S. Appl. No. 17/250,203, Response filed Jun. 2, 2022 to Non Final Office Action mailed Jan. 24, 2022", 80 pgs.
"U.S. Appl. No. 17/250,203, Response filed Aug. 29, 2022 to Final Office Action mailed Jun. 27, 2022", 78 pgs.
"Australian Application Serial No. 2019285034, First Examination Report mailed Dec. 17, 2021", 3 pgs.
"Australian Application Serial No. 2019285034, Response filed Aug. 31, 2022 to First Examination Report mailed Dec. 17, 2021", 129 pgs.
"Canadian Application Serial No. 3,103,144, Office Action mailed Feb. 25, 2022", 3 pgs.
"Canadian Application Serial No. 3,103,144, Response filed Jun. 9, 2022 to Office Action mailed Feb. 25, 2022", 624 pgs.
"Canadian Application Serial No. 3,103,144, Voluntary Amendment filed Feb. 1, 2023", 40 pgs.
"European Application Serial No. 19819613.1, Extended European Search Report mailed Mar. 14, 2022", 11 pgs.
"European Application Serial No. 19819613.1, Indication of deficiencies in a request under Rule 22 EPC mailed Sep. 23, 2022", 2 pgs.
"European Application Serial No. 19819613.1, Response filed Sep. 7, 2022 to Extended European Search Report mailed Mar. 14, 2022", 217 pgs.
"European Application Serial No. 19819613.1, Response to Communication pursuant to Rules 161(2) and 162 EPC filed Apr. 19, 2021", 173 pgs.
"International Application No. PCT/US2019/036897, Communication re Third Party Observation mailed Oct. 14, 2020", (Oct. 14, 2020), 1 pg.
"International Application No. PCT/US2019/036897, International Search Report and Written Opinion mailed Oct. 18, 2019", (Oct. 18, 2019), 9 pgs.
"International Application No. PCT/US2019/036897, Third Party Observation", (Oct. 9, 2020), 3 pgs.
"Japanese Application Serial No. 2020-568988, Notification of Reasons for Refusal mailed Mar. 9, 2022", with English translation, 8 pages.
"Japanese Application Serial No. 2020-568988, Notification of Reasons for Refusal mailed Nov. 21, 2022", w/ English Translation, 6 pgs.
"Japanese Application Serial No. 2020-568988, Response filed Jan. 10, 2023 to Notification of Reasons for Refusal mailed Nov. 21, 2022", w/ English claims, 39 pgs.
"Japanese Application Serial No. 2020-568988, Response filed Aug. 5, 2022 to Notification of Reasons for Refusal mailed Mar. 9, 2022", w/ English claims, 78 pgs.
"Korean Application Serial No. 10-2021-7000761, Notice of Preliminary Rejection mailed Dec. 15, 2022", w/ English Translation, 11 pgs.
"Pubchem CID 131465882", Create Date: Oct. 9, 2017, p. 2, (Oct. 9, 2017), 6 pgs.
"Pubchem CID 24178121", Create Date: Feb. 22, 2008, p. 2, (Feb. 22, 2008), 13 pgs.
Antoine, Thessicar E., et al., "Inhibition of myosin light chain kinase can be targeted for the development of new therapies against herpes simplex virus type-1 infection", Antiviral Therapy, 19, (2014), 15-29.
Arii, Jun, et al., "Non-musclemyosin IIAis a functional entry receptor for herpes simplex virus-1", Nature, vol. 467, (2010), 859-862 (6 pgs).

Arii, Jun, et al., "Nonmuscle Myosin Heavy Chain IIB Mediates Herpes Simplex Virus 1 Entry", Journal of Virology, Feb. 2015, vol. 89, No. 3, (Nov. 26, 2014), 1879-1888.
Arora, Pamma D., et al., "Flightless I interacts with NMMIIA to promote cell extension formation, which enables collagen remodeling", Mol Biol Cell., 26(12), (2015), 2279-2297.
Atluri, K., et al., "Blebbistatin-Loaded Poly(D,L-lactide-co-glycolide) Particles For Treating Arthrofibrosis", ACS Biomaterials Science & Engineering, 2, (2016), 1097-1105.
Babayeva, Sima, et al., "Plasma from a case of recurrent idiopathic FSGS perturbs non-muscle myosin IIA (MYH9 protein) in human podocytes", Pediatr Nephrol (2011) 26:1071-1081; DOI 10.1007/s00467-011-1831-z, (Mar. 6, 2011), 1071-1081.
Betapudi, Venkaiah, et al., "Distinct Roles of Nonmuscle Myosin II Isoforms in the Regulation of MDA-MB-231 Breast Cancer Cell Spreading and Migration", Cancer Res 2006; 66: (9). May 1, 2006, (May 1, 2006), 4725-4733.
Betapudi, Venkaiah, et al., "Life without double-headed non-muscle myosin II motor proteins", Frontiers in Chemistry, vol. 2, Article 45, (Jul. 7, 2014), 13 pgs.
Bond, Jennifer E., et al., "Angiotensin-II Mediates Nonmuscle Myosin II Activation and Expression and Contributes to Human Keloid Disease Progression", Mol Med, 17(11-12), (2011), 1196-1203.
Bond, Jennifer E., et al., "Temporal spatial expression and function of non-muscle myosin II isoforms IIA and IIB in scar remodeling", Laboratory Investigation (2011) 91, 499-508, (Apr. 2011), 499-508.
Bondzie, Philip A., et al., "Non-Muscle Myosin-IIA Is Critical for Podocyte F-Actin Organization, Contractility, and Attenuation of Cell Motility", Cytoskeleton, Aug. 2016, 73:377-395 (doi: 10.1002/cm.21313), (Aug. 2016), 377-395.
Bowers, Robert R., et al., "Sulfiredoxin Redox-Sensitive Interaction with S100A4 and Non-Muscle Myosin IIA Regulates Cancer Cell Motility", Biochemistry 2012, 51, 7740-7754 / dx.doi.org/10.1021/bi301006w, (Aug. 30, 2012), 7740-7754.
Brozovich, F. V., et al., "Mechanisms of Vascular Smooth Muscle Contraction and the Basis for Pharmacologic Treatment of Smooth Muscle Disorders", Pharmacological Reviews, 68, (Apr. 2016), 476-532.
Brunet, Alain, et al., "Reduction of PTSD Symptoms With Pre-Reactivation Propranolol Therapy: A Randomized Controlled Trial", Am J Psychiatry, 175:5, (May 2018), 427-433.
Chen, Ping, et al., "The expression and functional activities of smooth muscle myosin and non-muscle myosin isoforms in rat prostate", J. Cell. Mol. Med., 22(1), (2018), 576-588.
Chou, Chung-Lin, et al., "Non-muscle Myosin II and Myosin Light Chain Kinase Are Downstream Targets for Vasopressin Signaling in the Renal Collecting Duct", vol. 279, No. 47, Issue of Nov. 19, pp. 49026-49035, 2004, (Aug. 30, 2004), 49026-49035.
Coaxum, Sonya D., et al., "The tumor suppressor capability of p53 is dependent on nonmuscle myosin IIA function in head and neck cancer", Oncotarget, 2017, vol. 8, (No. 14), pp. 22991-23007, (Feb. 1, 2017), 22991-23007.
Coelho, Nuno M., et al., "Discoidin Domain Receptor 1 Mediates Myosin- Dependent Collagen Contraction", Cell Reports 18, 1774-1790, Feb. 14, 2017, (Feb. 14, 2017), 1774-1790.
Cooke Bailey, Jessica N., et al., "Kidney Disease Genetics and the Importance of Diversity in Precision Medicine", Pacific Symposium on Biocomputing 2016, (2016), 12 pgs.
Cymerys, J., et al., "Function of myosin during entry and egress of equid herpesvirus type 1 in primary murine neurons", Acta virologica, 60, (2016), 410-416.
Das, Provas, et al., "Phosphorylation of Nonmuscle myosin II-A regulatory light chain resists Sendai virus fusion with host cells", Scientific Reports | 5:10395 | DOI: 10.1038/srep10395, (May 20, 2015), 15 pgs.
Derycke, Lara, et al., "The role of non-muscle myosin IIA in aggregation and invasion of human MCF-7 breast cancer cells", Int. J. Dev. Biol. 55: 835-840; doi: 10.1387/ijdb.113336ld, (Nov. 29, 2011), 835-840.
Doller, Anke, et al., "The cytoskeletal inhibitors latrunculin A and blebbistatin exert antitumorigenic properties in human hepatocel-

(56) References Cited

OTHER PUBLICATIONS lular carcinoma cells by interfering with intracellular HuR trafficking", Experimental Cell Research 330, (2015), 66-80.

Du, Hongzhi, et al., "DT-13 inhibits cancer cell migration by regulating NMIIA indirectly in the tumor microenvironment", Oncology Reports 36: 721-728, 2016, (2016), 721-728.

Du, Min, et al., "S100P Dissociates Myosin IIA Filaments and Focal Adhesion Sites to Reduce Cell Adhesion and Enhance Cell Migration", The Journal of Biological Chemistry vol. 287, No. 19, pp. 15330-15344, May 4, 2012, (May 4, 2012), 15330-15344.

Duxbury, Mark S., et al., "Inhibition of pancreatic adenocarcinoma cellular invasiveness by blebbistatin: a novel myosin II inhibitor", Biochemical and Biophysical Research Communications, 313, (2004), 992-997.

Elliott, Paul R., et al., "Asymmetric Mode of Ca2+-S100A4 Interaction with Nonmuscle Myosin IIA Generates Nanomolar Affinity Required for Filament Remodeling", Structure 20, 654-666, Apr. 4, 2012, (Apr. 4, 2012), 654-666.

Epstein, David L., et al., "Acto-Myosin Drug Effects and Aqueous Outflow Function", Invest Ophthalmol Vis Sci., 40(1), (Jan. 1999), 74-81.

Espay, Albernto J., et al., "Chronic isolated hemifacial spasm as a manifestation of epilepsia partialis continua", NIH Public Access, Author Manuscript, published in final edited form as: Epilepsy Behav., 12(2), (2008), 332-226, (2008), 7 pgs.

Fan, Xueping, et al., "SLIT2/ROBO2 signaling pathway inhibits nonmuscle myosin IIA activity and destabilizes kidney podocyte adhesion", JCI Insight. 2016;1(19):e86934 / doi: 10.1172/jci.insight.86934, (Nov. 17, 2016), 16 pgs.

Feghhi, Shirin, et al., "Nonmuscle Myosin IIA Regulates Platelet Contractile Forces Through Rho Kinase and Myosin Light-Chain Kinase", Journal of Biomechanical Engineering, vol. 138, (Oct. 2016), 4 pgs.

Foley, Peter L., et al., "Prevalence and natural history of pain in adults with multiple sclerosis: Systematic review and meta-analysis", Pain, 154, (2013), 632-642.

Freedman, Barry I., et al., "Non-muscle myosin heavy chain 9 gene MYH9 associations in African Americans with clinically diagnosed type 2 diabetes mellitus-associated ESRD", Nephrol Dial Transplant (2009) 24: 3366-3371 / doi: 10.1093/ndt/gfp316, (Jun. 30, 2009), 3366-3371.

Freedman, Barry I., et al., "Polymorphisms in the non-muscle myosin heavy chain 9 gene (MYH9) are strongly associated with end-stage renal disease historically attributed to hypertension in African Americans", Kidney International (2009) 75, 736-745; doi:10.1038/ki.2008.701, (Jan. 28, 2009), 736-745.

Fritz, D., et al., "Progress Towards Discovery of Antifibrotic Drugs Targeting Synthesis of Type I Collagen", Current Medicinal Chemistry, 2011, 18(22), 3410-3416, (2011), 3410-3416.

Fukuda, Shota P., et al., "Cellular force assay detects altered contractility caused by a nephritis-associated mutation in nonmuscle myosin IIA", Develop. Growth Differ. (2017) 59, 423-433, (2017), 423-433.

Gao, Jiming, et al., "MYH9 is an Essential Factor for Porcine Reproductive and Respiratory Syndrome Virus Infection", Scientific Reports | 6:25120 | DOI: 10.1038/srep25120, (Apr. 26, 2016), 13 pgs.

Grant, Jon E., et al., "Expanding the Definition of Addiction: DSM-5 vs. ICD-11", Europe PMC Funders Group, CNS Spectr. Author Manuscript, published in final edited form as: CNS Spectr., 21(4), (2016), 300-303, (2016), 6 pgs.

Haque, Fahim, et al., "Non-muscle myosin II deletion in the developing kidney causes ureter-bladder misconnection and apical extrusion of the nephric duct lineage epithelia", Developmental Biology 427 (2017) 121-130, (May 3, 2017), 121-130.

Hays, Thomas, et al., "Proteomics Analysis of the Non-Muscle Myosin Heavy Chain IIa-Enriched Actin-Myosin Complex Reveals Multiple Functions within the Podocyte", PLoS ONE 9(6): e100660. doi:10.1371/journal.pone.0100660, (Jun. 20, 2014), 11 pgs.

Hirayama, Jiro, et al., "Relationship between low-back pain, muscle spasm and pressure pain thresholds in patients with lumbar disc herniation", Eur Spine J, 15, (2006), 41-47.

Ivkovic, Sanja, et al., "Direct inhibition of myosin II effectively blocks glioma invasion in the presence of multiple motogens", Molecular Biology of the Cell, vol. 23, (2012), 533-542.

Jacobs, Koen, et al., "P-cadherin counteracts myosin II-B function: implications in melanoma progression", Molecular Cancer 2010, 9:255, (2010), 12 pgs.

Jiang, L., et al., "Substrate stiffness of endothelial cells directs LFA-1/ICAM-1 interaction: A physical trigger of immune-related diseases", Clin Hemorheol Microcirc, 61(4), (2015), 633-643.

Johnstone, Duncan B., et al., "Podocyte-Specific Deletion of Myh9 Encoding Nonmuscle Myosin Heavy Chain 2A Predisposes Mice to Glomerulopathy", Molecular and Cellular Biology, 31(10), May 2011, p. 2162-2170, (Mar. 14, 2011), 2162-2170.

Kampourakis, Thomas, et al., "Omecamtiv mercabil and blebbistatin modulate cardiac contractility by perturbing the regulatory state of the myosin filament", J Physiol, 596(1), (2018), 31-46.

Keeling, Brett H., et al., "Keloids and non-diabetic kidney disease: Similarities and the APOL1-MYH9 haplotype as a possible genetic link", Medical Hypotheses 81 (2013) 908-910, (2013), 908-910.

Khan, Ghulam Jilany, et al., "TGF-ß1 Causes EMT by Regulating N-Acetyl Glucosaminyl Transferases via Downregulation of Non Muscle Myosin II-A through JNK/P38/PI3K Pathway in Lung Cancer", Current Cancer Drug Targets, 2018, 18(2), 209-219 // DOI: 10.2174/1568009617666170807120304, (2018), 209-219.

Kim, Jong Hyun, et al., "LPA1-Induced Migration Requires Nonmuscle Myosin II Light Chain Phosphorylation in Breast Cancer Cells", J. Cell. Physiol. 226: 2881-2893, 2011, (Feb. 1, 2011), 2881-2893.

Kiss, Bence, et al., "Crystal structure of the S100A4—nonmuscle myosin IIA tail fragment complex reveals an asymmetric target binding mechanism", PNAS, vol. 109, No. 16, (Apr. 17, 2012), 6048-6053.

Kopp, Jeffrey B., "Glomerular pathology in autosomal dominant MYH9 spectrum disorders: what are the clues telling us about disease mechanism?", Kidney International (2010) 78, 130-133. doi: 10.1038/ki.2010.82, (2010), 130-133.

Kopp, Jeffrey B., et al., "MYH9 is a major-effect risk gene for focal segmental glomerulosclerosis", Nature Genetics, vol. 40, No. 10, Oct. 2008, (Sep. 14, 2008), 1175-1184.

Kubo, Takekazu, et al., "The therapeutic effects of Rho-ROCK inhibitors on CNS disorders", Therapeutics and Clinical Risk Management, 4(3), (2008), 605-615.

Kumakura, Michiko, et al., "Actin-myosin network is required for proper assembly of influenza virus particles", Virology, 476, (2015), 141-150.

Lawson, Christopher P. A. T., et al., "Application of the copper catalysed N-arylation of amidines in the synthesis of analogues of the chemical tool, blebbistatin", Chemical Communications, vol. 47, No. 3, (Jan. 1, 2011), 1057-1059.

Lawson, Christopher P.A.T., et al., "Supplementary Information Application of the copper-catalysed N-arylation of amidines in the synthesis of analogues of the chemical tool, Blebbistatin", <https://mm.rsc.org/suppdata/cc/c0/c0cc03624b/c0cc03624b.pdf>, (Jan. 1, 2011), 3 pages.

Lee, Wanho, et al., "The role of myosin II in glioma invasion: A mathematical model", PLoS ONE 12(2): e0171312, (2017), 43 pgs.

Liu, Dongning, et al., "Clinicopathological Significance of NMIIA Overexpression in Human Gastric Cancer", Int. J. Mol. Sci. 2012, 13, 15291-15304; doi:10.3390/ijms131115291, (Nov. 19, 2012), 15291-15304.

Liu, Tao, et al., "Downregulation of non-muscle myosin IIA expression inhibits migration and invasion of gastric cancer cells via the c-Jun N-terminal kinase signaling pathway", Molecular Medicine Reports 13: 1639-1644, 2016, (2016), 1639-1644.

Liu, Zhenan, et al., "Blebbistatin inhibits contraction and accelerates migration in mouse hepatic stellate cells", British Journal of Pharmacology, 159, (2010), 304-315.

Liu, Zhenan, et al., "Distinct roles for non-muscle myosin II isoforms in mouse hepatic stellate cells", Journal of Hepatology; 2011; vol. 54; 132-141, (Aug. 26, 2010), 132-141.

(56) References Cited

OTHER PUBLICATIONS

Lucas-Lopez, Cristina, et al., "The small molecule tool (S)-(—)-blebbistatin: novel insights of relevance to myosin inhibitor design", Org Biomol Chem. Jun. 21, 2008; 6(12): 2076-2084, (Jun. 21, 2008), 2076-2084.

Luo, Cheng, et al., "Molecular inhibition mechanisms of cell migration and invasion by coix polysaccharides in A549 NSCLC cells via targeting S100A4", Molecular Medicine Reports 17: 309-316, 2017, (2017), 309-316.

Ma, Xuefei, et al., "Conditional Ablation of Nonmuscle Myosin II-B Delineates Heart Defects in Adult Mice", Circulation Research; DOI: 10.1161/CIRCRESAHA.109.200303, (2009), 1102-1109.

Maher, Chris, et al., "Non-specific low back pain", Lancet, 389, (2017), 736-747.

Mameniškiene, Ruta, et al., "Epilepsia partialis continua: A review", Seizure, 44, (2017), 74-80.

Marini, Monica, et al., "Non-muscle myosin heavy chain IIA and IIB interact and co- localize in living cells: Relevance for MYH9-related disease", International Journal of Molecular Medicine 17: 729-736, 2006, (2006), 729-736.

Matsha, Tandi Edith, "Polymorphisms in the Non-Muscle Myosin Heavy Chain Gene (MYH9) Are Associated with Lower Glomerular Filtration Rate in Mixed Ancestry Diabetic Subjects from South Africa", PLoS ONE 7(12): e52529. doi:10.1371/journal.pone.0052529, (Dec. 20, 2012), 7 pgs.

Michael, Simon K., et al., "High blood pressure arising from a defect in vascular function", Proc. Natl. Acad. Sci. USA, 105(18), (2008), 6702-6707.

Mohamed, R. M. P., et al., "Try to Remember: Interplay between Memory and Substance Use Disorder", Current Drug Targets, 20(2), (2019), 158-165.

Muller, Tobias, et al., "Non-muscle myosin IIA is required for the development of the zebrafish glomerulus", Kidney International (2011) 80, 1055-1063; doi:10.1038/ki.2011.256, (Aug. 17, 2011), 1055-1063.

Nabet, Behnam, et al., "Identification of a Putative Network of Actin-Associated Cytoskeletal Proteins in Glomerular Podocytes Defined by Co-Purified mRNAs", PLoS ONE 4(8): e6491. doi:10.1371/journal.pone.0006491, (Aug. 4, 2009), 15 pgs.

Noris, Marina, et al., "Non-muscle myosins and the podocyte", Clin Kidney J (2012) 5: 94-101 / doi: 10.1093/ckj/sfs032, (2012), 94-101.

Ochala, Julien, et al., "Novel myosin-based therapies for congenital cardiac and skeletal myopathies", J Med Genet, 53, (2016), 651-654.

Pacik, Peter T., "Understanding and treating vaginismus: a multimodal approach", Int Urogynecol J, 25, (2014), 1613-1620.

Pecci, Alessandro, et al., "MYH9: Structure, functions and role of non-muscle myosin IIA in human disease", Gene 664 (2018) 152-167, (Apr. 19, 2018), 152-167.

Picariello, Hannah S., et al., "Myosin IIA suppresses glioblastoma development in a mechanically sensitive manner", Proc. Natl. Acad. Sci. USA, 116(31), (2019), 15550-15559.

Poincloux, Renaud, et al., "Contractility of the cell rear drives invasion of breast tumor cells in 3D Matrigel", Proc. Natl. Acad. Sci. USA, 108(5), (2011), 1943-1948.

Roman, Bart I, et al., "Medicinal Chemistry and Use of Myosin II Inhibitor (S)-Blebbistatin and Its Derivatives", Journal of Medicinal Chemistry, 61(21), (2018), 9410-28.

Roman, Bart I, et al., "Recovering Actives in Multi-Antitarget and Target Design of Analogs of the Myosin II Inhibitor Blebbistatin", Frontiers in Chemistry, vol. 6, (May 24, 2018).

Sekine, Takashi, et al., "Patients with Epstein-Fechtner syndromes owing to MYH9 R702 mutations develop progressive proteinuric renal disease", Kidney International (2010) 78, 207-214, (Mar. 3, 2010), 207-214.

Si, Jin, et al., "Inhibiting nonmuscle myosin II impedes inflammatory infiltration and ameliorates progressive renal disease", Laboratory Investigation, 90, (2010), 448-458.

Sigrid, Verhasselt, et al., "Improved synthesis and comparative analysis of the tool properties of new and existing D-ring modified ( S )-blebbistatin analogs", European Journal of Medicinal Chemistry, vol. 136, (Aug. 18, 2017), 85-103.

Sirigu, Serena, et al., "Highly selective inhibition of myosin motors provides the basis of potential therapeutic application", Proc. Natl. Acad. Sci. USA, 113 (47), (2016), E7448-E7455.

Soeter, Marieke, et al., "An Abrupt Transformation of Phobic Behavior After a Post-Retrieval Amnesic Agent", Biology Psychiatry, 78, (2015), 880-886.

Southern, Brian D., et al., "Matrix-driven Myosin II Mediates the Pro-fibrotic Fibroblast Phenotype", The Journal of Biological Chemistry, 291(12), (2016), 6083-6095.

Stefanovic, Branko, "RNA protein interactions governing expression of the most abundant protein in human body, type I collagen", WIREs RNA 2013, 4:535-545. doi: 10.1002/wrna.1177, (Sep. 2013), 535-545.

Sun, Yinyan, et al., "Nonmuscle Myosin Heavy Chain IIA Is a Critical Factor Contributing to the Efficiency of Early Infection of Severe Fever with Thrombocytopenia Syndrome Virus", Journal of Virology, 88(1), (Jan. 2014), 237-248.

Tan, Lei, et al., "Non-muscle Myosin II: Role in Microbial Infection and Its Potential as a Therapeutic Target", Front. Microbiol. 10:401 // doi: 10.3389/fmich.2019.00401, (Mar. 2019), 11 pgs.

Thomas, Dustin G., "Non-muscle myosin IIB is critical for nuclear translocation during 3D invasion", J. Cell Biol., vol. 210, No. 4, 583-594 / www.jcb.org/cgi/doi/10.1083/jcb.201502039, (2015), 583-594.

Tomii, Shohei, et al., "Cortical Actin Alteration at the Matrix-Side Cytoplasm in Lung Adenocarcinoma Cells and Its Significance in Invasion", Pathobiology, 84, (2017), 171-183.

Van Leeuwen, Hans, et al., "Evidence of a Role for Nonmuscle Myosin II in Herpes Simplex Virus Type 1 Egress", Journal of Virology, Apr. 2002, p. 3471-3481, vol. 76, No. 7, 0022-538X/02/$04.00+0; DOI: 10.1128/JVI.76.7.3471-3481.2002, (Apr. 2022), 3471-3481.

Veettil, Mohanan Valiya, et al., "Interaction of c-Cbl with Myosin IIA Regulates Bleb Associated Macropinocytosis of Kaposi's Sarcoma-Associated Herpesvirus", PLoS Pathog 6(12): e1001238. doi:10.1371/journal.ppat.1001238, (Dec. 23, 2010), 16 pgs.

Verhasselt, S, et al., "Discovery of (S)-3'-hydroxyblebbistatin and (S)-3'-aminoblebbistatin: polar myosin II inhibitors with superior research tool properties", Organic & Biomolecular Chemistry, 15(9), (2017), 2104-2118.

Verhasselt, Sigrid, et al., "Insights into the myosin II inhibitory potency of A-ring modified (S)-blebbistatin analogs", Bioorg Med Chem Lett., Jul. 2017, vol. 27(13), (Jul. 2017), 2986-2989.

Wang, Hao, et al., "Role of LARP6 and Nonmuscle Myosin in Partitioning of Collagen mRNAs to the ER Membrane", PLoS ONE 9(10): e108870. doi:10.1371/journal.pone.0108870, (Oct. 1, 2014), 14 pgs.

Wang, Jianfeng, et al., "RhoA Signaling and Synaptic Damage Occur Within Hours in a Live Pig Model of CNS Injury, Retinal Detachment", Investigative Ophthalmology & Visual Science, 57(8), (Jul. 2016), 3892-3906.

Wang, Yan, et al., "Myosin IIA-related Actomyosin Contractility Mediates Oxidative Stress-induced Neuronal Apoptosis", Frontiers in Molecular Neuroscience, 10: 75, (Mar. 2017), 1-20.

Wasik, Anita A., et al., "Septin 7 reduces nonmuscle myosin IIA activity in the SNAP23 complex and hinders GLUT4 storage vesicle docking and fusion", Experimental Cell Research 350 (2017) 336-348, (Dec. 20, 2016), 336-348.

Wei, Xiao-Hui, et al., "DT-13 attenuates human lung cancer metastasis via regulating NMIIA activity under hypoxia condition", Oncology Reports, 36, (2016), 991-999.

Wigton, Eric J., et al., "Myosin-IIA regulates leukemia engraftment and brain infiltration in a mouse model of acute lymphoblastic leukemia", Journal of Leukocyte Biology, vol. 100, (Jul. 2016), 143-152.

Wu, D., et al., "Myosin-interacting guanine exchange factor (MyoGEF) regulates the invasion activity of MDA-MB-231 breast cancer cells through activation of RhoA and RhoC", Oncogene (2009) 28, 2219-2230, (May 4, 2009), 2219-2230.

(56) References Cited

OTHER PUBLICATIONS

Xiong, Dan, et al., "Nonmuscle myosin heavy chain IIA mediates Epstein-Barr virus infection of nasopharyngeal epithelial cells", PNAS, vol. 112, No. 35, (Sep. 1, 2015), 11036-11041.

Xu, Xiaopeng, et al., "VP15R from infectious spleen and kidney necrosis virus is a non-muscle myosin-II-binding protein", Arch Virol (2011) 156:53-61, (Sep. 30, 2010), 53-61.

Yoshimoto, Tetsuya, et al., "Aggregatibacter actinomycetemcomitans outer membrane protein 29 (Omp29) induces TGF-ß-regulated apoptosis signal in human gingival epithelial cells via fibronectin/integrinß1/FAK cascade", Cellular Microbiology, 18(12), (2016), 1723-1738.

Young, Erica J., et al., "Nonmuscle myosin II inhibition disrupts methamphetamine-associated memory in females and adolescents", HHS Public Access, Neurobiol Learn Mem., Author Manuscript, Published in final edited form as: Neurobiol. Learn. Mem., 139, (2017), 109-116, (2017), 15 pgs.

Young, Erica J., et al., "Nonmuscle myosin IIB as a therapeutic target for the prevention of relapse to methamphetamine use", HHS Public Access, Author Manuscript, Published in final edited form as: Mol. Psychiatry, 21(5), (2016), 615-623, (2016), 22 pgs.

Yu, Xiao-Wen, et al., "Synergistic combination of DT-13 and topotecan inhibits human gastric cancer via myosin IIA-induced endocytosis of EGF receptor in vitro and in vivo", Oncotarget, vol. 7, No. 22, (Apr. 20, 2016), 32990-33003.

Zhai, Kefeng, et al., "NMMHC IIA inhibition impedes tissue factor expression and venous thrombosis via Akt/GSK3ß-NF-?B signalling pathways in the endothelium", HHS Public Access, Author Manuscript, Published in final edited form as: Thromb Haemost, 114(1), (2015), 173-185, (2015), 26 pgs.

Zhang, Min, et al., "Blebbistatin, a Novel Inhibitor of Myosin II ATPase Activity, Increases Aqueous Humor Outflow Facility in Perfused Enucleated Porcine Eyes", Investigative Ophthalmology & Visual Science, 46(11), (Nov. 2005), 4130-4138.

Zhang, X., et al., "In vitro and in vivo relaxation of corpus cavernosum smooth muscle by the selective myosin II inhibitor, blebbistatin", J Sex Med, 6, (2009), 2661-2671.

Zhang, Xinhua, et al., "In vitro and in vivo relaxation of urinary bladder smooth muscle by the selective myosin II inhibitor, blebbistatin", BJU International 107(2), (2010), 310-317.

Zhang, Yuanyuan, et al., "The Myosin II Inhibitor, Blebbistatin, Ameliorates FeCI3-induced Arterial Thrombosis via the GSK3ß-NF-?B Pathway", International Journal of Biological Sciences, 13(5), (2017), 630-639.

Zhao, Jia-Wang, "Acute Effects of Rho-Kinase Inhibitor Fasudil on Pulmonary Arterial Hypertension in Patients With Congenital Heart Defects", Circulation Journal, 79, (2015), 1342-1348.

Zvibel, Isabel, et al., "Thyroid hormones induce activation of rat hepatic stellate cells through increased expression of p75 neurotrophin receptor and direct activation of Rho", Laboratory Investigation, 90, (2010), 674-684.

"Korean Application Serial No. 10-2021-7000761, Response filed Feb. 10, 2023 to Notice of Preliminary Rejection mailed Dec. 15, 2022", w English claims, 46 pgs.

"Chinese Application Serial No. 201980039813.2, Office Action mailed Feb. 21, 2023", w English Translation, 20 pgs.

Roman, Bart I, "The Medicinal Chemistry and Use of Myosin II Inhibitor (S)-Blebbistatin and Its Derivatives", Journal of Medicinal Chemistry, 61, 21, (Jun. 7, 2018).

"Australian Application Serial No. 2019285034, Office Action mailed Apr. 14, 2023", 1 pg.

"Chinese Application Serial No. 201980039813.2, Response filed Jul. 10, 2023 to Office Action mailed Feb. 21, 2023", w English claims, 40 pgs.

"Chinese Application Serial No. 201980039813.2, Office Action mailed Sep. 5, 2023", W English Translation, 11 pgs.

"Chinese Application Serial No. 201980039813.2, Response filed Nov. 17, 2023 to Office Action mailed Sep. 5, 2023", w English claims, 101 pgs.

"Chinese Application Serial No. 201980039813.2, Decision of Rejection mailed Apr. 29, 2024", W English Translation, 13 pgs.

"Australian Application Serial No. 2022283724, First Examination Report mailed May 30, 2024", 2 pgs.

"Australian Application Serial No. 2022283724, Response filed Aug. 21, 2024 to First Examination Report mailed May 30, 2024", 9 pgs.

"Chinese Application Serial No. 201980039813.2, Request for Reexamination filed Jul. 26, 2024", W/English Claims, 108 pgs.

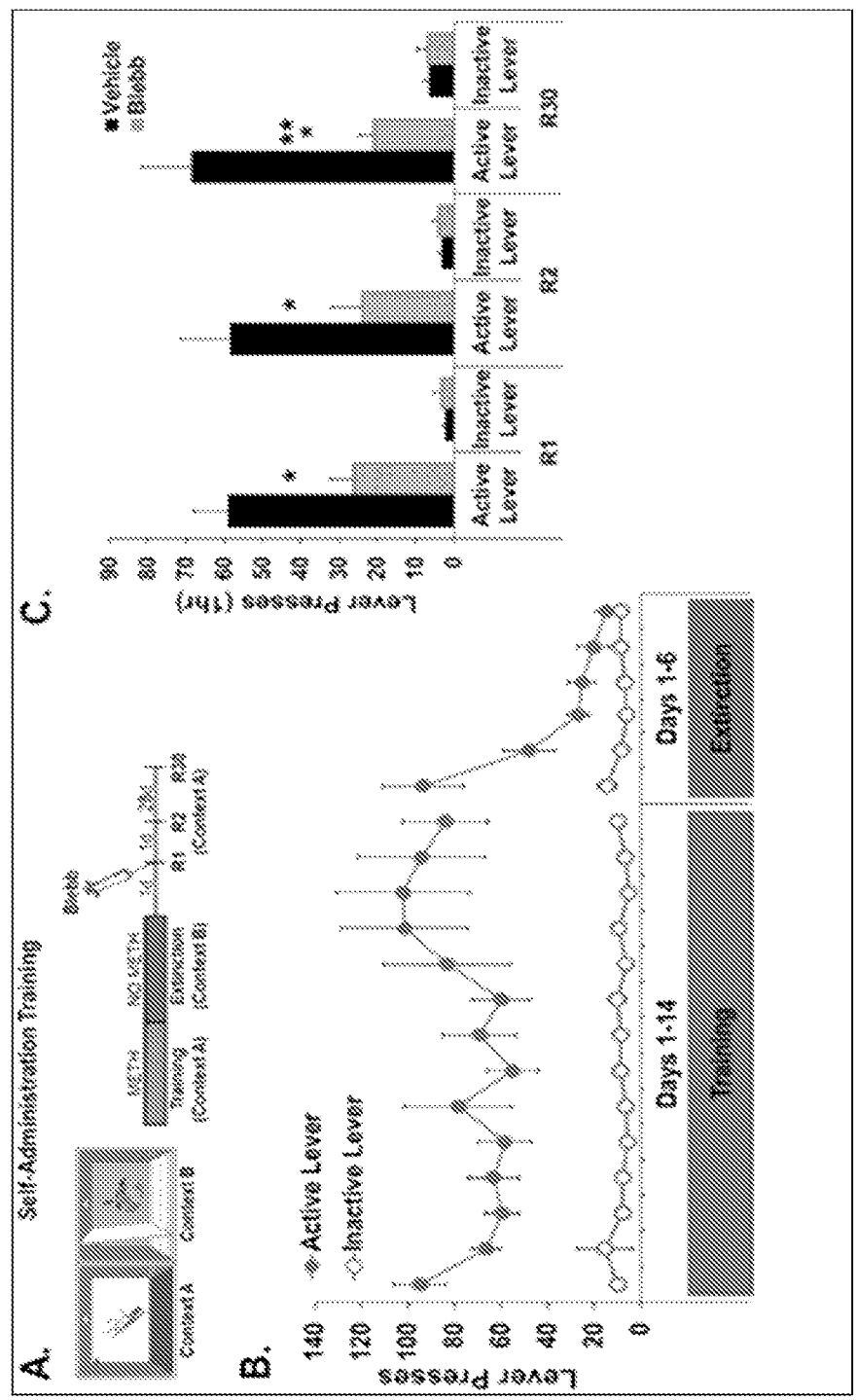
Fig. 1(A, B, C)

Fig. 3(A, B, C, D)
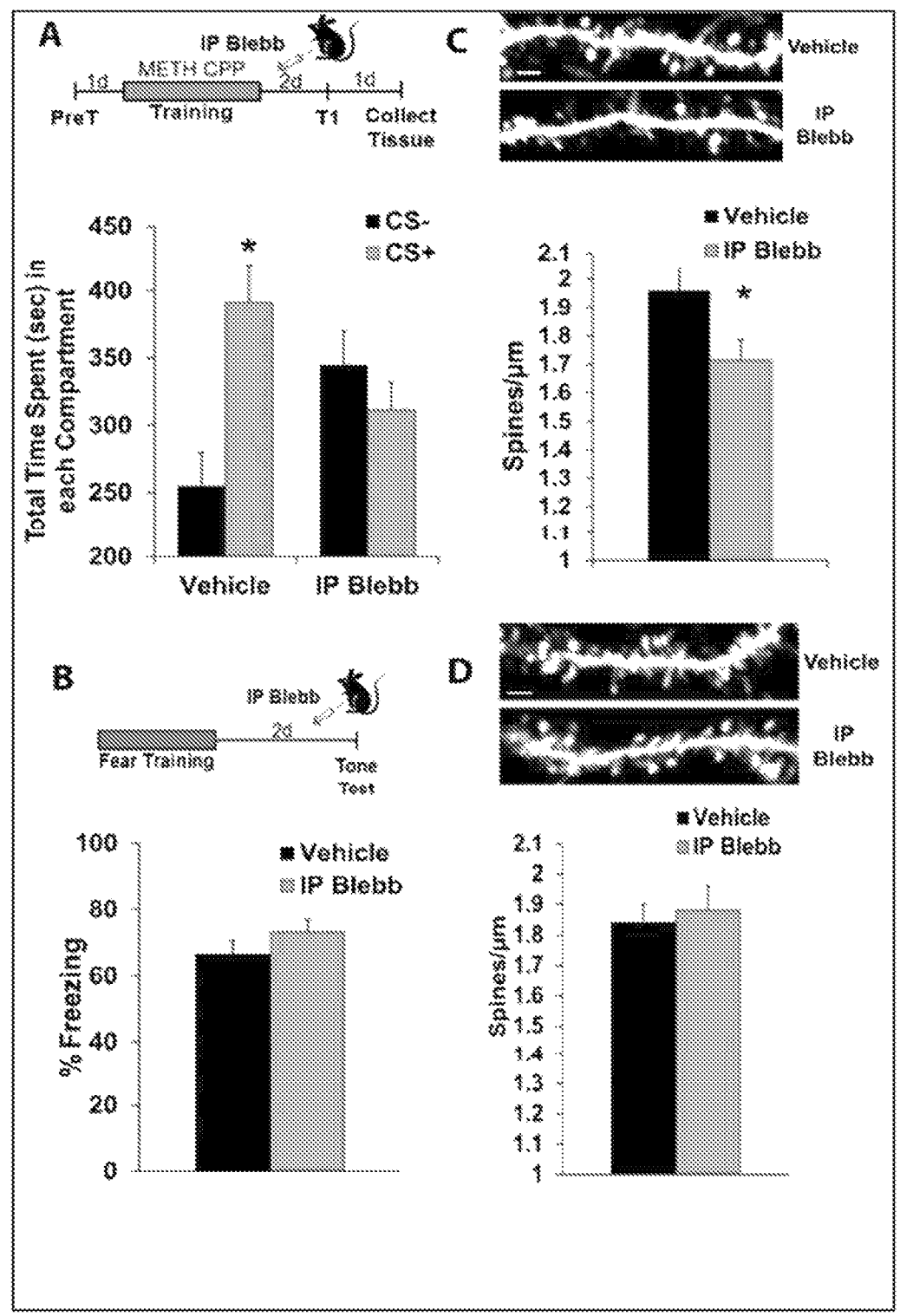

Fig. 7
| Identifier | NMII (EC50 uM) | CMII (KI uM) |
|---|---|---|
| Blebbistatin | 1.90 | 1.50 |
| BPN-0026496 | 2.60 | 83.0 |
| BPN-0026499 | 0.43 | 6.30 |
Group 1: 26496, n = 3
Group 2: 26499, n = 2
Group 3: Blebb, n = 2
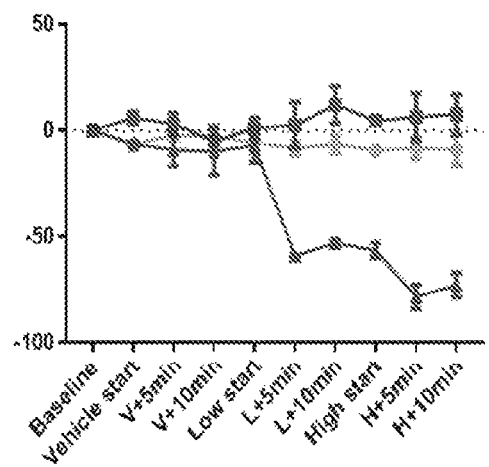
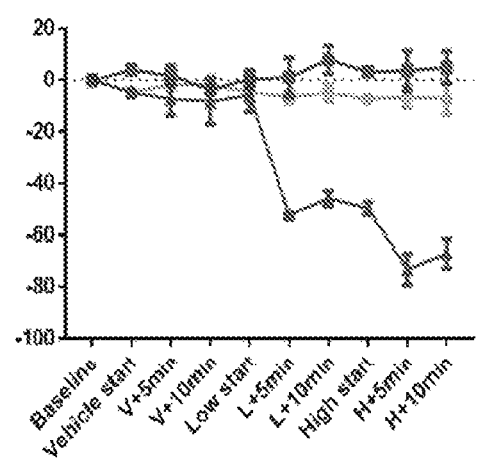
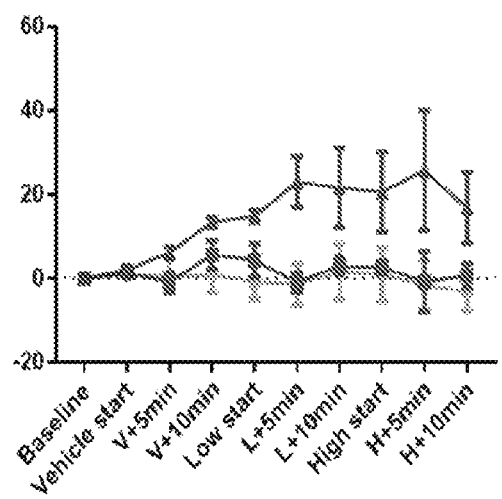
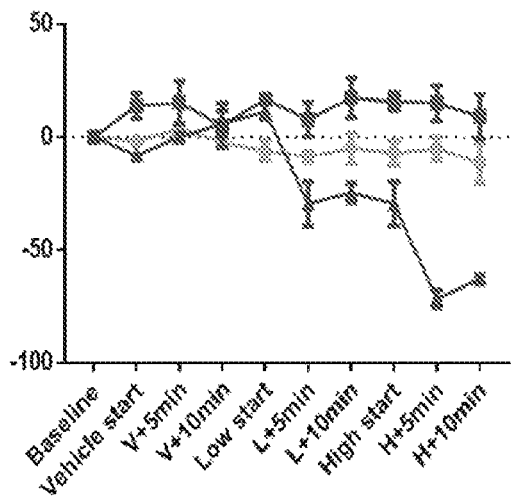

NONMUSCLE MYOSIN II INHIBITORS

CROSS-REFERENCE TO RELATED APPLICATIONS

The subject patent application is a continuation of U.S. patent application Ser. No. 17/250,203 filed on Dec. 14, 2020, which is U.S. national stage filing under 35 U.S.C. § 371 from International Application No. PCT/US2019/036897, filed on Jun. 13, 2019, and published as WO 2019/241469 on Dec. 19, 2019, and claims the benefit of priority to U.S. Provisional Patent Application No. 62/685,158, filed Jun. 14, 2018, the benefit of priority of each application of which is claimed herein, and which applications and publication are hereby incorporated herein by reference in their entirety.

STATEMENT OF GOVERNMENT SUPPORT

This invention was made with government support under grant number NS096833 awarded by the National Institutes of Health. The government has certain rights in the invention.

BACKGROUND

Substance abuse disorder is a chronic, relapsing disorder with no relapse preventing pharmacotherapies available for any drug of abuse. This is a major treatment challenge, as deeply engrained drug seeking behaviors persist long after the cessation of drug use. Numerous associations form between the drug's central and peripheral effects and components of the environment present at the time of drug use, which can range from the obvious (e.g. drug paraphernalia) to the more abstract (e.g. music, snow, gum)[1]. The associations become highly motivating on their own, serving as rapid triggers to seek out the drug. Perhaps most troubling, drug-associated stimuli retain their ability to motivate drug seeking behavior after successful rehabilitation and prolonged drug-free periods, because of the persistence of associative memories.

SUMMARY

The invention is directed, in various embodiments, to compounds and methods useful for inhibition of nonmuscle myosin II, which can be selective inhibition of the nonmuscle myosin II with respect to cardiac myosin II. The compounds are analogs of (S)-blebbistatin ("Blebb").

In various embodiments, the invention can provide a compound of formula (I)

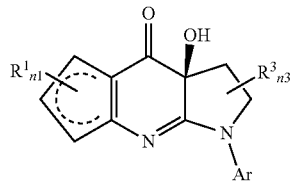

(I)

wherein
the ring bearing $R^1$ is a 5-membered, 6-membered, or 7-membered aryl or heteroaryl ring system comprising 0, 1, or 2 heteroatoms selected from the group consisting of S, O, N, and $NR^1$; wherein the ring can be fused with an aryl, heteroaryl, cycloalkyl, or heterocyclyl ring; wherein $R^1$ can be disposed on any one or more rings of a multiring system;

$R^1$ is independently at each occurrence (C1-C4)alkyl, (C1-C4)alkoxyl; (C1-C4)alkoxycarbonyl, (C1-C4)haloalkyl, cyano, nitro, or halo; n1=0, 1, 2, or 3;

Ar is a monocyclic or bicyclic aryl or heteroaryl ring system, wherein any aryl or heteroaryl thereof can be substituted with 0, 1, 2 or 3 $R^2$;

$R^2$ is independently at each occurrence (C1-C4)alkyl, (C1-C4)alkoxyl), (C1-C4)alkoxycarbonyl, (C1-C4)haloalkyl, hydroxymethyl, $R_2NCH_2$ wherein R is H or alkyl, cyano, nitro, or halo;

$R^3$ is independently at each occurrence (C1-C4)alkyl, halo, or (C1-C4)haloalkyl; n3=0, 1, 2, 3, or 4;

provided that the compound is not blebbistatin or a compound of any of formulas

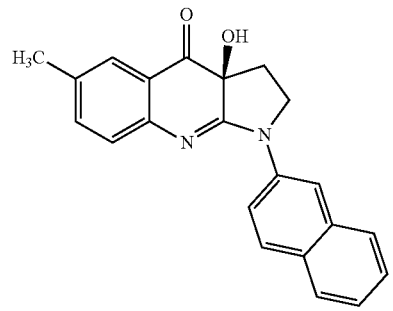

BPN-0025915

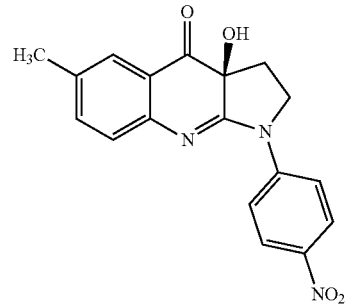

BPN-0025001

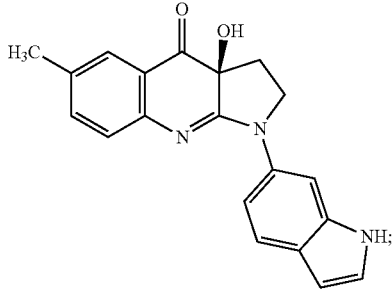

BPN-0026555 or a pharmaceutically acceptable salt thereof.

For example, the ring bearing $R^1$ can be phenyl, pyridyl, or thienyl.

More specifically, the compound of formula (I) can be a compound of formula (IIa) or (IIb)

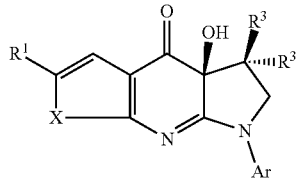
(IIa)

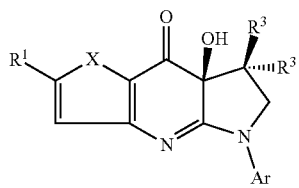
(IIb)

wherein
X is S, or X is a group of formula

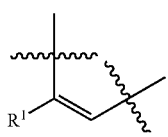

wherein wavy lines indicate points of bonding;
R$^1$ is independently at each occurrence H, (C1-C4)alkyl, CF$_3$, or halo;
provided that when X is a group of formula

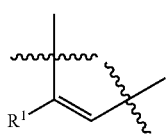

and Ar is unsubstituted phenyl, at least one R$^1$ group is other than H or (C1-C4)alkyl;
Ar is aryl or heteroaryl, wherein any aryl or heteroaryl thereof can be substituted with 0, 1, 2 or 3 R$^2$;
R$^2$ is independently at each occurrence halo, cyano, nitro, CF$_3$, (C1-C4)alkyl, or (C1-C4)alkoxyl);
R$^3$ is independently at each occurrence H or CH$_3$;
or a pharmaceutically acceptable salt thereof.

For example, for the compound of formula (II), X can be S.

In other embodiments, for the compound of formula (II), X can be a group of formula

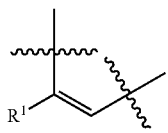

wherein wavy lines indicate points of bonding. In these embodiments, at least one R$^1$ group of formula (I) can be methyl, halo or CF$_3$.

In other embodiments of formula (I), Ar can be a group of formula

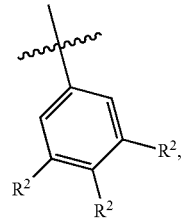

wherein a wavy line indicates a point of bonding.

In other embodiments, Ar can be a pyrazolyl, thiophenyl, isoquinolinyl, benzoxazolyl, quinazolinyl, isoxazolyl, cinnolinyl, quinoxalinyl, benzisoxazolyl, benzothiadiazolyl, pyrazolopyridinyl, imidazopyridinyl, thieopyridinyl, dihydrobenzoxazinyl, triazolopyridinyl, dihydropyridoxazinyl, tetrahydrobenzoxazepinyl, dihydrobenzodioxinyl, dihydrobenzothiazinyl, tetrahydroquinolinyl, tetrahydronaphthyl, or chromanyl, ring system, any of which can be unsubstituted or substituted with 1, 2, or 3 R$^2$.

In various specific embodiments of a compound of formula (I) of the invention, the compound can be any one of the compounds depicted in Table 3, with the exception of blebbistatin itself and the three compounds excluded by proviso as described above.

In various embodiments, the invention can provide a method of inhibiting nonmuscle myosin II, comprising contact the nonmuscle myosin II with an effective amount or concentration of a compound of formula (I)

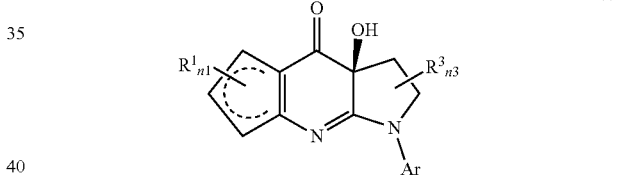
(I)

wherein
the ring bearing R$^1$ is a 5-membered, 6-membered, or 7-membered aryl or heteroaryl ring system comprising 0, 1, or 2 heteroatoms selected from the group consisting of S, O, N, and NR$^1$; wherein the ring can be fused with an aryl, heteroaryl, cycloalkyl, or heterocyclyl ring; wherein R$^1$ can be disposed on any one or more rings of a multiring system;
R$^1$ is independently at each occurrence (C1-C4)alkyl, (C1-C4)alkoxyl; (C1-C4)alkoxycarbonyl, (C1-C4)haloalkyl, cyano, nitro, or halo; n1=0, 1, 2, or 3;
Ar is a monocyclic or bicyclic aryl or heteroaryl ring system, wherein any aryl or heteroaryl thereof can be substituted with 0, 1, 2 or 3 R$^2$;
R$^2$ is independently at each occurrence (C1-C4)alkyl, (C1-C4)alkoxyl), (C1-C4)alkoxycarbonyl, (C1-C4)haloalkyl, hydroxymethyl, dialkylaminomethyl, cyano, nitro, or halo;
R$^3$ is independently at each occurrence (C1-C4)alkyl, halo, or (C1-C4)haloalkyl; n3=0, 1, 2, 3, or 4;
provided that the compound is not blebbistatin;
or a pharmaceutically acceptable salt thereof.

Compounds BPN-0025915, BPN-0025001, and BPN-0026555 (see Table 3) are included in the set of compounds useful for practice of an embodiment of the methods of the invention.

In other embodiments, the invention can provide a method of treatment of substance use relapse in a patient, comprising administering to the patient an effective dose of a compound of formula (I).

In various embodiments, a compound useful for practice of a method of the invention can include:

a compound of formula (I) wherein the ring bearing $R^1$ is phenyl, pyridyl, or thienyl;

a compound of formula (I) being of formula (IIa) or (IIb)

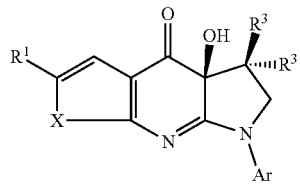

(IIa)

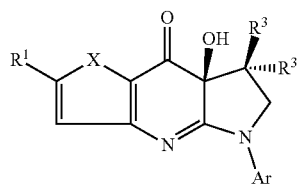

(IIb)

wherein

X is S, or X is a group of formula

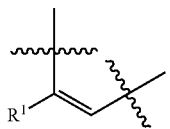

wherein wavy lines indicate points of bonding;

$R^1$ is independently at each occurrence H, (C1-C4)alkyl, $CF_3$, or halo;

provided that when X is a group of formula

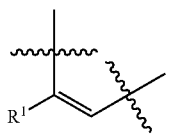

and Ar is unsubstituted phenyl, at least one $R^1$ group is other than H or (C1-C4)alkyl;

Ar is aryl or heteroaryl, wherein any aryl or heteroaryl thereof can be substituted with 0, 1, 2 or 3 $R^2$;

$R^2$ is independently at each occurrence halo, cyano, nitro, $CF_3$, (C1-C4)alkyl, or (C1-C4)alkoxyl);

$R^3$ is independently at each occurrence H or $CH_3$;

or a pharmaceutically acceptable salt thereof.

In various embodiments of a compound of formula (II) for practice of a method of the invention, X can be S; or X can be a group of formula

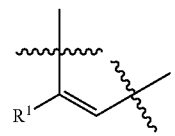

wherein wavy lines indicate points of bonding. In these embodiments, at least one $R^1$ group of formula (I) can be methyl, halo or $CF_3$.

In other embodiments of a compound of formula (I) useful for practice of a method of the invention, Ar can be a group of formula

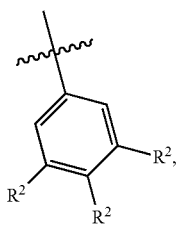

wherein a wavy line indicates a point of bonding.

In other embodiments, Ar can be a pyrazolyl, thiophenyl, isoquinolinyl, benzoxazolyl, quinazolinyl, isoxazolyl, cinnolinyl, quinoxalinyl, benzisoxazolyl, benzothiadiazolyl, pyrazolopyridinyl, imidazopyridinyl, thieopyridinyl, dihydrobenzoxazinyl, triazolopyridinyl, dihydropyridoxazinyl, tetrahydrobenzoxazepinyl, dihydrobenzodioxinyl, dihydrobenzothiazinyl, tetrahydroquinolinyl, tetrahydronaphthyl, or chromanyl, ring system, any of which can be unsubstituted or substituted with 1, 2, or 3 $R^2$.

For practice of a method of the invention, in various embodiments a specific example of a compound of formula (I) can be any of the compounds shown in Table 3 other than blebbistatin itself.

In various embodiments, the compound can be more effective, on a molar basis, in inhibition of nonmuscle myosin II relative to myosin II derived from cardiac muscle.

In another aspect, described herein provides a method of treating a disease, disorder, or medical condition in a patient, comprising modulating myosin II ATPase, wherein the modulating of myosin II ATPase comprises administering to the patient at least one compound of Formula (I) or Formula (II) or a pharmaceutically acceptable salt thereof, in a dose, at a frequency, and for a duration to provide a beneficial effect to the patient. In various embodiments, the disease, disorder, or medical condition is selected from the group consisting of renal disease[2], cancer and metastasis, including hepatocarcinoma[3], pancreatic adenocarcinoma[4], breast cancer[5-6], lung carcinoma[7], glioblastoma[8-11], benign prostate hyperplasia[12] hemostasis or thrombosis[13-15], nerve injury[16] including retinal damage[17], lung fibrosis[18], liver fibrosis[19], arthrofibrosis[20], wound healing[21-23], spinal cord injury[24], periodontitis[25], glaucoma[26-27] and immune-related diseases including multiple sclerosis[28]. In certain embodiments, the disease, disorder, or medical condition is selected from the group consisting of viral infection including herpes virus[29-33], high blood pressure[34], pulmonary hypertension[35], chronic respiratory diseases[36], cardiovascular disease[37], erectile disfunctions[38], thrombotic disorders[13], overactive bladder[39], cardiomyopathies[40], spasms[41-46], skeletal myopathies[47], and psychiatric disorders, including substance use[48], anxiety disorders (e.g. phobias)[49] and stress disorders (e.g. posttraumatic stress disorder)[50]. Addiction can include abuse of or addiction to anything classified as a Substance-Related or Addictive Disorder in the Diagnostic and Statistical Manual of Mental Disorders (DSM), such as, but not limited to, cocaine, opioids, amphetamines[51-52], ethanol, cannabis/marijuana, nicotine, and activities (e.g. gambling)[53].

BRIEF DESCRIPTION OF THE FIGURES

FIG. 1(A,B,C): Long-lasting disruption of METH (methamphetamine)-associated memory by intra-amygdala administration of (S)-blebbistatin ("Blebb") (90 ng/ul).

FIG. 3(A,B,C,D): Systemic NMII inhibition selectively targets the storage of (A) a METH-associated memory, (B) having no effect on an auditory fear memory. Similarly, spine density associated with a METH-associated memory (C), but not a fear memory (D), is reduced.

FIG. 7: Cardiac safety Characterization for Selected Blebbistatin Analogs: Echocardiography assessment in vivo with IV drug infusion

DETAILED DESCRIPTION

Figure 2A:
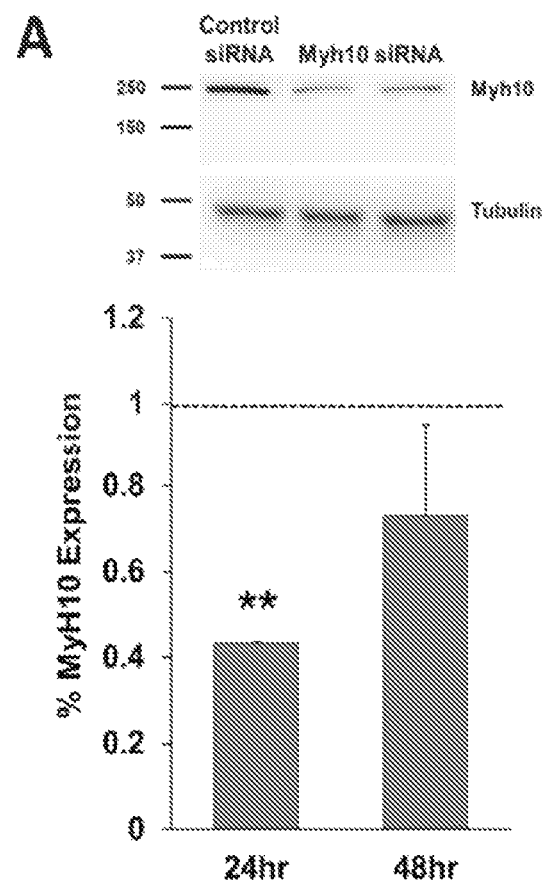
FIGS. 2A, 2B, 2C, 2D: Post-consolidation loss of NMIIB (A-B) produces a lasting disruption of METH-associated memory (C-D). *P<0.05.

The physical storage site of memory is dendritic spines[54]. Spines are the small, highly dynamic postsynaptic structures found at the majority of forebrain excitatory synapses. At the time of learning, spines undergo structural and functional changes critical to the formation of lasting memories[55-56]. The workhorse of this spine plasticity is actin polymerization, the process of linking actin monomers into complex, branched filaments (F-actin)[57-58]. Disrupting F-actin dynamics at the time of learning prevents the formation of long-term memories[59-63]. However, actin rapidly stabilizes after synaptic stimulation, such that the cytoskeleton and associated memory become impervious to disruption by actin depolymerizing agents, such as Latrunculin A (LatA), within minutes of stimulation[59, 62-64]. In stark contrast to this, we discovered that the F-actin supporting METH-associated memories in the basolateral amygdala complex (BLC), a subregion of the amygdala (AMY) and the brain's emotional memory center and a hub for drug-associated memories, remains dynamic long after learning. This revealed an unexpected weakness of pathogenic drug associations, providing a mechanism to selectively target the storage of METH-associated memories[65].

Importantly, other types of memories are not disrupted by LatA and a single home cage treatment is sufficient to produce an immediate and long-lasting disruption of memory-induced drug seeking. Thus, it is possible to selectively manipulate drug-associated memories without retrieval[65].

Given these results, actin depolymerization would seem to be a promising therapeutic target. However, β-actin, the isoform implicated in neuronal plasticity[66-69], is ubiquitously expressed throughout the body and critical for a multitude of processes, such as cell division and cardiac function. Therefore, we turned our focus to nonmuscle myosin II (NMII), a direct regulator of the synaptic actin cytoskeleton. NMII is a molecular motor we have shown to be a critical, temporally restricted player in synaptic actin polymerization and fear memory[59, 63]. (S)-Blebbistatin, the active enantiomer of blebbistatin, is the first and, until recently, the only inhibitor known to have activity against nonmuscle myosin IIs[70-73].

The terms blebblistatin and Blebb as used throughout refer to (S)-blebbistatin. The blebbistatin analogs of the present invention are all likewise (S)-enantiomers. Blebbistatin is commercially available (e.g. Tocris, Sigma) at >98% purity. Using blebbistatin, we have recapitulated all of the LatA findings including a single treatment being sufficient to prevent drug seeking for at least one month in an animal relapse model[52, 74].

Justification for the proposed discovery and development work is based on several key discoveries made over the past few years with regards to NMII as a target for drug seeking induced by METH-associated memories[65, 74].

In 2013, we published the finding that depolymerization of actin in the AMY disrupts the storage of METH-associated memories in a selective, retrieval-independent manner[65]. Because of the limited clinical potential of actin depolymerizing agents, we turned to NMII, a molecular motor we previously found to be a key regulator of memory, synaptic plasticity (long-term potentiation [LTP]) and actin polymerization in dendritic spines[59, 63]. Through a series of experiments in a recently published studies, we detailed NMII's potential as a therapeutic target for SUD relapse[52, 74-76]. For instance, through a single intra-BLC or IP administration of blebbistatin, we have found that METH-associated memory (conditioned place preference [CPP] assay) is disrupted in adult and adolescent male and female mice and rats (inactive enantiomer used as control with intra-BLC drug delivery or racemic blebbistatin used with systemic drug delivery due to solubility limitations)[52, 65].

Further, blebbistatin prevents context-induced reinstatement of METH seeking (FIG. 1A; P<0.05-0.005), a gold standard animal model of relapse[52, 74]. FIG. 1B shows lever pressing for METH during the self-administration training period in Context A, and subsequent extinction of lever pressing in Context B, when METH is removed. FIG. 1C shows lever pressing during the METH-free reinstatement sessions on Days 1, 2 and 30, when animals are returned to the METH-paired environment (Context A). Reinstatement testing on Day 1 was performed 30 minutes after a single intra-BLC administration of blebbistatin or the inactive enantiomer. No blebbistatin was given prior to Reinstatement sessions on Days 2 or 30, indicating the long-lasting memory disruption produced by a single administration of blebbistatin (at least one month), with no spontaneous renewal of the memory.

Figure 2B:
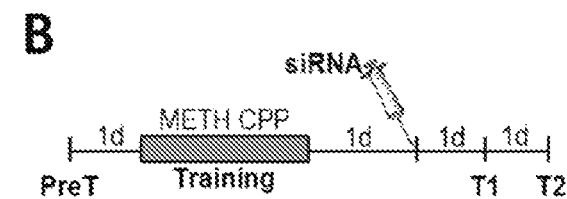
Figure 2C:
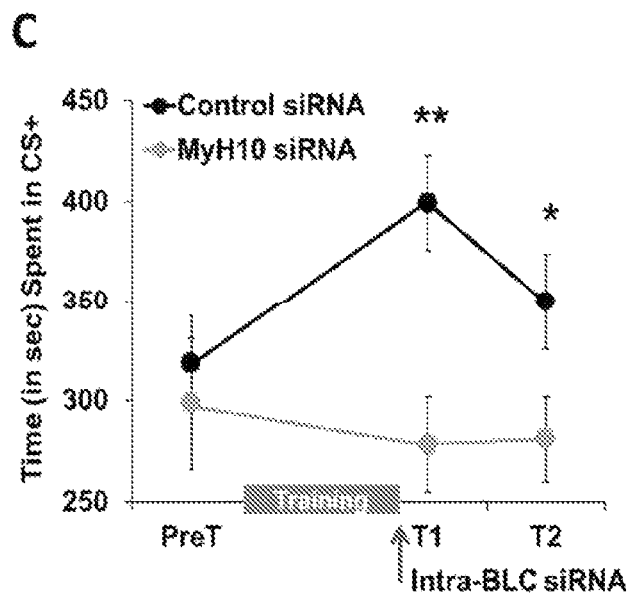
Figure 2D:
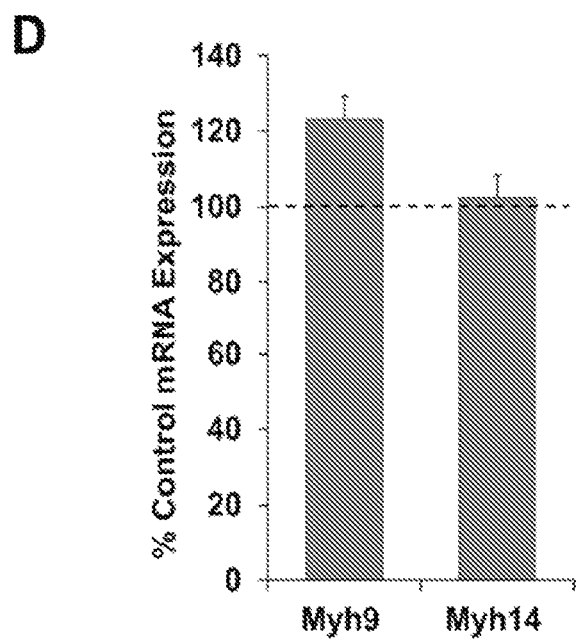

Blebbistatin has been shown to inhibit all classes of myosin IIs[77-79]. Myosin IIs are made of light chains, which are interchangeable across classes, and heavy chains, which are unique to each myosin II isoform. The heavy chain contains actin and ATP binding sites, as well as the force generating motor head that moves actin. According to RNA-Seq data from the Miller lab, none of the skeletal muscle heavy chain isoforms are expressed in the BLC of adult mice. However, two of the cardiac muscle myosin II's, Myh7 and Myh7b, the smooth muscle myosin II (Myh11) and all three nonmuscle myosin heavy chain isoforms (Myh14, Myh10, Myh9) are, with Myh10 expression being the highest by several fold. All six myosin IIs are found at the synapse. Therefore, we employed a genetic method of acute, focal knockdown of MYH10 in the BLC and found its post-training loss (FIG. 2A) to be sufficient to disrupt an established METH-associated memory (FIG. 2B-C)[74]. Interestingly, while protein expression data is not available, myosin II transcript levels in the human AMY (Allen Brain Atlas) suggests that a focus on the NMII class as a whole, as opposed to solely NMIIB, may be wise from a drug development perspective, as mRNA for NMIIA, B and C are expressed at equal levels. It is important to note that the NMIIs are a highly conserved class of actin-based molecular motors. For instance, *M.musculus* Myh10 has 99.1% sequence homology to *H.sapiens*.

The potential for systemic NMII inhibition to selectively target METH-associated memories in the way that intra-AMY administration does was also investigated. Results with IP administered Blebb indicate that it crosses the blood brain barrier at a high enough concentration to disrupt a METH-associated memory (IP, 10 mg/kg [brain levels=90 µM]; FIG. 3A). Yet, the effect remains selective, having no similarly immediate effect on a fear memory (FIG. 3B), or memories associated with food reward 75. IP administered Blebbistatin also disrupts reconsolidation of memories for cocaine, nicotine and mephedrone, a result with additional potential therapeutic relevance in treating relapse[75-76]. In addition, the BLC spine density increase that accompanies a METH-associated memory is reversed by Blebbistatin (FIG. 3C), without altering the spine density increase associated with a fear memory (FIG. 3D)[65, 74].

Figure 6:
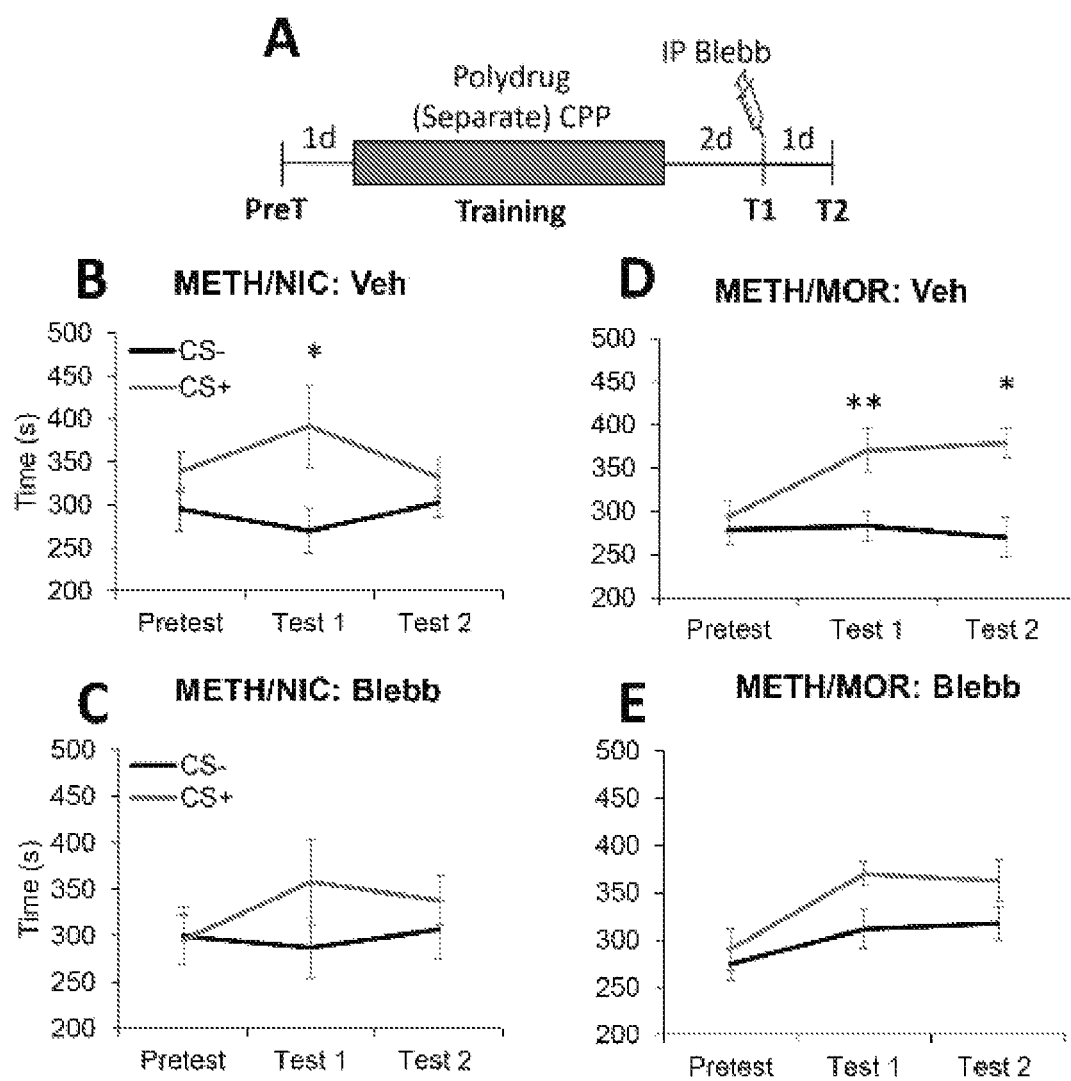
FIG. 6(A,B,C,D,E): Nonmuscle myosin II inhibition disrupts polydrug-associated memories when the drugs are administered on alternating days (A) Schematic of the experimental design. (B) Vehicle-treated mice demonstrated a significant METH/NIC CPP during Test 1, but not during Test 2. (C) Blebb-treated mice did not demonstrate a significant METH/NIC CPP during either test. (D) Veh-treated mice demonstrated a significant METH/MOR CPP during Test 1 and 2. (E) Blebb-treated mice did not demonstrate a significant METH/MOR CPP during either test. METH/NIC: Veh n=10; METH/NIC: Blebb n=10; METH/MOR: Veh n=19; METH/MOR: Blebb n=19; * p<0.05,  p<0.01, * p<0.001. Error bars represent ±s.e.m.

The vast majority of individuals with substance use disorder are polydrug users. For example, most METH users also smoke. We recently made an unexpected discovery with direct relevance to polydrug use[76]. When animals are treated with both METH and a drug that is impervious to Blebb on its own (nicotine or morphine), either concurrently or on alternating days, the nicotine and morphine memories become susceptible to immediate disruption by Blebb, akin to the effect on METH alone memories (FIG. 6). Thus, memories for previously impervious drugs of abuse become susceptible to NMII inhibition when METH associations are also formed. Importantly, this occurs when associative training is performed with METH and the other drug of abuse being administered simultaneously or separately, on different days. We are currently expanding our analysis to other commonly abused drugs, including other opioids, such as heroin, alcohol, cocaine and synthetic cathinones.

Figure 4:
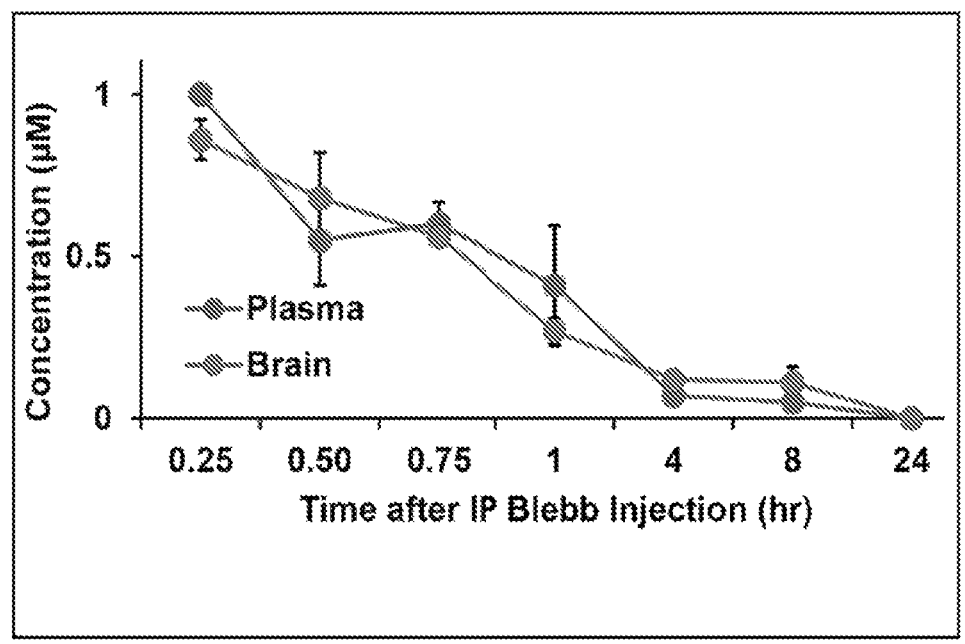
FIG. 4: Brain and plasma distribution of blebbistatin after IP dosing at 10 mg/kg in mice.

In addition to its efficacy in animal relapse models, several properties make Blebb an excellent scaffold for medicinal chemistry. Paramount among these are the molecule's small size, high brain penetration, rapid clearance from plasma and brain (short-acting is sufficient and reduces unwanted peripheral and central effects; FIG. 4). In addition, we have observed no effect of systemically administered racemic Blebb in a broad panel of rodent behaviors[74].

Blebb, identified in an HTS campaign in the early 2000s via an ATPase assay[70], and its few derivatives (FIG. 5) were until very recently, the only small molecules reported to have inhibitory activity toward NMII. BDM (2,3-butanedione monoxime)[80] some N-benzylsulphonamides and hydroxycoumarines[81] inhibit some myosin IIs, but they are either not active against NMII and/or lack selectivity and thus, cannot be used as viable probes, even for in vitro studies. Blebb has been widely used as an in vitro probe since its discovery. Due to photoinactivation upon exposure to blue light[73], analogs made through simple modifications, including a nitro-derivative, have been developed to establish the photostability.[82-84] More discussion of these compounds can be found in the next section.

Figure 5:
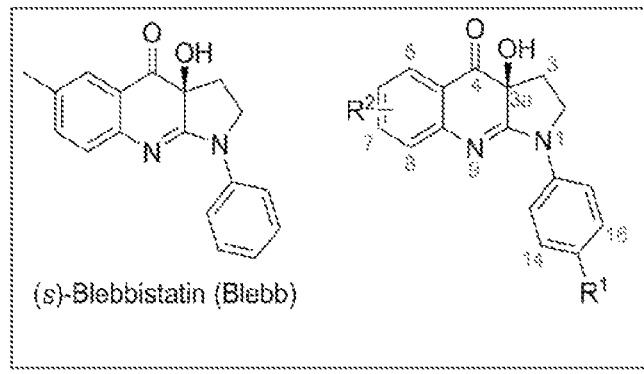
FIG. 5: Structure of (S)-blebbistatin, and compound numbering scheme.

Blebb is the (s)-configuration of Blebbistatin (FIG. 5). Since its discovery, its biochemical and cell potency have been assayed against many myosin ATPases[70, 73, 77, 85-88] and in a number of cells/tissues.[77, 86-92] The biochemical $IC_{50}$ values reported for Blebb in various myosin IIs are 1.8-9 µM[77]. Specific $IC_{50}$ values in cell-based assays have not been reported, but Blebb has been shown to be effective across a wide concentration range from ~900 nM to 90 µM,[79, 86-87, 93-94], indicating that Blebb is cell penetrant, consistent with our own data. Limited SAR has been performed around Blebb's core structure[70], likely due to the therapeutic potentials of NMII inhibitors having only been realized in the past few years. Modifications and optimization to Blebb are needed in order to obtain more selective NMII inhibitors to serve as viable drug candidates.

The current class of blebbistatin analogs have been synthesized as generally described in Synthetic Schemes 1-7 (below) and are characterized in vitro in Table 1. Chemical structures of compounds of the invention listed in Table 1 are shown in Table 3, below. Synthetic Scheme 1 is an overview of a synthetic method that can be used in preparation of the specific examples and the structures read upon by the generic structural claim, and Synthetic Schemes 2-7 are examples of different embodiments of synthetic methods for certain of the specific examples and the structures read upon by the generic structural claim.

Table 1 lists properties of compounds of the invention, analogs of blebbistatin having an inhibitory selectivity for nonmuscle myosin II relative to cardiac myosin II of greater than 3.0. Compounds having significantly less inhibitory activity (higher Ki) for cardiac myosin II can exhibit lower cardiac toxicity of the compound relative to blebbistatin, as discussed below.

Table 1 lists the selective inhibitory compounds, defined by this ratio of Ki/EC50, the structures of which are shown in Table 3, according to a unique compound identifier also shown with the corresponding chemical structure in the Figures. All compounds of the invention are of the same absolute configuration as (S)-blebbistatin, and are based on the parent ring structure

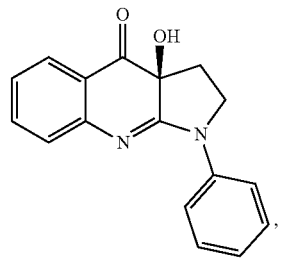 [SMILES: O=C1c2ccccc2N=C2N(c3ccccc3)CC[C@@]12O]

(S)-3a-hydroxy-1-phenyl-1,2,3,3a-tetrahydro-4H-pyrrolo[2,3-b]quinolin-4-one. The phenyl rings in (S)-blebbistatin can be substituted, and can be replaced by various heteroaryl rings, unsubstituted or substituted, in certain of the analogs, compounds of the invention.

The top row of data are provided for blebbistatin itself for purposes of comparison. Blebbistatin has a ratio (CMMII/NMII) of 0.789, showing that the Ki value of the parent compound with respect to inhibition of cardiac myosin II is lower than is the EC50 value of nonmuscle myosin II, i.e., the compound has more potent inhibitory activity of the cardiac form of myosin II than it does towards the nonmuscle form of myosin II. All the compounds of the invention or compounds for practice of methods of the invention, indicated in Table 1, have at least a three-fold higher Ki value for inhibition of cardiac myosin II relative to the EC50 value of the compound for inhibition of nonmuscle myosin II.

The first column of Table 1 provides a unique numerical identifier of the compound, the structure of each of which is indicated in Table 3. The second, third, and fourth columns of Table 1 provide data concerning the photostability of the indicated compound. In comparison with blebbistatin, many compounds used for practice of methods of the invention exhibit a significantly higher photostability than does blebbistatin. These columns (Photostability), provide values for the percentage remaining undegraded of the compound under conditions after 4 and 24 hours illumination, compared to percentage remaining undegraded in the dark under comparable conditions. Blebbistatin is known to be somewhat photo-unstable, and improvement of photostability is a benefit in formulation of pharmaceutical compositions for administration to patients undergoing treatment.

The fifth column of Table 1 provides EC50 values (μM) determined for inhibition of nonmuscle myosin II by the indicated compound. These figures were obtained as described in the bioassays section. The sixth and seventh columns give the Ki values (μM) of inhibition of cardiac myosin II and the ratio of cardiac muscle myosin inhibition relative to non-muscle myosin II. The eighth column gives skeletal myosin II inhibition. For compounds marked as NMII selective ("NMII-sel"), no Ki value for cardiac myosin II could be determined; the compounds had no detectable inhibitory properties versus the cardiac myosin II. The ninth column shows the chiral purity of the sample tested.

TABLE 1

In vitro characterization data for selected blebbistatin analogs

| Identifier | Photostability | | | NMII | CMMII | Ratio CMMII: | SKMMII | Chiral HPLC |
|---|---|---|---|---|---|---|---|---|
| | 4 hours | 24 hours | Dark (24 h) | EC50 (μM) | $K_i$ (μM) | NMII Ki/EC50 | $K_i$ (μM) | Purity % |
| Blebbistatin | 82.9 | 9.3 | >99 | 1.9 | 1.5 | 0.8 | 0.36 | >99 |
| BPN-0025044 | 90.3 | 12.1 | >99 | 5.2 | 28.0 | 5.4 | 7.00 | 97.0 |
| BPN-0025059 | 96.1 | 48.6 | >99 | 5.1 | 120.0 | 23.5 | 22.00 | >99 |
| BPN-0025100 | 82.8 | 4.7 | 99.0 | 7.5 | 48.0 | 6.4 | 9.70 | >99 |
| BPN-0025110 | 6.6 | 2.6 | >99 | 3.2 | 22.0 | 6.9 | 8.00 | >99 |
| BPN-0025240 | 93.0 | 28.6 | 94.7 | 10.2 | 400.0 | 39.2 | 35.00 | >99 |
| BPN-0025254 | 92.5 | 39.4 | >99 | 4.6 | n/a | NMII-sel | 7.70 | >99 |
| BPN-0025903 | 39.8 | 7.5 | 98.3 | 6.4 | n/a | NMII-sel | 11.00 | 95.4 |
| BPN-0025919 | ND | ND | ND | 3.9 | 18.0 | 4.6 | 1.80 | 91.7 |
| BPN-0026282 | 64.0 | 7.0 | >99 | 48.0 | n/a | NMII-sel | n/a | 87.5 |
| BPN-0026283 | 39.4 | 10.8 | 92.0 | 3.5 | n/a | NMII-sel | 5.00 | 96.7 |
| BPN-0026285 | 51.9 | 8.2 | 94.7 | 1.6 | 9.1 | 5.7 | 0.90 | >99 |
| BPN-0026324 | 98.5 | 90.4 | >99 | 2.2 | 30.0 | 13.6 | 3.50 | >99 |
| BPN-0026325 | 89.0 | 14.0 | 97.8 | 5.3 | n/a | NMII-sel | 13.00 | >99 |
| BPN-0026387 | 85.2 | 18.0 | 93.5 | 2.5 | 13.0 | 5.2 | 1.20 | 98.2 |
| BPN-0026393 | 97.9 | 75.0 | >99 | 3.4 | 11.0 | 3.2 | 1.70 | >99 |
| BPN-0026394 | >99 | 98.7 | >99 | 3.8 | n/a | NMII-sel | 4.80 | 98.25 |
| BPN-0026401 | 81.2 | 9.6 | 97.7 | 3.0 | 50.0 | 16.7 | 3.30 | 99.0 |
| BPN-0026404 | ND | ND | ND | 3.3 | 23.0 | 7.0 | 3.60 | >99 |
| BPN-0026413 | 94.3 | 82.2 | 97.3 | 36.0 | 110.0 | 3.1 | 33.00 | 49.5 |
| BPN-0026457 | 98.6 | 77.1 | >99 | 5.3 | n/a | NMII-sel | 15.00 | 96.5 |
| BPN-0026495 | 80.9 | 15.9 | 93.4 | 6.6 | n/a | NMII-sel | 20.00 | >99 |

TABLE 1-continued

In vitro characterization data for selected blebbistatin analogs

| | Photostability | | | NMII | CMMII | Ratio CMMII: NMII | SKMMII | Chiral HPLC |
|---|---|---|---|---|---|---|---|---|
| Identifier | 4 hours | 24 hours | Dark (24 h) | EC50 (μM) | $K_I$ (μM) | Ki/EC50 | $K_I$ (μM) | Purity % |
| BPN-0026496 | 41.7 | 3.5 | 97.9 | 2.6 | 83.0 | 31.9 | 15.00 | >99 |
| BPN-0026497 | 82.7 | 6.1 | 97.5 | 2.1 | 33.0 | 15.7 | 9.80 | >99 |
| BPN-0026499 | 97.7 | 84.9 | >99 | 0.5 | 5.7 | 12.4 | 0.18 | 92.7 |
| BPN-0026500 | 92.2 | 22.8 | >99 | 2.4 | n/a | NMII-sel | 23.00 | >99 |
| BPN-0026533 | 87.7 | 6.4 | 91.7 | 33.0 | n/a | NMII-sel | 60.00 | 47.7 |
| BPN-0026544 | 51.1 | 10.8 | 93.7 | 5.3 | n/a | NMII-sel | 4.80 | 93.0 |
| BPN-0026545 | 89.4 | 5.1 | >99 | 7.0 | n/a | NMII-sel | 12.00 | 92.1 |
| BPN-0026546 | 81.2 | 12.5 | 93.5 | 8.9 | n/a | NMII-sel | 22.00 | 85.1 |
| BPN-0026576 | 98.6 | >99 | >99 | 5.5 | 18.0 | 3.3 | 4.60 | 98.9 |
| BPN-0026579 | 77.3 | 8.5 | 93.7 | 1.0 | 5.0 | 5.0 | 0.37 | 98.5 |
| BPN-0026605 | 69.6 | 2.3 | 94.2 | 1.0 | 15.0 | 15.0 | 0.29 | >99 |
| BPN-0026606 | 85.9 | 4.1 | 95.5 | 5.9 | n/a | NMII-sel | n/a | 98.6 |
| BPN-0026607 | 98.5 | 84.7 | 98.1 | 6.1 | n/a | NMII-sel | 5.80 | 96.1 |
| BPN-0026608 | 86.7 | <1 | 97.5 | 4.3 | 50.0 | 11.6 | 1.70 | 95.3 |
| BPN-0026609 | ND | ND | ND | 1.5 | 5.5 | 3.7 | 0.43 | 98.5 |
| BPN-0026618 | 92.3 | 17.2 | 96.6 | 4.8 | 18.0 | 3.8 | 5.90 | >99 |
| BPN-0026619 | 77.4 | <1 | 91.0 | 1.6 | 36.0 | 22.5 | 2.50 | 99.0 |
| BPN-0026620 | 94.1 | 27.8 | 92.8 | 6.4 | n/a | NMII-sel | 16.00 | >99 |
| BPN-0026621 | 93.3 | 61.4 | 93.5 | 5.7 | 40.0 | 7.0 | 3.40 | 83.0 |
| BPN-0026624 | 90.5 | 88.2 | 92.2 | 15.0 | 210.0 | 14.0 | 24.00 | >99 |
| BPN-0026638 | 87.9 | 71.9 | 91.6 | 1.7 | 12.0 | 7.1 | 0.37 | 94.3 |
| BPN-0026639 | 89.8 | 49.5 | >99 | 3.3 | 14.0 | 4.2 | 1.10 | >99 |
| BPN-0026640 | 71.1 | 17.8 | 96.8 | 2.0 | 8.0 | 4.0 | 0.53 | 89.6 |
| BPN-0026643 | 64.0 | <1 | 85.1 | 4.8 | 17.0 | 3.5 | 1.90 | >99 |
| BPN-0026648 | 94.3 | 84.3 | 97.7 | 4.7 | 56.0 | 11.9 | 4.50 | 91.3 |
| BPN-0026650 | 80.5 | 5.5 | >99 | 4.9 | n/a | NMII-sel | 4.30 | >99 |
| BPN-0026651 | 73.0 | 5.8 | 97.5 | 3.3 | n/a | NMII-sel | 3.90 | 96.3 |
| BPN-0026659 | 72.1 | 17.9 | 91.1 | 2.6 | 9.0 | 3.5 | 0.93 | 93.2 |
| BPN-0026660 | 87.4 | 7.6 | 93.8 | 8.2 | n/a | NMII-sel | 33.00 | >99 |
| BPN-0026661 | 95.5 | 65.4 | 98.2 | 2.4 | 53.0 | 22.1 | 2.20 | 89.4 |
| BPN-0026662 | 85.4 | 7.5 | >99 | 1.1 | 6.0 | 5.5 | 0.19 | 97.6 |
| BPN-0026663 | 40.7 | 2.0 | 97.3 | 0.8 | 2.8 | 3.5 | 0.12 | >99 |
| BPN-0026664 | 30.3 | <1 | 97.7 | 0.9 | 29.0 | 33.3 | 1.50 | 95.8 |
| BPN-0026665 | 2.7 | <1 | 97.4 | 0.6 | 4.2 | 6.7 | 0.14 | >99 |
| BPN-0026667 | 85.7 | 2.9 | >99 | 1.2 | 6.2 | 5.2 | 0.33 | 98.6 |
| BPN-0026669 | 87.8 | 11.2 | >99 | 5.3 | 25.0 | 4.7 | 1.20 | >99 |

TABLE 1-continued

In vitro characterization data for selected blebbistatin analogs

| Identifier | Photostability | | | NMII EC50 (μM) | CMMII $K_l$ (μM) | Ratio CMMII: NMII Ki/EC50 | SKMMII $K_l$ (μM) | Chiral HPLC Purity % |
| --- | --- | --- | --- | --- | --- | --- | --- | --- |
| | 4 hours | 24 hours | Dark (24 h) | | | | | |
| BPN-0026693 | 34.1 | 1.7 | >99 | 0.6 | 3.5 | 6.0 | 0.27 | 53.0 |
| BPN-0026708 | 40.7 | <1 | >99 | 1.7 | 5.3 | 3.1 | 1.40 | 83.5 |
| BPN-0026709 | 98.7 | 93.0 | 98.2 | 1.2 | 30.6 | 25.5 | 1.30 | 95.7 |
| BPN-0026710 | 6.6 | <1 | >99 | 1.7 | 5.2 | 3.1 | 0.95 | 92.2 |
| BPN-0026726 | 76.3 | 24.1 | 95.4 | 6.0 | n/a | NMII-sel | 4.40 | 95.8 |
| BPN-0026745 | >99 | 94.2 | >99 | 2.9 | 73.0 | 25.2 | 2.60 | 97.7 |
| BPN-0026746 | 58.8 | 10.6 | >99 | 4.5 | 17.0 | 3.8 | 3.60 | 98.3 |
| BPN-0026748 | 88.2 | 22.4 | >99 | 3.0 | 14.0 | 4.7 | 2.60 | 96.7 |
| BPN-0026749 | 87.8 | <5 | >99 | 3.2 | n/a | NMII-sel | 23.00 | >99 |
| BPN-0026770 | >99 | 92.9 | >99 | 3.8 | n/a | NMII-sel | 1.50 | >99 |
| BPN-0026774 | 86.7 | 18.1 | >99 | 2.6 | 8.9 | 3.4 | 1.10 | >99 |
| BPN-0026785 | 95.8 | 59.3 | 91.6 | 7.4 | 23.0 | 3.1 | 5.90 | >99 |
| BPN-0026786 | 87.8 | 66.6 | 96.0 | 11.0 | n/a | NMII-sel | n/a | >99 |
| BPN-0026813 | 82.0 | <1 | >99 | 0.5 | 1.6 | 3.1 | 0.11 | >99 |
| BPN-0026815 | 91.2 | 88.2 | 90.2 | 0.8 | 2.8 | 3.6 | 0.27 | 91.2 |
| BPN-0026819 | 96.6 | 84.8 | 97.3 | 1.8 | 50.0 | 27.8 | 1.70 | >99 |
| BPN-0026847 | 99.0 | 91.8 | >99 | 13.0 | n/a | NMII-sel | n/a | >99 |
| BPN-0026848 | >99 | 98.7 | >99 | 26.0 | 320.0 | 12.3 | 61.00 | 66.7 |
| BPN-0026849 | 98.5 | 91.8 | >99 | 1.0 | 16.0 | 16.0 | 0.77 | >99 |
| BPN-0026852 | 62.4 | 3.8 | 85.1 | 2.6 | 25.0 | 9.6 | 5.60 | 81.8 |
| BPN-0026853 | 91.2 | 88.2 | 90.2 | 12.0 | n/a | NMII-sel | n/a | 98.9 |
| BPN-0026881 | 70.9 | 1.8 | >99 | 1.8 | 11.0 | 6.1 | 0.80 | >99 |
| BPN-0026882 | 98.8 | 96.8 | >99 | 5.8 | 21.0 | 3.6 | 4.50 | >99 |
| BPN-0026886 | >99 | 98.5 | >99 | 2.7 | 19.0 | 7.0 | 4.20 | 87.8 |
| BPN-0027036 | 90.2 | 24.7 | 97.4 | 3.0 | 22.0 | 7.3 | 4.90 | >99 |
| BPN-0027037 | >99 | >99 | >99 | 24.0 | n/a | NMII-sel | 18.00 | 69.1 |
| BPN-0027038 | >99 | 98.7 | >99 | 2.7 | 17.0 | 6.3 | 0.61 | >99 |
| BPN-0027039 | 89.8 | 31.3 | 95.9 | 22.0 | 68.0 | 3.1 | 4.60 | 49.3 |
| BPN-0027040 | 94.8 | 21.4 | 95.7 | 1.2 | 37.0 | 30.8 | 2.60 | 94.1 |
| BPN-0027042 | 92.7 | 13.8 | >99 | 6.7 | n/a | NMII-sel | 10.00 | >99 |
| BPN-0027043 | 97.7 | 72.3 | >99 | 2.9 | n/a | NMII-sel | 15.00 | 89.1 |
| BPN-0027071 | >99 | 95.3 | >99 | 10.0 | n/a | NMII-sel | 20.00 | 45.6 |
| BPN-0027072 | >99 | >99 | >99 | 10.0 | 31.0 | 3.1 | 5.00 | 96.3 |
| BPN-0027074 | 95.8 | 93.4 | 94.5 | 21.0 | 77.0 | 3.7 | 16.00 | >99 |
| BPN-0027080 | 98.1 | 88.1 | >99 | 3.0 | n/a | NMII-sel | 4.80 | >99 |
| BPN-0027081 | 97.0 | 46.3 | 96.9 | 1.1 | 9.0 | 8.2 | 0.29 | 89.8 |

TABLE 1-continued

In vitro characterization data for selected blebbistatin analogs

| | Photostability | | | NMII | CMMII | Ratio CMMII: NMII | SKMMII | Chiral HPLC |
|---|---|---|---|---|---|---|---|---|
| Identifier | 4 hours | 24 hours | Dark (24 h) | EC50 ($\mu$M) | $K_I$ ($\mu$M) | Ki/EC50 | $K_I$ ($\mu$M) | Purity % |
| BPN-0027108 | >99 | 97.0 | >99 | 2.8 | n/a | NMII-sel | 10.00 | >99 |
| BPN-0027109 | 82.5 | 29.4 | >99 | 0.5 | 11.0 | 21.2 | 0.27 | 91.4 |
| BPN-0027118 | 68.6 | 9.2 | 94.4 | 1.2 | 5.5 | 4.6 | 0.68 | 84.2 |
| BPN-0027121 | 75.6 | 6.5 | 98.6 | 2.5 | 19.0 | 7.6 | 2.70 | 70.3 |
| BPN-0027122 | 69.5 | 5.3 | 97.1 | 1.7 | 45.0 | 26.5 | 5.90 | 82.7 |
| BPN-0027159 | 89.9 | 22.5 | >99 | 14.0 | n/a | NMII-sel | 330.00 | >99 |
| BPN-0027160 | 95.5 | 73.0 | >99 | 2.9 | 30.0 | 10.3 | 0.20 | 81.9 |
| BPN-0027161 | 78.6 | 60.2 | 98.3 | 1.1 | 24.0 | 21.8 | 0.24 | 73.7 |
| BPN-0027162 | 98.5 | 95.9 | >99 | 7.9 | 52.0 | 6.6 | 4.50 | 77.2 |
| BPN-0027163 | 95.0 | 44.6 | >99 | 4.2 | 21.0 | 5.0 | 5.90 | 92.4 |
| BPN-0027181 | >99 | 99.0 | >99 | 2.7 | 91.0 | 33.7 | 3.10 | 97.5 |
| BPN-0027196 | 94.9 | 7.1 | >99 | 7.5 | n/a | NMII-sel | 12.00 | 75.2 |
| BPN-0027197 | >99 | 36.4 | >99 | 2.5 | n/a | NMII-sel | 2.40 | 58.8 |
| BPN-0027198 | 89.9 | 21.4 | >99 | 2.9 | 10.5 | 3.6 | 0.88 | 72.8 |
| BPN-0027213 | 46.3 | 1.0 | 85.0 | 2.9 | 33.0 | 11.4 | 0.45 | 79.2 |
| BPN-0027215 | 73.2 | 9.2 | 97.3 | 0.4 | n/a | NMII-sel | 1.00 | >99 |
| BPN-0027216 | 97.2 | 85.0 | >99 | 2.7 | 31.0 | 11.5 | 4.60 | >99 |
| BPN-0027217 | 97.9 | 76.0 | >99 | 7.8 | 160.0 | 20.5 | 21.00 | >99 |
| BPN-0027218 | 90.0 | 4.4 | 95.5 | 6.9 | n/a | NMII-sel | 40.00 | 49.1 |
| BPN-0027219 | 46.2 | 3.8 | 98.3 | 39.0 | n/a | NMII-sel | n/a | 50.0 |
| BPN-0027228 | >99 | 89.1 | >99 | 28.0 | 300.0 | 10.7 | 4.60 | 70.8 |
| BPN-0027236 | >99 | 84.9 | >99 | 5.9 | N/A | NMII-sel | 5.00 | 55.9 |
| BPN-0027237 | 79.8 | 15.8 | 82.7 | 11.0 | 50.0 | 4.5 | 6.70 | 40.8 |
| BPN-0027238 | >99 | >99 | >99 | 4.1 | n/a | NMII-sel | 3.70 | 90.8 |
| BPN-0027240 | 94.1 | 74.6 | 98.0 | 3.8 | n/a | NMII-sel | n/a | 82.3 |
| BPN-0027241 | 91.6 | 87.0 | 97.4 | 13.0 | 100.0 | 7.7 | 7.20 | 54.2 |
| BPN-0027250 | 45.8 | 2.7 | 70.1 | 1.0 | n/a | NMII-sel | 1.00 | 78.1 |
| BPN-0027255 | 82.4 | 42.2 | 98.3 | 1.9 | n/a | NMII-sel | 0.80 | 71.5 |
| BPN-0027257 | 97.0 | 78.0 | 97.4 | 5.9 | 40.0 | 6.8 | 4.20 | 96.7 |
| BPN-0027289 | 91.9 | 26.3 | 97.0 | 1.7 | 50.0 | 29.4 | 1.00 | 95.8 |
| BPN-0027330 | 92.7 | 64.6 | >99 | 10.0 | 80.0 | 8.0 | 4.20 | >99 |
| BPN-0027346 | 97.7 | 98.7 | 98.1 | 4.8 | 33.0 | 6.9 | 2.00 | >99 |
| BPN-0027374 | 96.9 | 86.4 | >99 | 8.7 | n/a | NMII-sel | 0.82 | 68.8 |
| BPN-0027376 | 90.4 | 2.8 | 97.0 | 5.9 | 46.0 | 7.8 | 6.70 | 89.5 |
| BPN-0027393 | 95.2 | 83.9 | 97.5 | 5.2 | 30.0 | 5.8 | 3.50 | 96.3 |
| BPN-0027394 | 92.2 | 57.2 | 98.7 | 4.1 | 14.0 | 3.4 | 1.10 | >99 |

TABLE 1-continued

In vitro characterization data for selected blebbistatin analogs

| | Photostability | | | NMII | CMMII | Ratio CMMII: NMII | SKMMII | Chiral HPLC |
|---|---|---|---|---|---|---|---|---|
| Identifier | 4 hours | 24 hours | Dark (24 h) | EC50 (μM) | $K_I$ (μM) | Ki/EC50 | $K_I$ (μM) | Purity % |
| BPN-0027396 | 85.5 | 23.5 | >99 | 1.8 | 9.5 | 5.3 | 1.10 | 74.1 |
| BPN-0027406 | 75.7 | 1.6 | >99 | 53.0 | 200.0 | 3.8 | 7.50 | 84.0 |
| BPN-0027410 | 91.5 | 41.8 | >99 | 3.4 | 25.0 | 7.4 | 1.60 | 96.8 |
| BPN-0027411 | 81.8 | 6.4 | 98.8 | 6.3 | 51.0 | 8.1 | 1.10 | 74.7 |
| BPN-0027412 | 90.8 | 67.7 | 95.5 | 5.8 | 21.0 | 3.6 | 2.70 | >99 |
| BPN-0027441 | 97.2 | 71.4 | 91.8 | 50.0 | 230.0 | 4.6 | 12.00 | 64.4 |
| BPN-0027468 | 83.3 | 77.5 | 98.3 | 4.0 | n/a | NMII-sel | 1.20 | 62.6 |
| BPN-0027469 | 58.8 | 44.3 | >99 | 2.0 | n/a | NMII-sel | 0.68 | 90.6 |
| BPN-0027488 | 49.4 | 20.0 | 96.4 | 0.8 | n/a | NMII-sel | 0.90 | >99 |
| BPN-0027489 | 76.1 | 8.5 | >99 | 0.8 | 26.0 | 33.3 | 0.94 | 85.0 |
| BPN-0027490 | 80.8 | 6.8 | 98.5 | 0.7 | n/a | NMII-sel | 0.41 | 97.0 |
| BPN-0027491 | 54.0 | 6.7 | 97.1 | 2.3 | 24.0 | 10.4 | 0.68 | 84.9 |
| BPN-0027492 | 95.1 | 66.9 | >99 | 2.9 | n/a | NMII-sel | 2.60 | 89.5 |
| BPN-0027494 | 63.5 | <1.0 | 88.4 | 4.2 | n/a | NMII-sel | 4.70 | Inconclusive |
| BPN-0028550 | 92.7 | 77.6 | 89.4 | 9.3 | 70.0 | 7.5 | 9.40 | 50.7 |
| BPN-0028552 | 87.7 | 62.2 | 91.8 | 1.2 | 26.0 | 21.7 | 2.50 | 71.1 |
| BPN-0028554 | 87.6 | 35.9 | 97.6 | 9.7 | 120.0 | 12.4 | 9.00 | 91.6 |
| BPN-0028555 | 4.7 | <1 | 93.6 | 0.8 | 4.6 | 6.1 | 1.50 | 64.2 |
| BPN-0028616 | 93.2 | 71.0 | 89.4 | 15.0 | 200.0 | 13.3 | 11.00 | 50.8 |
| BPN-0028625 | 84.4 | 84.6 | 81.8 | 5.3 | 300.0 | 56.6 | 8.90 | 46.3 |
| BPN-0028646 | >99 | 97.1 | 98.2 | 4.5 | n/a | NMII-sel | 1.30 | >99 |
| BPN-0028648 | 52.5 | <1 | 98.4 | 1.3 | 4.4 | 3.4 | 0.26 | 82.7 |
| BPN-0028649 | 96.7 | 73.1 | 98.4 | 4.2 | 30.0 | 7.1 | 2.70 | 62.9 |
| BPN-0028650 | 88.7 | 62.6 | 93.4 | 9.1 | 40.0 | 4.4 | 12.00 | 70.0 |
| BPN-0028652 | 86.2 | 22.8 | 98.5 | 8.3 | 80.0 | 9.6 | 1.30 | >99 |
| BPN-0028694 | 55.3 | 11.2 | 98.0 | 1.9 | 16.0 | 8.4 | 1.70 | 82.0 |
| BPN-0028697 | 88.4 | 25.4 | 97.3 | 8.0 | 60.0 | 7.5 | 1.90 | 98.4 |
| BPN-0028731 | 37.6 | 7.4 | >99 | 5.2 | 40 | 7.7 | 2.2 | 81.1 |
| BPN-0028733 | 82.1 | 14.8 | 96.6 | 8.7 | 27 | 3.1 | 6.8 | 74.8 |
| BPN-0028734 | 76 | <1 | 96.3 | 3 | 15 | 5.0 | 2.9 | 86.1 |
| BPN-0028736 | 64 | 2 | 95.3 | 13 | 90 | 6.9 | 1.5 | 91.1 |
| BPN-0028758 | 90.9 | 55.3 | 93.3 | 51 | 210 | 4.1 | 40 | 91 |
| BPN-0028760 | 87.9 | 83 | 87.6 | 3.7 | 16 | 4.3 | 0.94 | 40.3 |
| BPN-0028790 | 92.7 | 64 | 95.3 | 0.63 | 2.4 | 3.8 | 1 | >99 |
| BPN-0028820 | 80.9 | 62.7 | 94.2 | 7.2 | N/A | NMII-sel | 3 | 85.2 |
| BPN-0028821 | 89.8 | 29.1 | 98.5 | 0.96 | 12 | 12.5 | 0.77 | 84.1 |

TABLE 1-continued

In vitro characterization data for selected blebbistatin analogs

| Identifier | Photostability 4 hours | Photostability 24 hours | Dark (24 h) | NMII EC50 (µM) | CMMII $K_I$ (µM) | Ratio CMMII: NMII Ki/EC50 | SKMMII $K_I$ (µM) | Chiral HPLC Purity % |
|---|---|---|---|---|---|---|---|---|
| BPN-0028863 | 98.8 | 94.7 | 99 | 2.6 | N/A | NMII-sel | 2.8 | 91.2 |
| BPN-0028864 | 97.4 | 88.4 | 98.4 | 7 | N/A | NMII-sel | 12 | 65.4 |
| BPN-0028866 | 77.8 | 2.9 | 97.8 | 10 | N/A | NMII-sel | 400 | 82.8 |
| BPN-0028867 | 69.9 | 1 | 98.7 | 2.8 | N/A | NMII-sel | 1.3 | 88.2 |
| BPN-0028868 | 46.7 | 43.3 | 98.9 | 0.76 | 24 | 31.6 | 0.23 | 88.5 |
| BPN-0028897 | 82.8 | 5.4 | 98.4 | 9 | 300 | 33.3 | 110 | 52.4 |
| BPN-0028898 | 93.4 | 58.1 | 96.4 | 3 | 95 | 31.7 | 1.9 | >99 |
| BPN-0028899 | 70.8 | 29.7 | 97.8 | 1.5 | N/A | NMII-sel | 3.8 | 86.1 |
| BPN-0028918 | 54.2 | 7.8 | >99 | 2 | 11 | 5.5 | 0.64 | 97.2 |
| BPN-0028919 | 48.4 | <1 | 98.5 | 2.8 | N/A | NMII-sel | 1.4 | 95.4 |
| BPN-0028920 | 36.6 | 2.5 | 98.4 | 3.2 | N/A | NMII-sel | 3.9 | 97.5 |
| BPN-0028921 | 2.8 | 3.1 | 97.2 | 0.75 | 8.4 | 11.2 | 1 | 95.9 |
| BPN-0028922 | 86.1 | 27.7 | 94.8 | 1.1 | 9.7 | 8.8 | 0.77 | 95.3 |
| BPN-0028923 | 77.5 | 1 | 98.1 | 3.5 | 30 | 8.6 | 6 | >99 |
| BPN-0028924 | 44.7 | <1 | 97.7 | 1.7 | 20 | 11.8 | 2.6 | 88 |
| BPN-0028925 | 85.9 | 24.7 | 93.7 | 0.8 | 5.8 | 7.3 | 0.7 | 99 |

Table 2 and FIG. 7, below, provide data summarizing two different cardiac safety assays. The first (results shown in Table 2) assesses the effects of our compounds on the contractility of cardiomyocytes. As the cardiac Ki increases, the contractility effects dramatically decrease. However, unlike in the adult heart, the hiPS cardiomyocytes used in this assay express NMII, which likely accounts for the residual contractility effects seen at the highest dose tested. For that reason, we moved to in vivo echocardiograms, which assess contractility in live animals (FIG. 7). Similar to our results with the cardiomyocytes, increasing the cardiac Ki protects against the substantial contractility effects observed with Blebbistatin, regardless of NMII potency. Accordingly, the compounds of the invention and compounds used for practice of methods of the invention can produce less cardiac toxicity than does blebbistatin.

TABLE 2

Cardiac safety Characterization for Selected Blebbistatin Analogs I: Assessment of beating parameters in hiPS-derived cardiomyocyte.

| Compound | NMII EC50 | CMMII Ki | CMMII/NMII Ratio | Qualitative impact on Complete inhibition of Qualitative impact on contractility (e.g. Full = contraction) | Change in amplitude at 1 uM @ 15 min |
|---|---|---|---|---|---|
| Blebbistatin | 1.2 uM | 0.67 uM | 0.56 | NOTE: Baseline 0.1 uM: No 0.3 uM: Partial 1.0u M: Full 3.0 uM: Full | −57.9 ± 12.8% |
| BPN-0025059 | 5.1 uM | 47.2 uM | 9.25 | NOTE: Reduced potency, improved selectivity, solubility, photostability 0.1 uM-1.0 uM: No effect; 3.0 uM: Small effect | +1.1 ± 0.1% |
| BPN-0025060 | 0.78 uM | 0.48 uM | 0.62 | NOTE: Improved potency, selectivity slightly improved, worse solubility/photostab Similar to Blebb | −81.8 ± 86.9% |
| BPN-0025100 | 7.5 uM | 26.3 uM | 3.51 | NOTE: Reduced potency, but reasonable improvement in selectivity and solubility | −7.8 ± 1.3% |

TABLE 2-continued

Cardiac safety Characterization for Selected Blebbistatin Analogs I:
Assessment of beating parameters in hiPS-derived cardiomyocyte.

| Compound | NMII EC50 | CMMII Ki | CMMII/NMII Ratio | Qualitative impact on Complete inhibition of Qualitative impact on contractility (e.g. Full = contraction) | Change in amplitude at 1 uM @ 15 min |
|---|---|---|---|---|---|
| BPN-0025002 | 2.6 uM | 1.97 uM | 0.76 | 0.1 uM-1.0 uM: No effect; 3.0 uM: Small effect NOTE: Slightly reduced potency, but slight improvement in selectivity | −38.9 ± 2.4% |
| BPN-0025046 | 26.8 uM | 1.74 uM | 0.07 | Similar to Blebb NOTE: Reduced potency and large shift towards cardiac selectivity | −47.6 ± 5.2% |
| BPN-0025098 | Inactive | Inactive | N/A | Similar to Blebb NOTE: Inactive in cytokinesis, improved solubility (86 uM vs Blebb = 9.3 uM) No effect at any dose | +2.0 ± 2.8% |

Table 3: Structures of Compounds for Methods of Invention

TABLE 3

Structures of Compounds for Methods of Invention

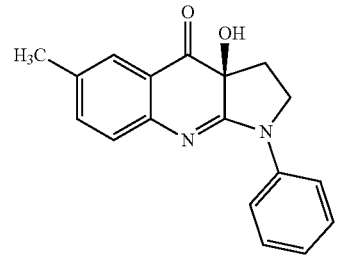

BPN-0024998 (blebbistatin, control)

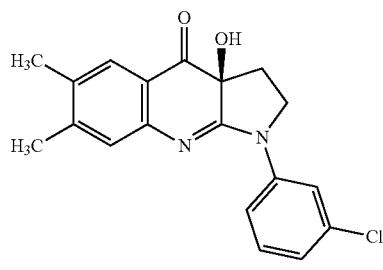

BPN-0026500

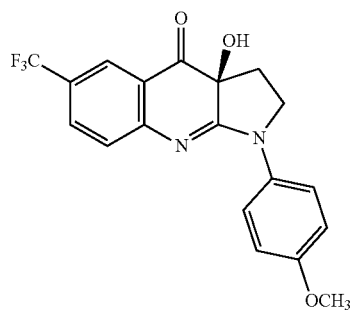 [SMILES: COc1ccc(N2CC[C@@]3(O)C(=O)c4cc(C(F)(F)F)ccc4N=C23)cc1]

BPN-0026393

TABLE 3-continued

Structures of Compounds for Methods of Invention

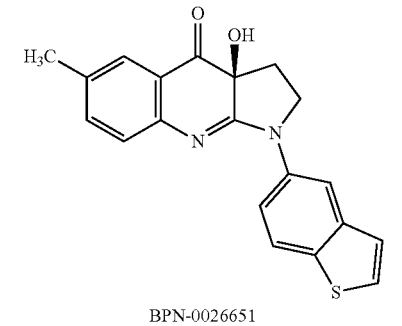

BPN-0026651

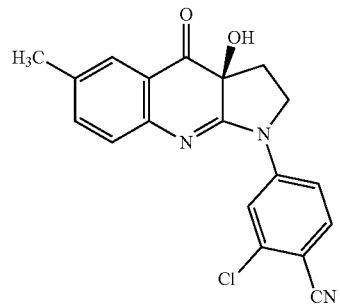 [SMILES: Cc1ccc2c(c1)C(=O)[C@]1(O)CCN(c3ccc(C#N)c(Cl)c3)C1=N2]

BPN-0026394/002

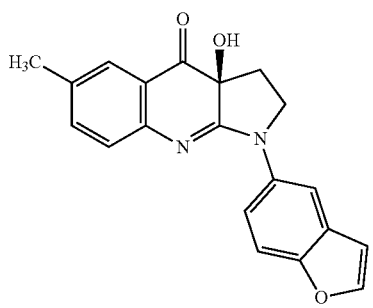 [SMILES: Cc1ccc2c(c1)C(=O)[C@]1(O)CCN(c3ccc4occc4c3)C1=N2]

BPN-0026283

TABLE 3-continued
Structures of Compounds for Methods of Invention
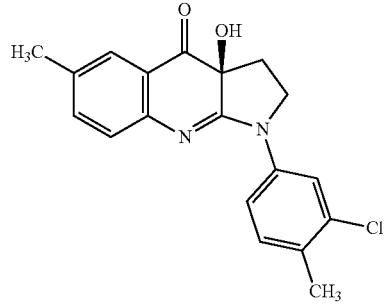 [SMILES: Cc1ccc2c(c1)C(=O)[C@]1(O)CCN(c3ccc(C)c(Cl)c3)C1=N2]
BPN-0025254
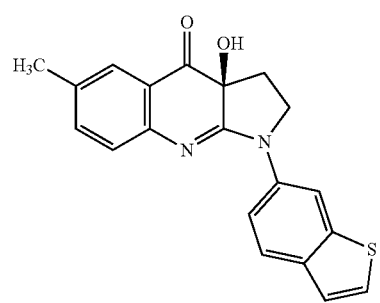 [SMILES: Cc1ccc2c(c1)C(=O)[C@]1(O)CCN(c3ccc4ccsc4c3)C1=N2]
BPN-0026650
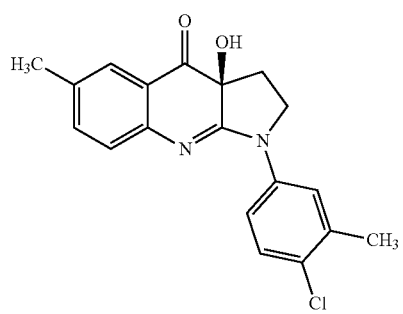
BPN-0026325
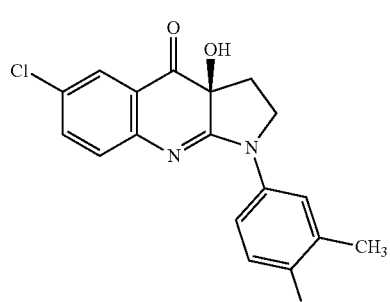
BPN-0026457
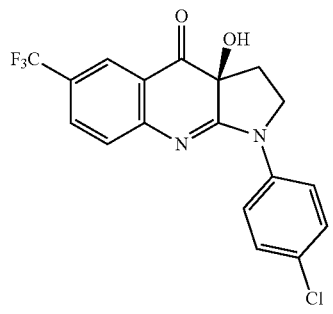 [SMILES: O=C1c2cc(C(F)(F)F)ccc2N=C2N(c3ccc(Cl)cc3)CC[C@@]12O]
BPN-0026544
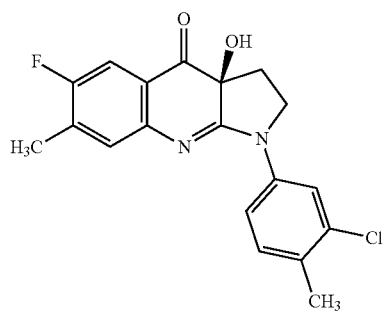 [SMILES: Cc1cc2c(cc1F)C(=O)[C@]1(O)CCN(c3ccc(C)c(Cl)c3)C1=N2]
BPN-0026606
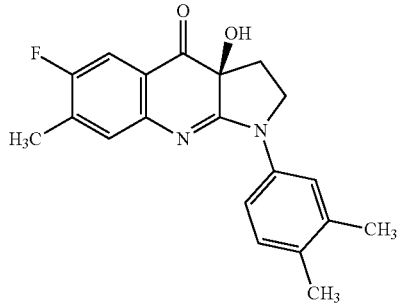 [SMILES: Cc1ccc(N2CC[C@@]3(O)C(=O)c4cc(F)c(C)cc4N=C23)cc1C]
BPN-0026607
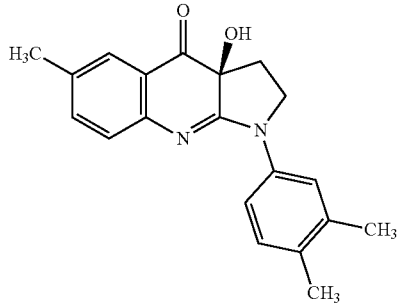
BPN-0025903
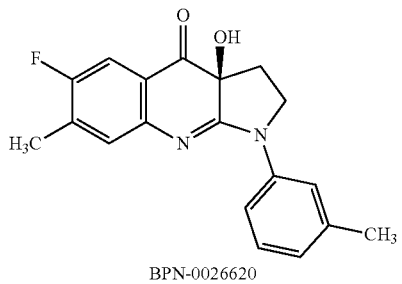
BPN-0026620

TABLE 3-continued
Structures of Compounds for Methods of Invention
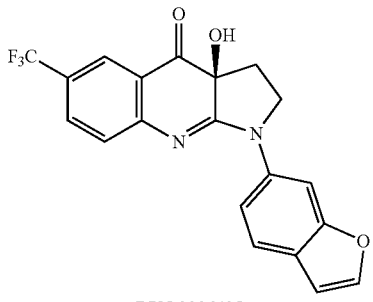 [SMILES: O=C1c2cc(C(F)(F)F)ccc2N=C2N(c3ccc4ccoc4c3)CC[C@@]12O]
BPN-0026495
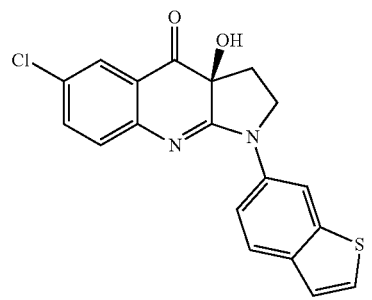 [SMILES: O=C1c2cc(Cl)ccc2N=C2N(c3ccc4ccsc4c3)CC[C@@]12O]
BPN-0026545
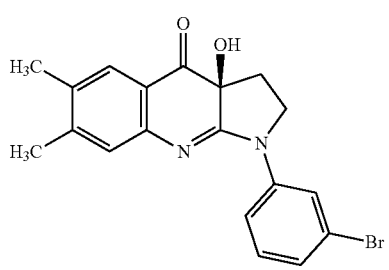
BPN-0026660
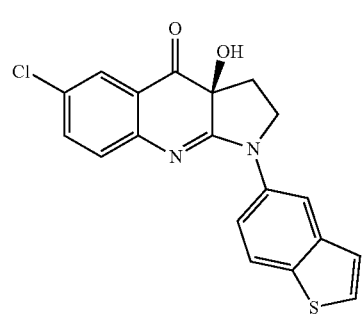 [SMILES: O=C1c2cc(Cl)ccc2N=C2N(c3ccc4sccc4c3)CC[C@@]12O]
BPN-0026546
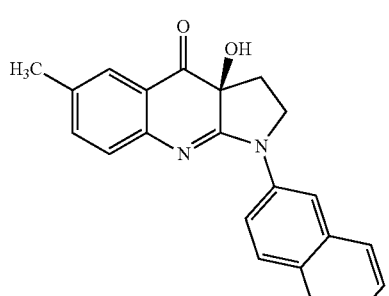
BPN-0025915
TABLE 3-continued
Structures of Compounds for Methods of Invention
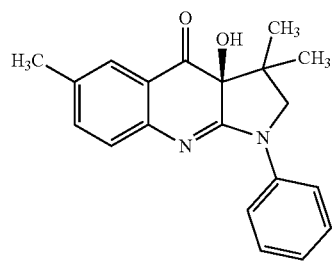 [SMILES: Cc1ccc2c(c1)C(=O)[C@@]1(O)C(=N2)N(c2ccccc2)CC1(C)C]
BPN-0026282
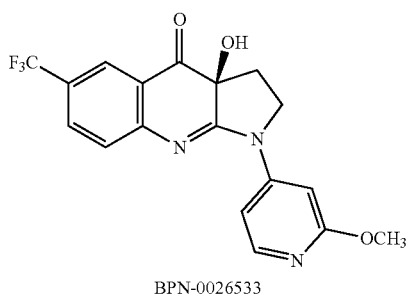
BPN-0026533
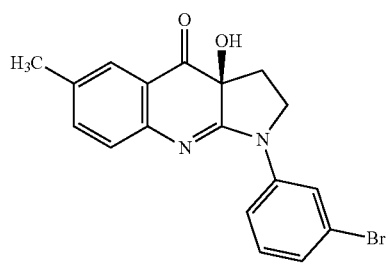 [SMILES: Cc1ccc2c(c1)C(=O)[C@]1(O)CCN(c3cccc(Br)c3)C1=N2]
BPN-0025240
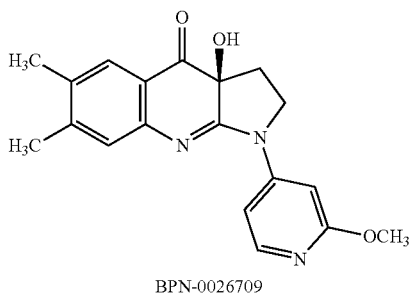
BPN-0026709
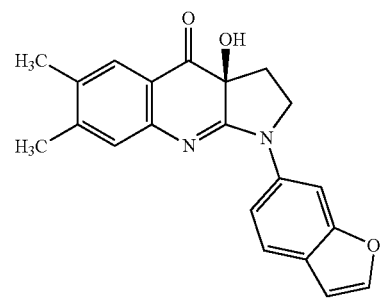
BPN-0026664

TABLE 3-continued
Structures of Compounds for Methods of Invention
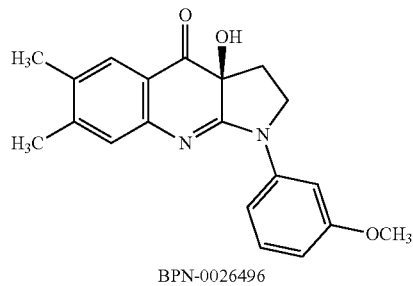
BPN-0026496
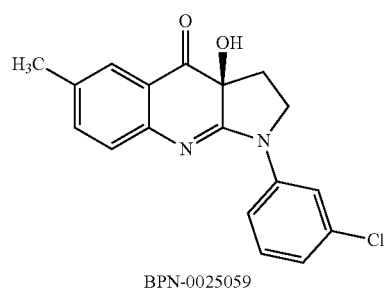
BPN-0025059
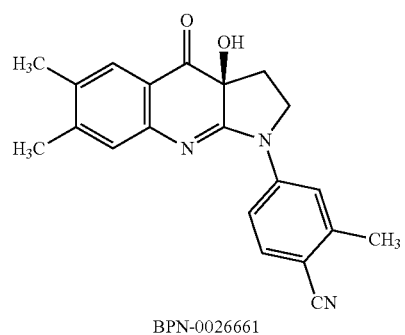
BPN-0026661
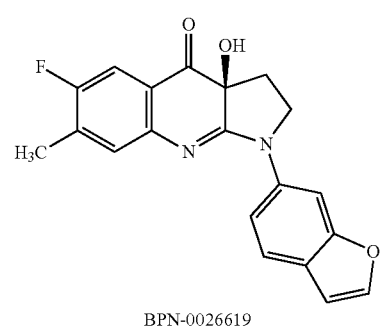
BPN-0026619
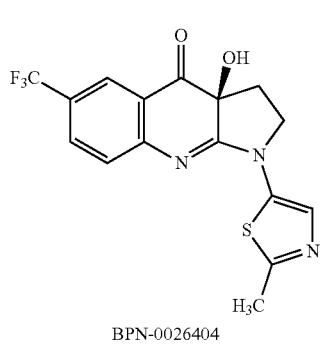
BPN-0026404
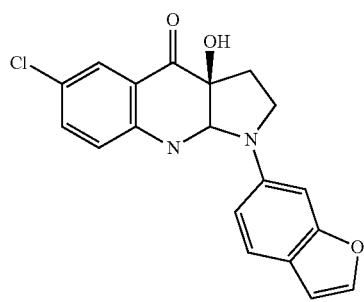 [SMILES: O=C1c2cc(Cl)ccc2NC2N(c3ccc4ccoc4c3)CC[C@@]12O]
BPN-0026401
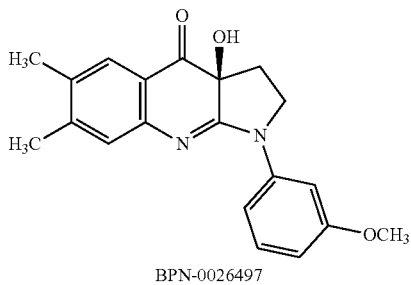
BPN-0026497
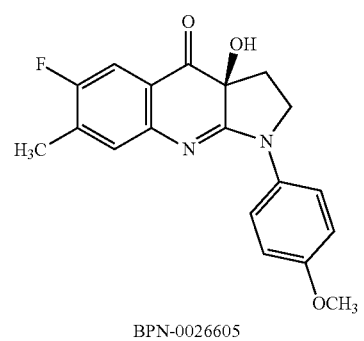
BPN-0026605
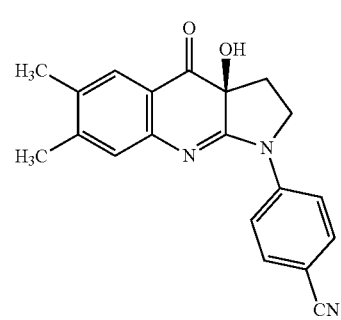 [SMILES: Cc1cc2c(cc1C)C(=O)[C@]1(O)CCN(c3ccc(C#N)cc3)C1=N2]
BPN-0026499
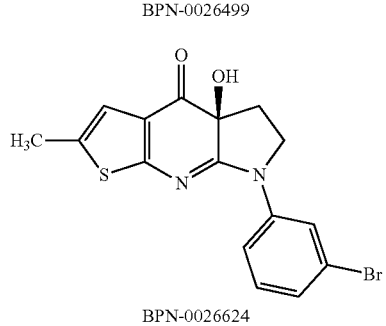
BPN-0026624

TABLE 3-continued
Structures of Compounds for Methods of Invention
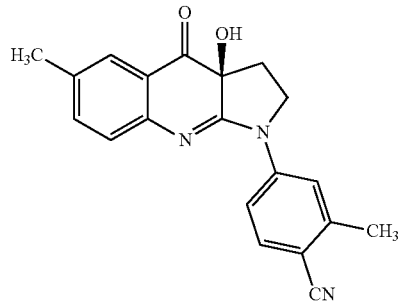
BPN-0026324
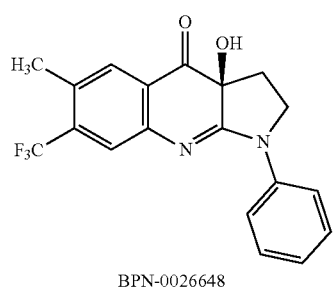
BPN-0026648
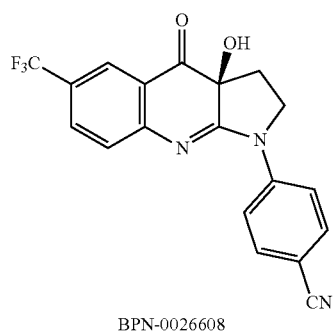
BPN-0026608
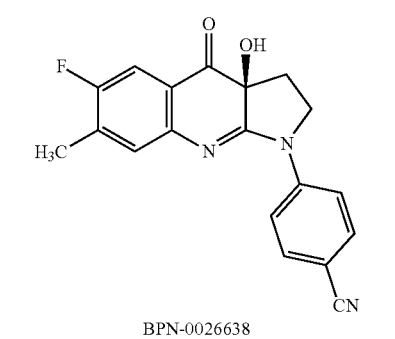
BPN-0026638
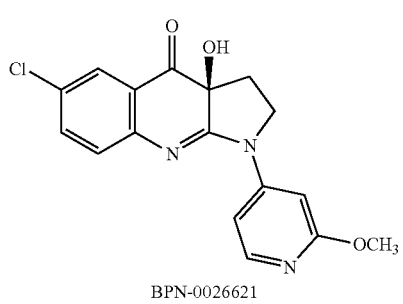
BPN-0026621
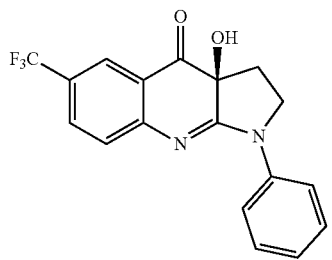 [SMILES: O=C1c2cc(C(F)(F)F)ccc2N=C2N(c3ccccc3)CC[C@@]12O]
BPN-0025110
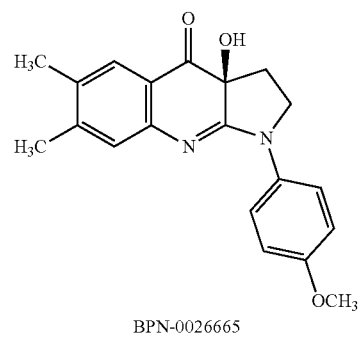
BPN-0026665
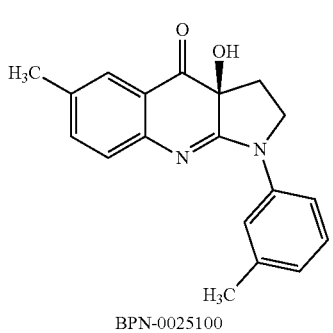
BPN-0025100
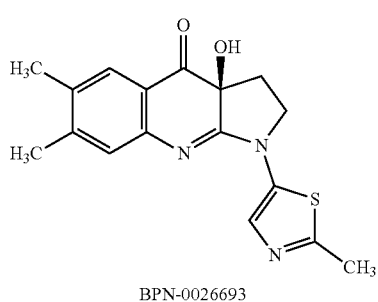
BPN-0026693
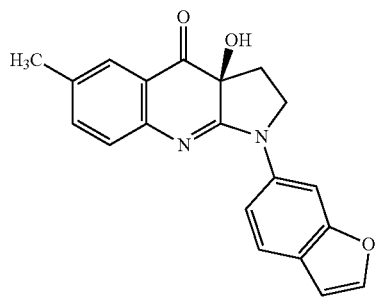 [SMILES: Cc1ccc2c(c1)C(=O)[C@]1(O)CCN(c3ccc4ccoc4c3)C1=N2]
BPN-0026285

TABLE 3-continued
Structures of Compounds for Methods of Invention
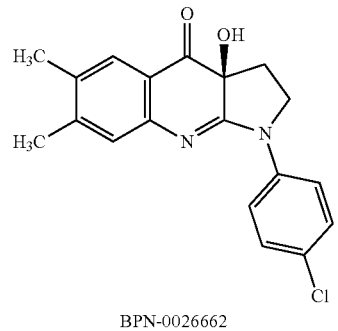
BPN-0026662
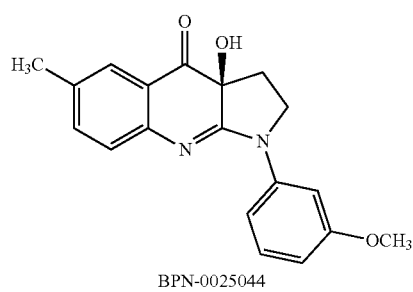
BPN-0025044
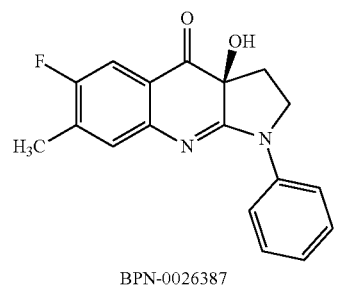
BPN-0026387
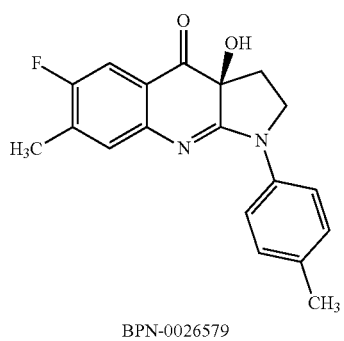
BPN-0026579
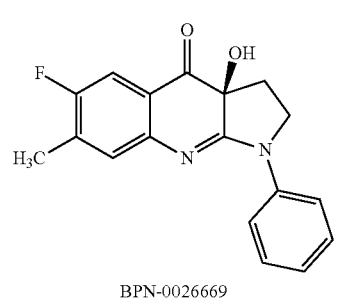
BPN-0026669
TABLE 3-continued
Structures of Compounds for Methods of Invention
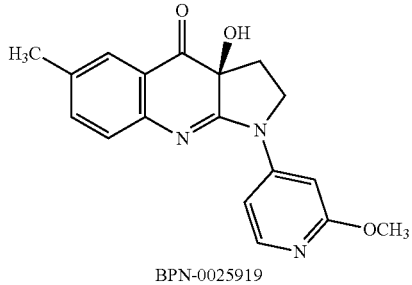
BPN-0025919
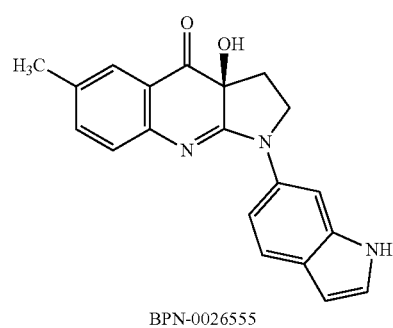
BPN-0026555
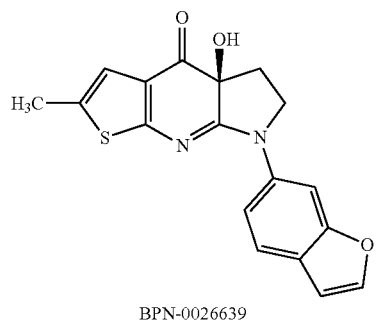
BPN-0026639
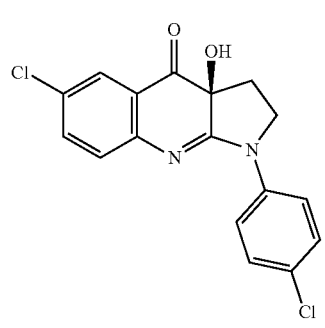 [SMILES: O=C1c2cc(Cl)ccc2N=C2N(c3ccc(Cl)cc3)CC[C@@]12O]
BPN-0026640
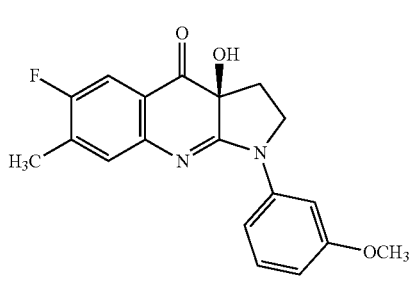 [SMILES: COc1cccc(N2CC[C@@]3(O)C(=O)c4cc(F)c(C)cc4N=C23)c1]
BPN-0026618

TABLE 3-continued
Structures of Compounds for Methods of Invention
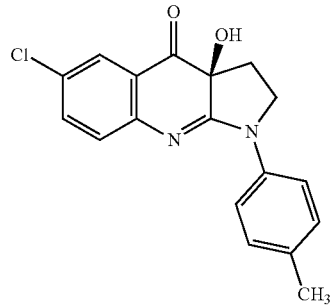 [SMILES: Cc1ccc(N2CC[C@@]3(O)C(=O)c4cc(Cl)ccc4N=C23)cc1]
BPN-0026609
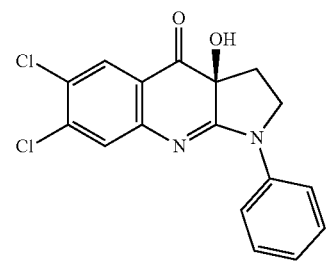 [SMILES: O=C1c2cc(Cl)c(Cl)cc2N=C2N(c3ccccc3)CC[C@@]12O]
BPN-0026643
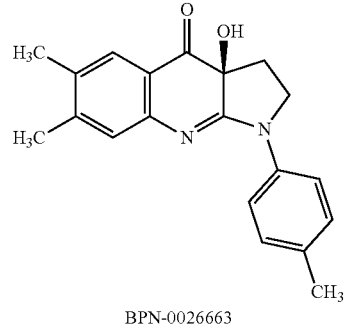
BPN-0026663
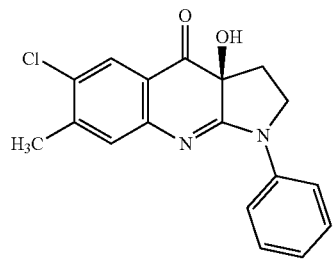 [SMILES: Cc1cc2c(cc1Cl)C(=O)[C@]1(O)CCN(c3ccccc3)C1=N2]
BPN-0026659
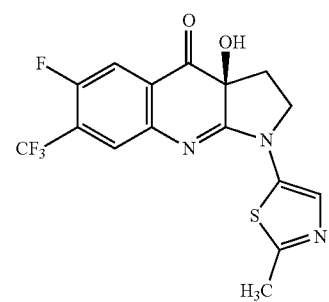 [SMILES: Cc1ncc(N2CC[C@@]3(O)C(=O)c4cc(F)c(C(F)(F)F)cc4N=C23)s1]
BPN-0026667
TABLE 3-continued
Structures of Compounds for Methods of Invention
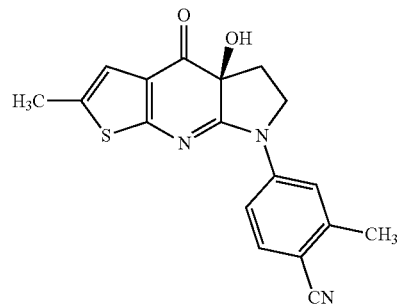
BPN-0026576
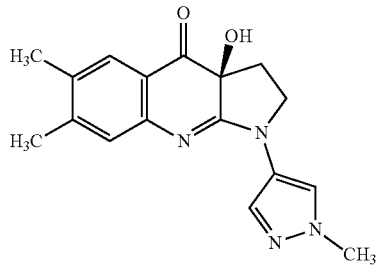
BPN-0026710
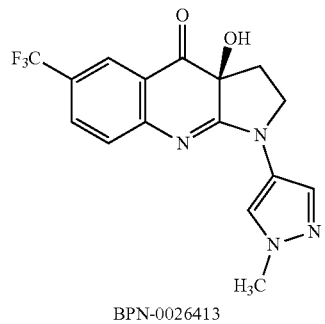
BPN-0026413
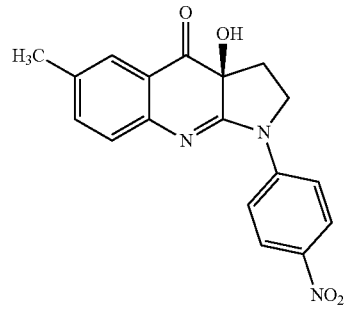 [SMILES: Cc1ccc2c(c1)C(=O)[C@]1(O)CCN(c3ccc([N+](=O)[O-])cc3)C1=N2]
BPN-0025001
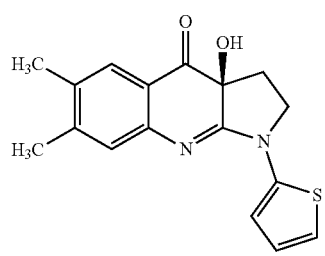 [SMILES: Cc1cc2c(cc1C)C(=O)[C@]1(O)CCN(c3cccs3)C1=N2]
BPN-0026708

TABLE 3-continued
Structures of Compounds for Methods of Invention
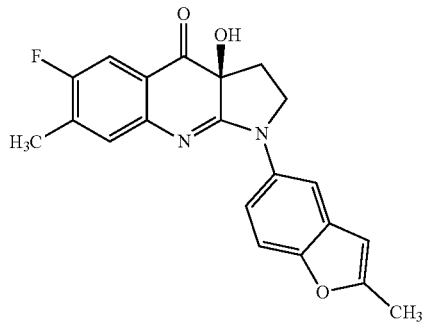
BPN-0026726
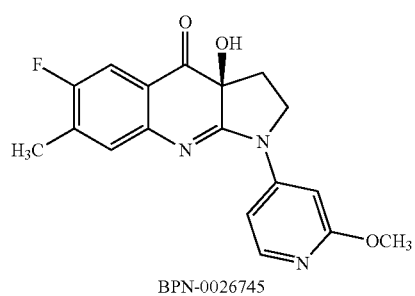
BPN-0026745
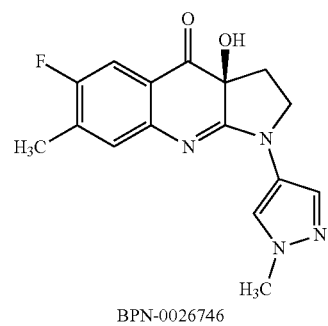
BPN-0026746
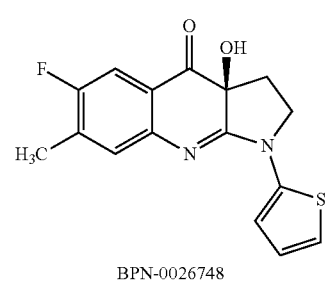
BPN-0026748
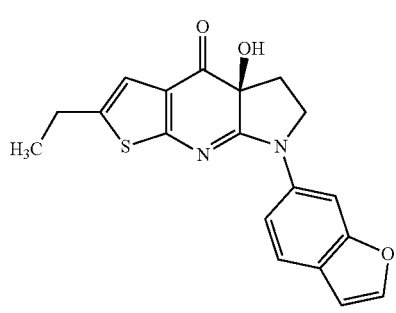 [SMILES: CCc1cc2c(s1)N=C1N(c3ccc4ccoc4c3)CC[C@@]1(O)C2=O]
BPN-0026749
TABLE 3-continued
Structures of Compounds for Methods of Invention
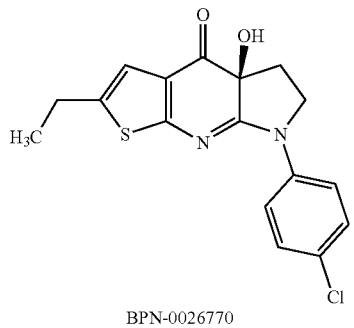
BPN-0026770
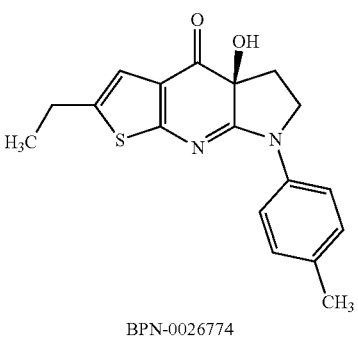
BPN-0026774
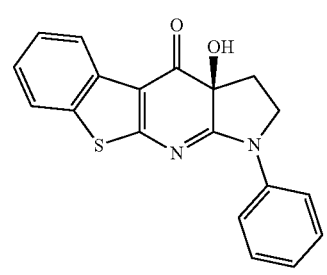 [SMILES: O=C1c2c(sc3ccccc23)N=C2N(c3ccccc3)CC[C@@]12O]
BPN-0026785
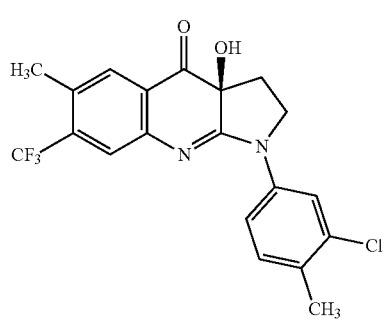 [SMILES: Cc1ccc(N2CC[C@@]3(O)C(=O)c4cc(C)c(C(F)(F)F)cc4N=C23)cc1Cl]
BPN-0026786
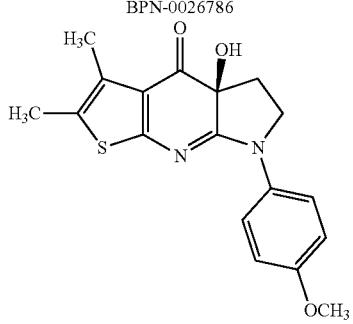
BPN-0026813

TABLE 3-continued
Structures of Compounds for Methods of Invention
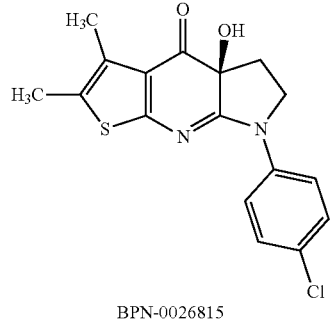
BPN-0026815
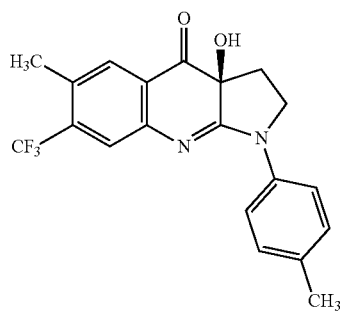 [SMILES: Cc1ccc(N2CC[C@@]3(O)C(=O)c4cc(C)c(C(F)(F)F)cc4N=C23)cc1]
BPN-0026819
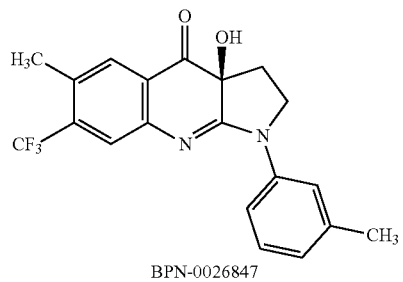
BPN-0026847
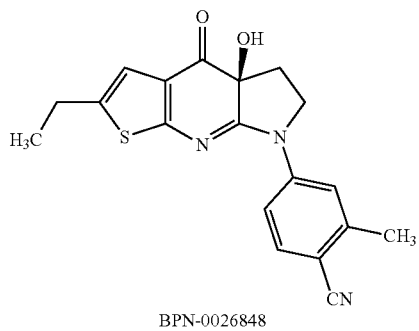
BPN-0026848
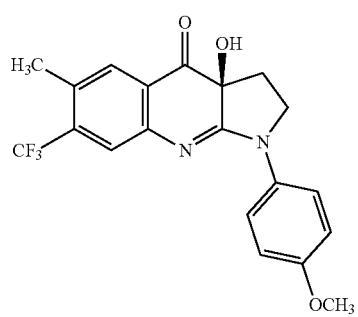 [SMILES: COc1ccc(N2CC[C@@]3(O)C(=O)c4cc(C)c(C(F)(F)F)cc4N=C23)cc1]
BPN-0026849
TABLE 3-continued
Structures of Compounds for Methods of Invention
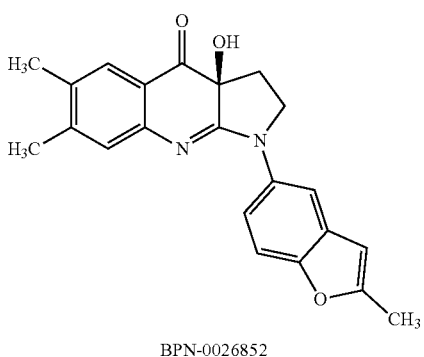
BPN-0026852
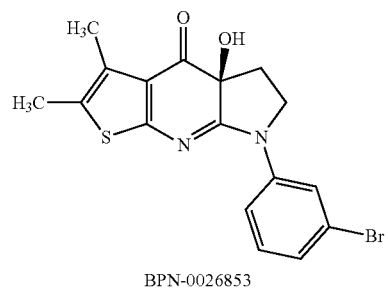
BPN-0026853
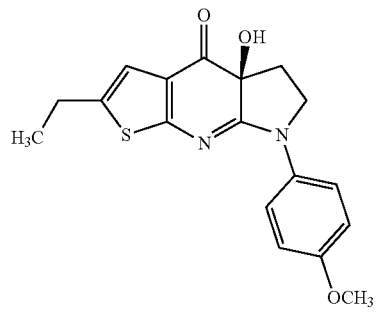 [SMILES: CCc1cc2c(s1)N=C1N(c3ccc(OC)cc3)CC[C@@]1(O)C2=O]
BPN-0026881
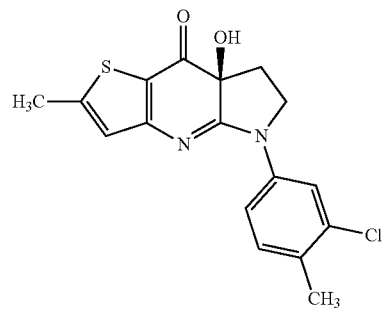 [SMILES: Cc1cc2c(s1)C(=O)[C@]1(O)CCN(c3ccc(C)c(Cl)c3)C1=N2]
BPN-0026882

TABLE 3-continued
Structures of Compounds for Methods of Invention
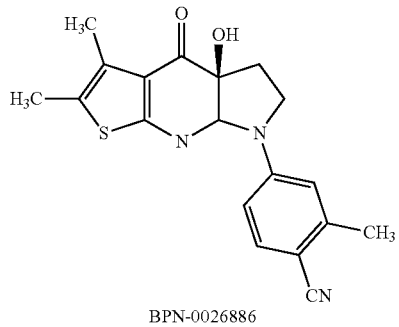
BPN-0026886
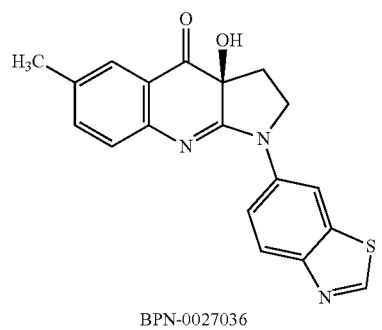
BPN-0027036
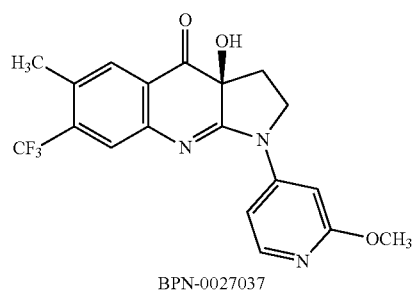
BPN-0027037
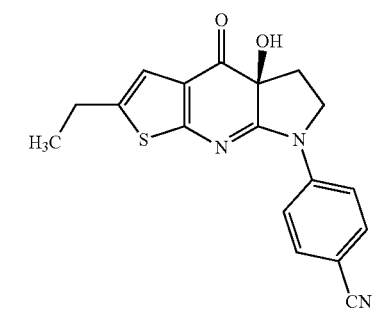 [SMILES: CCc1cc2c(s1)N=C1N(c3ccc(C#N)cc3)CC[C@@]1(O)C2=O]
BPN-0027038
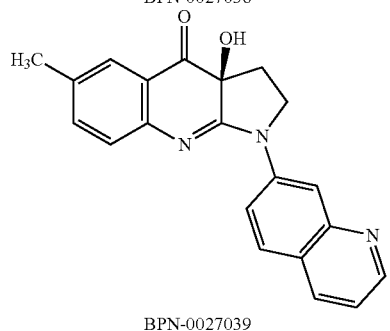
BPN-0027039
TABLE 3-continued
Structures of Compounds for Methods of Invention
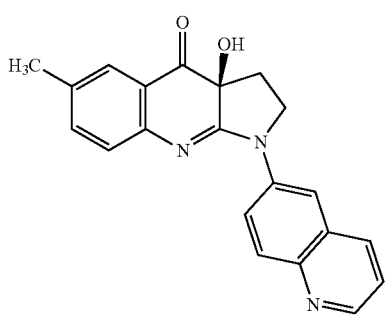 [SMILES: Cc1ccc2c(c1)C(=O)[C@]1(O)CCN(c3ccc4cccnc4c3)C1=N2]
BPN-0027040
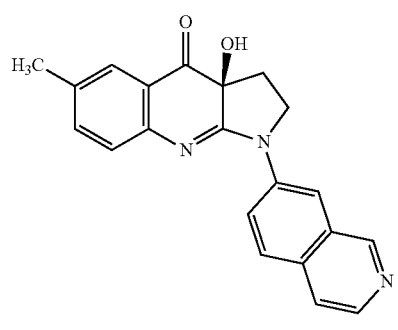 [SMILES: Cc1ccc2c(c1)C(=O)[C@]1(O)CCN(c3ccc4ccncc4c3)C1=N2]
BPN-0027042
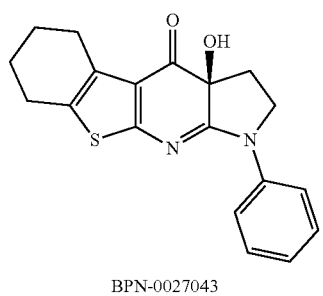
BPN-0027043
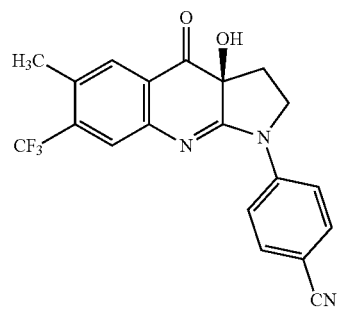 [SMILES: Cc1cc2c(cc1C(F)(F)F)N=C1N(c3ccc(C#N)cc3)CC[C@@]1(O)C2=O]
BPN-0027071

TABLE 3-continued
Structures of Compounds for Methods of Invention
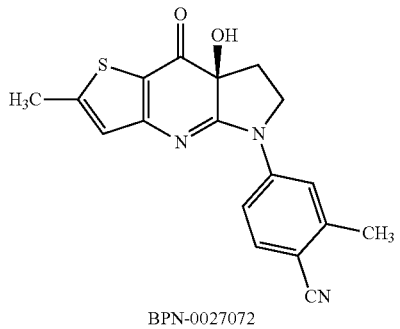
BPN-0027072
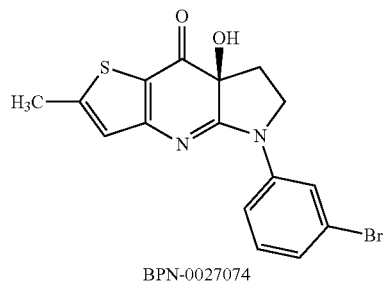
BPN-0027074
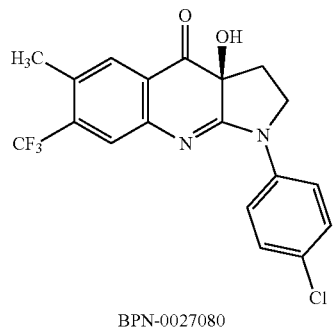
BPN-0027080
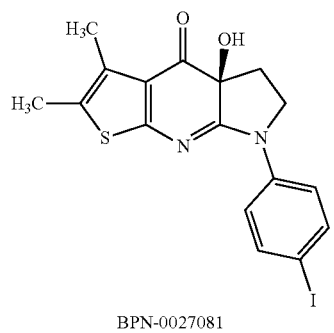
BPN-0027081
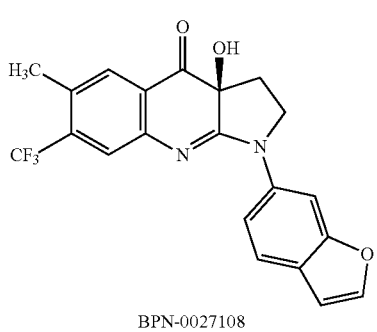
BPN-0027108
TABLE 3-continued
Structures of Compounds for Methods of Invention
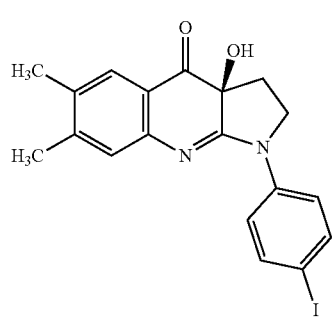 [SMILES: Cc1cc2c(cc1C)C(=O)[C@]1(O)CCN(c3ccc(I)cc3)C1=N2]
BPN-0027109
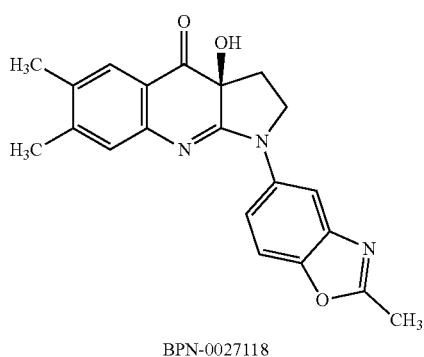
BPN-0027118
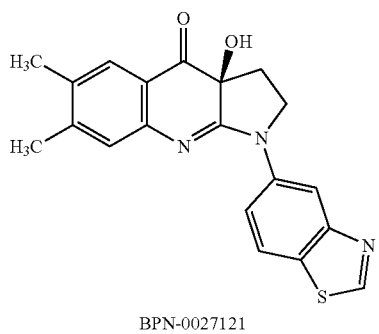
BPN-0027121
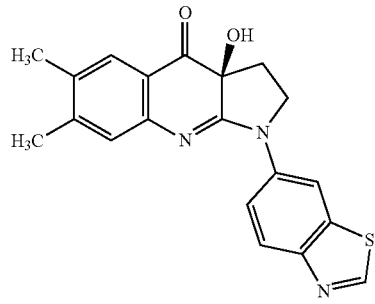 [SMILES: Cc1cc2c(cc1C)C(=O)[C@]1(O)CCN(c3ccc4ncsc4c3)C1=N2]
BPN-0027122

TABLE 3-continued
Structures of Compounds for Methods of Invention
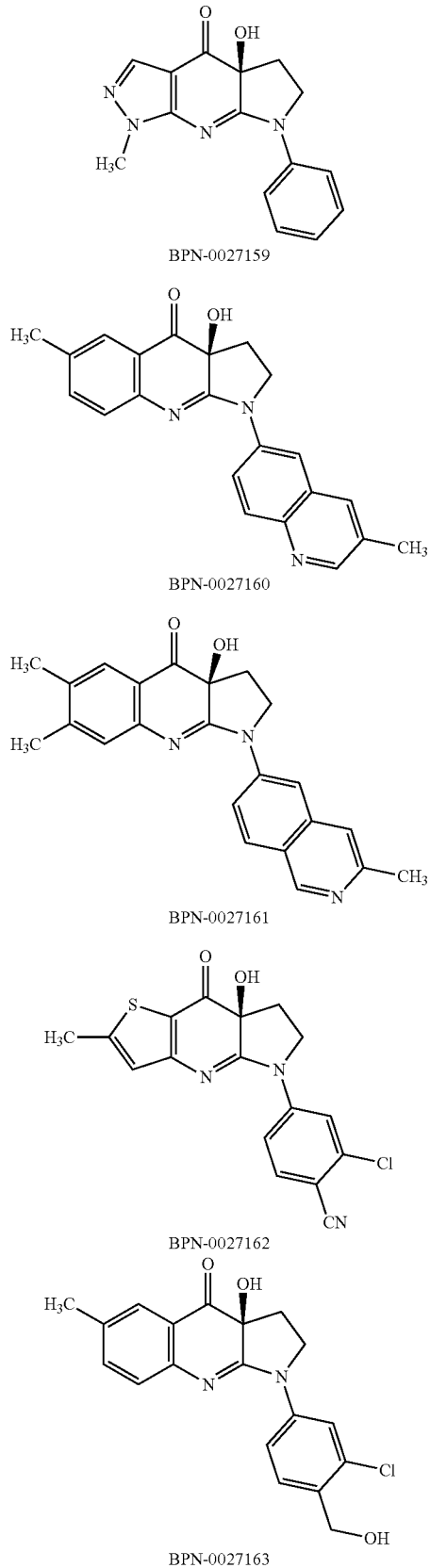
BPN-0027159
BPN-0027160
BPN-0027161
BPN-0027162
BPN-0027163
TABLE 3-continued
Structures of Compounds for Methods of Invention
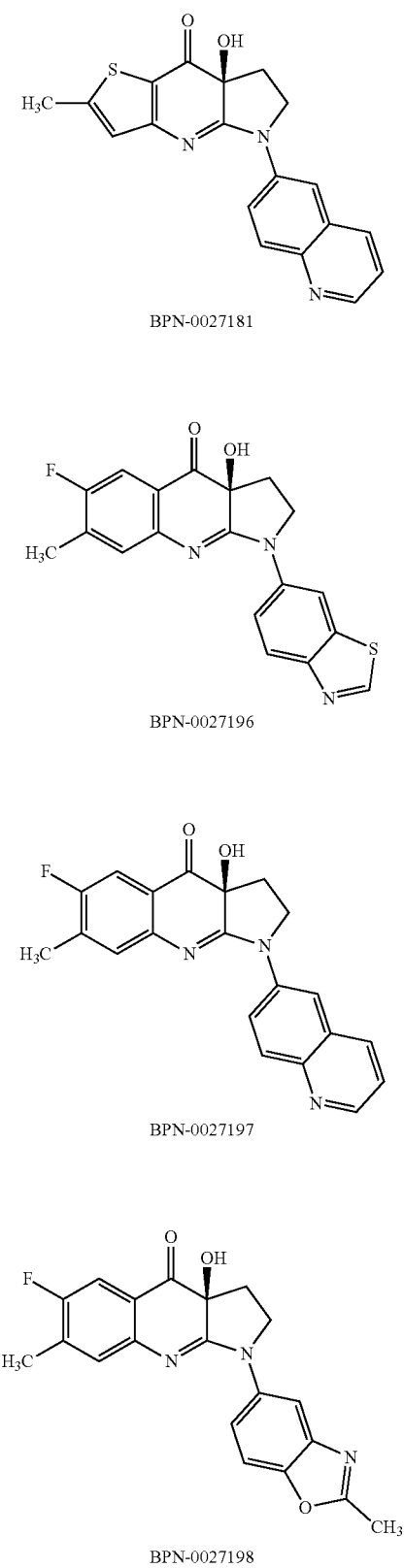
BPN-0027181
BPN-0027196
BPN-0027197
BPN-0027198

TABLE 3-continued
Structures of Compounds for Methods of Invention
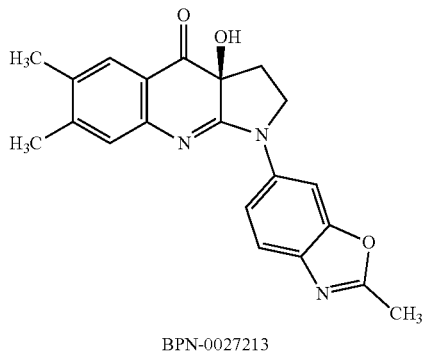
BPN-0027213
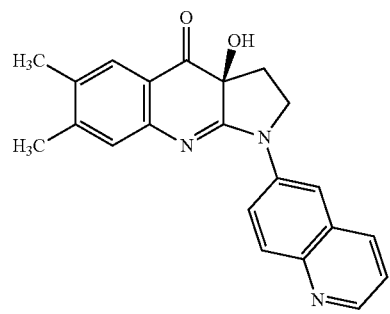 [SMILES: Cc1cc2c(cc1C)C(=O)[C@]1(O)CCN(c3ccc4ncccc4c3)C1=N2]
BPN-0027215
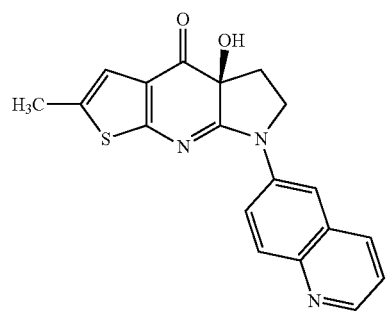 [SMILES: Cc1cc2c(s1)N=C1N(c3ccc4ncccc4c3)CC[C@@]1(O)C2=O]
BPN-0027216
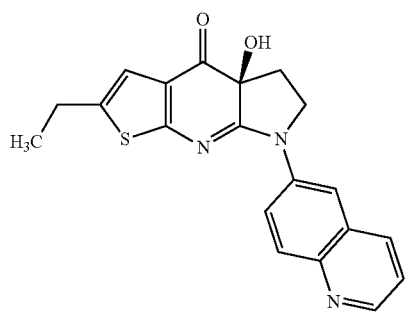 [SMILES: CCc1cc2c(s1)N=C1N(c3ccc4ncccc4c3)CC[C@@]1(O)C2=O]
BPN-0027217
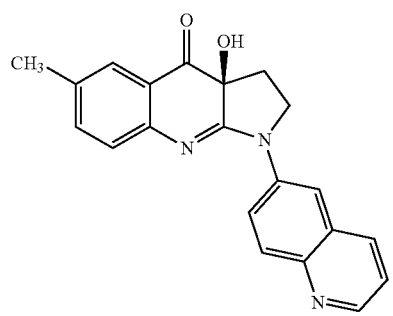 [SMILES: Cc1ccc2c(c1)C(=O)[C@]1(O)CCN(c3ccc4ncccc4c3)C1=N2]
BPN-0027218
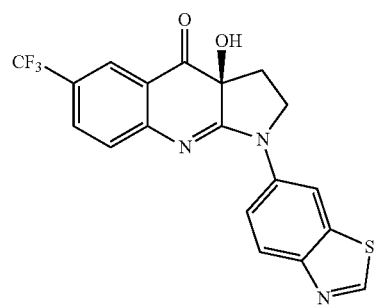 [SMILES: O=C1c2cc(C(F)(F)F)ccc2N=C2N(c3ccc4ncsc4c3)CC[C@@]12O]
BPN-0027219
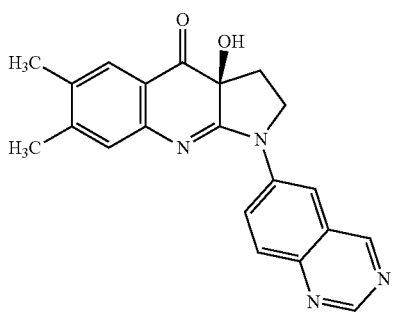 [SMILES: Cc1cc2c(cc1C)C(=O)[C@]1(O)CCN(c3ccc4ncncc4c3)C1=N2]
BPN-0027228
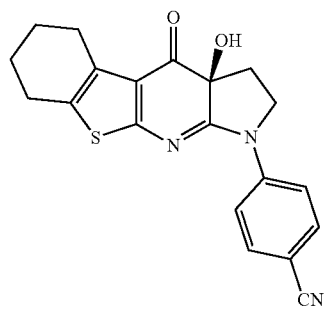 [SMILES: N#Cc1ccc(N2CC[C@@]3(O)C(=O)c4c(sc5c4CCCC5)N=C23)cc1]
BPN-0027236

TABLE 3-continued
Structures of Compounds for Methods of Invention
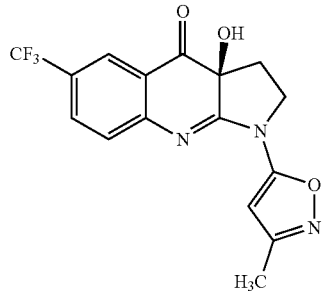 [SMILES: Cc1cc(N2CC[C@@]3(O)C(=O)c4cc(C(F)(F)F)ccc4N=C23)on1]
BPN-0027237
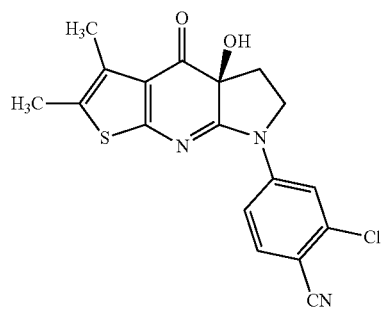 [SMILES: Cc1sc2c(c1C)C(=O)[C@]1(O)CCN(c3ccc(C#N)c(Cl)c3)C1=N2]
BPN-0027238
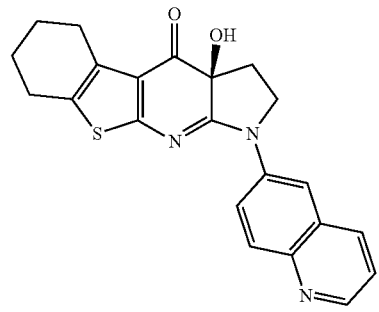 [SMILES: O=C1c2c(sc3c2CCCC3)N=C2N(c3ccc4ncccc4c3)CC[C@@]12O]
BPN-0027240
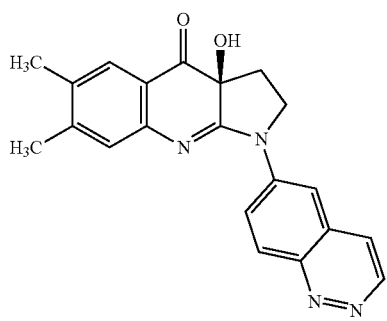 [SMILES: Cc1cc2c(cc1C)C(=O)[C@]1(O)CCN(c3ccc4nnccc4c3)C1=N2]
BPN-0027241
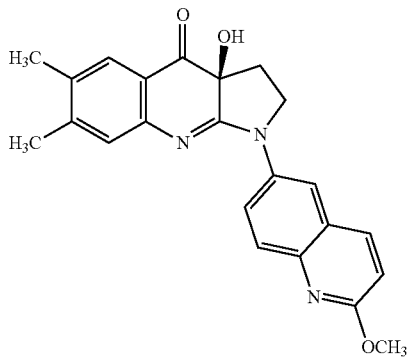 [SMILES: COc1ccc2cc(N3CC[C@@]4(O)C(=O)c5cc(C)c(C)cc5N=C34)ccc2n1]
BPN-0027250
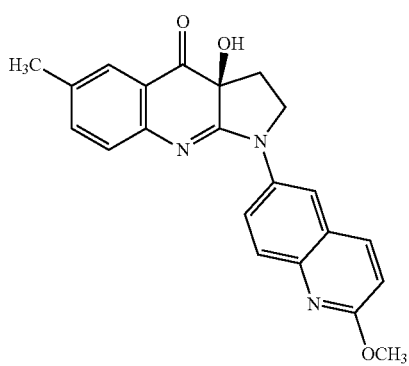 [SMILES: COc1ccc2cc(N3CC[C@@]4(O)C(=O)c5cc(C)ccc5N=C34)ccc2n1]
BPN-0027255
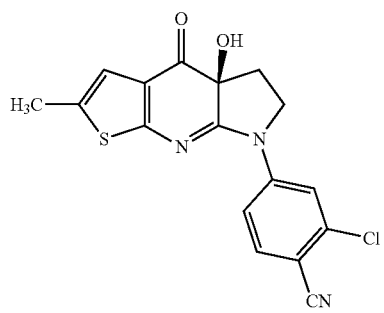 [SMILES: Cc1cc2c(s1)N=C1N(c3ccc(C#N)c(Cl)c3)CC[C@@]1(O)C2=O]
BPN-0027257
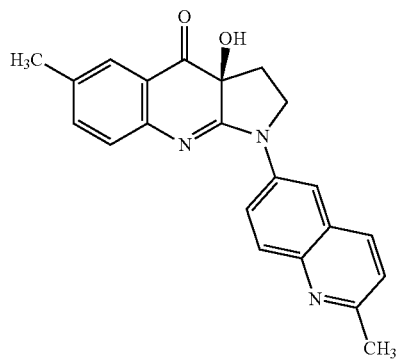 [SMILES: Cc1ccc2c(c1)C(=O)[C@]1(O)CCN(c3ccc4nc(C)ccc4c3)C1=N2]
BPN-0027289

TABLE 3-continued
Structures of Compounds for Methods of Invention
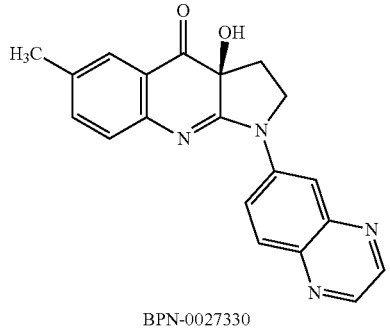
BPN-0027330
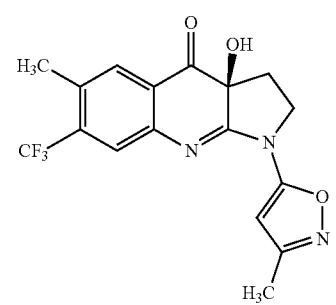 [SMILES: Cc1cc(N2CC[C@@]3(O)C(=O)c4cc(C)c(C(F)(F)F)cc4N=C23)on1]
BPN-0027346
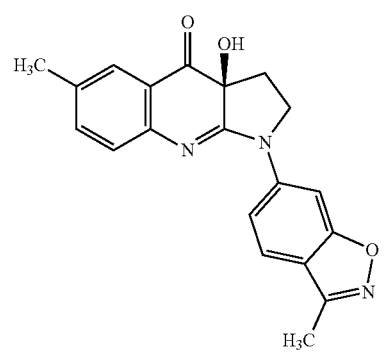 [SMILES: Cc1ccc2c(c1)C(=O)[C@]1(O)CCN(c3ccc4c(C)noc4c3)C1=N2]
BPN-0027374
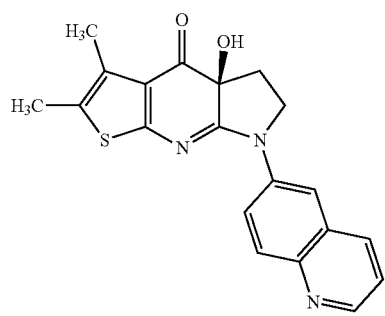 [SMILES: Cc1sc2c(c1C)C(=O)[C@]1(O)CCN(c3ccc4ncccc4c3)C1=N2]
BPN-0027376
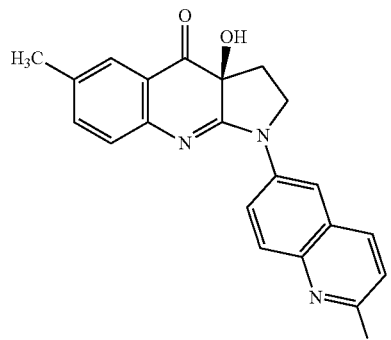
BPN-0027393
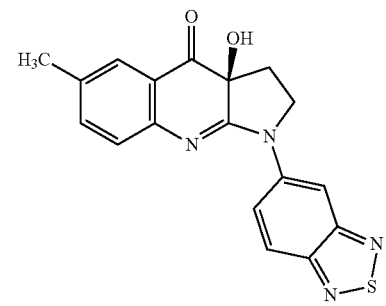 [SMILES: Cc1ccc2c(c1)C(=O)[C@]1(O)CCN(c3ccc4nsnc4c3)C1=N2]
BPN-0027394
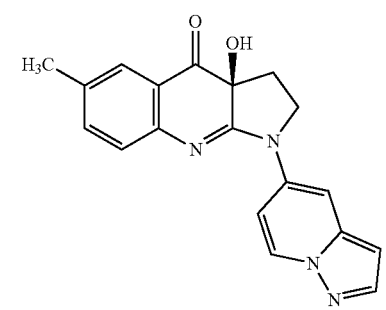 [SMILES: Cc1ccc2c(c1)C(=O)[C@]1(O)CCN(c3ccn4nccc4c3)C1=N2]
BPN-0027396
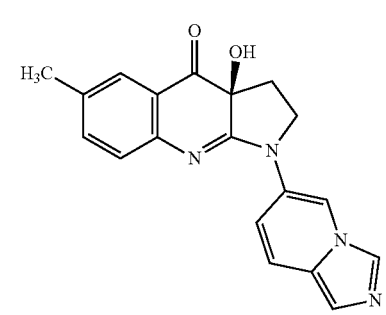 [SMILES: Cc1ccc2c(c1)C(=O)[C@]1(O)CCN(c3ccc4cncn4c3)C1=N2]
BPN-0027406

TABLE 3-continued
Structures of Compounds for Methods of Invention
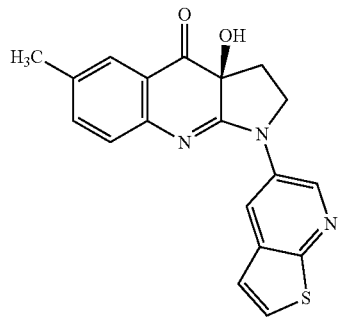 [SMILES: Cc1ccc2c(c1)C(=O)[C@]1(O)CCN(c3cnc4sccc4c3)C1=N2]
BPN-0027410
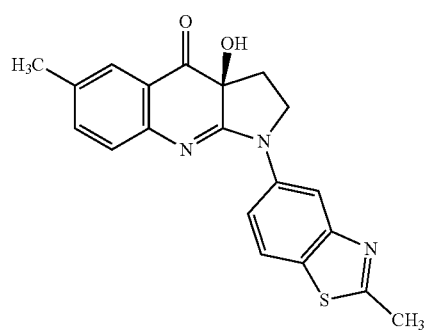
BPN-0027411
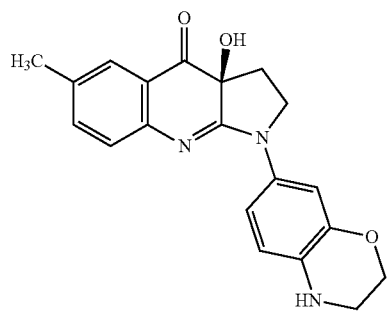 [SMILES: Cc1ccc2c(c1)C(=O)[C@]1(O)CCN(c3ccc4c(c3)OCCN4)C1=N2]
BPN-0027412
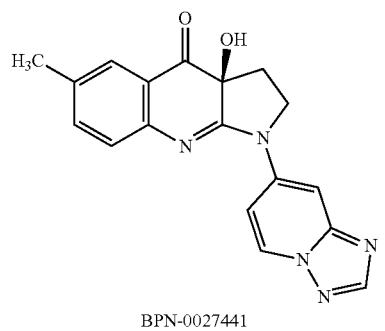
BPN-0027441
TABLE 3-continued
Structures of Compounds for Methods of Invention
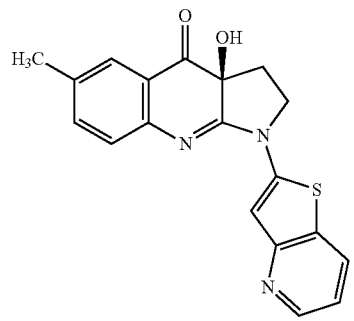 [SMILES: Cc1ccc2c(c1)C(=O)[C@]1(O)CCN(c3cc4ncccc4s3)C1=N2]
BPN-0027468
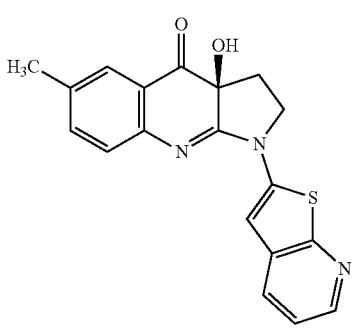 [SMILES: Cc1ccc2c(c1)C(=O)[C@]1(O)CCN(c3cc4cccnc4s3)C1=N2]
BPN-0027469
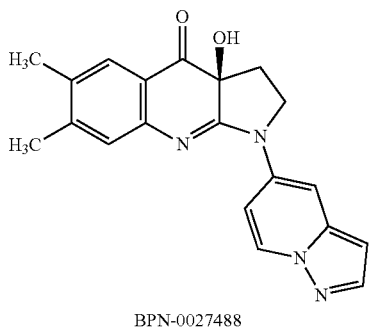
BPN-0027488
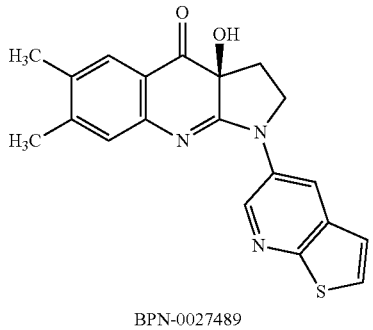
BPN-0027489

TABLE 3-continued

Structures of Compounds for Methods of Invention

BPN-0027490

BPN-0027491

BPN-0027492

BPN-0027494

BPN-0028550

BPN-0028552

BPN-0028554

BPN-0028555

TABLE 3-continued
Structures of Compounds for Methods of Invention
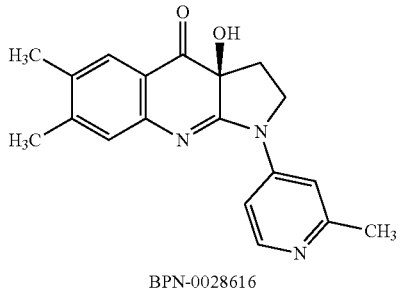
BPN-0028616
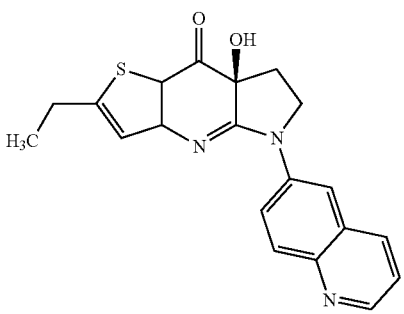 [SMILES: CCC1=CC2N=C3N(c4ccc5ncccc5c4)CC[C@@]3(O)C(=O)C2S1]
BPN-0028625
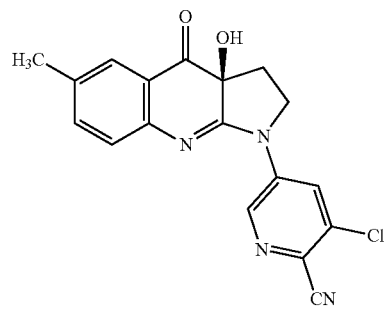 [SMILES: Cc1ccc2c(c1)C(=O)[C@]1(O)CCN(c3cnc(C#N)c(Cl)c3)C1=N2]
BPN-0028646
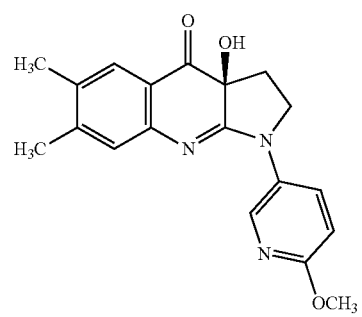 [SMILES: COc1ccc(N2CC[C@@]3(O)C(=O)c4cc(C)c(C)cc4N=C23)cn1]
BPN-0028648
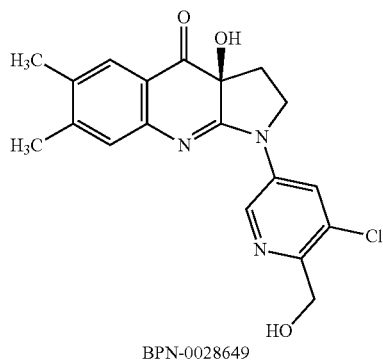
BPN-0028649
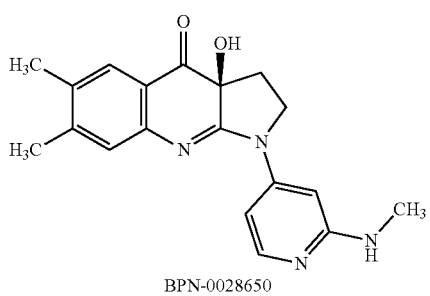
BPN-0028650
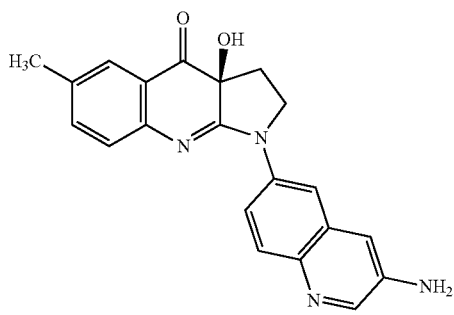 [SMILES: Cc1ccc2c(c1)C(=O)[C@]1(O)CCN(c3ccc4ncc(N)cc4c3)C1=N2]
BPN-0028652
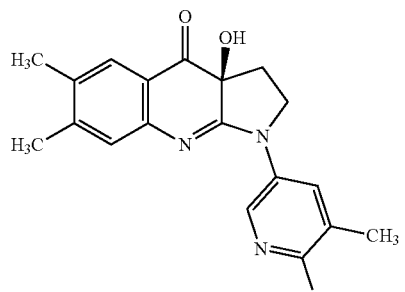
BPN-0028694

TABLE 3-continued
Structures of Compounds for Methods of Invention
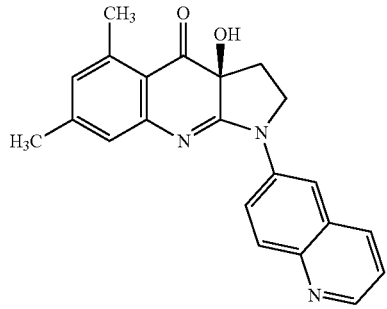 [SMILES: Cc1cc(C)c2c(c1)N=C1N(c3ccc4ncccc4c3)CC[C@@]1(O)C2=O]
BPN-0028697
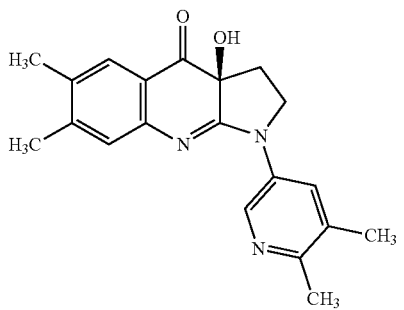
BPN-0028731
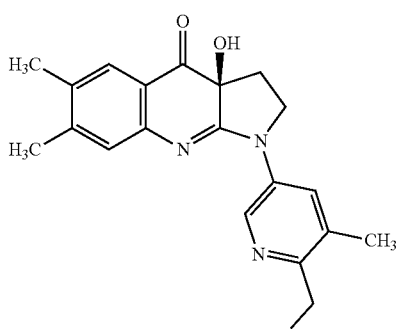
BPN-0028733
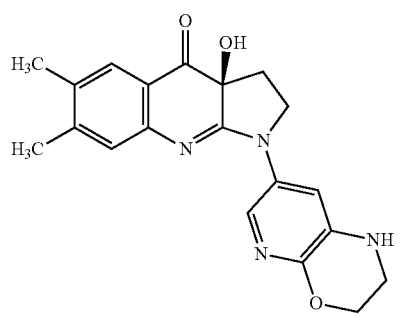 [SMILES: Cc1cc2c(cc1C)C(=O)[C@]1(O)CCN(c3cnc4c(c3)NCCO4)C1=N2]
BPN-0028734
TABLE 3-continued
Structures of Compounds for Methods of Invention
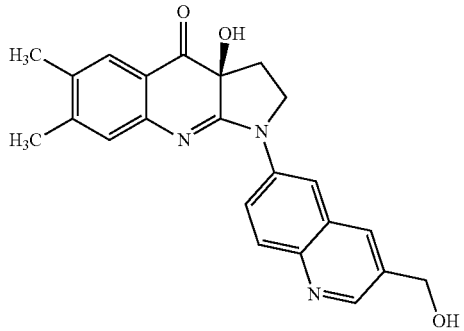 [SMILES: Cc1cc2c(cc1C)C(=O)[C@]1(O)CCN(c3ccc4ncc(CO)cc4c3)C1=N2]
BPN-0028736
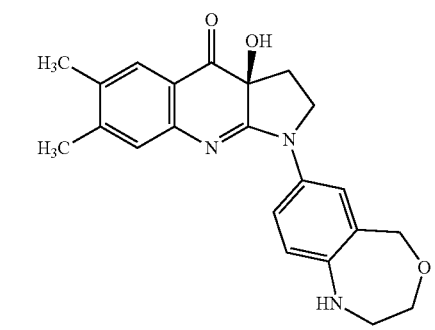 [SMILES: Cc1cc2c(cc1C)C(=O)[C@]1(O)CCN(c3ccc4c(c3)COCCN4)C1=N2]
BPN-0028758
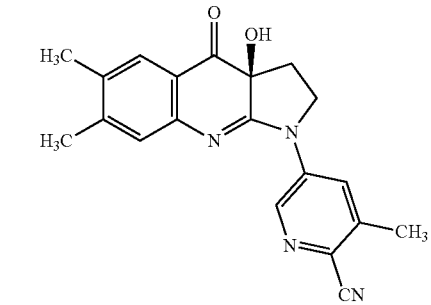
BPN-0028760
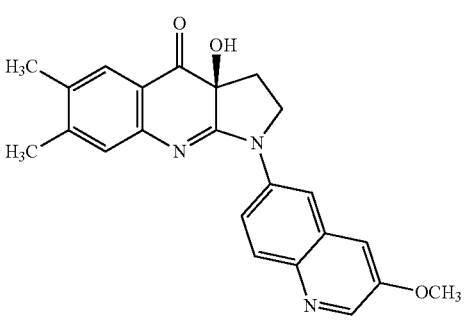 [SMILES: COc1cnc2ccc(N3CC[C@@]4(O)C(=O)c5cc(C)c(C)cc5N=C34)cc2c1]
BPN-0028788

TABLE 3-continued
Structures of Compounds for Methods of Invention
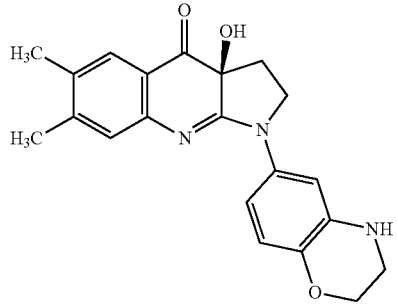
BPN-0028790
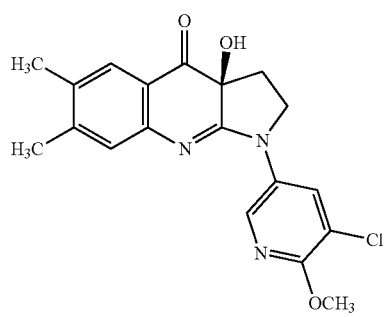 [SMILES: COc1ncc(N2CC[C@@]3(O)C(=O)c4cc(C)c(C)cc4N=C23)cc1Cl]
BPN-0028820
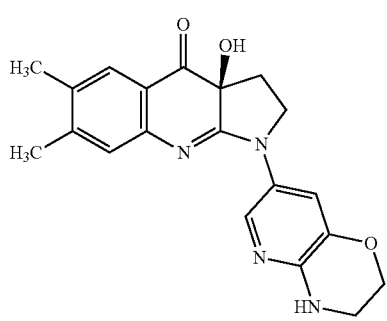 [SMILES: Cc1cc2c(cc1C)C(=O)[C@]1(O)CCN(c3cnc4c(c3)OCCN4)C1=N2]
BPN-0028821
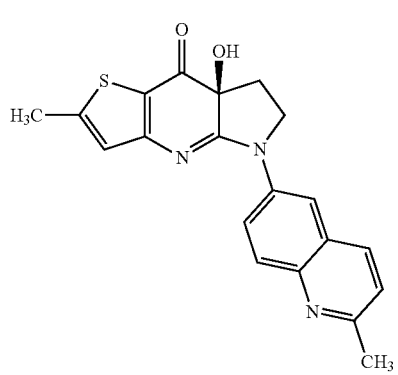 [SMILES: Cc1ccc2cc(N3CC[C@@]4(O)C(=O)c5sc(C)cc5N=C34)ccc2n1]
BPN-0028863
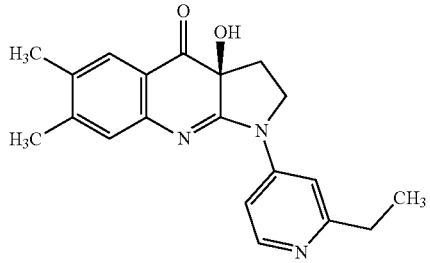 [SMILES: CCc1cc(N2CC[C@@]3(O)C(=O)c4cc(C)c(C)cc4N=C23)ccn1]
BPN-0028864
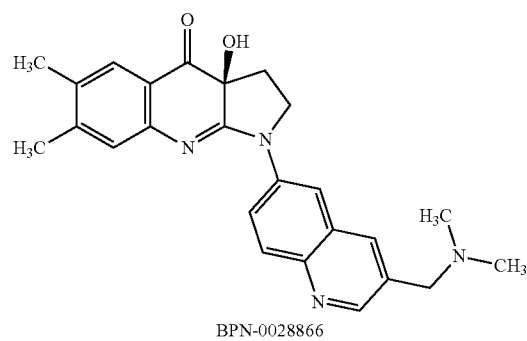
BPN-0028866
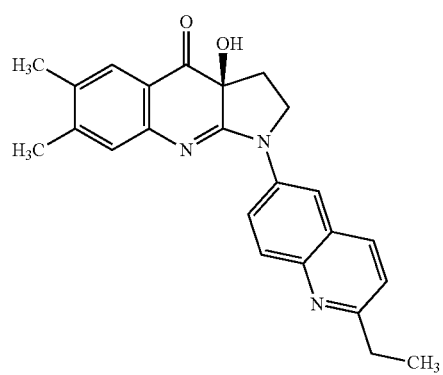 [SMILES: CCc1ccc2cc(N3CC[C@@]4(O)C(=O)c5cc(C)c(C)cc5N=C34)ccc2n1]
BPN-0028867
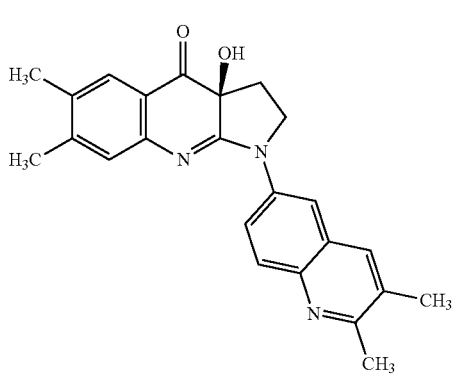
BPN-0028868

TABLE 3-continued
Structures of Compounds for Methods of Invention
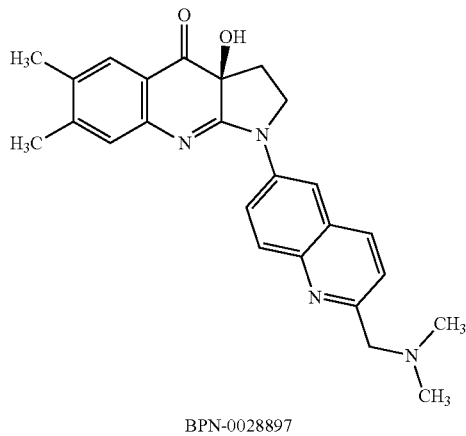
BPN-0028897
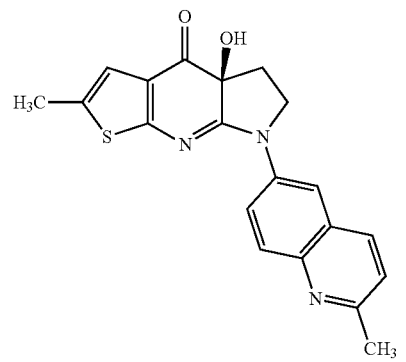 [SMILES: Cc1ccc2cc(N3CC[C@@]4(O)C(=O)c5cc(C)sc5N=C34)ccc2n1]
BPN-0028898
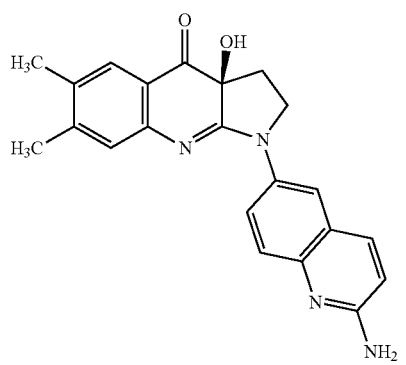 [SMILES: Cc1cc2c(cc1C)C(=O)[C@]1(O)CCN(c3ccc4nc(N)ccc4c3)C1=N2]
BPN-0028899
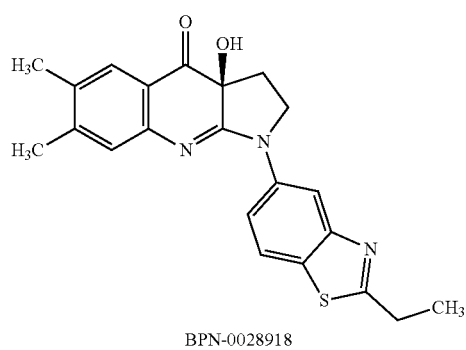
BPN-0028918
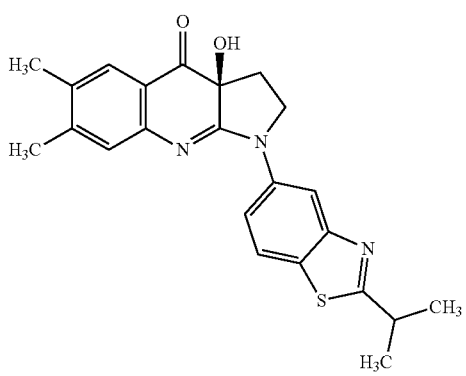 [SMILES: Cc1cc2c(cc1C)C(=O)[C@]1(O)CCN(c3ccc4sc(C(C)C)nc4c3)C1=N2]
BPN-0028919
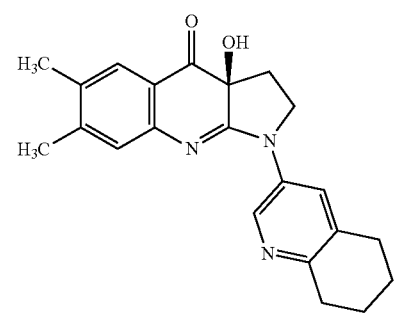 [SMILES: Cc1cc2c(cc1C)C(=O)[C@]1(O)CCN(c3cnc4c(c3)CCCC4)C1=N2]
BPN-0028920
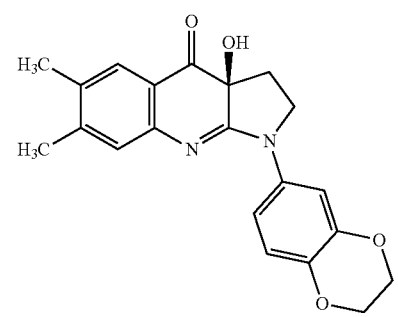 [SMILES: Cc1cc2c(cc1C)C(=O)[C@]1(O)CCN(c3ccc4c(c3)OCCO4)C1=N2]
BPN-0028921
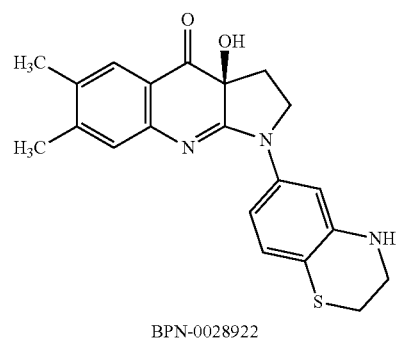
BPN-0028922

TABLE 3-continued

Structures of Compounds for Methods of Invention

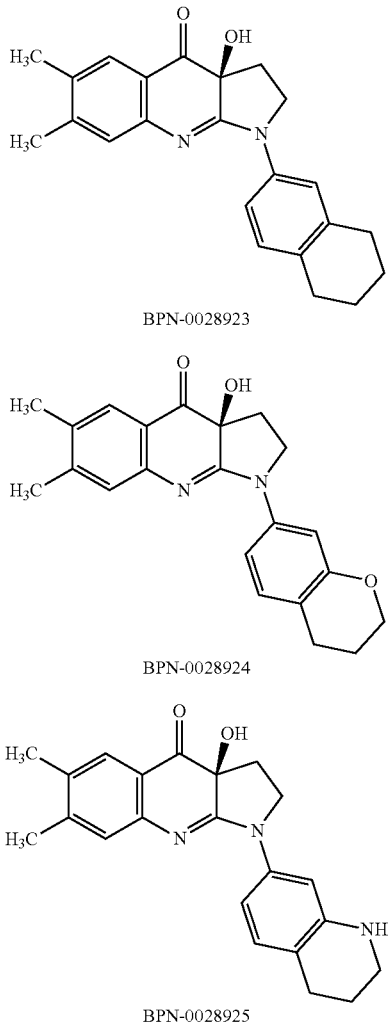

BPN-0028923

BPN-0028924

BPN-0028925

Blebbistatin Analog Bioassay Methods

1. Assaying Cardiac Muscle Myosin II

The cardiac muscle myosin II actin-activated ATPase assay is a biochemical assay. Specifically, it is an NADH (nicotinamide adenine dinucleotide)-coupled ATPase assay that relies on NADH fluorescence as a readout. Cardiac myosin is a mechanochemical energy transducer that hydrolyzes ATP to generate force in the presence of its activator, F-actin. The resulting ADP is regenerated to ATP by pyruvate kinase (PK) that transforms one molecule of phosphoenolpyruvate (PEP) to pyruvate in parallel. Subsequently, pyruvate is reduced to lactate by lactate dehydrogenase (LDH) that, in turn, oxidizes one molecule of NADH to NAD. Therefore, the decrease in NADH concentration as a function of time equals the ATP hydrolysis rate. Bovine cardiac myosin is obtained from a commercial source, Cytoskeleton. PK, LDH, ATP, PEP, and NADH are obtained from Sigma. F-actin is prepared in house from Rabbit Muscle Acetone Powder. The assay is run at 25° C. in 384 well black-wall polystyrene microplates with a total volume of 20 µl per well. NADH fluorescence is monitored for 30 minutes with an EnVision Multimode Plate Reader. The slope of the fluorescence response, which is proportional to the reaction rate, is determined by simple linear regression. Final assay conditions are 300 nM cardiac myosin, 10 µM actin, 40 U/ml LDH, 200 U/ml PK, 220 µM NADH, 1 mM PEP, 1 mM ATP in a buffer containing 10 mM 3-(N-morpholino)propanesulfonic acid (pH=7.0), 2 mM $MgCl_2$, 0.15 mM ethylene glycol-bis(β-aminoethyl ether)-N,N,N', N'-tetraacetic acid, 0.1 mg/mL bovine serum albumin, 0.5% (V/V) dimethyl sulfoxide (DMSO) and 1 mM dithiothreitol. Prior to testing the inhibitory activity of the compounds, a two-fold dilution series starting at 10 mM compound concentration is prepared in DMSO. Subsequently, 100 nl is transferred to each well of the measuring plate containing a mixture of myosin, LDH and PK. The enzymatic reaction is started with the addition of a mixture containing ATP, PEP, NADH and actin. The highest final compound concentration is 50 uM. 20 µM para-aminoblebbistatin in 0.5% DMSO serves as the positive control and 0.5% DMSO alone is the negative control. Reaction rates are determined by using the fluorescence responses of a dilution series of NADH included in all plates and plotted as a function of inhibitor concentration. All measurements are carried out in triplicate. Inhibitory constants are determined by fitting the 16 point dose-response data to a quadratic equation corresponding to a simple one-to-one binding model. Small molecules showing no observable inhibition at or below their solubility are reported as inactive.

2. Assaying Skeletal Muscle Myosin II

The skeletal muscle myosin II actin-activated ATPase assay is performed the same as for cardiac muscle myosin II with the following exceptions: Rabbit skeletal myosin is obtained from Cytoskeleton and the final assay conditions contain 20 nM skeletal muscle myosin II.

3. Assaying Nonmuscle Myosin II

Cytokinesis is a cell-based assay to assess nonmuscle myosin II function, performed using COS7 cells. The assay is run in a 96 well plate, with 2,000 cells plated per well. Total incubation time is 48 hours, with 24 hours of treatment with the compound of interest. Prior to treatment with small molecules, a two-fold dilution series of compound solutions is prepared in DMSO. Starting concentrations are determined based on compound solubility. Compound solutions are further diluted in DMEM medium to a final DMSO concentration of 2% (50-fold dilution). Subsequently, 100 µl diluted solution is transferred to each well of the plate containing 100 µl of cell culture (achieving 1% final DMSO concentration). All measurements are carried out in triplicate. Cells are stained by fluorescein diacetate (6 µM), a cell viability dye, the cell-permeant Hoescht33342 (10 µM) and the membrane-impermeant propidium iodide (4 µM) to label all nuclei and those belonging to dead cells, respectively. Dye solutions are replaced by fresh media after 10 minutes of incubation. An INCell Analyzer 6000 is used for imaging. The signal of interest is the ratio of nuclei to cell numbers, as nonmuscle myosin II inhibition prevents cellular blebbing, resulting in multinucleated cells. Cytotoxicity is also assayed and quantified as the ratio of dead nuclei to total nuclei. 20 µM para-aminoblebbistatin in 1% DMSO serves as the positive control and 1% DMSO alone is the negative control. Half maximal effective concentration ($EC_{50}$) is determined by fitting the 6-point dose-response data to the Hill equation. Small molecules showing no observable inhibition are reported as inactive.

4. Assaying Cardiac Safety (Assay 1)

The spontaneous contractions of cardiomyocytes (CMs) is measured label-free in real time using the ACEA xCELLigence RTCA Cardio instrument. All measurements are performed at 37° C. in a cell culture incubator, allowing for spontaneous beating of CMs at physiological conditions. Cor.4U CMs are seeded at 3×104 cells/well in 180 µl/well maintenance medium. Prior to seeding, a background impedance measurement (plate plus medium) is performed. The contraction of CMs involves cyclic modulation of cell morphology and adhesion inducing a delta change in impedance. From the cyclic changes in impedance a beating frequency, amplitude and effects on beating pattern can be calculated. Time point "0" (baseline) is recorded 10× for 20 seconds at 1 minute intervals. Thereafter, compounds and control (0.1% DMSO) are added to the wells and effects are measured 30 minutes later. Vehicle control is 0.1% DMSO and positive control is 100 nM isoproterenol. Compounds are tested at 0.1, 0.3, 1.0 and 3.0 uM. Data is collected at 5, 10, 15, 20 and 30 minutes, and 1, 4, 6, 12 and 24 hours post-incubation.

5. Assaying Cardiac Safety (Assay 2)

Male Sprague-Dawley rats are acclimated for approximately 1 week prior to use. Rats are lightly anesthetized using isoflurane and an intravenous catheter is placed for dosing purposes. Baseline 2-D echocardiograms are collected (standard SAX B-mode and M-mode at the level of the papillary muscle). Each rat receives a total of 3 IV treatments. Vehicle (10% DMSO, 10% Tween 80 and 80% water) is first administered, followed 10 minutes later by two subsequent infusions, separated by 10 minutes. Infusions of the positive control, Blebbistatin, are delivered at 0.5 mg/kg IV. Test compound concentrations vary depending upon the compound and experimental question. However, when available, dose is adjusted based on plasma pharmacokinetics and NMII potency. Standard SAX ECHO images are collected at the initiation of and at 1, 5, and 10 min after the initiation of each treatment. Measurements including fractional shortening, ejection fraction, heart rate and cardiac output are calculated.

Compounds of the invention were prepared according to the Synthetic Schemes 1-7, below, and all compounds disclosed and claimed herein can be prepared according to these Schemes, in conjunction with ordinary skill and knowledge of a synthetic organic chemist and illustrated by the detailed procedures for specific examples further provided below.

HPLC Conditions:
Method A
　Column: Waters Symmetry 5 µm C18 (250×4.6 mm)
　Mobile Phase A: Water containing 0.1% v/v Trifluoroacetic Acid
　Mobile Phase B: Acetonitrile containing 0.1% v/v Trifluoroacetic Acid
　Detection: 254 nm
Method A Gradient

| Time (min) | Flow (mL/min) | % A | % B |
|---|---|---|---|
| 0.0 | 1.0 | 98.0 | 2.0 |
| 20.0 | 1.0 | 0.0 | 100.0 |
| 25.0 | 1.0 | 0.0 | 100.0 |

Method B
　Column: YMC ODS-AQ C18 120 Å (150×4.6 mm)
　Mobile Phase A: Water containing 0.1% v/v Trifluoroacetic Acid
　Mobile Phase B: Acetonitrile containing 0.1% v/v Trifluoroacetic Acid
　Detection: 254 nm
Method B Gradient

| Time (min) | Flow (mL/min) | % A | % B |
|---|---|---|---|
| 0.0 | 1.0 | 98.0 | 2.0 |
| 15.0 | 1.0 | 0.0 | 100.0 |
| 19.0 | 1.0 | 0.0 | 100.0 |

Method C
　Column: xBridge 3.5 µm C18 (150×4.6 mm)
　Mobile Phase A: Water containing 0.1% v/v Trifluoroacetic Acid
　Mobile Phase B: Acetonitrile containing 0.1% v/v Trifluoroacetic Acid
　Detection: 254 nm
Method C Gradient

| Time (min) | Flow (mL/min) | % A | % B |
|---|---|---|---|
| 0.0 | 1.0 | 95.0 | 5.0 |
| 20.0 | 1.0 | 0.0 | 100.0 |
| 25.0 | 1.0 | 0.0 | 100.0 |

Method D
　Column: YMC ODS-AQ C18 120 Å (150×4.6 mm)
　Mobile Phase A: Water containing 0.1% v/v Trifluoroacetic Acid
　Mobile Phase B: Acetonitrile containing 0.1% v/v Trifluoroacetic Acid
　Detection: 254 nm
Method D Gradient

| Time (min) | Flow (mL/min) | % A | % B |
|---|---|---|---|
| 0.0 | 1.0 | 95.0 | 5.0 |
| 20.0 | 1.0 | 0.0 | 100.0 |
| 25.0 | 1.0 | 0.0 | 100.0 |

Method E
　Column: YMC ODS-AQ C18 120 Å (150×4.6 mm)
　Mobile Phase A: Water containing 0.1% v/v Trifluoroacetic Acid
　Mobile Phase B: Acetonitrile containing 0.1% v/v Trifluoroacetic Acid
　Detection: 254 nm
Method E Gradient

| Time (min) | Flow (mL/min) | % A | % B |
|---|---|---|---|
| 0.0 | 1.0 | 100.0 | 0.0 |
| 5.0 | 1.0 | 100.0 | 0.0 |
| 15.0 | 1.0 | 0.0 | 100.0 |
| 18.0 | 1.0 | 0.0 | 100.0 |

Method F
　Column: Waters Symmetry 5 µm C18 (250×4.6 mm)
　Mobile Phase A: Water containing 0.1% v/v Trifluoroacetic Acid
　Mobile Phase B: Acetonitrile containing 0.1% v/v Trifluoroacetic Acid
　Detection: 290 nm Method F Gradient

| Time (min) | Flow (mL/min) | % A | % B |
|---|---|---|---|
| 0.0 | 1.0 | 95.0 | 5.0 |
| 20.0 | 1.0 | 0.0 | 100.0 |
| 25.0 | 1.0 | 0.0 | 100.0 |

UPLC Conditions:
Method A
  Column: Acquity UPLC BEH 1.7 μm C18 (75×2.1 mm)
  Mobile Phase A: Water containing 0.1% v/v Trifluoroacetic Acid
  Mobile Phase B: Acetonitrile containing 0.1% v/v Trifluoroacetic Acid
  Detection: 254 nm
Method A Gradient

| Time (min) | Flow mL/min | % A | % B |
|---|---|---|---|
| 0.0 | 0.5 | 95.0 | 5.0 |
| 6.0 | 0.5 | 0.0 | 100.0 |
| 8.0 | 0.5 | 0.0 | 100.0 |

Chiral HPLC Conditions:
Method A
  Column: Chiralpak AD 5 μm (250×4.6 mm)
  Mobile Phase A: Heptane
  Mobile Phase B: i-Propyl Alcohol
  Detection: 254 nm
Method A Gradient

| Time (min) | Flow (mL/min) | % A | % B |
|---|---|---|---|
| 0.0 | 1.0 | 90.0 | 10.0 |
| 5.0 | 1.0 | 90.0 | 10.0 |
| 20.0 | 1.0 | 50.0 | 50.0 |
| 35.0 | 1.0 | 50.0 | 50.0 |

Method B
  Column: Chiralpak AD 5 μm (250×4.6 mm)
  Mobile Phase A: Heptane
  Mobile Phase B: i-Propyl Alcohol
  Detection: 290 nm
Method B Gradient

| Time (min) | Flow (mL/min) | % A | % B |
|---|---|---|---|
| 0.0 | 1.0 | 90.0 | 10.0 |
| 5.0 | 1.0 | 90.0 | 10.0 |
| 20.0 | 1.0 | 50.0 | 50.0 |
| 35.0 | 1.0 | 50.0 | 50.0 |

Chiral SFC Conditions:
Method A
  Column: Chiralcel OJ-H 5 μm (100×4.6 mm)
  Mobile Phase A: CO$_2$
  Mobile Phase B: i-Propyl Alcohol
  Detection: 254 nm Method A Gradient

| Time (min) | Flow (mL/min) | % A | % B |
|---|---|---|---|
| 0.0 | 1.5 | 95.0 | 5.0 |
| 8.0 | 1.5 | 60.0 | 40.0 |

Method B
  Column: Chiralcel OJ-H 5 μm (100×4.6 mm)
  Mobile Phase A: CO$_2$
  Mobile Phase B: Methanol
  Detection: 254 nm
Method B Gradient

| Time (min) | Flow (mL/min) | % A | % B |
|---|---|---|---|
| 0.0 | 1.5 | 95.0 | 5.0 |
| 8.0 | 1.5 | 60.0 | 40.0 |

Synthetic Schemes
Scheme 1: Synthetic Approach to Compounds

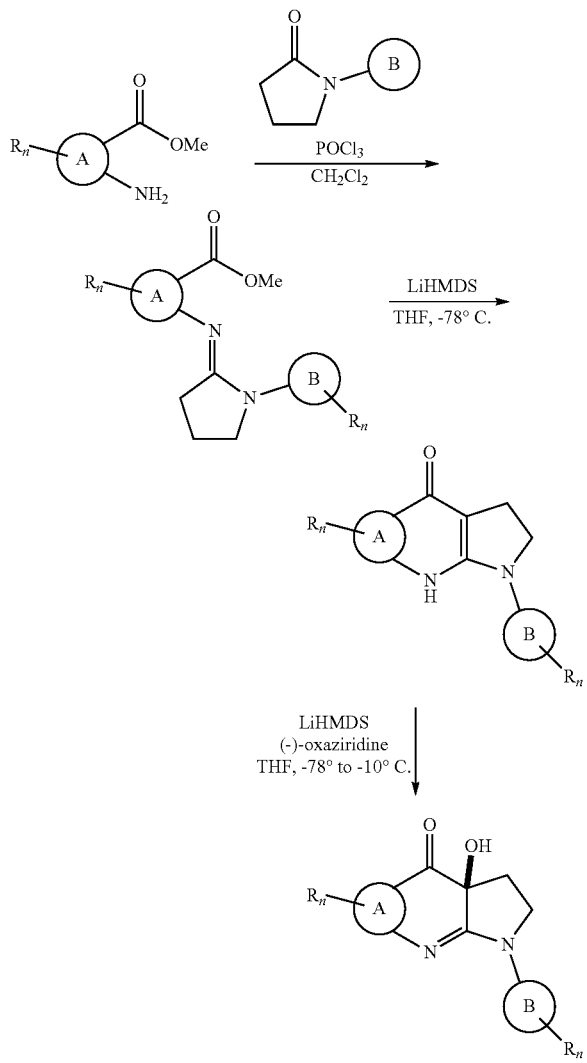

Scheme 1: Synthetic approach to compounds

Scheme 2: BPN-0025002

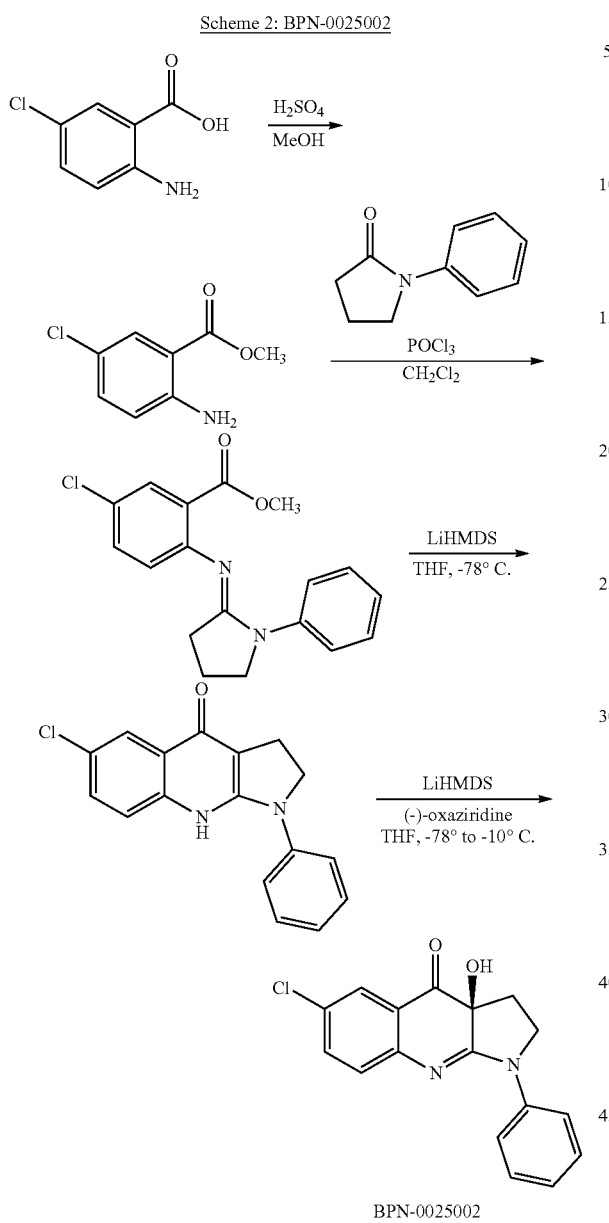

Preparation of Methyl 2-amino-5-chlorobenzoate

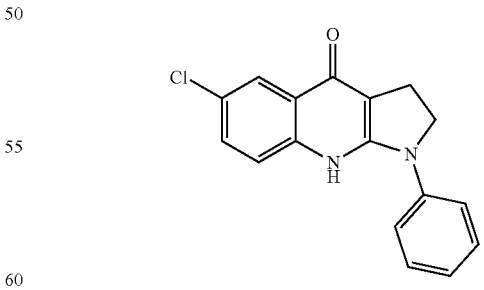

A solution of 2-amino-5-chlorobenzoic acid (5.00 g, 29.1 mmol) in methanol (75 mL) was treated with concentrated sulfuric acid (7.5 mL) and heated at 60° C. under a nitrogen atmosphere for 72 h. After this time, the reaction mixture was concentrated under reduced pressure to remove the volatiles. The resulting residue was carefully treated with saturated aqueous sodium bicarbonate (150 mL) and extracted with ethyl acetate (3×100 mL). The combined organics were dried over sodium sulfate, filtered, and concentrated under reduced pressure to provide methyl 2-amino-5-chlorobenzoate (5.10 g, 94%) as a brown solid: $^1$H NMR (500 MHz, DMSO-$d_6$) δ 7.63 (d, J=2.5 Hz, 1H), 7.28 (dd, J=8.5, 2.5 Hz, 1H), 6.81 (d, J=8.5 Hz, 1H), 6.77 (br s, 2H), 3.80 (s, 3H).

Preparation of Methyl 5-chloro-2-((1-phenylpyrrolidin-2-ylidene)amino)benzoate

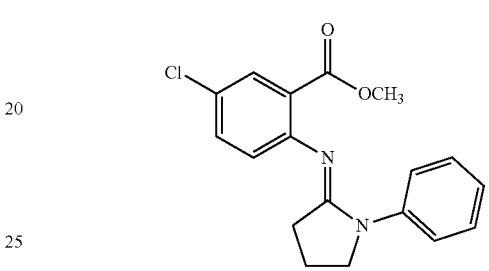

A solution of 1-phenylpyrrolidin-2-one (1.04 g, 6.45 mmol) in methylene chloride (13 mL) was treated with phosphorous oxychloride (0.60 mL, 0.99 g, 6.4 mmol) and stirred under a nitrogen atmosphere at ambient temperature for 3 h. The mixture was treated with a solution of methyl 2-amino-5-chlorobenzoate (1.00 g, 5.39 mmol) in methylene chloride (3 mL) and heated at 50° C. for 16 h. After this time, the reaction mixture was allowed to cool to ambient temperature, diluted with methylene chloride (25 mL), washed with saturated aqueous sodium bicarbonate (2×25 mL) and brine (25 mL), dried over sodium sulfate, filtered, and concentrated under reduced pressure. The crude residue was purified by column chromatography (silica gel, 0-30% ethyl acetate/methylene chloride) to provide methyl 5-chloro-2-((1-phenylpyrrolidin-2-ylidene)amino)benzoate (0.72 g, 41%) as a light tan oil: ESI MS m/z 329 $[C_{18}H_{17}ClN_2O_2+H]^+$.

Preparation of 6-Chloro-1-phenyl-2,3-dihydro-1H-pyrrolo[2,3-b]quinolin-4(9H)-one A solution of methyl 5-chloro-2-((1-phenylpyrrolidin-2-ylidene)amino)benzoate (715 mg, 2.17 mmol) in tetrahydrofuran (10 mL) was cooled in a dry ice/acetone bath under a nitrogen atmosphere and treated dropwise with a 1.0 M solution of lithium bis(trimethylsilyl)amide in tetrahydrofuran (5.4 mL, 5.4 mmol). The mixture was stirred for 3.5 h, during which time the bath temperature increased to ~0° C. After this time, the mixture was treated with chilled saturated aqueous ammonium chloride (50 mL) and stirred rapidly for 1 h. The resulting solids were isolated by filtration, washed with water and ethyl acetate, and dried under vacuum to provide 6-chloro-1-phenyl-2,3-dihydro-1H-pyrrolo[2,3-b]quinolin-4(9H)-one (435 mg, 67%) as a light orange solid: $^1$H NMR (500 MHz, DMSO-$d_6$) δ 10.77 (s, 1H), 8.05 (d, J=8.0 Hz, 2H), 7.93 (d, J=2.5 Hz, 1H), 7.60 (d, J=8.5 Hz, 1H), 7.47 (dd, J=8.5, 2.5 Hz, 1H), 7.39 (apparent t, J=7.5 Hz, 2H), 7.02 (apparent t, J=7.5 Hz, 1H), 4.11 (t, J=8.0 Hz, 2H), 3.19 (t, J=8.0 Hz, 2H); ESI MS m/z 297 [$C_{17}H_{13}ClN_2O+H$]$^+$.

Preparation of (S)-6-Chloro-3a-hydroxy-1-phenyl-3,3a-dihydro-1H-pyrrolo[2,3-b]quinolin-4(2H)-one

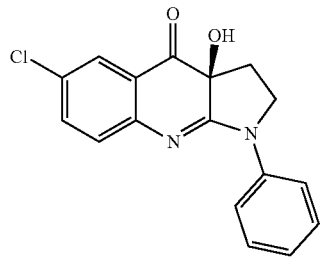

BPN-0025002

A solution of 6-chloro-1-phenyl-2,3-dihydro-1H-pyrrolo[2,3-b]quinolin-4(9H)-one (101 mg, 0.339 mmol) in tetrahydrofuran (6 mL) was cooed in a dry ice/acetone bath and treated with a 1.0 M solution of lithium bis(trimethylsilyl)amide in tetrahydrofuran (0.41 mL, 0.41 mmol) under a nitrogen atmosphere. After stirring for 45 min, the mixture was treated with a solution of (−)-(8,8-dichlorocamphorylsulfonyl)oxaziridine (245 mg, 0.821 mmol) in tetrahydrofuran (3 mL). The mixture was stirred for 2 h while the bath temperature increased to ~0° C. The acetone bath was replaced by a wet ice/brine bath, and the mixture was stirred for 3 h. After this time, the mixture was treated with saturated aqueous ammonium iodide (6 mL) followed by saturated aqueous sodium thiosulfate (25 ml) and extracted with ethyl acetate (3×25 mL). The organics were extracted with 0.3 M hydrochloric acid (3×25 mL). The combined acid layers were adjusted to pH~8 with 2.0 M aqueous sodium hydroxide and extracted with ethyl acetate (4×25 mL). The organics were dried over sodium sulfate, filtered, and concentrated under reduced pressure. The crude product was recrystallized from hot acetonitrile to provide (S)-6-chloro-3a-hydroxy-1-phenyl-3,3a-dihydro-1H-pyrrolo[2,3-b]quinolin-4(2H)-one (37 mg, 35%) as a yellow solid: mp=199-200° C. decomposed; $^1$H NMR (500 MHz, DMSO-$d_6$) δ 8.06 (dd, J=7.5, 1.0 Hz, 2H), 7.64 (d, J=2.5 Hz, 1H), 7.56 (dd, J=8.5, 2.5 Hz, 1H), 7.44 (apparent t, J=7.0 Hz, 2H), 7.22 (d, J=8.5 Hz, 1H), 7.17 (apparent t, J=7.0 Hz, 1H), 6.96 (s, 1H), 4.14-4.08 (m, 1H), 3.98 (apparent t, J=9.0 Hz, 1H), 2.37-2.31 (m, 1H), 2.26 (dd, J=13.5, 6.0 Hz, 1H); ESI MS m/z 313 [$C_{17}H_{13}ClN_2O_2+H$]$^+$; HPLC (Method A) >99% (AUC), $t_R$=11.17 min; Chiral HPLC (Chiralpak AD, Method A) >99% (AUC), $t_R$=11.17 min.

Scheme 3: BPN-0025881

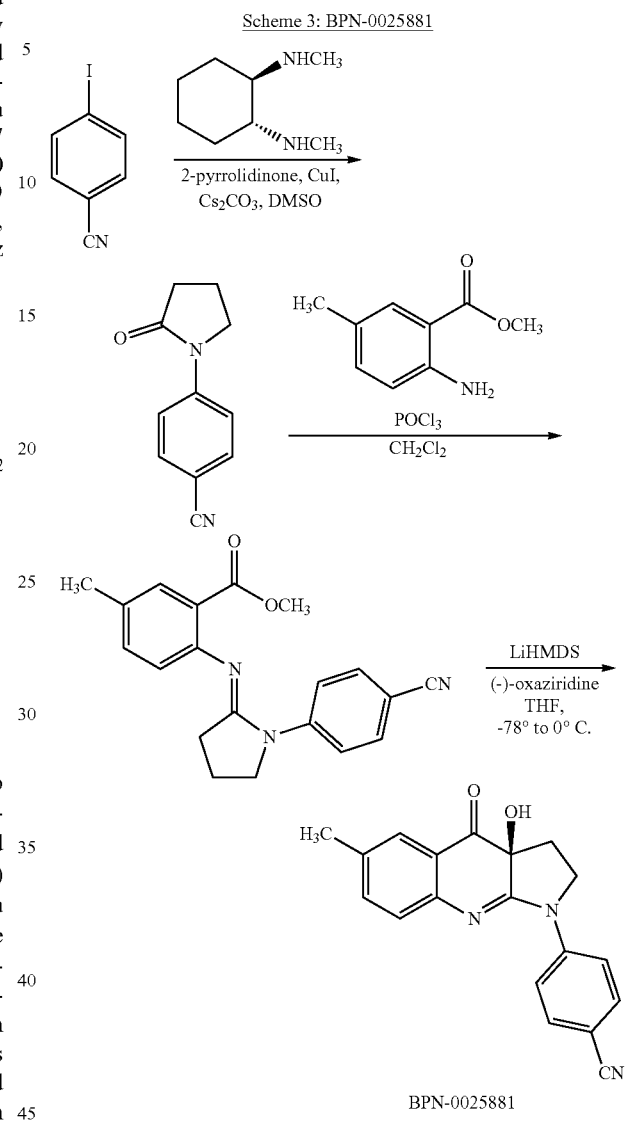

Preparation of 4-(2-Oxopyrrolidin-1-yl)benzonitrile

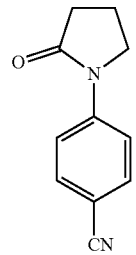 [SMILES: N#Cc1ccc(N2CCCC2=O)cc1]

A solution of 4-iodobenzonitrile (1.00 g, 4.36 mmol) in dimethyl sulfoxide (10 mL) was treated with 2-pyrrolidinone (331 μL, 4.36 mmol), copper iodide (83.0 mg, 0.436 mmol), cesium carbonate (4.26 g, 13.1 mmol) and N,N'-dimethyl-(1R,2R)-1,2-cyclohexanediamine (137 μL, 0.872 mmol) and heated at 110° C. under a nitrogen atmosphere for 16 h. After this time, the reaction mixture was allowed to cool to ambient temperature, diluted with water (50 mL), and extracted with ethyl acetate (4×50 mL). The combined organics were washed with water (4×10 mL), dried over sodium sulfate, filtered, and concentrated under reduced pressure. The crude residue was purified by column chromatography (silica gel, 0-100% ethyl acetate/heptane) to provide 4-(2-oxopyrrolidin-1-yl)benzonitrile (514 mg, 63%) as an off-white solid: $^1$H NMR (300 MHz, DMSO-$d_6$) δ 7.90-7.82 (m, 4H), 3.87 (t, J=7.2 Hz, 2H), 2.56 (t, J=3.9 Hz, 2H), 2.12-2.05 (m, 2H).

Preparation of Methyl 2-((1-(4-Cyanophenyl)pyrrolidin-2-ylidene)amino)-5-methylbenzoate

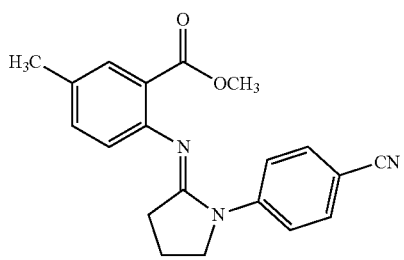 [SMILES: COC(=O)c1cc(C)ccc1/N=C1\CCCN1c1ccc(C#N)cc1]

A solution of 4-(2-oxopyrrolidin-1-yl)benzonitrile (400 mg, 2.14 mmol) in methylene chloride (9 mL) was treated with phosphorous oxychloride (0.30 mL, 3.2 mmol) and stirred under a nitrogen atmosphere at ambient temperature for 16 h. The mixture was treated with a solution of methyl 2-amino-5-methylbenzoate (355 mg, 2.14 mmol) in methylene chloride (2 mL) and heated at 45° C. for 5 d. After this time, the reaction mixture was allowed to cool to ambient temperature, quenched with saturated aqueous sodium bicarbonate (15 mL), and extracted with ethyl acetate. The organics were dried over sodium sulfate, filtered, and concentrated under reduced pressure. The crude residue was dissolved in ethyl acetate and extracted with 0.3 M hydrochloric acid (2×20 mL). The combined acid layers were adjusted to pH~11 with 2.0 M aqueous sodium hydroxide and extracted with ethyl acetate (3×25 mL). The organics were dried over sodium sulfate, filtered, and concentrated under reduced pressure to provide methyl 2-((1-(4-cyanophenyl)pyrrolidin-2-ylidene)amino)-5-methylbenzoate (226 mg, 32%) as a yellow oil, which was used without further purification: ESI MS m/z 334 $[C_{20}H_{19}N_3O_2+H]^+$.

Preparation of (S)-4-(3a-Hydroxy-6-methyl-4-oxo-2,3,3a,4-tetrahydro-1H-pyrrolo[2,3-b]quinolin-1-yl)benzonitrile

BPN-0025881

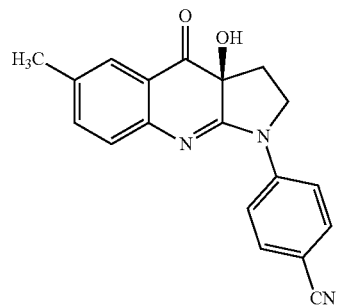

A solution of methyl 2-((1-(4-cyanophenyl)pyrrolidin-2-ylidene)amino)-5-methylbenzoate (226 mg, 0.678 mmol) in tetrahydrofuran (12 mL) was cooled in a dry ice/acetone bath under a nitrogen atmosphere and treated with a 1.0 M solution of lithium bis(trimethylsilyl)amide in tetrahydrofuran (2.03 mL, 2.03 mmol). The acetone bath was replaced by a wet ice/water bath, and the mixture was stirred for 3 h. After stirring for 3 h, the mixture was treated with a solution of (−)-(8,8-dichlorocamphorylsulfonyl)oxaziridine (505 mg, 1.70 mmol) in tetrahydrofuran (8 mL). The mixture was stirred for 2 h at ~0° C. After this time, the mixture was treated sequentially with saturated aqueous ammonium iodide (0.7 mL), saturated aqueous sodium thiosulfate (2.3 mL), and brine (20 mL). The aqueous layer was extracted with ethyl acetate (3×25 mL). The organics were combined, dried over sodium sulfate, filtered, and concentrated under reduced pressure. The crude residue was purified by column chromatography (silica gel, 0-100% ethyl acetate/heptane) to obtain a yellow gum, which was re-purified by column chromatography (silica gel, 0-80% ethyl acetate/heptane) and recrystallization from hot acetonitrile to provide (S)-4-(3a-hydroxy-6-methyl-4-oxo-2,3,3a,4-tetrahydro-1H-pyrrolo[2,3-b]quinolin-1-yl)benzonitrile (39 mg, 18%) as a yellow solid: mp=222-223° C.; $^1$H NMR (500 MHz, DMSO-$d_6$) δ 8.32 (dd, J=7.0, 2.0 Hz, 2H), 7.88 (dd, J=7.0, 2.0 Hz, 2H), 7.57 (apparent d, J=2.0 Hz, 1H), 7.42 (dd, J=8.5, 1.5 Hz, 1H), 7.20 (d, J=8 Hz, 1H), 6.92 (s, 1H), 4.06-4.02 (m, 2H), 2.32 (s, 3H), 2.29-2.27 (m, 2H); ESI MS m/z 318 $[C_{19}H_{15}N_3O_2+H]^+$; HPLC (Method B) >99% (AUC), $t_R$=9.48 min.

Scheme 4: BPN-0026543

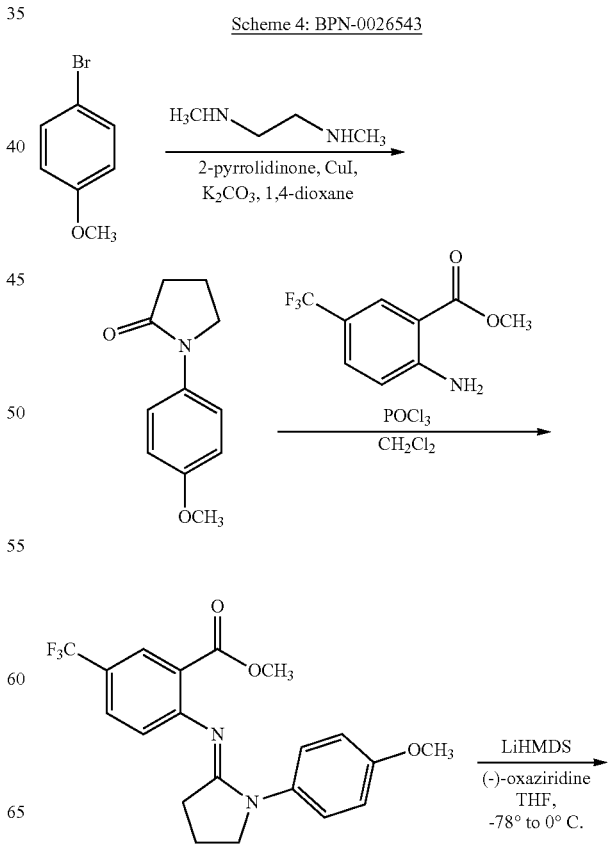

77

-continued

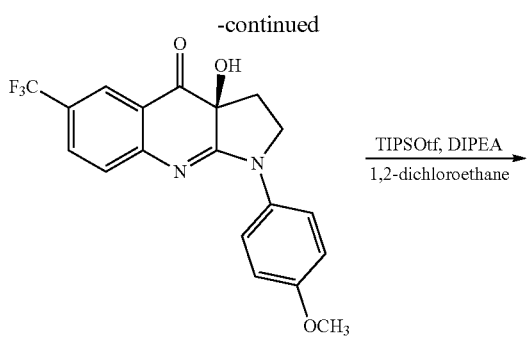

TIPSOtf, DIPEA
─────────────────
1,2-dichloroethane

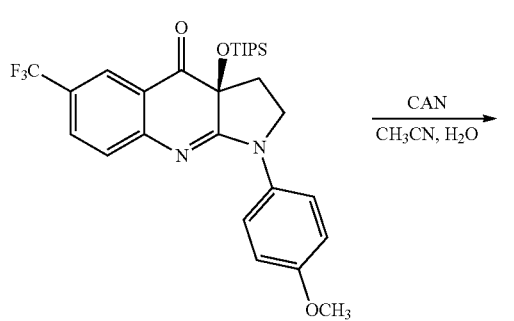

CAN
─────────
CH₃CN, H₂O

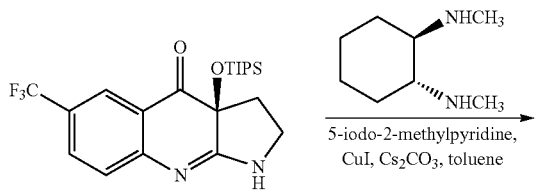

5-iodo-2-methylpyridine,
CuI, Cs₂CO₃, toluene

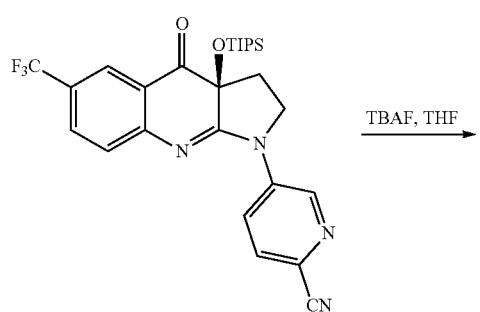

TBAF, THF

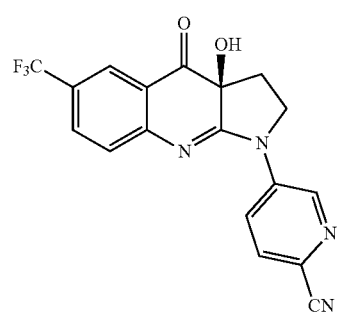

BPN-0026543

78

Preparation of Methyl 2-((1-(4-Methoxyphenyl)pyrrolidin-2-ylidene)amino)-5-(trifluoromethyl)benzoate

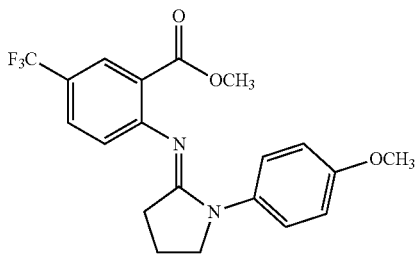 [SMILES: COC(=O)c1cc(C(F)(F)F)ccc1/N=C1\CCCN1c1ccc(OC)cc1]

A solution of 1-(4-methoxyphenyl)pyrrolidin-2-one (2.00 g, 10.5 mmol) in methylene chloride (20 mL) was treated with phosphorous oxychloride (1.46 mL, 15.7 mmol) and stirred under a nitrogen atmosphere at ambient temperature for 7 h. The mixture was treated with a solution of methyl 2-amino-5-(trifluoromethyl)benzoate (3.21 g, 14.6 mmol) in methylene chloride (20 mL) and heated at 45° C. for 2 d. After this time, the reaction mixture was allowed to cool to ambient temperature, quenched with saturated aqueous sodium bicarbonate (40 mL), and extracted with ethyl acetate. The organics were dried over sodium sulfate, filtered, and concentrated under reduced pressure. The crude residue was purified by column chromatography (silica gel, 12-100% ethyl acetate/heptane) to provide methyl 2-((1-(4-methoxyphenyl)pyrrolidin-2-ylidene)amino)-5-(trifluoromethyl)benzoate (2.19 g, 53%) as a clear gum: ¹H NMR (500 MHz, CDCl₃) δ 8.10 (s, 1H), 7.63 (d, J=8.5 Hz, 2H), 7.56 (dd, J=8.5, 1.5 Hz, 1H), 6.90 (d, J=8.5 Hz, 3H), 3.88-3.85 (m, 5H), 3.79 (s, 3H), 2.47 (t, J=7.5 Hz, 2H), 2.11-2.05 (m, 2H).

Preparation of (S)-3a-Hydroxy-1-(4-methoxyphenyl)-6-(trifluoromethyl)-1,2,3,3a-tetrahydro-4H-pyrrolo[2,3-b]quinolin-4-one

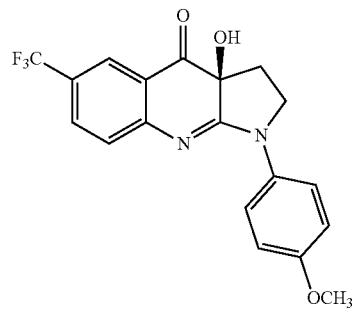 [SMILES: COc1ccc(N2CC[C@@]3(O)C(=O)c4cc(C(F)(F)F)ccc4N=C23)cc1]

A solution of methyl 2-((1-(4-methoxyphenyl)pyrrolidin-2-ylidene)amino)-5-(trifluoromethyl)benzoate (2.19 g, 5.59 mmol) in tetrahydrofuran (35 mL) was cooled in a dry ice/acetone bath under a nitrogen atmosphere and treated with a 1.0 M solution of lithium bis(trimethylsilyl)amide in tetrahydrofuran (16.8 mL, 16.8 mmol). The acetone bath was replaced by a wet ice/water bath, and the mixture was stirred for 1 h. After this time, the mixture was treated with a solution of (−)-(8,8-dichlorocamphorylsulfonyl)oxaziridine (4.17 g, 14.0 mmol) in tetrahydrofuran (20 mL). The mixture was stirred for 1 h at ~0° C. After this time, the mixture was treated sequentially with saturated aqueous ammonium iodide (20 mL), saturated aqueous sodium thiosulfate (37 mL), and brine (50 mL). The aqueous layer was extracted with ethyl acetate (3×50 mL). The organics were combined, dried over sodium sulfate, filtered, and concentrated under reduced pressure. The crude residue was triturated in hot acetonitrile to provide (S)-3a-hydroxy-1-(4-methoxyphenyl)-6-(trifluoromethyl)-1,2,3,3a-tetrahydro-4H-pyrrolo[2,3-b]quinolin-4-one (1.26 g, 60%) as a yellow-brown solid: $^1$H NMR (500 MHz, DMSO-d$_6$) δ 7.93 (dd, J=7.0, 2.5 Hz, 2H), 7.90 (d, J=1.5 Hz, 1H), 7.81 (dd, J=8.5, 2.5 Hz, 1H), 7.29 (d, J=8.0 Hz, 1H), 7.03 (dd, J=7.0, 2.5 Hz, 2H), 6.99 (s, 1H), 4.16-4.12 (m, 1H), 3.98-3.94 (m, 1H), 3.79 (s, 3H), 2.42-2.35 (m, 1H), 2.28-2.25 (m, 1H).

Preparation of (S)-1-(4-Methoxyphenyl)-6-(trifluoromethyl)-3a-((triisopropylsilyl)oxy)-1,2,3,3a-tetrahydro-4H-pyrrolo[2,3-b]quinolin-4-one

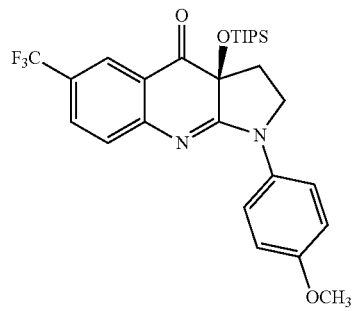

A solution of (S)-3a-hydroxy-1-(4-methoxyphenyl)-6-(trifluoromethyl)-1,2,3,3a-tetrahydro-4H-pyrrolo[2,3-b]quinolin-4-one (730 mg, 1.94 mmol) in 1,2-dichloroethane (30 mL) was treated with N,N-diisopropylethylamine (1.35 mL, 7.76 mmol) and triisopropylsilyl trifluoromethanesulfonate (1.56 mL, 5.82 mmol) and stirred under a nitrogen atmosphere at 90° C. for 16 h. After this time, the reaction mixture was allowed to cool to ambient temperature. The mixture was treated with cold deionized water (17 mL) followed by saturated aqueous ammonium chloride (40 mL). The aqueous layer was extracted with ethyl acetate (3×50 mL). The organics were dried over sodium sulfate, filtered, and concentrated under reduced pressure. The crude residue was purified by column chromatography (silica gel, 0-60% ethyl acetate/heptane) to provide (S)-1-(4-methoxyphenyl)-6-(trifluoromethyl)-3a-((triisopropylsilyl)oxy)-1,2,3,3a-tetrahydro-4H-pyrrolo[2,3-b]quinolin-4-one (870 mg, 84%) as a yellow solid: $^1$H NMR (500 MHz, DMSO-d$_6$) δ 7.93-7.88 (m, 3H), 7.82 (d, J=8.5 Hz, 1H), 7.30 (d, J=8.5 Hz, 1H), 7.04 (d, J=9.0 Hz, 2H), 4.10-4.05 (m, 2H), 3.79 (s, 3H), 2.57-2.50 (m, 1H), 2.33-2.30 (m, 1H), 0.86-0.80 (m, 21H).

Preparation of (S)-6-(Trifluoromethyl)-3a-((triisopropylsilyl)oxy)-1,2,3,3a-tetrahydro-4H-pyrrolo[2,3-b]quinolin-4-one

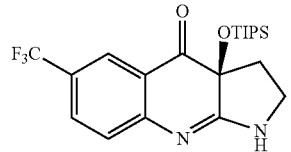

A solution of (S)-1-(4-methoxyphenyl)-6-(trifluoromethyl)-3a-((triisopropylsilyl)oxy)-1,2,3,3a-tetrahydro-4H-pyrrolo[2,3-b]quinolin-4-one (870 mg, 1.63 mmol) in acetonitrile (24 mL) was cooled in a wet ice/water bath under a nitrogen atmosphere and treated dropwise with a solution of ammonium cerium(IV) nitrate (3.58 g, 6.53 mmol) in deionized water (6 mL) and stirred for 2 h at ~0° C. The mixture was treated with an additional solution of ammonium cerium(IV) nitrate (1.79 g, 3.27 mmol) in deionized water (3 mL) and acetonitrile (12 mL) and stirred for 3 h at ~0° C. After this time, the mixture was treated with sodium thiosulfate pentahydrate (3.67 g) in deionized water (6 mL) and acetonitrile (25 mL) followed by saturated aqueous sodium bicarbonate (50 mL) to form a slurry. The solid was removed by filtration through diatomaceous earth and rinsed with ethyl acetate. The filtrate was extracted with ethyl acetate (3×50 mL). The organics were combined and washed with saturated sodium bicarbonate, water, and brine. The organics were dried over sodium sulfate, filtered, and concentrated under reduced pressure. The crude residue was purified by column chromatography (silica gel, 12-100% ethyl acetate/heptane) to provide (S)-6-(trifluoromethyl)-3a-((triisopropylsilyl)oxy)-1,2,3,3a-tetrahydro-4H-pyrrolo[2,3-b]quinolin-4-one (358 mg, 52%) as a yellow solid: $^1$H NMR (300 MHz, DMSO-d$_6$) δ 7.84 (s, 1H), 7.80 (d, J=8.7 Hz, 1H), 7.15 (d, J=8.7 Hz, 1H), 3.70 (br s, 2H), 2.39-2.34 (m, 1H), 2.17-2.16 (m, 1H), 0.90-0.81 (m, 21H); NH proton not observed.

Preparation of (S)-1-(6-Methylpyridin-3-yl)-6-(trifluoromethyl)-3a-((triisopropylsilyl)oxy)-1,2,3,3a-tetrahydro-4H-pyrrolo[2,3-b]quinolin-4-one

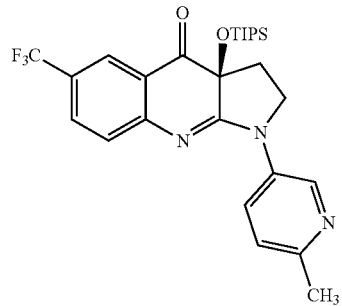

A solution of (S)-6-(trifluoromethyl)-3a-((triisopropylsilyl)oxy)-1,2,3,3a-tetrahydro-4H-pyrrolo[2,3-b]quinolin-4-one (125 mg, 0.293 mmol) in toluene (3 mL) was treated with 5-iodo-2-methylpyridine (96 mg, 0.44 mmol), copper iodide (6.0 mg, 0.029 mmol), cesium carbonate (286 mg, 0.879 mmol), and N,N'-dimethyl-(1R,2R)-1,2-cyclohexanediamine (9 μL, 0.06 mmol) and heated at 105° C. in a sealed vial for 16 h. After this time, the reaction mixture was allowed to cool to ambient temperature. The solids were removed by filtration and washed with ethyl acetate. The filtrate was concentrated under reduced pressure. The crude residue was purified by column chromatography (silica gel, 12-100% ethyl acetate/heptane) to provide (S)-1-(6-methylpyridin-3-yl)-6-(trifluoromethyl)-3a-((triisopropylsilyl)oxy)-1,2,3,3a-tetrahydro-4H-pyrrolo[2,3-b]quinolin-4-one (143 mg, 94%) as a yellow gum: ESI MS m/z 518 $[C_{27}H_{34}F_3N_3O_2Si+H]^+$.

Preparation of provide (S)-3a-Hydroxy-1-(6-methylpyridin-3-yl)-6-(trifluoromethyl)-1,2,3,3a-tetrahydro-4H-pyrrolo[2,3-b]quinolin-4-one

BPN-0226543

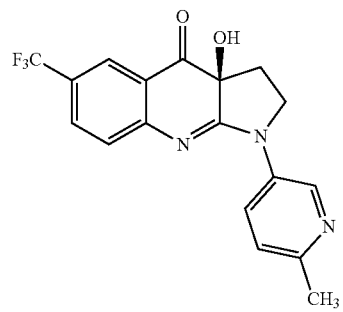

A solution of (S)-1-(6-methylpyridin-3-yl)-6-(trifluoromethyl)-3a-((triisopropylsilyl)oxy)-1,2,3,3a-tetrahydro-4H-pyrrolo[2,3-b]quinolin-4-one (143 mg, 0.276 mmol) in tetrahydrofuran (5 mL) under a nitrogen atmosphere was treated with a 1.0 M solution of tetrabutylammonium fluoride in tetrahydrofuran (0.829 mL, 0.829 mmol), and the mixture was stirred for 1 h. After this time, the mixture was concentrated under reduced pressure. The crude residue was purified by column chromatography (silica gel, 0-20% methanol/methylene chloride) to provide (S)-3a-hydroxy-1-(6-methylpyridin-3-yl)-6-(trifluoromethyl)-1,2,3,3a-tetrahydro-4H-pyrrolo[2,3-b]quinolin-4-one (84 mg, 84%) as a yellow solid: mp=237-240° C. decomposed; $^1$H NMR (300 MHz, DMSO-$d_6$) δ 9.09 (d, J=2.4 Hz, 1H), 8.39 (dd, J=8.7, 2.7 Hz, 1H), 7.93 (s, 1H), 7.87 (d, J=8.4 Hz, 1H), 7.36 (dd, J=8.4, 4.8 Hz, 2H), 7.08 (s, 1H), 4.19-4.12 (m, 1H), 4.06-4.00 (m, 1H), 2.32-2.27 (m, 2H), CH$_3$ protons obscured by solvent; ESI MS m/z 362 $[C_{18}H_{14}F_3N_3O_2+H]^+$; HPLC (Method C) >99% (AUC), $t_R$=12.49 min; Chiral HPLC (Chiralpak AD, Method A) 49.7% (AUC), $t_R$=16.24 min. Scheme 5: BPN-0026581

Scheme 5: BPN-0026581

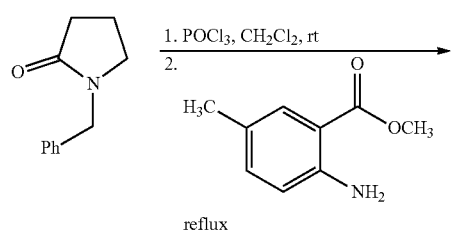

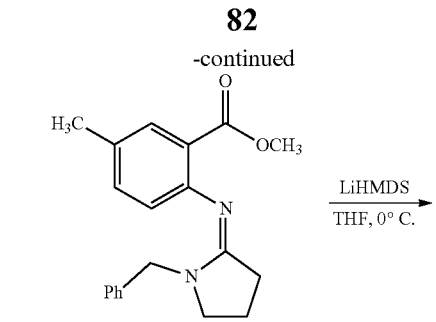

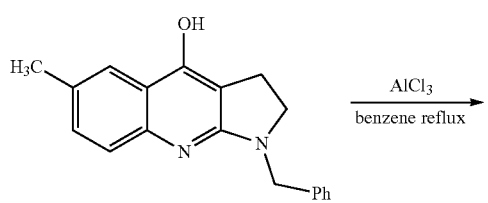

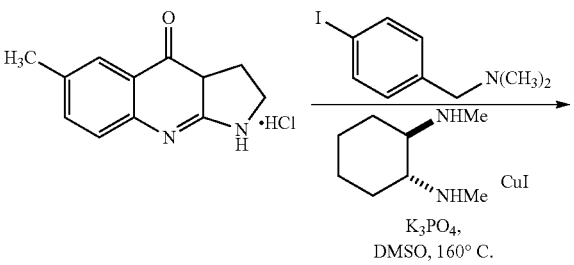

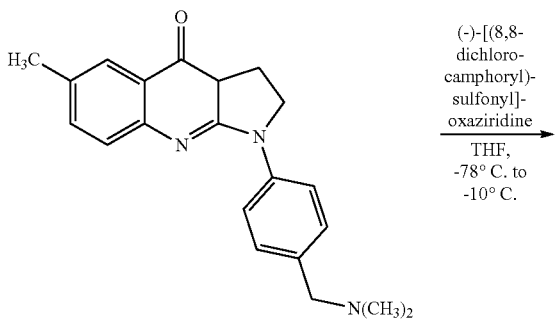

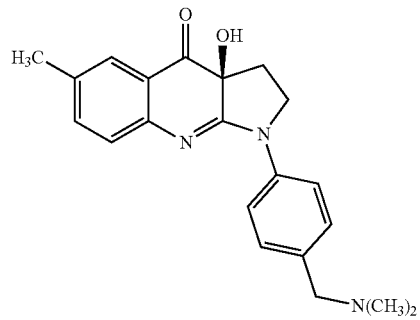

BPN-0026581

Preparation of Methyl 2-((1-benzylpyrrolidin-3-ylidene)amino)-5-methylbenzoate

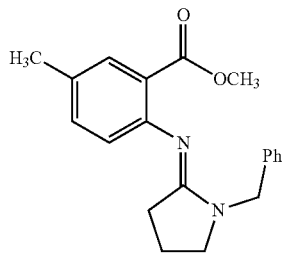 [SMILES: COC(=O)c1cc(C)ccc1/N=C1\CCCN1Cc1ccccc1]

A solution of 1-benzylpyrrolidin-2-one (6.30 g, 35.9 mmol) in methylene chloride (200 mL) was treated with phosphorous oxychloride (4.50 mL, 49.2 mmol) and stirred under a nitrogen atmosphere at ambient temperature for 4 h. The mixture was treated with a solution of methyl 2-amino-5-methylbenzoate (5.30 g, 32.1 mmol) in methylene chloride (20 mL) and heated at reflux for 48 h. After this time, the reaction mixture was allowed to cool to ambient temperature and concentrated under reduced pressure. The residue was diluted with ethyl acetate, washed with saturated aqueous sodium bicarbonate and then water. The organic layer was extracted with 0.4 M hydrochloric acid, and the aqueous extract was basified to pH~12 by adding sodium hydroxide. The mixture was extracted with ethyl acetate, dried over sodium sulfate, filtered, and concentrated under reduced pressure to provide methyl 2-((1-benzylpyrrolidin-3-ylidene)amino)-5-methylbenzoate (8.40 g, 81%) as a pale yellow oil: ESI MS m/z 323 $[C_{20}H_{22}N_2O_2+H]^+$.

Preparation of 1-Benzyl-6-methyl-2,3-dihydro-1H-pyrrolo[2,3-b]quinolin-4-ol

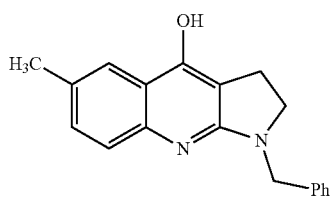 [SMILES: Cc1ccc2nc3c(c(O)c2c1)CCN3Cc1ccccc1]

A solution of methyl 2-((1-benzylpyrrolidin-3-ylidene)amino)-5-methylbenzoate (8.40 g, 26.1 mmol) in tetrahydrofuran (200 mL) under a nitrogen atmosphere at 0° C. was treated dropwise with a 1.0 M solution of lithium bis(trimethylsilyl)amide in tetrahydrofuran (55 mL, 55 mmol) and stirred for 3 h. After this time, a saturated solution of ammonium chloride (100 mL) was added, and the mixture was stirred for 30 min. The precipitate was collected by filtration, washed with water and diethyl ether and dried under high vacuum to provide 1-benzyl-6-methyl-2,3-dihydro-1H-pyrrolo[2,3-b]quinolin-4-ol (3.18 g, 42%) as an off-white solid: ESI MS m/z 291 $[C_{19}H_{18}N_2O+H]^+$.

Preparation of 6-Methyl-2,3-dihydro-1H-pyrrolo[2,3-b]quinolin-4-ol hydrochloride

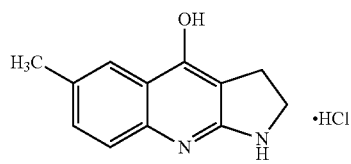

A mixture of 1-benzyl-6-methyl-2,3-dihydro-1H-pyrrolo[2,3-b]quinolin-4-ol (6.30 g, 21.7 mmol) and aluminum trichloride (12.8 g, 96.0 mmol) in benzene (140 mL) was stirred at reflux for 3 h. After this time, the mixture was cooled to room temperature and poured into stirred ice/water (250 mL). The mixture was stirred for 15 min and then the precipitate was collected by filtration, washed with diethyl ether and dried under high vacuum to provide 6-methyl-2,3-dihydro-1H-pyrrolo[2,3-b]quinolin-4-ol hydrochloride (5.1 g, quantitative): ESI MS m/z 201 $[C_{12}H_{12}N_2O+H]^+$.

Preparation of 1-(4-((Dimethylamino)methyl)phenyl)-6-methyl-2,3-dihydro-1H-pyrrolo[2,3-b]quinolin-4-ol

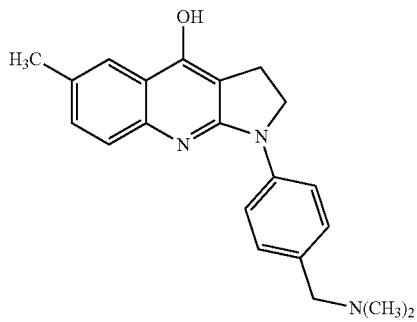 [SMILES: Cc1ccc2nc3c(c(O)c2c1)CCN3c1ccc(CN(C)C)cc1]

A solution of 6-methyl-2,3-dihydro-1H-pyrrolo[2,3-b]quinolin-4-ol hydrochloride (260 mg, 1.10 mmol) in dimethyl sulfoxide (4 mL) was treated with 1-(4-iodophenyl)-N,N-dimethylmethanamine (460 mg, 1.77 mmol), copper iodide (40 mg, 0.21 mmol), tripotassium phosphate (650 mg, 3.06 mmol), and trans-N,N'-dimethyl-1,2-cyclohexanediamine (58 mg, 0.41 mmol). The resulting mixture was heated in a microwave at 160° C. for 4 h. After this time, the reaction mixture was filtered through diatomaceous earth using 3/1 methylene chloride/methanol as eluent. The filtrate was concentrated under reduced pressure, and the residue was purified by column chromatography (silica gel, 0-80% (methylene chloride/methanol/ammonium hydroxide 80/18/2), methylene chloride) to provide 1-(4-((dimethylamino)methyl)phenyl)-6-methyl-2,3-dihydro-1H-pyrrolo[2,3-b]quinolin-4-ol (200 mg, 54%): ESI MS m/z 334 $[C_{21}H_{23}N_3O+H]^+$.

Preparation of (S)-1-(4-((Dimethylamino)methyl)phenyl)-3a-hydroxy-6-methyl-3,3a-dihydro-1H-pyrrolo[2,3-b]quinolin-4(2H)-one

BPN-0026581

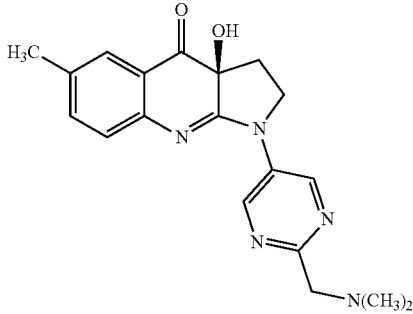

A solution of 1-(4-((dimethylamino)methyl)phenyl)-6-methyl-2,3-dihydro-1H-pyrrolo[2,3-b]quinolin-4-ol (200 mg, 0.60 mmol) in tetrahydrofuran (8 mL) at −78° C. was treated dropwise with a 1.0 M solution of lithium bis(trimethylsilyl)amide in tetrahydrofuran (1.0 mL, 1.0 mmol), followed by (−)-(8,8-dichlorocamphorylsulfonyl)oxaziridine (600 mg, 2.01 mmol) in one portion. The mixture was stirred while allowing the temperature to raise to −10° C. over 2 h. After this time, the mixture was treated with saturated aqueous ammonium iodide (4 mL) and stirred for 20 min. Saturated aqueous sodium thiosulfate (10 ml) was added, and the mixture was stirred for 20 min and then extracted with ethyl acetate. The organics were extracted with 0.8 M hydrochloric acid, and the aqueous extract was basified to pH~12 by adding sodium hydroxide. The mixture was extracted with ethyl acetate, dried over sodium sulfate, filtered, and concentrated under reduced pressure. The residue was crystallized from hot acetonitrile to provide (S)-1-(4-((dimethylamino)methyl)phenyl)-3a-hydroxy-6-methyl-3,3a-dihydro-1H-pyrrolo[2,3-b]quinolin-4(2H)-one (26 mg, 12%) as a yellow solid: mp=194-195° C.; $^1$H NMR (500 MHz, DMSO-$d_6$) δ 8.01 (d, J=8.7 Hz, 1H), 7.52 (d, J=1.5 Hz, 1H), 7.37 (d, J=8.2, 1.7 Hz, 1H), 7.32 (d, J=8.6 Hz, 1H), 7.10 (d, J=8.1 Hz, 1H), 6.80 (s, 1H), 4.08-4.02 (m, 1H), 3.97-3.93 (m, 1H), 3.37 (s, 2H), 2.30 (s, 3H), 2.27-2.23 (m, 2H), 2.14 (s, 6H); ESI MS m/z 350 $[C_{21}H_{23}N_3O_2+H]^+$; HPLC (Method C) 96.4% (AUC), $t_R$=9.73 min; Chiral HPLC (Chiralpak AD, Method A) 94.5% (AUC), $t_R$=15.86 min.

Scheme 6: BPN-0028736

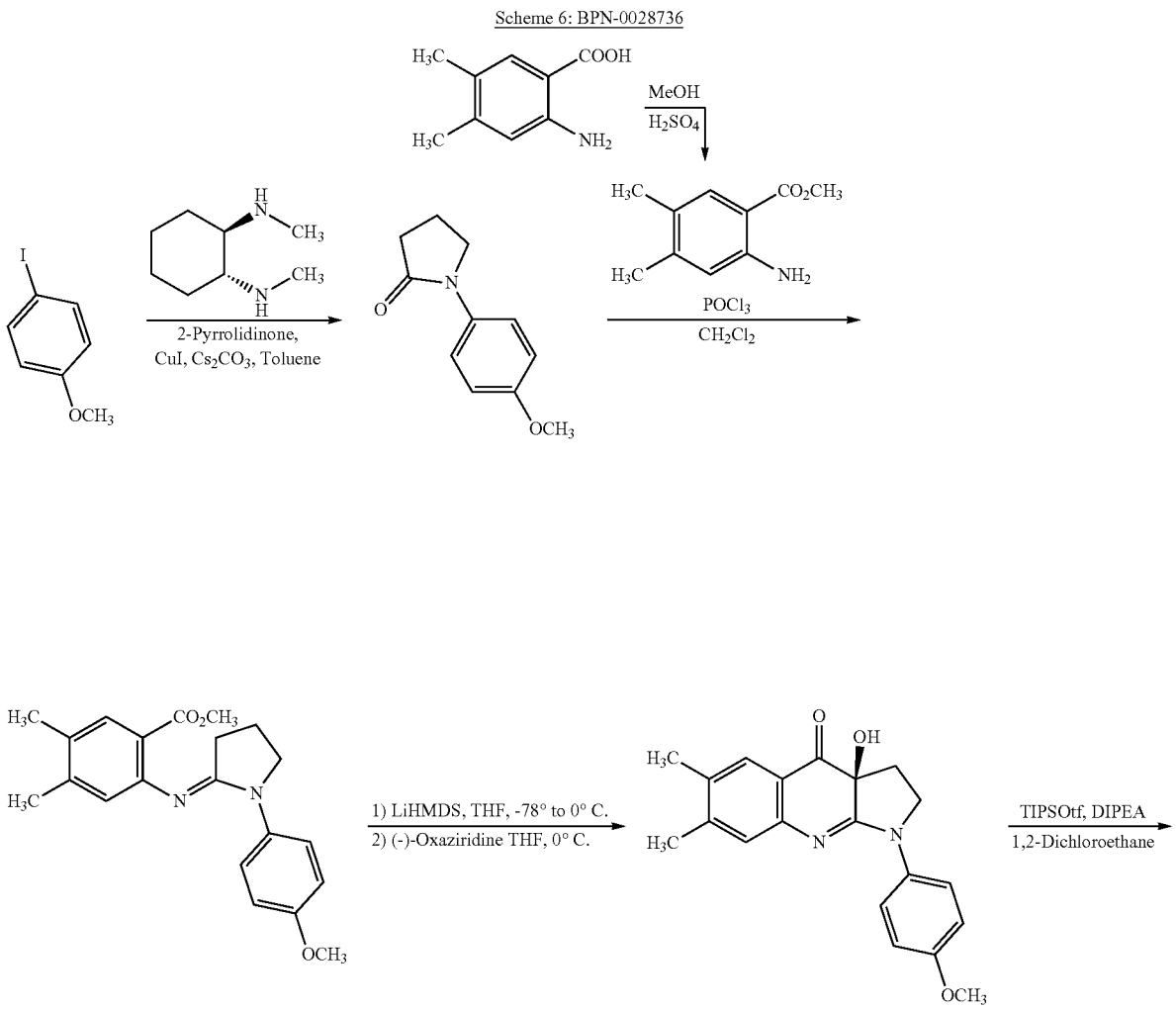

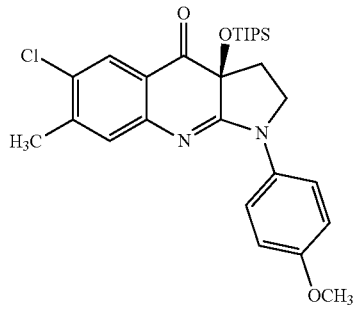
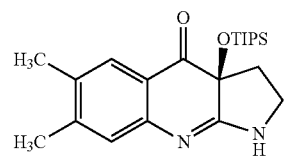
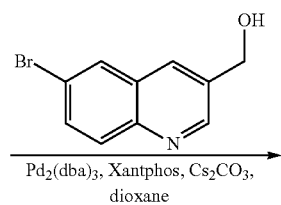

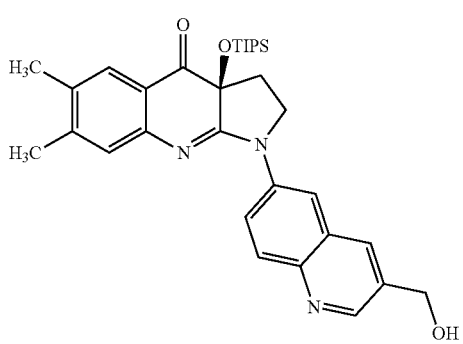
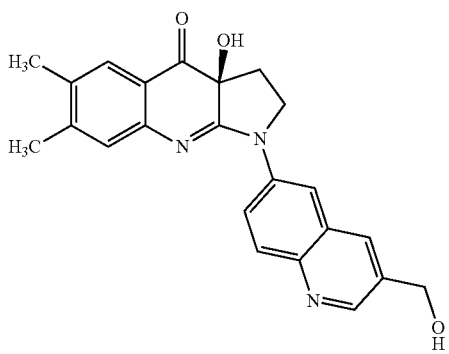

BPN-0028736

Preparation of 1-(4-Methoxyphenyl)pyrrolidin-2-one

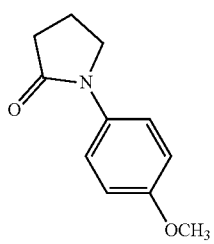 [SMILES: COc1ccc(N2CCCC2=O)cc1]

A solution of 1-iodo-4-methoxybenzene (8.00 g, 33.3 mmol) in toluene (50 mL) was treated with 2-pyrrolidinone (3.8 mL, 4.3 g, 50 mmol), copper iodide (638 mg, 3.35 mmol), cesium carbonate (26.1 g, 80.0 mmol) and (1R, 2R)—$N^1,N^2$-dimethylcyclohexane-1,2-diamine (1.1 mL, 0.99 g, 7.0 mmol) and heated at 110° C. under a nitrogen atmosphere for 22 h. After this time, the reaction mixture was allowed to cool to ambient temperature, filtered through celite, and the filtrate was concentrated under reduced pressure. The crude residue was purified by column chromatography (silica gel, 12-100% ethyl acetate/heptane) to provide 1-(4-methoxyphenyl)pyrrolidin-2-one (6.07 g, 95%) as a white solid: $^1$H NMR (300 MHz, DMSO-$d_6$) δ 7.54 (d, J=9.3 Hz, 2H), 6.93 (d, J=9.0 Hz, 2H), 3.78 (t, J=7.2 Hz, 2H), 3.74 (s, 3H), 2.45 (t, J=8.1 Hz, 2H), 2.09-1.99 (m, 2H); ESI MS m/z 192 $[C_{11}H_{13}NO_2+H]^+$.

Preparation of Methyl 2-Amino-4,5-dimethylbenzoate

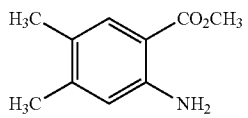

A solution of 2-amino-4,5-dimethylbenzoic acid (10.00 g, 60.54 mmol) in methanol (180 mL) was treated with concentrated sulfuric acid (18 mL) and heated at 60° C. under a nitrogen atmosphere for 64.5 h. After this time, the reaction mixture was concentrated under reduced pressure to remove the volatiles. The resulting residue was carefully treated with saturated aqueous sodium bicarbonate (800 mL) and extracted with ethyl acetate (2×300 mL). The combined organics were dried over sodium sulfate, filtered, and concentrated under reduced pressure to provide methyl 2-amino-4,5-dimethylbenzoate (10.14 g, 94%) as a light brown solid: $^1$H NMR (300 MHz, DMSO-$d_6$) δ 7.44 (s, 1H), 6.56 (s, 1H), 6.38 (s, 2H), 3.75 (s, 3H), 2.12 (s, 3H), 2.07 (s, 3H); ESI MS m/z 180 $[C_{10}H_{13}NO_2+H]^+$.

Preparation of Methyl 2-((1-(4-Methoxyphenyl)pyrrolidin-2-ylidene)amino)-4,5-dimethylbenzoate

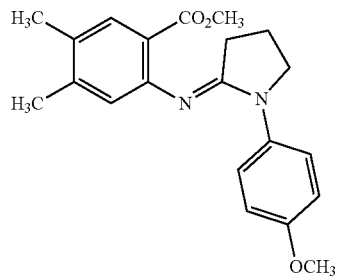 [SMILES: COC(=O)c1cc(C)c(C)cc1/N=C1\CCCN1c1ccc(OC)cc1]

A solution of 1-(4-methoxyphenyl)pyrrolidin-2-one (16.34 g, 85.45 mmol) in 1,2-dichloroethane (100 mL) was treated with phosphorous oxychloride (12 mL, 20 g, 130 mmol) and stirred under a nitrogen atmosphere at ambient temperature for 5.25 h. The mixture was treated with a solution of methyl 2-amino-4,5-dimethylbenzoate (15.36 g, 85.70 mmol) in 1,2-dichloroethane (100 mL) and refluxed at 80° C. for 67 h. After this time, the reaction mixture was allowed to cool to ambient temperature and was treated with sodium bicarbonate (200 mL). The organic and aqueous layers were separated, and the aqueous layer was washed with ethyl acetate. The combined organics were dried over sodium sulfate, filtered, and concentrated under reduced pressure. The residue was dissolved in ethyl acetate (200 mL) and extracted with 0.3 M hydrochloric acid. The combined acid layers were adjusted to pH~11 with 2.0 M aqueous sodium hydroxide and extracted with and ethyl acetate. The combined organics were dried over sodium sulfate, filtered, and concentrated under reduced pressure to provide methyl 2-((1-(4-methoxyphenyl)pyrrolidin-2-ylidene)amino)-4,5-dimethylbenzoate (25.93 g, 86%) as a brown oil: $^1$H NMR (300 MHz, DMSO-$d_6$) δ 7.75-7.70 (m, 2H), 7.51 (s, 1H), 6.94-6.88 (m, 2H), 6.58 (s, 1H), 3.79 (apparent t, J=6.9 Hz, 2H), 3.73-3.70 (m, 6H), 2.34 (apparent t, J=7.8 Hz, 2H), 2.19-2.18 (m, 6H), 1.97-1.90 (m, 2H); ESI MS m/z 353 $[C_{21}H_{24}N_2O_3+H]^+$.

Preparation of (S)-3a-Hydroxy-1-(4-methoxyphenyl)-6,7-dimethyl-1,2,3,3a-tetrahydro-4H-pyrrolo[2,3-b]quinolin-4-one

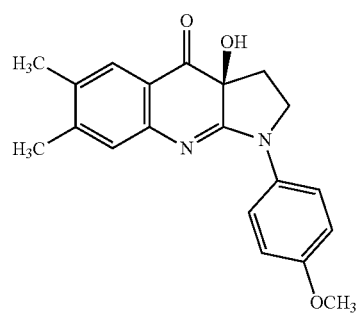 [SMILES: COc1ccc(N2CC[C@@]3(O)C(=O)c4cc(C)c(C)cc4N=C23)cc1]

A solution of methyl 2-((1-(4-methoxyphenyl)pyrrolidin-2-ylidene)amino)-4,5-dimethylbenzoate (1.87 g, 5.31 mmol) in tetrahydrofuran (10 mL) was cooled in a dry ice/acetone bath under a nitrogen atmosphere and treated dropwise with a 1.0 M solution of lithium bis(trimethylsilyl)amide in tetrahydrofuran (16 mL, 16 mmol). The mixture was stirred for 1 h, during which time the bath temperature increased to ~0° C. After 1 h, the mixture was treated with a solution of (−)-(8,8-dichlorocamphorylsulfonyl)oxaziridine (3.17 mg, 10.6 mmol) in tetrahydrofuran (10 mL) and stirred for 1 h. After this time, the mixture was treated with saturated aqueous ammonium iodide (6 mL) followed by saturated aqueous sodium thiosulfate (12 ml) and brine (40 mL). The organic and aqueous layers were separated, and the aqueous layer was washed with ethyl acetate. The combined organics were dried over sodium sulfate, filtered, and concentrated under reduced pressure. The residue was dissolved in ethyl acetate (25 mL) and extracted with 0.3 M hydrochloric acid (4×40 mL). The combined acid layers were adjusted to pH~8 with 2.0 M aqueous sodium hydroxide and extracted with ethyl acetate (3×100 mL). The organics were dried over sodium sulfate, filtered, and concentrated under reduced pressure. The crude product was purified by recrystallization from hot ethanol to provide (S)-3a-hydroxy-1-(4-methoxyphenyl)-6,7-dimethyl-1,2,3,3a-tetrahydro-4H-pyrrolo[2,3-b]quinolin-4-one (422 mg, 24%) as a yellow solid: mp=199-200° C.; $^1$H NMR (500 MHz, DMSO-$d_6$) δ 7.98-7.95 (m, 2H), 7.46 (s, 1H), 7.00-6.98 (m, 3H), 6.72 (s, 1H), 4.06-4.01 (m, 1H), 3.91-3.88 (m, 1H), 3.77 (s, 3H), 2.25 (s, 3H), 2.23-2.21 (m, 5H); ESI MS m/z 337 $[C_{20}H_{20}N_2O_3+H]^+$; HPLC (Method B) >99% (AUC), $t_R$=8.71 min; Chiral HPLC (Chiralpak AD, Method A) >99% (AUC), $t_R$=18.75 min.

Preparation of (S)-1-(4-Methoxyphenyl)-6,7-dimethyl-3a-((triisopropylsilyl)oxy)-1,2,3,3a-tetrahydro-4H-pyrrolo[2,3-b]quinolin-4-one

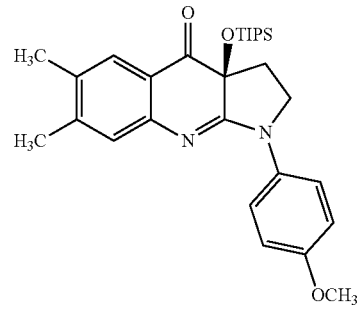

A solution of (S)-3a-hydroxy-1-(4-methoxyphenyl)-6,7-dimethyl-1,2,3,3a-tetrahydro-4H-pyrrolo[2,3-b]quinolin-4-one (725 mg, 2.16 mmol) in 1,2-dichloroethane (25 mL) was treated with N,N-diisopropylethylamine (1.5 mL, 1.1 g, 8.6 mmol) and triisopropylsilyl trifluoromethanesulfonate (1.8 mL, 2.0 g, 6.7 mmol) and stirred under a nitrogen atmosphere at 80° C. for 21 h. After this time, the reaction mixture was allowed to cool to ambient temperature. The mixture was treated with cold deionized water (25 mL), followed by saturated aqueous ammonium chloride (25 mL) and the organic and aqueous layers were separated. The aqueous layer was washed with ethyl acetate (2×25 mL). The organics were dried over sodium sulfate, filtered, and concentrated under reduced pressure. The crude residue was purified by column chromatography (silica gel, 5-40% ethyl acetate/heptane) to provide (S)-1-(4-methoxyphenyl)-6,7-dimethyl-3a-((triisopropylsilyl)oxy)-1,2,3,3a-tetrahydro-4H-pyrrolo[2,3-b]quinolin-4-one (690 mg, 65%) as an yellow oil: $^1$H NMR (300 MHz, DMSO-$d_6$) δ 7.96 (d, J=9.0 Hz, 2H), 7.46 (s, 1H), 7.02-6.99 (m, 3H), 4.02-3.96 (m, 2H), 3.77 (s, 3H), 2.33-2.26 (m, 5H), 2.20 (s, 3H), 0.83-0.81 (m, 21H); ESI MS m/z 493 $[C_{29}H_{40}N_2O_3Si+H]^+$.

Preparation of (S)-6,7-Dimethyl-3a-((triisopropylsilyl)oxy)-1,2,3,3a-tetrahydro-4H-pyrrolo[2,3-b]quinolin-4-one

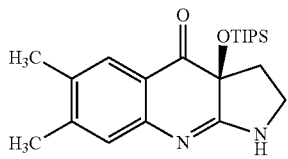

A solution of (S)-1-(4-methoxyphenyl)-6,7-dimethyl-3a-((triisopropylsilyl)oxy)-1,2,3,3a-tetrahydro-4H-pyrrolo[2,3-b]quinolin-4-one (1.24 g, 2.52 mmol) in acetonitrile (20 mL) was cooled in a wet ice/water bath and treated dropwise with a solution of ammonium cerium(IV) nitrate (5.52 g, 10.1 mmol) in deionized water (10 mL) and stirred under a nitrogen atmosphere at ~0° C. for 30 min. After this time, the mixture was treated with aqueous sodium thiosulfate (15 mL) and saturated aqueous sodium bicarbonate (15 mL). The mixture was filtered through celite and the solids were washed with ethyl acetate. The filtrate was extracted with ethyl acetate (2×100 mL). The combined organics were washed with saturated sodium bicarbonate, water, and brine. The organics were dried over sodium sulfate, filtered, and concentrated under reduced pressure. The crude residue was purified by column chromatography (silica gel, 5-100% ethyl acetate/heptane, 0-20% methanol/ethyl acetate) to provide (S)-6,7-dimethyl-3a-((triisopropylsilyl)oxy)-1,2,3,3a-tetrahydro-4H-pyrrolo[2,3-b]quinolin-4-one (589 mg, 61%) as a yellow-orange solid: $^1$H NMR (300 MHz, DMSO-$d_6$) δ 7.41 (s, 1H), 6.77 (s, 1H), 3.70-3.61 (m, 2H), 2.21-2.16 (m, 8H), 0.86-0.84 (m, 21H), NH proton not observed; ESI MS m/z 387 $[C_{22}H_{34}N_2O_2Si+H]^+$.

Preparation of (S)-1-(3-(Hydroxymethyl)quinolin-6-yl)-6,7-dimethyl-3a-((triisopropylsilyl)oxy)-1,2,3,3a-tetrahydro-4H-pyrrolo[2,3-b]quinolin-4-one

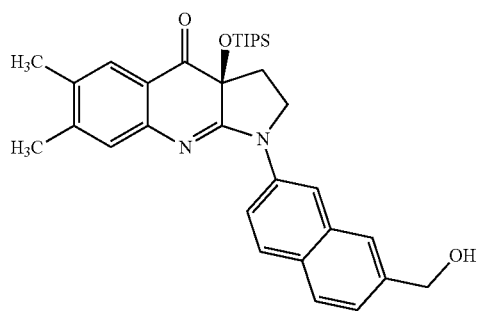

A solution of (S)-6,7-dimethyl-3a-((triisopropylsilyl)oxy)-1,2,3,3a-tetrahydro-4H-pyrrolo[2,3-b]quinolin-4-one (100 mg, 0.260 mmol), (6-bromoquinolin-3-yl)methanol (105 mg, 0.440 mmol), 4,5-bis(diphenylphosphino)-9,9-dimethylxanthene (xantphos) (90 mg, 0.16 mmol), and cesium carbonate (186 mg, 0.570 mmol) in 1,4-dioxane (6 mL) was degassed with argon for 15 min. Tris(dibenzylideneacetone)dipalladium(0) (25 mg, 0.026 mmol) was added, and the resulting mixture was heated at 105° C. for 3 h. After this time, the reaction mixture was filtered through diatomaceous earth using methylene chloride as an eluent. The filtrate was concentrated under reduced pressure, and the residue was purified by column chromatography (silica gel, 0-100% ethyl acetate/hexanes) to provide (S)-1-(3-(hydroxymethyl)quinolin-6-yl)-6,7-dimethyl-3a-((triisopropylsilyl)oxy)-1,2,3,3a-tetrahydro-4H-pyrrolo[2,3-b]quinolin-4-one (43 mg, 30%): ESI MS m/z 544 $[C_{32}H_{41}N_3O_3Si+H]^+$.

Preparation of (S)-3a-Hydroxy-1-(3-(hydroxymethyl)quinolin-6-yl)-6,7-dimethyl-1,2,3,3a-tetrahydro-4H-pyrrolo[2,3-b]quinolin-4-one

BPN-0028736

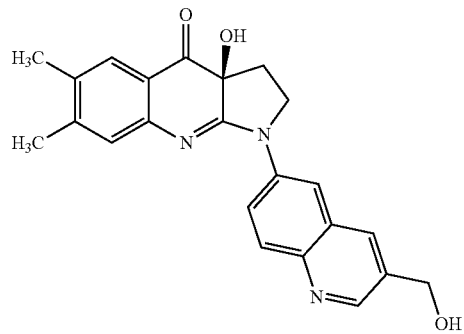

A solution of (S)-1-(3-(hydroxymethyl)quinolin-6-yl)-6,7-dimethyl-3a-((triisopropylsilyl)oxy)-1,2,3,3a-tetrahydro-4H-pyrrolo[2,3-b]quinolin-4-one (43 mg, 0.08 mmol) in tetrahydrofuran (3 mL) under a nitrogen atmosphere was treated with a 1.0 M solution of tetrabutylammonium fluoride in tetrahydrofuran (0.10 mL, 0.10 mmol), and the mixture was stirred for 4 h. After this time, the mixture was concentrated under reduced pressure. The crude residue was purified by column chromatography (silica gel, 0-20% methanol/methylene chloride) to provide (S)-3a-hydroxy-1-(3-(hydroxymethyl)quinolin-6-yl)-6,7-dimethyl-1,2,3,3a-tetrahydro-4H-pyrrolo[2,3-b]quinolin-4-one as a yellow solid: $^1$H NMR (300 MHz, DMSO-$d_6$) δ 8.78 (s, 1H), 8.70 (d, J=9.6 Hz, 1H), 8.49 (s, 1H), 8.23 (s, 1H), 8.05 (d, J=9.0 Hz, 1H), 7.52 (s, 1H), 7.15 (s, 1H), 6.87 (s, 1H), 5.47 (m, 1H), 4.73 (d, J=4.2 Hz, 2H) 4.19-4.13 (m, 2H), 2.31-2.24 (m, 8H); ESI MS m/z 388 $[C_{23}H_{21}N_3O_3+H]^+$; UPLC (Method A) 98.3% (AUC), $t_R$=10.24 min; Chiral HPLC (Chiralpak AD, Method A) 91.1% (AUC), $t_R$=19.45 min.

Scheme 7: BPN-0028821
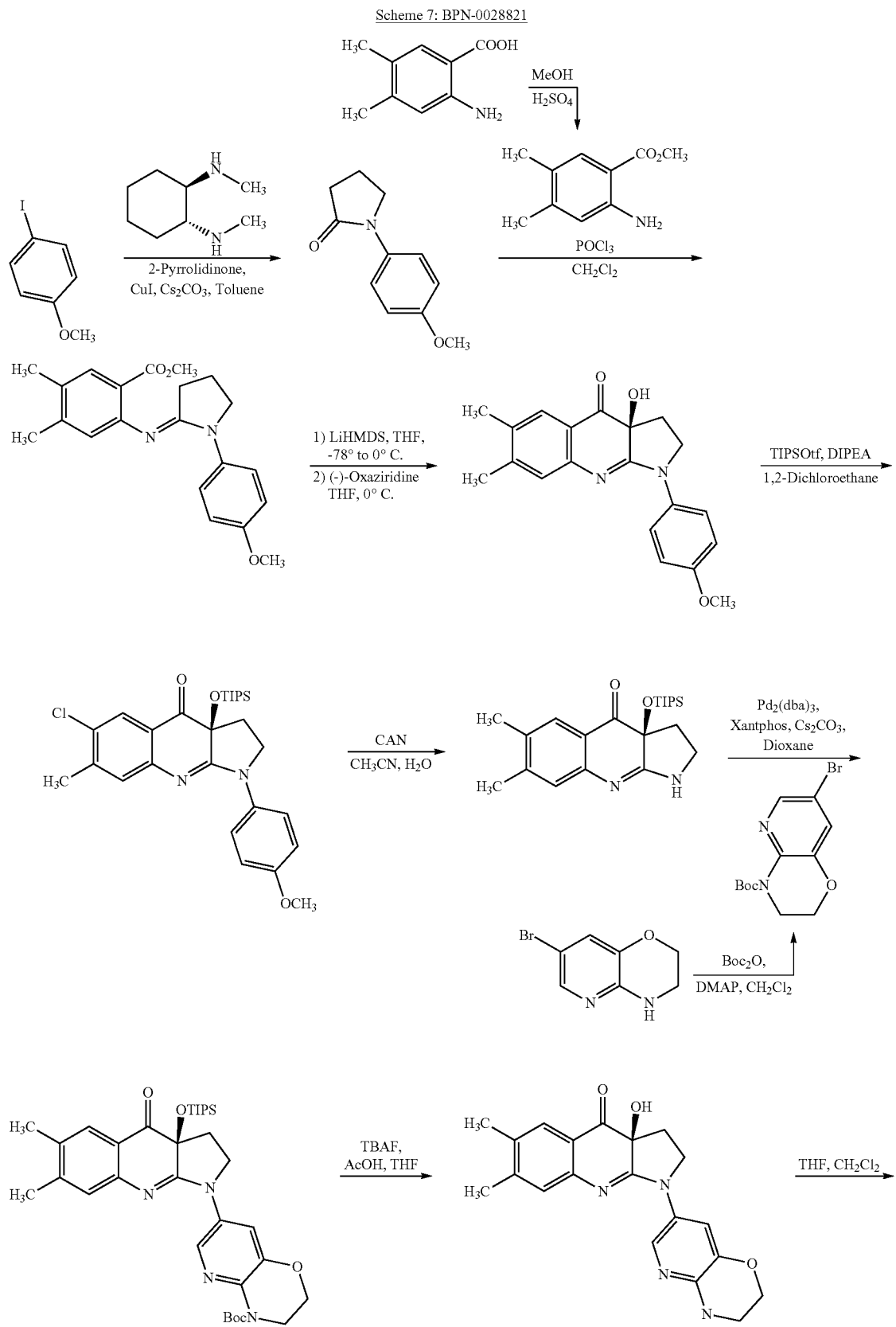

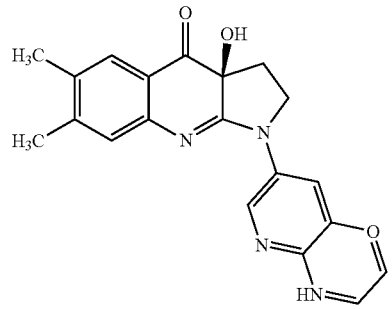

BPN-0028821

Preparation of 1-(4-Methoxyphenyl)pyrrolidin-2-one

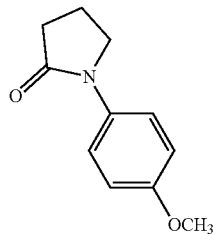

A solution of 1-iodo-4-methoxybenzene (8.00 g, 33.3 mmol) in toluene (50 mL) was treated with 2-pyrrolidinone (3.8 mL, 4.3 g, 50 mmol), copper iodide (638 mg, 3.35 mmol), cesium carbonate (26.1 g, 80.0 mmol) and (1R, 2R)—$N^1,N^2$-dimethylcyclohexane-1,2-diamine (1.1 mL, 0.99 g, 7.0 mmol) and heated at 110° C. under a nitrogen atmosphere for 22 h. After this time, the reaction mixture was allowed to cool to ambient temperature, filtered through celite, and the filtrate was concentrated under reduced pressure. The crude residue was purified by column chromatography (silica gel, 12-100% ethyl acetate/heptane) to provide 1-(4-methoxyphenyl)pyrrolidin-2-one (6.07 g, 95%) as a white solid: $^1$H NMR (300 MHz, DMSO-$d_6$) δ 7.54 (d, J=9.3 Hz, 2H), 6.93 (d, J=9.0 Hz, 2H), 3.78 (t, J=7.2 Hz, 2H), 3.74 (s, 3H), 2.45 (t, J=8.1 Hz, 2H), 2.09-1.99 (m, 2H); ESI MS m/z 192 $[C_{11}H_{13}NO_2+H]^+$.

Preparation of Methyl 2-Amino-4,5-dimethylbenzoate

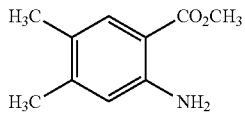

A solution of 2-amino-4,5-dimethylbenzoic acid (10.00 g, 60.54 mmol) in methanol (180 mL) was treated with concentrated sulfuric acid (18 mL) and heated at 60° C. under a nitrogen atmosphere for 64.5 h. After this time, the reaction mixture was concentrated under reduced pressure to remove the volatiles. The resulting residue was carefully treated with saturated aqueous sodium bicarbonate (800 mL) and extracted with ethyl acetate (2×300 mL). The combined organics were dried over sodium sulfate, filtered, and concentrated under reduced pressure to provide methyl 2-amino-4,5-dimethylbenzoate (10.14 g, 94%) as a light brown solid: $^1$H NMR (300 MHz, DMSO-$d_6$) δ 7.44 (s, 1H), 6.56 (s, 1H), 6.38 (s, 2H), 3.75 (s, 3H), 2.12 (s, 3H), 2.07 (s, 3H); ESI MS m/z 180 $[C_{10}H_{13}NO_2+H]^+$.

Preparation of Methyl 2-((1-(4-Methoxyphenyl)pyrrolidin-2-ylidene)amino)-4,5-dimethylbenzoate

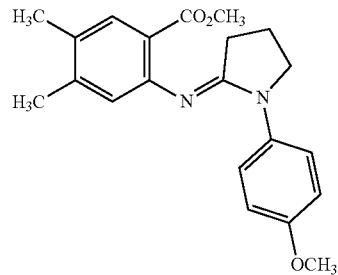 [SMILES: COC(=O)c1cc(C)c(C)cc1/N=C1\CCCN1c1ccc(OC)cc1]

A solution of 1-(4-methoxyphenyl)pyrrolidin-2-one (16.34 g, 85.45 mmol) in 1,2-dichloroethane (100 mL) was treated with phosphorous oxychloride (12. mL, 20. g, 130 mmol) and stirred under a nitrogen atmosphere at ambient temperature for 5.25 h. The mixture was treated with a solution of methyl 2-amino-4,5-dimethylbenzoate (15.36 g, 85.70 mmol) in 1,2-dichloroethane (100 mL) and refluxed at 80° C. for 67 h. After this time, the reaction mixture was allowed to cool to ambient temperature and was treated with saturated aqueous sodium bicarbonate (200 mL). The organic and aqueous layers were separated, and the aqueous layer was washed with ethyl acetate. The combined organics were dried over sodium sulfate, filtered, and concentrated under reduced pressure. The residue was dissolved in ethyl acetate (200 mL) and extracted with 0.3 M hydrochloric acid. The combined acid layers were adjusted to pH~11 with 2.0 M aqueous sodium hydroxide and extracted with ethyl acetate. The combined organics were dried over sodium sulfate, filtered, and concentrated under reduced pressure to provide methyl 2-((1-(4-methoxyphenyl)pyrrolidin-2-ylidene)amino)-4,5-dimethylbenzoate (25.93 g, 86%) as a brown oil: $^1$H NMR (300 MHz, DMSO-$d_6$) δ 7.75-7.70 (m, 2H), 7.51 (s, 1H), 6.94-6.88 (m, 2H), 6.58 (s, 1H), 3.79 (apparent t, J=6.9 Hz, 2H), 3.73-3.70 (m, 6H), 2.34 (apparent t, J=7.8 Hz, 2H), 2.19-2.18 (m, 6H), 1.97-1.90 (m, 2H); ESI MS m/z 353 $[C_{21}H_{24}N_2O_3+H]^+$.

Preparation of (S)-3a-Hydroxy-1-(4-methoxyphenyl)-6,7-dimethyl-1,2,3,3a-tetrahydro-4H-pyrrolo[2,3-b]quinolin-4-one

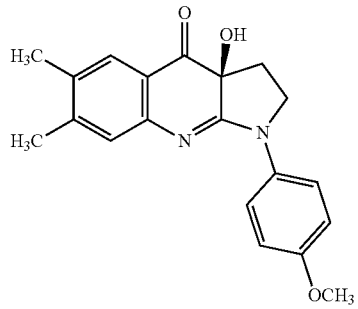 [SMILES: COc1ccc(N2CC[C@@]3(O)C(=O)c4cc(C)c(C)cc4N=C23)cc1]

A solution of methyl 2-((1-(4-methoxyphenyl)pyrrolidin-2-ylidene)amino)-4,5-dimethylbenzoate (1.87 g, 5.31 mmol) in tetrahydrofuran (10 mL) was cooled in a dry ice/acetone bath under a nitrogen atmosphere and treated dropwise with a 1.0 M solution of lithium bis(trimethylsilyl)amide in tetrahydrofuran (16 mL, 16 mmol). The mixture was stirred for 1 h, during which time the bath temperature increased to ~0° C. After 1 h, the mixture was treated with a solution of (−)-(8,8-dichlorocamphorylsulfonyl)oxaziridine (3.17 mg, 10.6 mmol) in tetrahydrofuran (10 mL) and stirred for 1 h. After this time, the mixture was treated with saturated aqueous ammonium iodide (6 mL) followed by saturated aqueous sodium thiosulfate (12 ml) and brine (40 mL). The organic and aqueous layers were separated, and the aqueous layer was washed with ethyl acetate. The combined organics were dried over sodium sulfate, filtered, and concentrated under reduced pressure. The residue was dissolved in ethyl acetate (25 mL) and extracted with 0.3 M hydrochloric acid (4×40 mL). The combined acid layers were adjusted to pH~8 with 2.0 M aqueous sodium hydroxide and extracted with ethyl acetate (3×100 mL). The organics were dried over sodium sulfate, filtered, and concentrated under reduced pressure. The crude product was purified by recrystallization from hot ethanol to provide (S)-3a-hydroxy-1-(4-methoxyphenyl)-6,7-dimethyl-1,2,3,3a-tetrahydro-4H-pyrrolo[2,3-b]quinolin-4-one (422 mg, 24%) as a yellow solid: mp=199-200° C.; $^1$H NMR (500 MHz, DMSO-$d_6$) δ 7.98-7.95 (m, 2H), 7.46 (s, 1H), 7.00-6.98 (m, 3H), 6.72 (s, 1H), 4.06-4.01 (m, 1H), 3.91-3.88 (m, 1H), 3.77 (s, 3H), 2.25 (s, 3H), 2.23-2.21 (m, 5H); ESI MS m/z 337 $[C_{20}H_{20}N_2O_3+H]^+$; HPLC (Method B) >99% (AUC), $t_R$=8.71 min; Chiral HPLC (Chiralpak AD, Method A) >99% (AUC), $t_R$=18.75 min.

Preparation of (S)-1-(4-Methoxyphenyl)-6,7-dimethyl-3a-((triisopropylsilyl)oxy)-1,2,3,3a-tetrahydro-4H-pyrrolo[2,3-b]quinolin-4-one

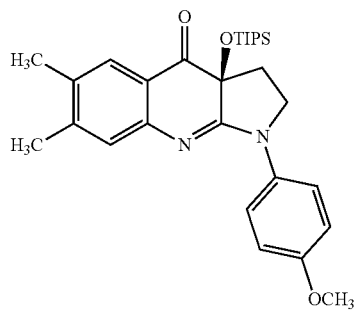

A solution of (S)-3a-hydroxy-1-(4-methoxyphenyl)-6,7-dimethyl-1,2,3,3a-tetrahydro-4H-pyrrolo[2,3-b]quinolin-4-one (725 mg, 2.16 mmol) in 1,2-dichloroethane (25 mL) was treated with N,N-diisopropylethylamine (1.5 mL, 1.1 g, 8.6 mmol) and triisopropylsilyl trifluoromethanesulfonate (1.8 mL, 2.0 g, 6.7 mmol) and stirred under a nitrogen atmosphere at 80° C. for 21 h. After this time, the reaction mixture was allowed to cool to ambient temperature. The mixture was treated with cold deionized water (25 mL), followed by saturated aqueous ammonium chloride (25 mL), and the organic and aqueous layers were separated. The aqueous layer was washed with ethyl acetate (2×25 mL). The organics were dried over sodium sulfate, filtered, and concentrated under reduced pressure. The crude residue was purified by column chromatography (silica gel, 5-40% ethyl acetate/heptane) to provide (S)-1-(4-methoxyphenyl)-6,7-dimethyl-3a-((triisopropylsilyl)oxy)-1,2,3,3a-tetrahydro-4H-pyrrolo[2,3-b]quinolin-4-one (690 mg, 65%) as an yellow oil: $^1$H NMR (300 MHz, DMSO-$d_6$) δ 7.96 (d, J=9.0 Hz, 2H), 7.46 (s, 1H), 7.02-6.99 (m, 3H), 4.02-3.96 (m, 2H), 3.77 (s, 3H), 2.33-2.26 (m, 5H), 2.20 (s, 3H), 0.83-0.81 (m, 21H); ESI MS m/z 493 $[C_{29}H_{40}N_2O_3Si+H]^+$.

Preparation of (S)-6,7-Dimethyl-3a-((triisopropylsilyl)oxy)-1,2,3,3a-tetrahydro-4H-pyrrolo[2,3-b]quinolin-4-one

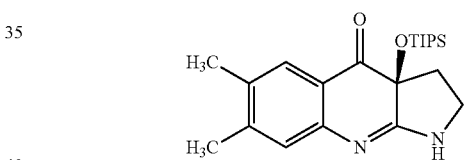

A solution of (S)-1-(4-methoxyphenyl)-6,7-dimethyl-3a-((triisopropylsilyl)oxy)-1,2,3,3a-tetrahydro-4H-pyrrolo[2,3-b]quinolin-4-one (1.24 g, 2.52 mmol) in acetonitrile (20 mL) was cooled in a wet ice/water bath and treated dropwise with a solution of ammonium cerium(IV) nitrate (5.52 g, 10.1 mmol) in deionized water (10 mL) and stirred under a nitrogen atmosphere at −0° C. for 30 min. After this time, the mixture was treated with aqueous sodium thiosulfate (15 mL) and saturated aqueous sodium bicarbonate (15 mL). The mixture was filtered through celite, and the solids were washed with ethyl acetate. The filtrate was extracted with ethyl acetate (2×100 mL). The combined organics were washed with saturated sodium bicarbonate, water, and brine. The organics were dried over sodium sulfate, filtered, and concentrated under reduced pressure. The crude residue was purified by column chromatography (silica gel, 5-100% ethyl acetate/heptane, 0-20% methanol/ethyl acetate) to provide (S)-6,7-dimethyl-3a-((triisopropylsilyl)oxy)-1,2,3,3a-tetrahydro-4H-pyrrolo[2,3-b]quinolin-4-one (589 mg, 61%) as a yellow-orange solid: $^1$H NMR (300 MHz, DMSO-$d_6$) δ 7.41 (s, 1H), 6.77 (s, 1H), 3.70-3.61 (m, 2H), 2.21-2.16 (m, 8H), 0.86-0.84 (m, 21H), NH proton not observed; ESI MS m/z 387 $[C22H34N_2O_2Si+H]^+$.

Preparation of tert-Butyl 7-Bromo-2,3-dihydro-4H-pyrido[3,2-b][1,4]oxazine-4-carboxylate

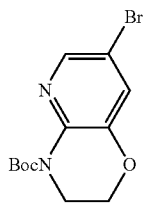

A solution of 7-bromo-3,4-dihydro-2H-pyrido[3,2-b][1,4]oxazine (305 mg, 1.42 mmol) and 4-dimethylaminopyridine (19 mg, 0.16 mmol) in dichloromethane (20 mL) was cooled in a wet ice/water bath and treated dropwise with a solution of 2M di-tert-butyl dicarbonate in dichloromethane (0.78 mL, 1.6 mmol). After 10 min, the reaction was warmed to room temperature and stirred for 24 h. After this time, water (20 mL) was added, and the organic and aqueous layers were separated. The organics were washed with brine, dried over sodium sulfate, filtered, and concentrated under reduced pressure to provide tert-butyl 7-bromo-2,3-dihydro-4H-pyrido[3,2-b][1,4]oxazine-4-carboxylate (353 mg, 79%) as a pink solid: $^1$H NMR (500 MHz, DMSO-$d_6$) δ 8.03 (d, J=2.2 Hz, 1H), 7.57 (d, J=2.2 Hz, 1H), 4.26-4.24 (m, 2H), 3.84-3.82 (m, 2H), 1.46 (s, 9H).

Preparation of tert-Butyl (S)-7-(6,7-Dimethyl-4-oxo-3a-((triisopropylsilyl)oxy)-2,3,3a,4-tetrahydro-1H-pyrrolo[2,3-b]quinolin-1-yl)-2,3-dihydro-4H-pyrido[3,2-b][1,4]oxazine-4-carboxylate

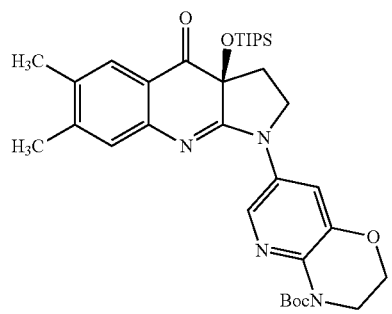

A solution of (S)-6,7-dimethyl-3a-((triisopropylsilyl)oxy)-1,2,3,3a-tetrahydro-4H-pyrrolo[2,3-b]quinolin-4-one (202 mg, 0.522 mmol), tert-butyl 7-bromo-2,3-dihydro-4H-pyrido[3,2-b][1,4]oxazine-4-carboxylate (250. mg, 0.793 mmol), and cesium carbonate (172 mg, 0.578 mmol) in 1,4-dioxane (10 mL) was degassed with argon for 10 min. Tris(dibenzylideneacetone)dipalladium(0) (61 mg, 0.067 mmol) and 4,5-bis(diphenylphosphino)-9,9-dimethylxanthene (xantphos) (188 mg, 0.325 mmol) were added and the resulting mixture was heated at 90° C. for 23.5 h in a sealed vial. After this time, the reaction mixture was filtered through diatomaceous earth using ethyl acetate as an eluent. The filtrate was concentrated under reduced pressure, and the residue was purified by column chromatography (silica gel, 12-100% ethyl acetate/hexanes) to provide tert-butyl (S)-7-(6,7-dimethyl-4-oxo-3a-((triisopropylsilyl)oxy)-2,3,3a,4-tetrahydro-1H-pyrrolo[2,3-b]quinolin-1-yl)-2,3-dihydro-4H-pyrido[3,2-b][1,4]oxazine-4-carboxylate (133 mg, 41%) as an orange solid: ESI MS m/z 621 $[C_{34}H_{48}N_4O_5Si+H]^+$.

Preparation of tert-Butyl (S)-7-(3a-Hydroxy-6,7-dimethyl-4-oxo-2,3,3a,4-tetrahydro-1H-pyrrolo[2,3-b]quinolin-1-yl)-2,3-dihydro-4H-pyrido[3,2-b][1,4]oxazine-4-carboxylate

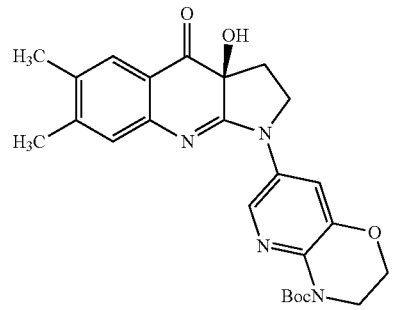 [SMILES: Cc1cc2c(cc1C)C(=O)[C@]1(O)CCN(c3cnc4c(c3)OCCN4C(=O)OC(C)(C)C)C1=N2]

A solution of tert-butyl (S)-7-(6,7-dimethyl-4-oxo-3a-((triisopropylsilyl)oxy)-2,3,3a,4-tetrahydro-1H-pyrrolo[2,3-b]quinolin-1-yl)-2,3-dihydro-4H-pyrido[3,2-b][1,4]oxazine-4-carboxylate (133 mg, 0.214 mmol) in tetrahydrofuran (5 mL) under a nitrogen atmosphere was treated with a 1.0 M solution of tetrabutylammonium fluoride in tetrahydrofuran (0.64 mL, 0.64 mmol) and acetic acid (0.07 mL, 0.07 g, 1 mmol), and the mixture was stirred. After 17 h, additional 1.0 M solution of tetrabutylammonium fluoride in tetrahydrofuran (0.21 mL, 0.21 mmol) was added, and the reaction continued to stir. After 12 h, additional 1.0 M solution of tetrabutylammonium fluoride in tetrahydrofuran (0.21 mL, 0.21 mmol) was added, and the reaction continued to stir. After 4 h, additional 1.0 M solution of tetrabutylammonium fluoride in tetrahydrofuran (0.21 mL, 0.21 mmol) was added, and the reaction continued to stir for 3 h. After this time, the mixture was concentrated under reduced pressure. The crude residue was purified by column chromatography (silica gel, 2-20% methanol/methylene chloride). The semi-crude product was dissolved in ethyl acetate (20 mL) and extracted with 0.3 M hydrochloric acid. The combined acid layers were adjusted to pH~8 with 2.0 M aqueous sodium hydroxide and extracted with ethyl acetate. The organics were dried over sodium sulfate, filtered, and concentrated under reduced pressure to provide a mixture of tert-butyl (S)-7-(3a-hydroxy-6,7-dimethyl-4-oxo-2,3,3a,4-tetrahydro-1H-pyrrolo[2,3-b]quinolin-1-yl)-2,3-dihydro-4H-pyrido[3,2-b][1,4]oxazine-4-carboxylate and (S)-1-(3,4-dihydro-2H-pyrido[3,2-b][1,4]oxazin-7-yl)-3a-hydroxy-6,7-dimethyl-1,2,3,3a-tetrahydro-4H-pyrrolo[2,3-b]quinolin-4-one (59 mg): ESI MS m/z 465 $[C_{25}H_{28}N_4O_5+H]^+$; ESI MS m/z 365 $[C_{20}H_{20}N_4O_3+H]^+$.

Preparation of (S)-1-(3,4-Dihydro-2H-pyrido[3,2-b][1,4]oxazin-7-yl)-3a-hydroxy-6,7-dimethyl-1,2,3,3a-tetrahydro-4H-pyrrolo[2,3-b]quinolin-4-one

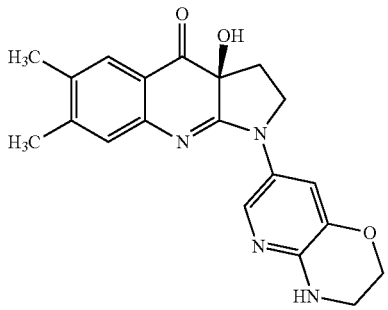

BPN-0028821

A mixture of tert-butyl (S)-7-(3a-hydroxy-6,7-dimethyl-4-oxo-2,3,3a,4-tetrahydro-1H-pyrrolo[2,3-b]quinolin-1-yl)-2,3-dihydro-4H-pyrido[3,2-b][1,4]oxazine-4-carboxylate and (S)-1-(3,4-dihydro-2H-pyrido[3,2-b][1,4]oxazin-7-yl)-3a-hydroxy-6,7-dimethyl-1,2,3,3a-tetrahydro-4H-pyrrolo[2,3-b]quinolin-4-one (59 mg) was dissolved in dichloromethane (5 mL) and treated with trifluoroacetic acid (0.01 mL, 0.01 g, 0.1 mmol). The reaction mixture was stirred under a nitrogen atmosphere at room temperature for 3.5 h. After this time, the mixture was diluted with dichloromethane (5 mL) and treated with sodium bicarbonate (10 mL). The organic and aqueous layers were separated, and the organics were dried over sodium sulfate, filtered, and concentrated under reduced pressure. The residue was crystallized from hot acetonitrile to provide (S)-1-(3,4-dihydro-2H-pyrido[3,2-b][1,4]oxazin-7-yl)-3a-hydroxy-6,7-dimethyl-1,2,3,3a-tetrahydro-4H-pyrrolo[2,3-b]quinolin-4-one (34 mg, 74%) as an orange solid: mp=231-232° C.; $^1$H NMR (500 MHz, DMSO-$d_6$) δ 8.03 (d, J=2.4 Hz, 1H), 7.93 (d, J=2.2 Hz, 1H), 7.45 (s, 1H), 6.96 (s, 1H), 6.70 (s, 1H), 6.67 (s, 1H), 4.15-4.13 (m, 2H), 4.00-3.95 (m, 1H), 3.87-3.83 (m, 1H), 3.42-3.39 (m, 2H), 2.25 (s, 3H), 2.20-2.19 (m, 5H); ESI MS m/z 365 [$C_{20}H_{20}N_4O_3$+H]$^+$; UPLC (Method A) 99.0% (AUC), $t_R$=2.66 min; Chiral HPLC (Chiralpak AD, Method A) 84.1% (AUC), $t_R$=20.76 min.

Preparation of (S)-1-(Benzo[b]thiophen-6-yl)-6-chloro-3a-hydroxy-1,2,3,3a-tetrahydro-4H-pyrrolo[2,3-b]quinolin-4-one

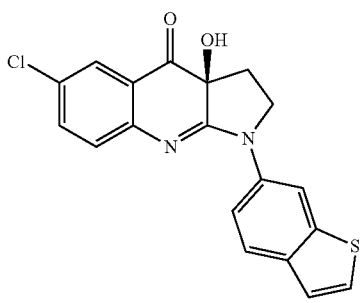

BPN-0026545

(S)-1-(Benzo[b]thiophen-6-yl)-6-chloro-3a-hydroxy-1,2,3,3a-tetrahydro-4H-pyrrolo[2,3-b]quinolin-4-one was prepared as an orange-red solid according to Synthetic Scheme 3: mp=221-229° C.; $^1$H NMR (300 MHz, DMSO-$d_6$) δ 8.72 (d, J=1.7, 1H), 8.15 (dd, J=8.8, 2.0 Hz, 1H), 7.92 (d, J=8.2 Hz, 1H), 7.73 (d, J=5.4 Hz, 1H), 7.65 (d, J=2.6 Hz, 1H), 7.58 (dd, J=8.6, 2.6 Hz, 1H), 7.45 (d, J=5.4 Hz, 1H), 7.28 (d, J=8.5 Hz, 1H), 7.01 (s, 1H), 4.22-4.04 (m, 2H), 2.36-2.27 (m, 2H); ESI MS m/z 369 [$C_{19}H_{13}ClN_2O_2S$+H]$^+$; HPLC (Method C) >99% (AUC), $t_R$=13.20 min; Chiral HPLC (Chiralpak AD, Method A) 92.1% (AUC), $t_R$=17.57 min.

Preparation of (S)-1-(Benzo[b]thiophen-5-yl)-6-chloro-3a-hydroxy-1,2,3,3a-tetrahydro-4H-pyrrolo[2,3-b]quinolin-4-one

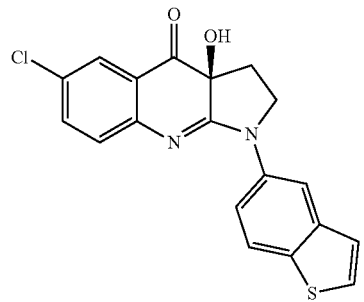

BPN-0026546

(S)-1-(Benzo[b]thiophen-5-yl)-6-chloro-3a-hydroxy-1,2,3,3a-tetrahydro-4H-pyrrolo[2,3-b]quinolin-4-one was prepared as a yellow solid according to Synthetic Scheme 3: mp=204-208° C.; $^1$H NMR (300 MHz, DMSO-$d_6$) δ 8.16 (d, J=2.1 Hz, 1H), 8.15 (d, J=2.0 Hz, 1H), 8.05 (d, J=8.9 Hz, 1H), 7.82 (d, J=5.4, 1H), 7.65 (dd, J=2.5, 2.6 Hz, 1H), 7.58 (d, J=3.7 Hz, 1H), 7.50 (d, J=5.4 Hz, 1H), 7.25 (d, J=8.6 Hz, 1H), 7.01 (s, 1H), 4.20-4.05 (m, 2H), 2.50-2.27 (m, 2H); ESI MS m/z 369 [$C_{19}H_{13}ClN_2O_2S$+H]$^+$; HPLC (Method C) >99% (AUC), $t_R$=13.15 min; Chiral HPLC (Chiralpak AD, Method A) 85.1% (AUC), $t_R$=18.25 min.

Preparation of (S)-6-Chloro-3a-hydroxy-1-(p-tolyl)-1,2,3,3a-tetrahydro-4H-pyrrolo[2,3-b]quinolin-4-one

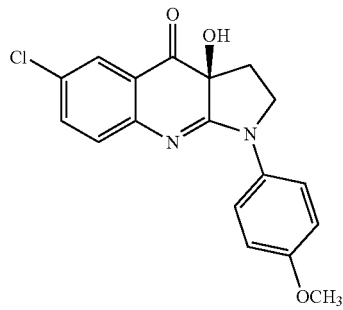

BPN-0026609

(S)-6-Chloro-3a-hydroxy-1-(p-tolyl)-1,2,3,3a-tetrahydro-4H-pyrrolo[2,3-b]quinolin-4-one was prepared as an orange solid according to Synthetic Scheme 2: mp=217-220° C.; $^1$H NMR (300 MHz, DMSO-$d_6$) δ 7.93 (d, J=8.5 Hz, 2H), 7.63

(d, J=2.5 Hz, 1H), 7.55 (dd, J=3.7 Hz, 1H), 7.22 (m, 3H), 6.96 (s, 1H), 4.02 (m, 2H), 2.31 (s, 3H), 2.27 (m, 2H); ESI MS m/z 327 [C$_{18}$H$_{15}$ClN$_2$O$_2$+H]$^+$; HPLC (Method C) 97.0% (AUC), t$_R$=12.45 min; Chiral HPLC (Chiralpak AD, Method A) 98.5% (AUC), t$_R$=14.31 min.

Preparation of (S)-6-Chloro-1-(4-chlorophenyl)-3a-hydroxy-3,3a-dihydro-1H-pyrrolo[2,3-b]quinolin-4(2H)-one

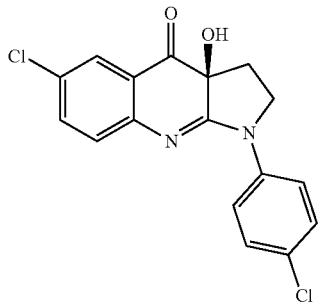

BPN-0026640

(S)-6-Chloro-1-(4-chlorophenyl)-3a-hydroxy-3,3a-dihydro-1H-pyrrolo[2,3-b]quinolin-4(2H)-one was prepared as a bright yellow solid according to Synthetic Scheme 2: mp=212-216° C.; $^1$H NMR (300 MHz, DMSO-d$_6$) δ 8.15-8.10 (m, 2H), 7.65 (d, J=2.6 Hz, 1H), 7.59 (dd, J=8.5, 2.6 Hz, 1H), 7.52-7.47 (m, 2H), 7.24 (d, J=8.5 Hz, 1H), 7.00 (s, 1H), 4.13-3.94 (m, 2H), 2.37-2.22 (m, 2H); ESI MS m/z 347 [C$_{17}$H$_{12}$Cl$_2$N$_2$O$_2$+H]$^+$; HPLC (Method C) 98.2% (AUC), t$_R$=13.45 min; Chiral HPLC (Chiralpak AD, Method A) 89.6% (AUC), t$_R$=19.74 min.

Preparation of (S)-6-Chloro-3a-hydroxy-7-methyl-1-phenyl-3,3a-dihydro-1H-pyrrolo[2,3-b]quinolin-4(2H)-one

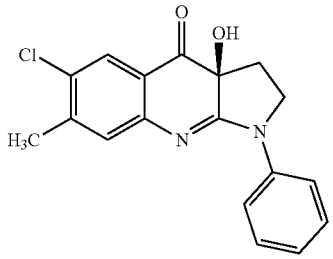

BPN-0026659

(S)-6-Chloro-3a-hydroxy-7-methyl-1-phenyl-3,3a-dihydro-1H-pyrrolo[2,3-b]quinolin-4(2H)-one was prepared as a light yellow solid according to Synthetic Scheme 2: mp=219-223° C.; $^1$H NMR (300 MHz, DMSO-d$_6$) δ 8.07 (d, J=8.0 Hz, 2H), 7.63 (s, 1H), 7.44 (apparent t, J=7.9 Hz, 2H), 7.24-7.15 (m, 2H), 6.94 (s, 1H), 4.14-3.94 (m, 2H), 2.37-2.21 (m, 5H); ESI MS m/z 327 [C$_{18}$H$_{15}$ClN$_2$O$_2$+H]$^+$; HPLC (Method C) 99.0% (AUC), t$_R$=12.69 min; Chiral HPLC (Chiralpak AD, Method A) 93.2% (AUC), t$_R$=18.38 min.

Preparation of (S)-3a-Hydroxy-1-(3-methoxyphenyl)-6-methyl-3,3a-dihydro-1H-pyrrolo[2,3-b]quinolin-4(2H)-one

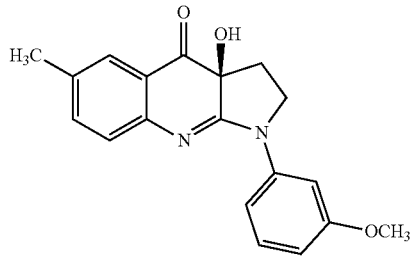

BPN-0025044

(S)-3a-Hydroxy-1-(3-methoxyphenyl)-6-methyl-3,3a-dihydro-1H-pyrrolo[2,3-b]quinolin-4(2H)-one was prepared as a yellow solid according to Synthetic Scheme 3: mp=196-197° C.; $^1$H NMR (500 MHz, DMSO-d$_6$) δ 7.99 (apparent t, J=2.1 Hz, 1H), 7.53 (d, J=1.2 Hz, 1H), 7.48-7.46 (m, 1H), 7.38 (dd, J=8.1, 2.0 Hz, 1H), 7.32 (apparent t, J=8.2 Hz, 1H), 7.12 (d, J=8.1 Hz, 1H), 6.81 (s, 1H), 6.73 (dd, J=8.2, 2.2 Hz, 1H), 4.06-4.01 (m, 1H), 3.97-3.94 (m, 1H), 3.80 (s, 3H), 2.30 (s, 3H), 2.26-2.24 (m, 2H); ESI MS m/z 323 [C$_{19}$H$_{18}$N$_2$O$_3$+H]$^+$; HPLC (Method C) >99% (AUC), t$_R$=12.05 min; Chiral HPLC (Chiralpak AD, Method A) 97.0% (AUC), t$_R$=15.07 min.

Preparation of (S)-1-(3-Chlorophenyl)-3a-hydroxy-6-methyl-3,3a-dihydro-1H-pyrrolo[2,3-b]quinolin-4(2H)-one

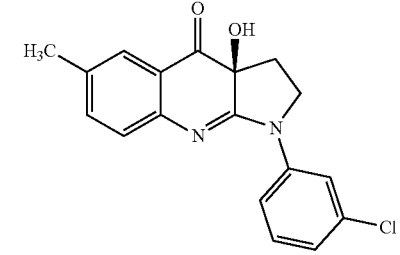

BPN-0025059

(S)-1-(3-Chlorophenyl)-3a-hydroxy-6-methyl-3,3a-dihydro-1H-pyrrolo[2,3-b]quinolin-4(2H)-one was prepared as an orange solid according to Synthetic Scheme 2: mp=199-200° C.; $^1$H NMR (500 MHz, DMSO-d$_6$) δ 8.39 (apparent t, J=2.1 Hz, 1H), 7.93 (ddd, J=8.4, 2.2, 0.7 Hz, 1H), 7.55 (d, J=1.6 Hz, 1H), 7.45 (apparent t, J=8.2 Hz, 1H), 7.41-7.39 (m, 1H), 7.19 (ddd, J=7.9, 1.9, 0.6 Hz, 1H), 7.15 (d, J=8.1 Hz, 1H), 6.86 (s, 1H), 4.07-3.96 (m, 2H), 2.31-2.25 (m, 5H); ESI MS m/z 327 [C$_{18}$H$_{15}$ClN$_2$O$_2$+H]$^+$; HPLC (Method C) >99% (AUC), t$_R$=12.18 min; Chiral HPLC (Chiralpak AD, Method A) >99% (AUC), t$_R$=14.59 min.

Preparation of (S)-3a-Hydroxy-6-methyl-1-(m-tolyl)-3,3a-dihydro-1H-pyrrolo[2,3-b]quinolin-4(2H)-one

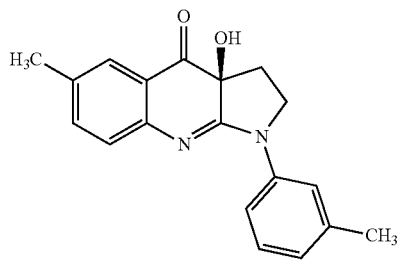

BPN-0025100

(S)-3a-Hydroxy-6-methyl-1-(m-tolyl)-3,3a-dihydro-1H-pyrrolo[2,3-b]quinolin-4(2H)-one was prepared as an orange solid according to Synthetic Scheme 3: mp=192-193° C.; $^1$H NMR (500 MHz, DMSO-d$_6$) δ 7.94 (dd, J=8.2, 2.0 Hz, 1H), 7.84 (s, 1H), 7.52 (d, J=2.0 Hz, 1H), 7.38-7.36 (m, 1H), 7.30 (apparent t, J=7.9 Hz, 1H), 7.11 (d, J=8.1 Hz, 1H), 6.96 (d, J=7.5 Hz, 1H), 6.79 (s, 1H), 4.07-4.02 (m, 1H), 3.96-3.93 (m, 1H), 2.36 (s, 3H), 2.30 (s, 3H), 2.26-2.23 (m, 2H); ESI MS m/z 307 [C$_{19}$H$_{18}$N$_2$O$_2$+H]$^+$; HPLC (Method C) >99% (AUC), t$_R$=14.48 min; Chiral HPLC (Chiralpak AD, Method A) >99% (AUC), t$_R$=12.51 min.

Preparation of (S)-1-(3-Bromophenyl)-3a-hydroxy-6-methyl-3,3a-dihydro-1H-pyrrolo[2,3-b]quinolin-4(2H)-one

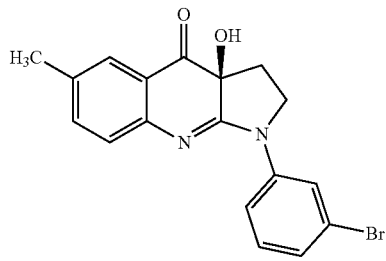

BPN-0025240

(S)-1-(3-Bromophenyl)-3a-hydroxy-6-methyl-3,3a-dihydro-1H-pyrrolo[2,3-b]quinolin-4(2H)-one was prepared as a yellow solid according to Synthetic Scheme 3: mp=195-196° C.; $^1$H NMR (500 MHz, DMSO-d$_6$) δ 8.53 (apparent t, J=2.0 Hz, 1H), 7.96 (ddd, J=8.3, 2.2, 0.9 Hz, 1H), 7.55 (d, J=1.8 Hz, 1H), 7.41-7.37 (m, 2H), 7.32 (ddd, J=7.9, 1.8, 0.9 Hz, 1H), 7.14 (d, J=8.1 Hz, 1H), 6.87 (s, 1H), 4.06-3.95 (m, 2H), 2.31 (s, 3H), 2.28-2.24 (m, 2H); ESI MS m/z 371 [C$_{18}$H$_{15}$BrN$_2$O$_2$+H]$^+$; HPLC (Method C) 96.2% (AUC), t$_R$=12.72 min; Chiral HPLC (Chiralpak AD, Method A) >99% (AUC), t$_R$=13.18 min.

Preparation of (S)-1-(3-Chloro-4-methylphenyl)-3a-hydroxy-6-methyl-3,3a-dihydro-1H-pyrrolo[2,3-b]quinolin-4(2H)-one

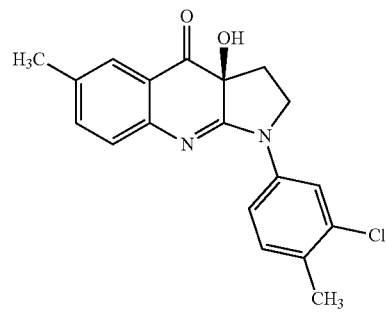

BPN-0025254

(S)-1-(3-Chloro-4-methylphenyl)-3a-hydroxy-6-methyl-3,3a-dihydro-1H-pyrrolo[2,3-b]quinolin-4(2H)-one was prepared as a yellow solid according to Synthetic Scheme 3: mp=213-214° C.; $^1$H NMR (500 MHz, DMSO-d$_6$) δ 8.37 (d, J=2.4 Hz, 1H), 7.82 (dd, J=8.4, 2.3 Hz, 1H), 7.54 (d, J=1.6 Hz, 1H), 7.39 (d, J=8.3 Hz, 2H), 7.12 (d, J=8.1 Hz, 1H), 6.84 (s, 1H), 4.05-3.93 (m, 2H), 2.33-2.31 (m, 6H), 2.27-2.22 (m, 2H); ESI MS m/z 341 [C$_{19}$H$_{17}$ClN$_2$O$_2$+H]$^+$; HPLC (Method C) >99% (AUC), t$_R$=2.30 min; Chiral HPLC (Chiralpak AD, Method A) >99% (AUC), t$_R$=14.28 min.

Preparation of (S)-1-(3,4-Dimethylphenyl)-3a-hydroxy-6-methyl-3,3a-dihydro-1H-pyrrolo[2,3-b]quinolin-4(2H)-one

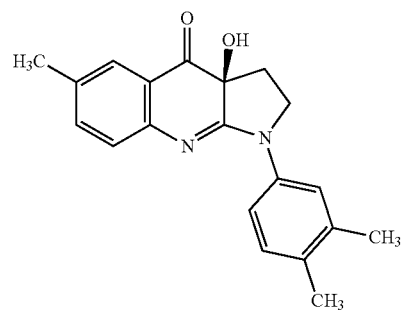

BPN-0025903

(S)-1-(3,4-Dimethylphenyl)-3a-hydroxy-6-methyl-3,3a-dihydro-1H-pyrrolo[2,3-b]quinolin-4(2H)-one was prepared as a yellow solid according to Synthetic Scheme 3: mp=197-199° C.; $^1$H NMR (500 MHz, DMSO-d$_6$) δ 7.83 (dd, J=8.5, 2.0 Hz, 1H), 7.78 (d, J=1.5 Hz, 1H), 7.51 (d, J=1.0 Hz, 1H), 7.35 (dd, J=7.5, 1.5 Hz, 1H), 7.17 (d, J=8.5 Hz, 1H), 7.09 (d, J=8.0 Hz, 1H), 6.77 (s, 1H), 4.05-4.00 (m, 1H), 3.94-3.90 (m, 1H), 2.29-2.22 (m, 11H); ESI MS m/z 321 [C$_{20}$H$_{20}$N$_2$O$_2$+H]$^+$; HPLC (Method F) 98.4% (AUC), t$_R$=14.99 min; Chiral HPLC (Chiralpak AD, Method A) 95.4% (AUC), t$_R$=13.05 min.

Preparation of (S)-1-(Benzofuran-6-yl)-3a-hydroxy-6-methyl-3,3a-dihydro-1H-pyrrolo[2,3-b]quinolin-4(2H)-one

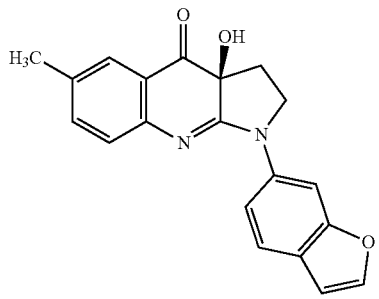

BPN-0026285

(S)-1-(Benzofuran-6-yl)-3a-hydroxy-6-methyl-3,3a-dihydro-1H-pyrrolo[2,3-b]quinolin-4(2H)-one was prepared as a red-orange solid according to Synthetic Scheme 3: mp=204-205° C.; $^1$H NMR (500 MHz, DMSO-d$_6$) δ 8.54 (s, 1H), 7.98 (d, J=2.5 Hz, 1H), 7.88 (dd, J=8.5, 2.0 Hz, 1H), 7.68 (d, J=8.5 Hz, 1H), 7.54 (d, J=1.5 Hz, 1H), 7.38 (dd, J=8.5, 2.0 Hz, 1H), 7.15 (d, J=8.0 Hz, 1H), 6.95 (dd, J=2.0, 2.0 Hz, 1H), 6.84 (s, 1H), 4.16-4.11 (m, 1H), 4.05-4.01 (m, 1H), 2.33-2.25 (m, 5H); ESI MS m/z 333 [C$_{20}$H$_{16}$N$_2$O$_3$+H]$^+$; HPLC (Method C) >99% (AUC), t$_R$=12.24 min; Chiral HPLC (Chiralpak AD, Method A) >99% (AUC), t$_R$=17.78 min.

Preparation of (S)-1-(4-Chloro-3-methylphenyl)-3a-hydroxy-6-methyl-3,3a-dihydro-1H-pyrrolo[2,3-b]quinolin-4(2H)-one

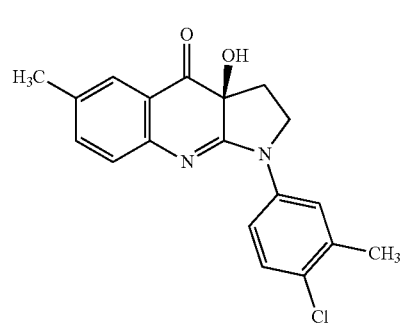

BPN-0026325

(S)-1-(4-Chloro-3-methylphenyl)-3a-hydroxy-6-methyl-3,3a-dihydro-1H-pyrrolo[2,3-b]quinolin-4(2H)-one was prepared as a yellow solid according to Synthetic Scheme 3: mp=203-204° C.; $^1$H NMR (500 MHz, DMSO-d$_6$) δ 8.06 (dd, J=9.0, 3.0 Hz, 1H), 8.01 (d, J=3.0 Hz, 1H), 7.53 (d, J=2.0 Hz, 1H), 7.44 (d, J=8.5 Hz, 1H), 7.38 (dd, J=8.5, 2.0 Hz, 1H), 7.14 (d, J=8.0 Hz, 1H), 6.83 (s, 1H), 4.05-4.00 (m, 1H), 3.97-3.93 (m, 1H), 2.38 (s, 3H), 2.31 (s, 3H), 2.27-2.24 (m, 2H); ESI MS m/z 341 [C$_{19}$H$_{17}$ClN$_2$O$_2$+H]$^+$; HPLC (Method C) >99% (AUC), t$_R$=13.07 min; Chiral HPLC (Chiralpak AD, Method A) >99% (AUC), t$_R$=13.68 min.

Preparation of (S)-1-(Benzofuran-6-yl)-6-chloro-3a-hydroxy-3,3a-dihydro-1H-pyrrolo[2,3-b]quinolin-4(2H)-one

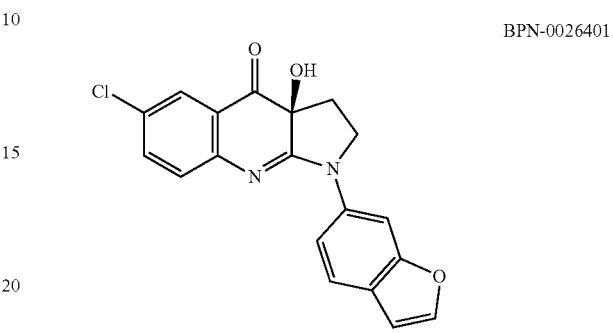

BPN-0026401

(S)-1-(Benzofuran-6-yl)-6-chloro-3a-hydroxy-3,3a-dihydro-1H-pyrrolo[2,3-b]quinolin-4(2H)-one was prepared as a yellow-orange solid according to Synthetic Scheme 3: mp=209-211° C.; $^1$H NMR (500 MHz, DMSO-d$_6$) δ 8.50 (s, 1H), 8.00 (d, J=2.0 Hz, 1H), 7.87 (dd, J=9.0, 2.0 Hz, 1H), 7.69 (d, J=9.0 Hz, 1H), 7.65 (d, J=2.5 Hz, 1H), 7.57 (dd, J=8.5, 2.5 Hz, 1H), 7.26 (d, J=8.5 Hz, 1H), 6.98 (s, 1H), 6.96 (dd, J=2.5, 1.0 Hz, 1H), 4.20-4.16 (m, 1H), 4.07-4.03 (m, 1H), 2.38-2.34 (m, 1H), 2.30-2.26 (m, 1H); ESI MS m/z 353 [C$_{19}$H$_{13}$ClN$_2$O$_3$+H]$^+$; HPLC (Method B) >99% (AUC), t$_R$=9.12 min; Chiral HPLC (Chiralpak AD, Method A) 99.0% (AUC), t$_R$=17.23 min.

Preparation of (S)-3a-Hydroxy-6,7-dimethyl-1-(m-tolyl)-3,3a-dihydro-1H-pyrrolo[2,3-b]quinolin-4(2H)-one

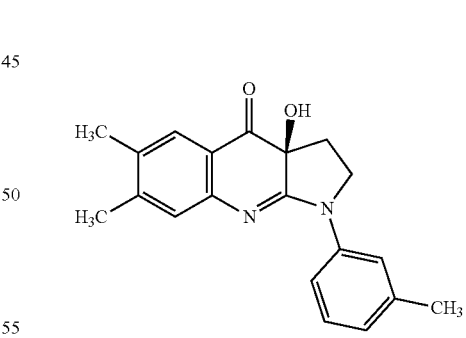

BPN-0026496

(S)-3a-Hydroxy-6,7-dimethyl-1-(m-tolyl)-3,3a-dihydro-1H-pyrrolo[2,3-b]quinolin-4(2H)-one was prepared as an orange solid according to Synthetic Scheme 3: mp=196-198° C.; $^1$H NMR (500 MHz, DMSO-d$_6$) δ 7.95 (d, J=8.5 Hz, 1H), 7.83 (s, 1H), 7.48 (s, 1H), 7.30 (apparent t, J=8.0 Hz, 1H), 7.03 (s, 1H), 6.96 (d, J=7.5 Hz, 1H), 6.74 (s, 1H), 4.06-4.01 (m, 1H), 3.95-3.92 (m, 1H), 2.36 (s, 3H), 2.27 (s, 3H), 2.24-2.20 (m, 5H); ESI MS m/z 321 [C$_{20}$H$_{20}$N$_2$O$_2$+H]$^+$; HPLC (Method C) >99% (AUC), t$_R$=12.62 min; Chiral HPLC (Chiralpak AD, Method A) >99% (AUC), t$_R$=13.47 min.

Preparation of (S)-3a-Hydroxy-1-(3-methoxyphenyl)-6,7-dimethyl-3,3a-dihydro-1H-pyrrolo[2,3-b]quinolin-4(2H)-one

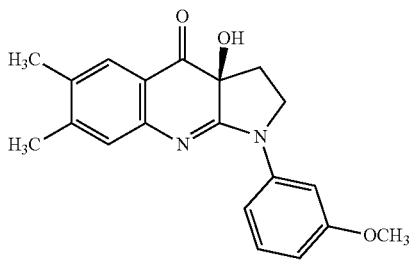

BPN-0026497

(S)-3a-Hydroxy-1-(3-methoxyphenyl)-6,7-dimethyl-3,3a-dihydro-1H-pyrrolo[2,3-b]quinolin-4(2H)-one was prepared as an yellow solid according to Synthetic Scheme 3: mp=176-178° C.; $^1$H NMR (500 MHz, DMSO-$d_6$) δ 7.97 (apparent t, J=2.0 Hz, 1H), 7.48 (dd, J=8.0, 2.5 Hz, 2H), 7.31 (apparent t, J=8.5 Hz, 1H), 7.04 (s, 1H), 6.76 (s, 1H), 6.73 (dd, J=8.0, 2.0 Hz, 1H), 4.05-4.00 (m, 1H), 3.96-3.93 (m, 1H), 3.80 (s, 3H), 2.27 (s, 3H), 2.24-2.21 (m, 5H); ESI MS m/z 337 $[C_{20}H_{20}N_2O_3+H]^+$; HPLC (Method C) >99% (AUC), $t_R$=12.41 min; Chiral HPLC (Chiralpak AD, Method A) >99% (AUC), $t_R$=16.05 min.

Preparation of (S)-4-(3a-Hydroxy-6,7-dimethyl-4-oxo-2,3,3a,4-tetrahydro-1H-pyrrolo[2,3-b]quinolin-1-yl)benzonitrile

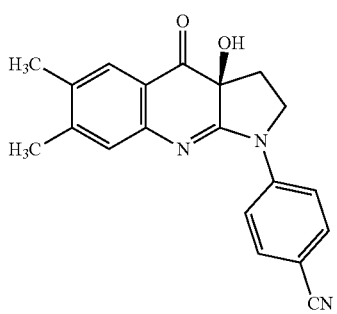

BPN-0026499

(S)-4-(3a-hydroxy-6,7-dimethyl-4-oxo-2,3,3a,4-tetrahydro-1H-pyrrolo[2,3-b]quinolin-1-yl)benzonitrile was prepared as a yellow-brown solid according to Synthetic Scheme 3: mp=229-231° C.; $^1$H NMR (500 MHz, DMSO-$d_6$) δ 8.32 (d, J=9.0 Hz, 2H), 7.87 (dd, J=7.5, 2.0 Hz, 2H), 7.52 (s, 1H), 7.13 (s, 1H), 6.86 (s, 1H), 4.07-3.99 (m, 2H), 2.29-2.24 (m, 8H); ESI MS m/z 332 $[C_{20}H_{17}N_3O_2+H]^+$; HPLC (Method C) >99% (AUC), $t_R$=12.60 min; Chiral HPLC (Chiralpak AD, Method A) 97.2% (AUC), $t_R$=19.40 min.

Preparation of (S)-1-(3-Chlorophenyl)-3a-hydroxy-6,7-dimethyl-3,3a-dihydro-1H-pyrrolo[2,3-b]quinolin-4(2H)-one

BPN-0026500

(S)-1-(3-Chlorophenyl)-3a-hydroxy-6,7-dimethyl-3,3a-dihydro-1H-pyrrolo[2,3-b]quinolin-4(2H)-one was prepared as a yellow solid according to Synthetic Scheme 3: mp=203-204° C.; $^1$H NMR (500 MHz, DMSO-$d_6$) δ 8.40 (apparent t, J=2.0 Hz, 1H), 7.92 (d, J=7.5 Hz, 1H), 7.50 (s, 1H), 7.44 (apparent t, J=8.5 Hz, 1H), 7.19 (d, J=7.5 Hz, 1H), 7.01 (s, 1H), 6.80 (s, 1H), 4.06-4.00 (m, 1H), 3.97-3.95 (m, 1H), 2.29 (s, 3H), 2.25-2.23 (m, 5H); ESI MS m/z 341 $[C_{19}H_{17}ClN_2O_2+H]^+$; HPLC (Method C) >99% (AUC), $t_R$=12.89 min; Chiral HPLC (Chiralpak AD, Method A) >99% (AUC), $t_R$=13.96 min.

Preparation of (S)-4-(4a-Hydroxy-2-methyl-4-oxo-5,6-dihydro-4H-pyrrolo[2,3-b]thieno[3,2-e]pyridin-7(4aH)-yl)-2-methylbenzonitrile

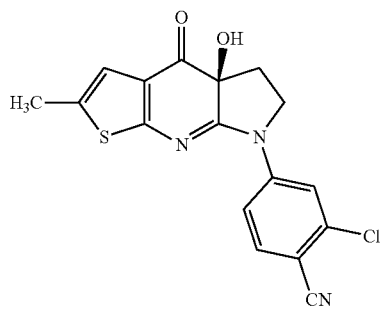

BPN-0026576

(S)-4-(4a-Hydroxy-2-methyl-4-oxo-5,6-dihydro-4H-pyrrolo[2,3-b]thieno[3,2-e]pyridin-7(4aH)-yl)-2-methylbenzonitrile was prepared as an orange solid according to Synthetic Scheme 3: mp=226-227° C.; $^1$H NMR (500 MHz, DMSO-$d_6$) δ 8.17 (dd, J=9.0, 2.5 Hz, 1H), 7.90 (dd, J=2.0 Hz, 1H), 7.83 (d, J=9.0 Hz, 1H), 6.97 (s, 1H), 6.84 (d, J=1.0 Hz, 1H), 4.15-4.06 (m, 2H), 2.52 (s, 3H), 2.37 (d, J=1.0, 3H), 2.25-2.21 (m, 2H); ESI MS m/z 338 $[C_{18}H_{15}N_3O_2S+H]^+$; HPLC (Method C) >99% (AUC), $t_R$=15.23 min; Chiral HPLC (Chiralpak AD, Method A) 98.9% (AUC), $t_R$=19.02 min.

Preparation of (S)-6-Chloro-3a-hydroxy-1-(2-methoxypyridin-4-yl)-3,3a-dihydro-1H-pyrrolo[2,3-b]quinolin-4(2H)-one

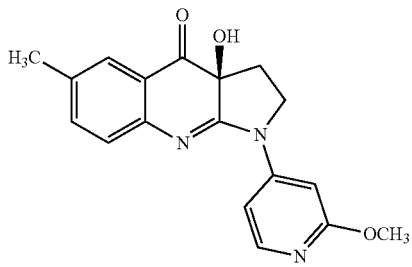

BPN-0026621

(S)-6-Chloro-3a-hydroxy-1-(2-methoxypyridin-4-yl)-3,3a-dihydro-1H-pyrrolo[2,3-b]quinolin-4(2H)-one was prepared as a yellow solid according to Synthetic Scheme 6: mp=230-231° C.; $^1$H NMR (500 MHz, DMSO-$d_6$) δ 8.14 (d, J=6.0 Hz, 1H), 7.72 (dd, J=6.0, 2.0 Hz, 1H), 7.68 (d, J=3.0 Hz, 1H), 7.63 (dd, J=8.5, 2.5 Hz, 1H), 7.56 (d, J=2.0 Hz, 1H), 7.34 (d, J=8.5 Hz, 1H), 7.04 (s, 1H), 4.02-4.00 (m, 2H), 3.87 (s, 3H), 2.39-2.32 (m, 1H), 2.26-2.23 (m, 1H); ESI MS m/z 344 $[C_{17}H_{14}ClN_3O_3+H]^+$; HPLC (Method C) 96.0% (AUC), $t_R$=13.01 min; Chiral HPLC (Chiralpak AD, Method A) 83.0% (AUC), $t_R$=14.71 min.

Preparation of (S)-7-(3-Bromophenyl)-4a-hydroxy-2-methyl-4a,5,6,7-tetrahydro-4H-pyrrolo[2,3-b]thieno[3,2-e]pyridin-4-one

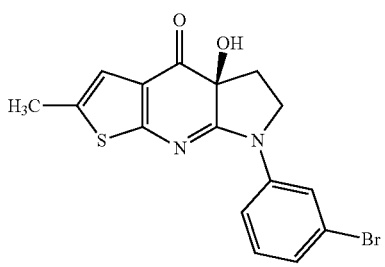

BPN-0026624

(S)-7-(3-Bromophenyl)-4a-hydroxy-2-methyl-4a,5,6,7-tetrahydro-4H-pyrrolo[2,3-b]thieno[3,2-e]pyridin-4-one was prepared as a red-orange solid according to Synthetic Scheme 3: mp=236-238° C.; $^1$H NMR (500 MHz, DMSO-$d_6$) δ 8.26 (apparent t, J=2.0 Hz, 1H), 7.90 (apparent dt, J=8.0, 1.5 Hz, 1H), 7.43-7.37 (m, 2H), 6.92 (s, 1H), 6.81 (d, J=1.0, 1H), 4.15-4.10 (m, 1H), 4.05-4.01 (m, 1H), 2.36 (d, J=1.0, 3H), 2.22-2.19 (m, 2H); ESI MS m/z 377 $[C_{16}H_{13}BrN_2O_2S+H]^+$; HPLC (Method C) 94.0% (AUC), $t_R$=16.31 min; Chiral HPLC (Chiralpak AD, Method A) >99% (AUC), $t_R$=16.36 min.

Preparation of (S)-7-(Benzofuran-6-yl)-4a-hydroxy-2-methyl-4a,5,6,7-tetrahydro-4H-pyrrolo[2,3-b]thieno[3,2-e]pyridin-4-one

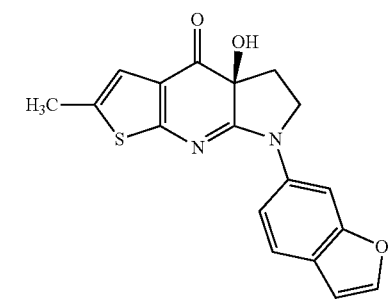

BPN-0026639

(S)-7-(Benzofuran-6-yl)-4a-hydroxy-2-methyl-4a,5,6,7-tetrahydro-4H-pyrrolo[2,3-b]thieno[3,2-e]pyridin-4-one was prepared as a red solid according to Synthetic Scheme 3: mp=247-248° C.; $^1$H NMR (500 MHz, DMSO-$d_6$) δ 8.29 (s, 1H), 8.02 (d, J=2.5 Hz, 1H), 7.81 (dd, J=8.5, 2.0 Hz, 1H), 7.71 (d, J=8.5 Hz, 1H), 7.97 (dd, J=2.0, 1.0 Hz, 1H), 6.90 (s, 1H), 6.79 (d, J=1.0, 1H), 4.25-4.20 (m, 1H), 4.11-4.08 (m, 1H), 2.35 (d, J=1.0, 3H), 2.26-2.22 (m, 2H); ESI MS m/z 339 $[C_{18}H_{14}N_2O_3S+H]^+$; HPLC (Method B) >99% (AUC), $t_R$=10.20 min; Chiral HPLC (Chiralpak AD, Method A) >99% (AUC), $t_R$=22.00 min.

Preparation of (S)-1-(3-Bromophenyl)-3a-hydroxy-6,7-dimethyl-3,3a-dihydro-1H-pyrrolo[2,3-b]quinolin-4(2H)-one

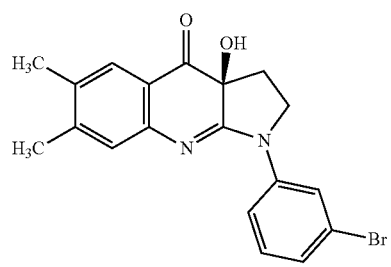

BPN-0026660

(S)-1-(3-Bromophenyl)-3a-hydroxy-6,7-dimethyl-3,3a-dihydro-1H-pyrrolo[2,3-b]quinolin-4(2H)-one was prepared as a yellow solid according to Synthetic Scheme 3: mp=223-224° C.; $^1$H NMR (500 MHz, DMSO-$d_6$) δ 8.52 (apparent t, J=2.0 Hz, 1H), 7.96 (ddd, J=8.3, 2.2, 1.0 Hz, 1H), 7.50 (s, 1H), 7.38 (apparent t, J=8.1 Hz, 1H), 7.32 (ddd, J=7.9, 1.7, 0.9 Hz, 1H), 7.05 (s, 1H), 6.81 (s, 1H), 4.05-4.00 (m, 1H), 3.98-3.94 (m, 1H), 2.28 (s, 3H), 2.25-2.23 (m, 5H); ESI MS m/z 385 $[C_{19}H_{17}BrN_2O_2+H]^+$; HPLC (Method C) 93.1% (AUC), $t_R$=13.27 min; Chiral HPLC (Chiralpak AD, Method A) >99% (AUC), $t_R$=14.35 min.

Preparation of (S)-4-(3a-Hydroxy-6,7-dimethyl-4-oxo-2,3,3a,4-tetrahydro-1H-pyrrolo[2,3-b]quinolin-1-yl)-2-methylbenzonitrile

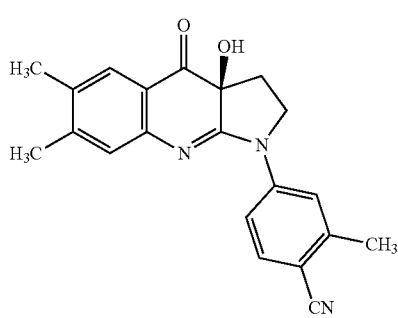

BPN-0026661

(S)-4-(3a-Hydroxy-6,7-dimethyl-4-oxo-2,3,3a,4-tetrahydro-1H-pyrrolo[2,3-b]quinolin-1-yl)-2-methylbenzonitrile was prepared as a yellow-brown solid according to Synthetic Scheme 3: mp=240-241° C.; $^1$H NMR (500 MHz, DMSO-$d_6$) δ 8.28 (dd, J=8.8, 2.2 Hz, 1H), 8.10 (d, J=1.9 Hz, 1H), 7.79 (d, J=8.7 Hz, 1H), 7.52 (s, 1H), 7.13 (s, 1H), 7.85 (s, 1H), 4.03-4.00 (m, 2H), 2.53 (s, 3H), 2.29 (s, 3H), 2.27-2.24 (m, 5H); ESI MS m/z 346 $[C_{21}H_{19}N_3O_2+H]^+$; HPLC (Method C) 98.6% (AUC), $t_R$=13.14 min; Chiral HPLC (Chiralpak AD, Method A) 88.1% (AUC), $t_R$=17.66 min.

Preparation of (S)-1-(4-Chlorophenyl)-3a-hydroxy-6,7-dimethyl-3,3a-dihydro-1H-pyrrolo[2,3-b]quinolin-4(2H)-one

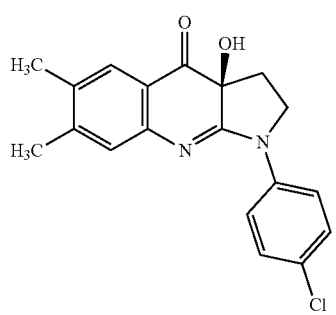

BPN-0026662

(S)-1-(4-Chlorophenyl)-3a-hydroxy-6,7-dimethyl-3,3a-dihydro-1H-pyrrolo[2,3-b]quinolin-4(2H)-one was prepared as a yellow solid according to Synthetic Scheme 3: mp=214-216° C.; $^1$H NMR (500 MHz, DMSO-$d_6$) δ 8.15-8.12 (m, 2H), 7.49-7.46 (m, 3H), 7.06 (s, 1H), 6.79 (s, 1H), 4.05-4.02 (m, 1H), 3.96-3.92 (m, 1H), 2.27 (s, 3H), 2.25-2.22 (m, 5H); ESI MS m/z 341 $[C_{19}H_{17}ClN_2O_2+H]^+$; HPLC (Method C) >99% (AUC), $t_R$=13.06 min; Chiral HPLC (Chiralpak AD, Method A) 97.6% (AUC), $t_R$=16.42 min.

Preparation of (S)-3a-Hydroxy-6,7-dimethyl-1-(p-tolyl)-3,3a-dihydro-1H-pyrrolo[2,3-b]quinolin-4(2H)-one

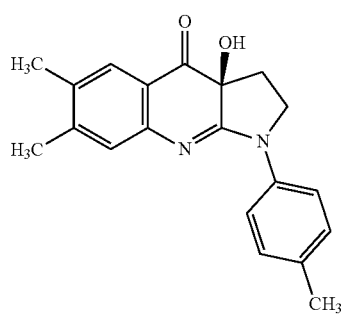

BPN-0026663

(S)-3a-Hydroxy-6,7-dimethyl-1-(p-tolyl)-3,3a-dihydro-1H-pyrrolo[2,3-b]quinolin-4(2H)-one was prepared as a yellow solid according to Synthetic Scheme 3: mp=219-220° C.; $^1$H NMR (500 MHz, DMSO-$d_6$) δ 7.96-3.94 (m, 2H), 7.47 (s, 1H), 7.22 (d, J=8.3 Hz, 2H), 7.02 (s, 1H), 6.73 (s, 1H), 4.05-4.00 (m, 1H), 3.93-3.89 (m, 1H), 2.31 (s, 3H), 2.26 (s, 3H), 2.24-2.21 (m, 5H); ESI MS m/z 321 $[C_{20}H_{20}N_2O_2+H]^+$; HPLC (Method B) >99% (AUC), $t_R$=8.97 min; Chiral HPLC (Chiralpak AD, Method A) >99% (AUC), $t_R$=15.61 min.

Preparation of (S)-1-(Benzofuran-6-yl)-3a-hydroxy-6,7-dimethyl-1,2,3,3a-tetrahydro-4H-pyrrolo[2,3-b]quinolin-4-one

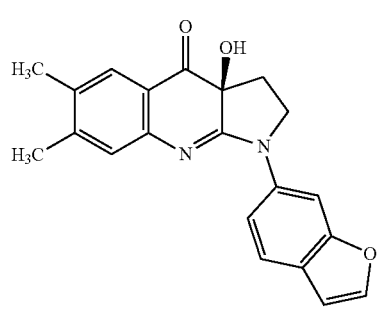

BPN-0026664

(S)-1-(Benzofuran-6-yl)-3a-hydroxy-6,7-dimethyl-1,2,3,3a-tetrahydro-4H-pyrrolo[2,3-b]quinolin-4-one was prepared as a red solid according to Synthetic Scheme 3: mp=213-214° C.; $^1$H NMR (500 MHz, DMSO-$d_6$) δ 8.56 (s, 1H), 7.98 (d, J=2.2 Hz, 1H), 7.88 (dd, J=8.6, 2.0 Hz, 1H), 7.67 (d, J=8.6 Hz, 1H), 7.49 (s, 1H), 7.09 (s, 1H), 6.50 (dd, J=2.2, 0.9 Hz, 1H), 6.79 (s, 1H), 4.15-4.10 (m, 1H), 4.04-4.00 (m, 1H), 2.28-2.25 (m, 5H), 2.23 (s, 3H); ESI MS m/z 347 $[C_{21}H_{18}N_2O_3+H]^+$; HPLC (Method B) >99% (AUC), $t_R$=9.10 min; Chiral HPLC (Chiralpak AD, Method A) 95.8% (AUC), $t_R$=19.08 min.

Preparation of (S)-3a-Hydroxy-1-(4-methoxyphenyl)-6,7-dimethyl-1,2,3,3a-tetrahydro-4H-pyrrolo[2,3-b]quinolin-4-one

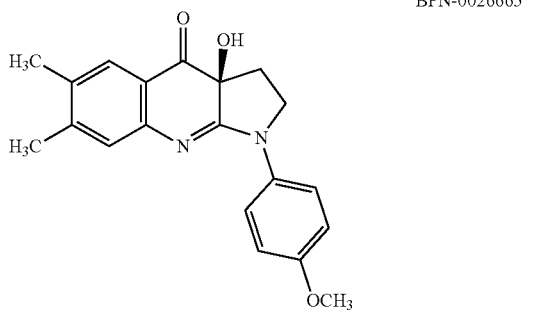

BPN-0026665

(S)-3a-Hydroxy-1-(4-methoxyphenyl)-6,7-dimethyl-1,2,3,3a-tetrahydro-4H-pyrrolo[2,3-b]quinolin-4-one was prepared as a yellow solid according to Synthetic Scheme 3: mp=199-200° C.; $^1$H NMR (500 MHz, DMSO-$d_6$) δ 7.98-7.95 (m, 2H), 7.46 (s, 1H), 7.00-6.98 (m, 3H), 6.72 (s, 1H), 4.06-4.01 (m, 1H), 3.91-3.88 (m, 1H), 3.77 (s, 3H), 2.25 (s, 3H), 2.23-2.21 (m, 5H); ESI MS m/z 337 $[C_{20}H_{20}N_2O_3+H]^+$; HPLC (Method B) >99% (AUC), $t_R$=8.71 min; Chiral HPLC (Chiralpak AD, Method A) >99% (AUC), $t_R$=18.75 min.

Preparation of (S)-3a-Hydroxy-6,7-dimethyl-1-(2-methylthiazol-5-yl)-1,2,3,3a-tetrahydro-4H-pyrrolo[2,3-b]quinolin-4-one

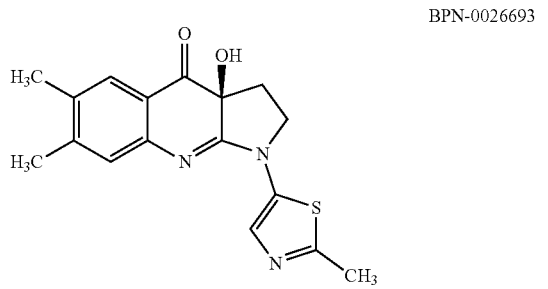

BPN-0026693

(S)-3a-hydroxy-6,7-dimethyl-1-(2-methylthiazol-5-yl)-1,2,3,3a-tetrahydro-4H-pyrrolo[2,3-b]quinolin-4-one was prepared as an orange-yellow solid according to Synthetic Scheme 6: mp=234-235° C.; $^1$H NMR (500 MHz, DMSO-$d_6$) δ 7.49 (s, 1H), 7.44 (s, 1H), 7.05 (s, 1H), 6.87 (s, 1H), 4.03-3.94 (m, 2H), 2.60 (s, 3H), 2.31-2.27 (m, 5H), 2.22 (s, 3H); ESI MS m/z 328 $[C_{17}H_{17}N_3O_2S+H]^+$; HPLC (Method C) >99% (AUC), $t_R$=12.84 min; Chiral HPLC (Chiralpak AD, Method A) 53.0% (AUC), $t_R$=15.14 min.

Preparation of (S)-3a-Hydroxy-6,7-dimethyl-1-(thiophen-2-yl)-1,2,3,3a-tetrahydro-4H-pyrrolo[2,3-b]quinolin-4-one

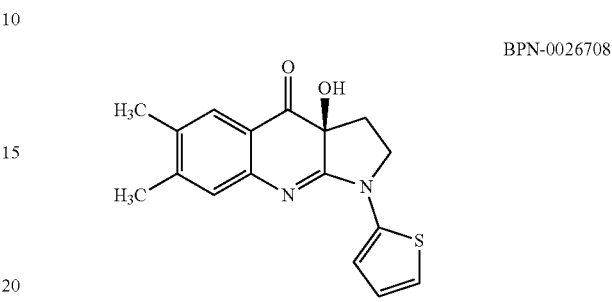

BPN-0026708

(S)-3a-Hydroxy-6,7-dimethyl-1-(thiophen-2-yl)-1,2,3,3a-tetrahydro-4H-pyrrolo[2,3-b]quinolin-4-one was prepared as an orange solid according to Synthetic Scheme 4: mp=229-231° C.; $^1$H NMR (500 MHz, DMSO-$d_6$) δ 7.49 (s, 1H), 7.14 (dd, J=5.5, 1.4 Hz, 1H), 7.05 (s, 1H), 6.96 (dd, J=5.4, 3.8 Hz, 1H), 6.83-6.82 (m, 2H), 4.07-3.97 (m, 2H), 2.37-2.35 (m, 2H), 2.28 (s, 3H), 2.22 (s, 3H); ESI MS m/z 313 $[C17H16N_2O_2S+H]^+$; HPLC (Method B) >99% (AUC), $t_R$=13.17 min; Chiral HPLC (Chiralpak AD, Method A) 83.5% (AUC), $t_R$=17.17 min.

Preparation of (S)-3a-Hydroxy-1-(2-methoxypyridin-4-yl)-6,7-dimethyl-1,2,3,3a-tetrahydro-4H-pyrrolo[2,3-b]quinolin-4-one

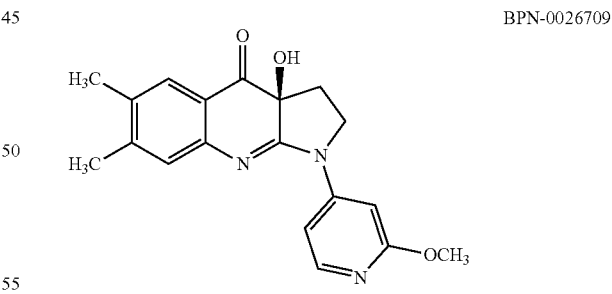

BPN-0026709

(S)-3a-Hydroxy-1-(2-methoxypyridin-4-yl)-6,7-dimethyl-1,2,3,3a-tetrahydro-4H-pyrrolo[2,3-b]quinolin-4-one was prepared as a yellow solid according to Synthetic Scheme 4: mp=218-220° C.; $^1$H NMR (500 MHz, DMSO-$d_6$) δ 8.12 (d, J=5.9 Hz, 1H), 7.69 (dd, J=5.9, 2.0 Hz, 1H), 7.59 (d, J=1.8 Hz, 1H), 7.52 (s, 1H), 7.14 (s, 1H), 6.86 (s, 1H), 3.97-3.94 (m, 2H), 3.87 (s, 3H), 2.30 (s, 3H), 2.26-2.23 (m, 5H); ESI MS m/z 338 $[C_{19}H_{19}N_3O_3+H]^+$; HPLC (Method B) >99% (AUC), $t_R$=9.04 min; Chiral HPLC (Chiralpak AD, Method A) 90.6% (AUC), $t_R$=15.27 min.

Preparation of (S)-3a-Hydroxy-6,7-dimethyl-1-(1-methyl-1H-pyrazol-4-yl)-1,2,3,3a-tetrahydro-4H-pyrrolo[2,3-b]quinolin-4-one

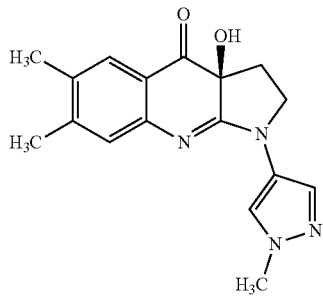

BPN-0026710

(S)-3a-Hydroxy-6,7-dimethyl-1-(1-methyl-1H-pyrazol-4-yl)-1,2,3,3a-tetrahydro-4H-pyrrolo[2,3-b]quinolin-4-one was prepared as a yellow solid according to Synthetic Scheme 4: mp=226-227° C.; $^1$H NMR (500 MHz, DMSO-$d_6$) δ 7.25 (s, 1H), 7.81 (s, 1H), 7.44 (s, 1H), 7.03 (s, 1H), 6.69 (s, 1H), 3.92-3.87 (m, 4H), 3.81-3.78 (m, 1H), 2.29-2.22 (m, 5H), 2.20 (s, 3H); ESI MS m/z 311 [$C_{17}H_{18}N_4O_2$+H]$^+$; HPLC (Method B) >99% (AUC), $t_R$=7.50 min; Chiral HPLC (Chiralpak AD, Method A) 92.2% (AUC), $t_R$=18.21 min.

Preparation of (S)-7-(Benzofuran-6-yl)-4a-hydroxy-2-ethyl-4a,5,6,7-tetrahydro-4H-pyrrolo[2,3-b]thieno[3,2-e]pyridin-4-one

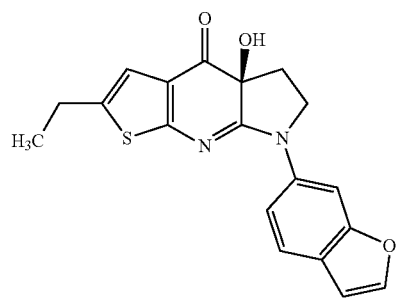

BPN-0026749

(S)-7-(Benzofuran-6-yl)-4a-hydroxy-2-ethyl-4a,5,6,7-tetrahydro-4H-pyrrolo[2,3-b]thieno[3,2-e]pyridin-4-one was prepared as a red-orange solid according to Synthetic Scheme 3: mp=233-235° C.; $^1$H NMR (500 MHz, DMSO-$d_6$) δ 8.30 (s, 1H), 8.02 (d, J=2.2 Hz, 1H), 7.81 (dd, J=8.6, 1.9 Hz, 1H), 7.71 (d, J=8.6 Hz, 1H), 6.97 (dd, J=2.0, 0.8 Hz, 1H), 6.91 (s, 1H), 6.82 (s, 1H), 4.26-4.21 (m, 1H), 4.11-4.08 (m, 1H), 2.70 (q, J=7.5, 2H), 2.28-2.20 (m, 2H), 1.22 (t, J=7.5 Hz, 3H); ESI MS m/z 353 [$C_{19}H_{16}N_2O_3S$+H]$^+$; HPLC (Method B) >99% (AUC), $t_R$=10.51 min; Chiral HPLC (Chiralpak AD, Method A) >99% (AUC), $t_R$=21.69 min.

Preparation of (S)-7-(4-Chlorophenyl)-4a-hydroxy-2-ethyl-4a,5,6,7-tetrahydro-4H-pyrrolo[2,3-b]thieno[3,2-e]pyridin-4-one

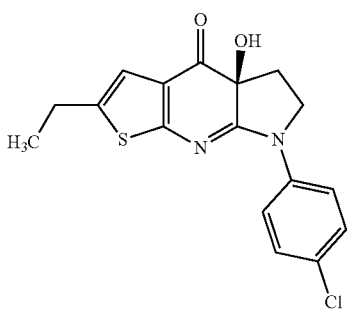

BPN-0026770

(S)-7-(4-Chlorophenyl)-4a-hydroxy-2-ethyl-4a,5,6,7-tetrahydro-4H-pyrrolo[2,3-b]thieno[3,2-e]pyridin-4-one was prepared as a red-orange solid according to Synthetic Scheme 3: mp=235-236° C.; $^1$H NMR (500 MHz, DMSO-$d_6$) δ 8.00-7.97 (m, 2H), 7.53-7.50 (m, 2H), 6.91 (s, 1H), 6.82 (apparent t, J=1.0 Hz, 1H), 4.16-4.11 (m, 1H), 4.03-4.00 (m, 1H), 2.70 (q, J=7.4 Hz, 2H), 2.23-2.20 (m, 2H), 1.21 (t, J=7.5 Hz, 3H); ESI MS m/z 347 [$C_{17}H_{15}ClN_2O_2S$+H]$^+$; HPLC (Method B) >99% (AUC), $t_R$=11.20 min; Chiral HPLC (Chiralpak AD, Method A) >99% (AUC), $t_R$=18.88 min.

Preparation of (S)-2-Ethyl-4a-hydroxy-7-(p-tolyl)-4a,5,6,7-tetrahydro-4H-pyrrolo[2,3-h]thieno[3,2-e]pyridin-4-one

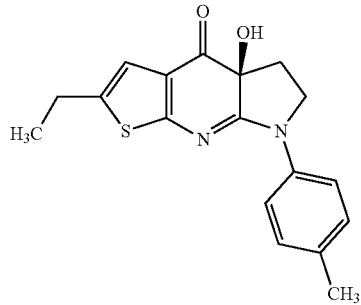

BPN-0026774

(S)-2-Ethyl-4a-hydroxy-7-(p-tolyl)-4a,5,6,7-tetrahydro-4H-pyrrolo[2,3-b]thieno[3,2-e]pyridin-4-one was prepared as a red solid according to Synthetic Scheme 3: mp=248-249° C.; $^1$H NMR (500 MHz, DMSO-$d_6$) δ 7.81-7.79 (m, 2H), 7.26-7.24 (m, 2H), 6.85 (s, 1H), 6.79 (apparent t, J=1.1 Hz, 1H), 4.15-4.10 (m, 1H), 4.01-3.98 (m, 1H), 2.71-2.66 (m, 2H), 2.31 (s, 3H), 2.25-2.15 (m, 2H), 2.21 (t, J=7.5 Hz, 3H); ESI MS m/z 327 [$C_{18}H_{18}N_2O_2S$+H]$^+$; HPLC (Method B) >99% (AUC), $t_R$=10.30 min; Chiral HPLC (Chiralpak AD, Method A) >99% (AUC), $t_R$=18.53 min.

Preparation of (S)-4a-Hydroxy-7-(4-methoxyphenyl)-2,3-dimethyl-4a,5,6,7-tetrahydro-4H-pyrrolo[2,3-b]thieno[3,2-e]pyridin-4-one

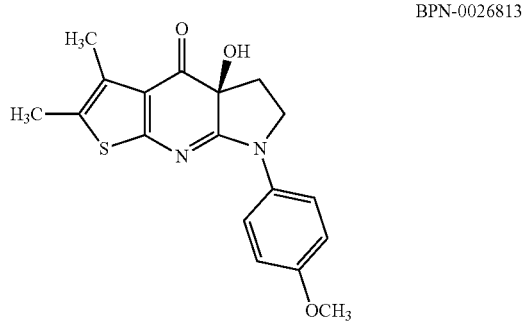 [SMILES: COc1ccc(N2CC[C@@]3(O)C(=O)c4c(sc(C)c4C)N=C23)cc1]

BPN-0026813

(S)-4a-Hydroxy-7-(4-methoxyphenyl)-2,3-dimethyl-4a,5,6,7-tetrahydro-4H-pyrrolo[2,3-b]thieno[3,2-e]pyridin-4-one was prepared as an orange solid according to Synthetic Scheme 3: mp=232-233° C.; $^1$H NMR (500 MHz, DMSO-$d_6$) δ 7.83-7.81 (m, 2H), 7.02-7.00 (m, 2H), 6.80 (s, 1H), 4.15-4.09 (m, 1H), 3.99-3.95 (m, 1H), 3.77 (s, 3H), 2.20-2.17 (m, 8H); ESI MS m/z 343 $[C_{18}H_{18}N_2O_3S+H]^+$; HPLC (Method B) >99% (AUC), $t_R$=9.49 min; Chiral HPLC (Chiralpak AD, Method A) 85.2% (AUC), $t_R$=18.94 min.

Preparation of (S)-7-(4-Chlorophenyl)-4a-hydroxy-2,3-dimethyl-4a,5,6,7-tetrahydro-4H-pyrrolo[2,3-b]thieno[3,2-e]pyridin-4-one

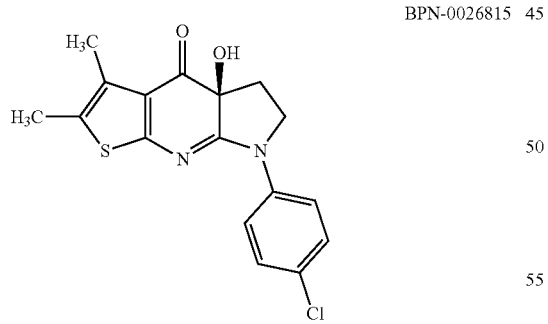

BPN-0026815

(S)-7-(4-Chlorophenyl)-4a-hydroxy-2,3-dimethyl-4a,5,6,7-tetrahydro-4H-pyrrolo[2,3-b]thieno[3,2-e]pyridin-4-one was prepared as a yellow-orange solid according to Synthetic Scheme 3: mp=257-258° C.; $^1$H NMR (500 MHz, DMSO-$d_6$) δ 7.99-7.98 (m, 2H), 7.51-7.49 (m, 2H), 6.88 (s, 1H), 4.14-4.09 (m, 1H), 4.03-4.00 (m, 1H), 2.22-2.19 (m, 8H); ESI MS m/z 347 $[C17H15ClN_2O_2S+H]^+$; HPLC (Method B) >99% (AUC), $t_R$=11.17 min; Chiral HPLC (Chiralpak AD, Method A) 91.2% (AUC), $t_R$=16.03 min.

Preparation of (S)-4-(2-Ethyl-4a-hydroxy-4-oxo-4,4a,5,6-tetrahydro-7H-pyrrolo[2,3-b]thieno[3,2-e]pyridin-7-yl)-2-methylbenzonitrile

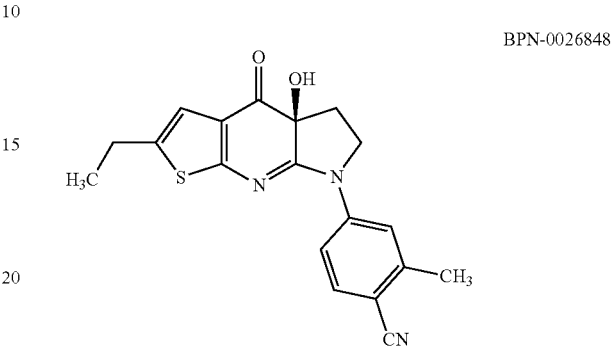

BPN-0026848

(S)-4-(2-Ethyl-4a-hydroxy-4-oxo-4,4a,5,6-tetrahydro-7H-pyrrolo[2,3-b]thieno[3,2-e]pyridin-7-yl)-2-methylbenzonitrile was prepared as an orange solid according to Synthetic Scheme 3: $^1$H NMR (500 MHz, DMSO-$d_6$) δ 8.16 (dd, J=8.6, 2.2 Hz, 1H), 7.91 (d, J=1.7 Hz, 1H), 7.83 (d, J=8.7 Hz, 1H), 6.98 (s, 1H), 6.86 (apparent t, J=1.0 Hz, 1H), 4.13-4.06 (m, 2H), 2.74-2.70 (m, 2H), 2.24-2.21 (m, 2H), 1.22 (t, J=7.5 Hz, 3H), 3H obscured by solvent peak; ESI MS m/z 352 $[C_{19}H_{17}N_3O_2S+H]^+$; HPLC (Method B) >99% (AUC), $t_R$=11.33 min; Chiral HPLC (Chiralpak AD, Method A) 66.7% (AUC), $t_R$=19.14 min.

Preparation of (S)-7-(3-Bromophenyl)-4a-hydroxy-2,3-dimethyl-4a,5,6,7-tetrahydro-4H-pyrrolo[2,3-b]thieno[3,2-e]pyridin-4-one

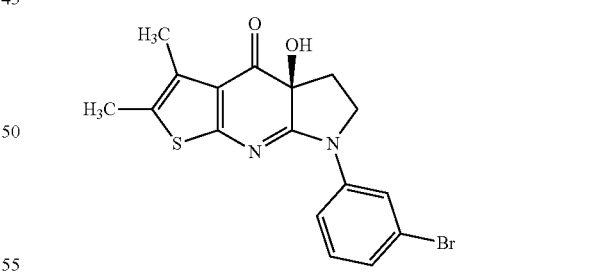

BPN-0026853

(S)-7-(3-Bromophenyl)-4a-hydroxy-2,3-dimethyl-4a,5,6,7-tetrahydro-4H-pyrrolo[2,3-b]thieno[3,2-e]pyridin-4-one was prepared as a yellow solid according to Synthetic Scheme 3: mp=259-260° C.; $^1$H NMR (500 MHz, DMSO-$d_6$) δ 8.27 (apparent t, J=1.9 Hz, 1H), 7.90 (ddd, J=8.0, 2.0, 1.3 Hz, 1H), 7.42-7.36 (m, 2H), 6.90 (s, 1H), 4.14-4.09 (m, 1H), 4.04-4.01 (m, 1H), 2.31-2.19 (m, 8H); ESI MS m/z 391 $[C_{17}H_{15}BrN_2O_2S+H]^+$; HPLC (Method C) 90.9% (AUC), $t_R$=18.45 min; Chiral HPLC (Chiralpak AD, Method A) 98.9% (AUC), $t_R$=14.50 min.

Preparation of (S)-2-Ethyl-4a-hydroxy-7-(4-methoxyphenyl)-4a,5,6,7-tetrahydro-4H-pyrrolo[2,3-b]thieno[3,2-e]pyridin-4-one

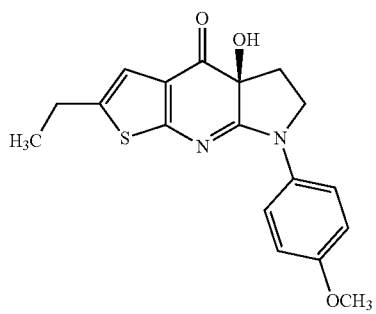

BPN-0026881

(S)-2-Ethyl-4a-hydroxy-7-(4-methoxyphenyl)-4a,5,6,7-tetrahydro-4H-pyrrolo[2,3-b]thieno[3,2-e]pyridin-4-one was prepared as an orange solid according to Synthetic Scheme 3: mp=228-229° C.; $^1$H NMR (500 MHz, DMSO-$d_6$) δ 7.83-7.80 (m, 2H), 7.03-7.00 (m, 2H), 6.83 (s, 1H), 6.78 (apparent t, J=1.2 Hz, 1H), 4.16-4.11 (m, 1H), 3.99-3.96 (m, 1H), 3.77 (s, 3H), 2.68 (q, J=7.4 Hz, 2H), 2.25-2.15 (m, 2H), 1.20 (t, J=7.5 Hz, 3H); ESI MS m/z 343 $[C_{18}H_{18}N_2O_3S+H]^+$; HPLC (Method B) >99% (AUC), $t_R$=10.28 min; Chiral HPLC (Chiralpak AD, Method A) >99% (AUC), $t_R$=22.29 min.

Preparation of (S)-4-(4a-Hydroxy-2,3-dimethyl-4-oxo-4,4a,5,6-tetrahydro-7H-pyrrolo[2,3-b]thieno[3,2-e]pyridin-7-yl)-2-methylbenzonitrile

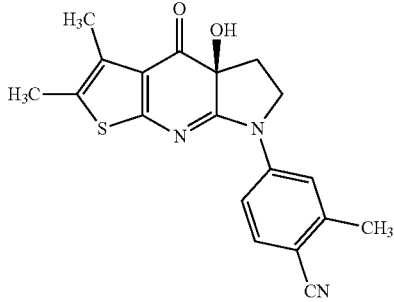

BPN-0026886

(S)-4-(4a-Hydroxy-2,3-dimethyl-4-oxo-4,4a,5,6-tetrahydro-7H-pyrrolo[2,3-b]thieno[3,2-e]pyridin-7-yl)-2-methylbenzonitrile was prepared as an orange solid according to Synthetic Scheme 3: mp=245-246° C.; $^1$H NMR (500 MHz, DMSO-$d_6$) δ 8.17 (dd, J=8.7, 1.9 Hz, 1H), 7.89 (d, J=1.9 Hz, 1H), 7.82 (d, J=8.6 Hz, 1H), 6.95 (s, 1H), 4.14-4.05 (m, 2H), 2.24-2.21 (m, 8H), 3H obscured by solvent peak; ESI MS m/z 352 $[C_{19}H_{17}N_3O_2S+H]^+$; HPLC (Method B) 98.6% (AUC), $t_R$=12.07 min; Chiral HPLC (Chiralpak AD, Method A) 87.8% (AUC), $t_R$=17.22 min.

Preparation of (S)-4-(2-Ethyl-4a-hydroxy-4-oxo-4,4a,5,6-tetrahydro-7H-pyrrolo[2,3-b]thieno[3,2-e]pyridin-7-yl)benzonitrile

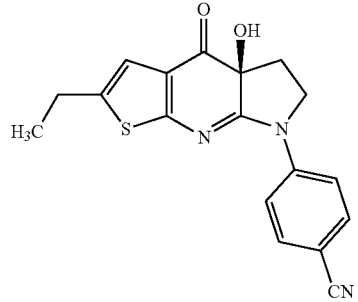

BPN-0027038

(S)-4-(2-Ethyl-4a-hydroxy-4-oxo-4,4a,5,6-tetrahydro-7H-pyrrolo[2,3-b]thieno[3,2-e]pyridin-7-yl)benzonitrile was prepared as an orange solid according to Synthetic Scheme 3: mp=238-239° C.; $^1$H NMR (500 MHz, DMSO-$d_6$) δ 8.19-8.17 (m, 2H), 7.92-7.90 (m, 2H), 6.99 (s, 1H), 6.87 (apparent t, J=1.0 Hz, 1H), 4.17-4.08 (m, 2H), 2.75-2.70 (m, 2H), 2.26-2.22 (m, 2H), 1.22 (t, J=7.5 Hz, 3H); ESI MS m/z 338 $[C_{18}H_{15}N_3O_2S+H]^+$; HPLC (Method B) >99% (AUC), $t_R$=11.89 min; Chiral HPLC (Chiralpak AD, Method A) >99% (AUC), $t_R$=21.29 min.

Preparation of (S)-3a-Hydroxy-6-methyl-1-(quinolin-7-yl)-1,2,3,3a-tetrahydro-4H-pyrrolo[2,3-b]quinolin-4-one

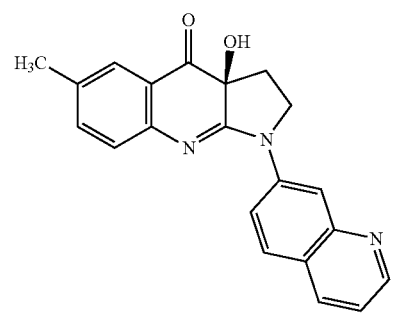

BPN-0027039

(S)-3a-Hydroxy-6-methyl-1-(quinolin-7-yl)-1,2,3,3a-tetrahydro-4H-pyrrolo[2,3-b]quinolin-4-one was prepared as a yellow solid according to Synthetic Scheme 4: mp=242-243° C.; $^1$H NMR (500 MHz, DMSO-$d_6$) δ 8.89 (dd, J=4.3, 1.8 Hz, 1H), 8.59 (d, J=2.2 Hz, 1H), 8.56 (dd, J=9.0, 2.3 Hz, 1H), 8.33 (dd, J=8.2, 1.1 Hz, 1H), 8.02 (d, J=9.0 Hz, 1H), 7.57 (d, J=1.5 Hz, 1H), 7.46 (dd, J=8.2, 4.2 Hz, 1H), 7.42 (dd, J=8.2, 1.9 Hz, 1H), 7.21 (d, J=8.0 Hz, 1H), 6.91 (s, 1H), 4.23-4.14 (m, 2H), 2.34-2.29 (m, 5H); ESI MS m/z 344 $[C_{21}H_{17}N_3O_2+H]^+$; HPLC (Method B) >99% (AUC), $t_R$=10.08 min; Chiral HPLC (Chiralpak AD, Method A) 49.3% (AUC), $t_R$=21.31 min.

Preparation of (S)-3a-Hydroxy-6-methyl-1-(quinolin-6-yl)-1,2,3,3a-tetrahydro-4H-pyrrolo[2,3-b]quinolin-4-one

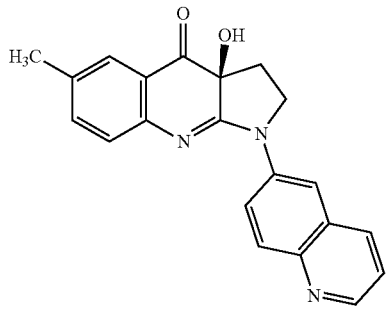

BPN-0027040

(S)-3a-Hydroxy-6-methyl-1-(quinolin-6-yl)-1,2,3,3a-tetrahydro-4H-pyrrolo[2,3-b]quinolin-4-one was prepared as a yellow solid according to Synthetic Scheme 3: mp=236-238° C.; $^1$H NMR (500 MHz, DMSO-d$_6$) δ 8.83 (dd, J=4.2, 1.7 Hz, 1H), 8.77 (dd, J=9.3, 2.6 Hz, 1H), 8.47 (d, J=2.5 Hz, 1H), 8.36 (dd, J=8.6, 0.9 Hz, 1H), 8.07 (d, J=9.3 Hz, 1H), 7.56 (d, J=1.7 Hz, 1H), 7.53 (dd, J=8.3, 4.2 Hz, 1H), 7.42 (dd, J=8.4, 1.9 Hz, 1H), 7.23 (d, J=8.0 Hz, 1H), 6.91 (s, 1H), 4.21-4.12 (m, 2H), 2.34-2.30 (m, 5H); ESI MS m/z 344 [C$_{21}$H$_{17}$N$_3$O$_2$+H]$^+$; HPLC (Method B) >99% (AUC), t$_R$=6.83 min; Chiral HPLC (Chiralpak AD, Method A) 94.1% (AUC), t$_R$=19.50 min.

Preparation of (S)-3a-Hydroxy-1-(isoquinolin-7-yl)-6-methyl-1,2,3,3a-tetrahydro-4H-pyrrolo[2,3-b]quinolin-4-one

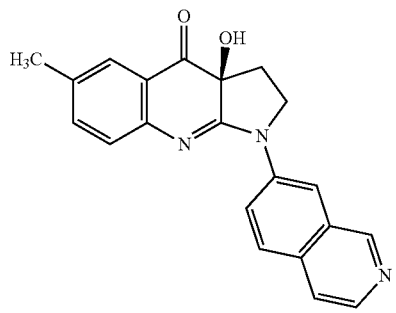

BPN-0027042

(S)-3a-Hydroxy-1-(isoquinolin-7-yl)-6-methyl-1,2,3,3a-tetrahydro-4H-pyrrolo[2,3-b]quinolin-4-one was prepared as a yellow solid according to Synthetic Scheme 4: mp=217-218° C.; $^1$H NMR (500 MHz, DMSO-d$_6$) δ 9.32 (s, 1H), 8.77 (dd, J=9.1, 2.3 Hz, 1H), 8.63 (d, J=2.0 Hz, 1H), 8.44 (d, J=5.7 Hz, 1H), 8.03 (d, J=9.1 Hz, 1H), 7.80 (d, J=5.7 Hz, 1H), 7.57 (d, J=1.5 Hz, 1H), 7.42 (dd, J=8.2, 1.9 Hz, 1H), 7.24 (d, J=8.1 Hz, 1H), 6.91 (s, 1H), 4.22-4.13 (m, 2H), 2.34-2.31 (m, 5H); ESI MS m/z 344 [C$_{21}$H$_{17}$N$_3$O$_2$+H]$^+$; HPLC (Method B) >99% (AUC), t$_R$=9.72 min; Chiral HPLC (Chiralpak AD, Method A) >99% (AUC), t$_R$=20.95 min.

Preparation of (S)-4a-Hydroxy-7-(4-iodophenyl)-2,3-dimethyl-4a,5,6,7-tetrahydro-4H-pyrrolo[2,3-b]thieno[3,2-e]pyridin-4-one

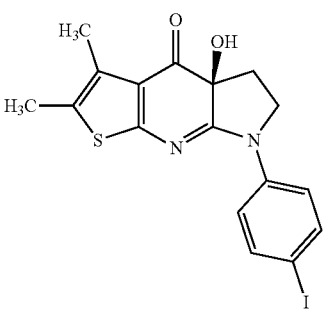

BPN-0027081

(S)-4a-Hydroxy-7-(4-iodophenyl)-2,3-dimethyl-4a,5,6,7-tetrahydro-4H-pyrrolo[2,3-b]thieno[3,2-e]pyridin-4-one was prepared as an orange solid according to Synthetic Scheme 3: mp=251-252° C.; $^1$H NMR (500 MHz, DMSO-d$_6$) δ 7.78 (s, 4H), 6.88 (s, 1H), 4.12-4.07 (m, 1H), 4.01-3.96 (m, 1H), 2.22-2.18 (m, 8H); ESI MS m/z 439 [C$_{17}$H$_{15}$IN$_2$O$_2$S+H]$^+$; HPLC (Method B) >99% (AUC), t$_R$=11.15 min; Chiral HPLC (Chiralpak AD, Method A) 89.8% (AUC), t$_R$=17.96 min.

Preparation of (S)-3a-Hydroxy-1-(4-iodophenyl)-6,7-dimethyl-1,2,3,3a-tetrahydro-4H-pyrrolo[2,3-b]quinolin-4-one

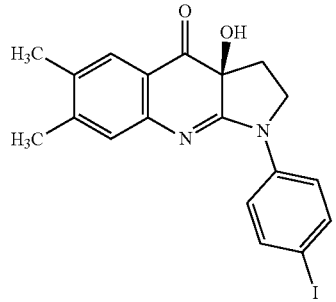

BPN-0027109

(S)-3a-Hydroxy-1-(4-iodophenyl)-6,7-dimethyl-1,2,3,3a-tetrahydro-4H-pyrrolo[2,3-b]quinolin-4-one was prepared as a yellow solid according to Synthetic Scheme 3: mp=240-241° C.; $^1$H NMR (500 MHz, DMSO-d$_6$) δ 7.95-7.93 (m, 2H), 7.75-7.73 (m, 2H), 7.49 (s, 1H), 7.05 (s, 1H), 6.79 (s, 1H), 4.01-3.96 (m, 1H), 3.94-3.89 (m, 1H), 2.27 (s, 3H), 2.25-2.22 (m, 5H); ESI MS m/z 433 [C$_{19}$H$_{17}$IN$_2$O$_2$+H]$^+$; HPLC (Method B) >99% (AUC), t$_R$=8.61 min; Chiral HPLC (Chiralpak AD, Method A) 91.4% (AUC), t$_R$=18.01 min.

Preparation of (S)-1-(Benzo[d]thiazol-5-yl)-3a-hydroxy-6,7-dimethyl-1,2,3,3a-tetrahydro-4H-pyrrolo[2,3-b]quinolin-4-one

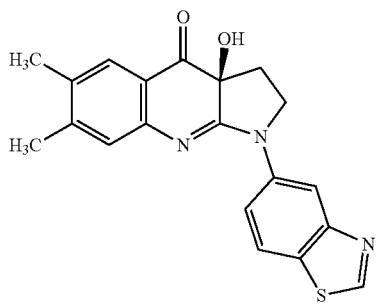

BPN-0027121

(S)-1-(Benzo[d]thiazol-5-yl)-3a-hydroxy-6,7-dimethyl-1,2,3,3a-tetrahydro-4H-pyrrolo[2,3-b]quinolin-4-one was prepared as a yellow solid according to Synthetic Scheme 6: $^1$H NMR (500 MHz, DMSO-$d_6$) δ 9.42 (s, 1H), 8.85 (d, J=2.1 Hz, 1H), 8.28 (dd, J=8.9, 2.2 Hz, 1H), 8.19 (d, J=8.9 Hz, 1H), 7.51 (s, 1H), 7.10 (s, 1H), 6.82 (s, 1H), 4.19-4.14 (m, 1H), 4.09-4.06 (m, 1H), 2.30-2.28 (m, 5H), 2.23 (s, 3H); ESI MS m/z 364 [$C_{20}H_{17}N_3O_2S$+H]$^+$; HPLC (Method B) 95.3% (AUC), $t_R$=8.01 min; Chiral HPLC (Chiralpak AD, Method A) 70.3% (AUC), $t_R$=27.20 min.

Preparation of (S)-1-(Benzo[d]thiazol-6-yl)-3a-hydroxy-6,7-dimethyl-1,2,3,3a-tetrahydro-4H-pyrrolo[2,3-b]quinolin-4-one

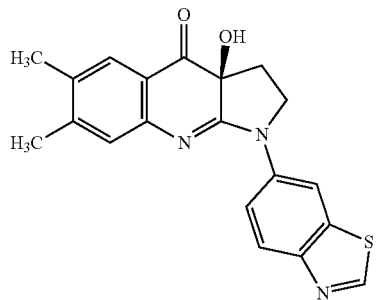

BPN-0027122

(S)-1-(Benzo[d]thiazol-6-yl)-3a-hydroxy-6,7-dimethyl-1,2,3,3a-tetrahydro-4H-pyrrolo[2,3-b]quinolin-4-one was prepared as a yellow solid according to Synthetic Scheme 6: $^1$H NMR (500 MHz, DMSO-$d_6$) δ 9.32 (s, 1H), 8.90 (d, J=2.3 Hz, 1H), 8.35 (dd, J=9.0, 2.3 Hz, 1H), 8.12 (d, J=9.0 Hz, 1H), 7.51 (s, 1H), 7.13 (s, 1H), 6.82 (s, 1H), 4.17-4.12 (m, 1H), 4.07-4.04 (m, 1H), 2.30-2.29 (m, 5H), 2.23 (s, 3H); ESI MS m/z 364 [$C_{20}H_{17}N_3O_2S$+H]$^+$; HPLC (Method B) 97.5% (AUC), $t_R$=7.92 min; Chiral HPLC (Chiralpak AD, Method A) 83.3% (AUC), $t_R$=21.14 min.

Preparation of (S)-3a-Hydroxy-6-methyl-1-(3-methylquinolin-6-yl)-1,2,3,3a-tetrahydro-4H-pyrrolo[2,3-b]quinolin-4-one

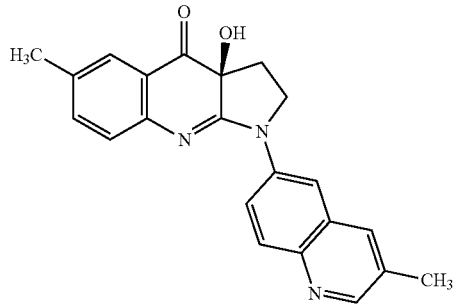

BPN-0027160

(S)-3a-Hydroxy-6-methyl-1-(3-methylquinolin-6-yl)-1,2,3,3a-tetrahydro-4H-pyrrolo[2,3-b]quinolin-4-one was prepared as a yellow solid according to Synthetic Scheme 4: mp=263-264° C.; $^1$H NMR (500 MHz, DMSO-$d_6$) δ 8.69 (d, J=2.1 Hz, 1H), 8.63 (dd, J=9.3, 2.5 Hz, 1H), 8.43 (d, J=2.5 Hz, 1H), 8.12 (s, 1H), 8.01 (d, J=9.3 Hz, 1H), 7.56 (d, J=1.6 Hz, 1H), 7.41 (dd, J=8.4, 2.0 Hz, 1H), 7.22 (d, J=8.1 Hz, 1H), 6.89 (s, 1H), 4.20-4.10 (m, 2H), 2.32-2.31 (m, 5H), 3H obscured by solvent peak; ESI MS m/z 358 [$C_{22}H_{19}N_3O_2$+H]$^+$; HPLC (Method C) 97.1% (AUC), $t_R$=11.24 min; Chiral HPLC (Chiralpak AD, Method A) 81.9% (AUC), $t_R$=18.76 min.

Preparation of (S)-3a-Hydroxy-6,7-dimethyl-1-(3-methylisoquinolin-6-yl)-1,2,3,3a-tetrahydro-4H-pyrrolo[2,3-b]quinolin-4-one

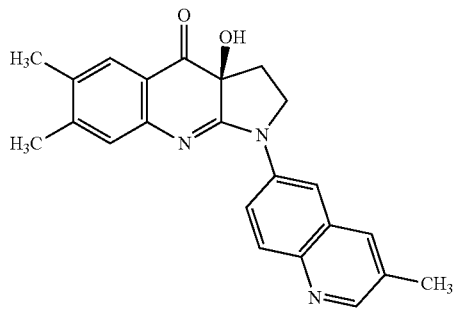

BPN-0027161

(S)-3a-Hydroxy-6,7-dimethyl-1-(3-methylisoquinolin-6-yl)-1,2,3,3a-tetrahydro-4H-pyrrolo[2,3-b]quinolin-4-one was prepared as a yellow solid according to Synthetic Scheme 4: mp=265-267° C.; $^1$H NMR (500 MHz, DMSO-$d_6$) δ 8.69 (d, J=2.1 Hz, 1H), 8.63 (dd, J=9.3, 2.6 Hz, 1H), 8.43 (d, J=2.5 Hz, 1H), 8.12 (s, 1H), 8.01 (d, J=9.2 Hz, 1H), 7.51 (s, 1H), 7.14 (s, 1H), 6.84 (s, 1H), 4.19-4.09 (m, 2H), 2.32-2.30 (m, 5H), 2.24 (s, 3H), 3H obscured by solvent peak; ESI MS m/z 372 [$C_{23}H_{21}N_3O_2$+H]$^+$; HPLC (Method B) >99% (AUC), $t_R$=7.61 min; Chiral HPLC (Chiralpak AD, Method A) 73.7% (AUC), $t_R$=19.44 min.

Preparation of (S)-3a-Hydroxy-6,7-dimethyl-1-(quinolin-6-yl)-1,2,3,3a-tetrahydro-4H-pyrrolo[2,3-b]quinolin-4-one

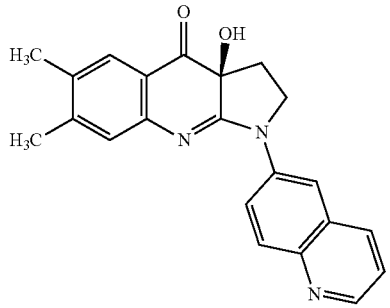

BPN-0027215

(S)-3a-Hydroxy-6,7-dimethyl-1-(quinolin-6-yl)-1,2,3,3a-tetrahydro-4H-pyrrolo[2,3-b]quinolin-4-one was prepared as a yellow solid according to Synthetic Scheme 4: mp=246-247° C.; $^1$H NMR (500 MHz, DMSO-d$_6$) δ 8.83 (dd, J=4.2, 1.7 Hz, 1H), 8.79 (dd, J=9.3, 2.6 Hz, 1H), 8.45 (d, J=2.5 Hz, 1H), 8.36 (d, J=7.6 Hz, 1H), 8.06 (d, J=9.3 Hz, 1H), 7.54-7.52 (m, 2H), 7.15 (s, 1H), 6.85 (s, 1H), 4.20-4.09 (m, 2H), 2.33-2.30 (m, 5H), 2.24 (s, 3H); ESI MS m/z 358 [C$_{22}$H$_{19}$N$_3$O$_2$+H]$^+$; HPLC (Method B) >97.9% (AUC), t$_R$=8.10 min; Chiral HPLC (Chiralpak AD, Method A) 61.1% (AUC), t$_R$=20.30 min.

Preparation of (S)-4a-Hydroxy-2-methyl-7-(quinolin-6-yl)-4a,5,6,7-tetrahydro-4H-pyrrolo[2,3-b]thieno[3,2-e]pyridin-4-one

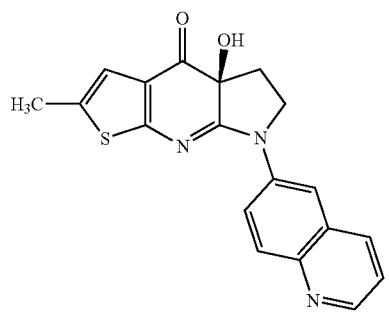

BPN-0027216

(S)-4a-Hydroxy-2-methyl-7-(quinolin-6-yl)-4a,5,6,7-tetrahydro-4H-pyrrolo[2,3-b]thieno[3,2-e]pyridin-4-one was prepared as a red-orange solid according to Synthetic Scheme 3: mp=242-243° C.; $^1$H NMR (500 MHz, DMSO-d$_6$) δ 8.86 (dd, J=4.2, 1.6 Hz, 1H), 8.60 (dd, J=9.3, 2.6 Hz, 1H), 8.37 (d, J=7.6 Hz, 1H), 8.31 (d, J=2.5 Hz, 1H), 8.09 (d, J=9.3 Hz, 1H), 7.55 (dd, J=8.3, 4.2 Hz, 1H), 6.97 (s, 1H), 6.82 (d, J=1.3 Hz, 1H), 4.30-4.25 (m, 1H), 4.21-4.18 (m, 1H), 2.37-2.36 (m, 3H), 2.30-2.27 (m, 2H); ESI MS m/z 350 [C$_{19}$H$_{15}$N$_3$O$_2$S+H]$^+$; HPLC (Method C) 98.7% (AUC), t$_R$=11.45 min; Chiral HPLC (Chiralpak AD, Method A) >99% (AUC), t$_R$=21.33 min.

Preparation of (S)-2-Ethyl-4a-hydroxy-7-(quinolin-6-yl)-4a,5,6,7-tetrahydro-4H-pyrrolo[2,3-b]thieno[3,2-e]pyridin-4-one

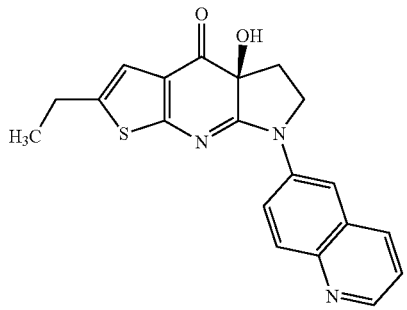

BPN-0027217

(S)-4a-Hydroxy-2-methyl-7-(quinolin-6-yl)-4a,5,6,7-tetrahydro-4H-pyrrolo[2,3-b]thieno[3,2-e]pyridin-4-one was prepared as an orange-brown solid according to Synthetic Scheme 3: mp=217-219° C.; $^1$H NMR (500 MHz, DMSO-d$_6$) δ 8.86 (dd, J=4.2, 1.6 Hz, 1H), 8.59 (dd, J=9.3, 2.6 Hz, 1H), 8.37 (d, J=8.5 Hz, 1H), 8.32 (d, J=2.4 Hz, 1H), 8.09 (d, J=9.3 Hz, 1H), 7.55 (dd, J=8.3, 4.2 Hz, 1H), 6.97 (s, 1H), 6.85 (s, 1H), 4.30-4.25 (m, 1H), 4.21-4.18 (m, 1H), 2.72 (q, J=7.5 Hz, 2H), 2.31-2.27 (m, 2H), 2.23 (t, J=7.5 Hz, 3H); ESI MS m/z 364 [C$_{20}$H$_{17}$N$_3$O$_2$S+H]$^+$; HPLC (Method C) >99% (AUC), t$_R$=12.26 min; Chiral HPLC (Chiralpak AD, Method A) >99% (AUC), t$_R$=20.87 min.

Preparation of (S)-4-(3a-Hydroxy-4-oxo-2,3,3a,4,5,6,7,8-octahydro-1H-benzo[4,5]thieno[2,3-b]pyrrolo[3,2-e]pyridin-1-yl)benzonitrile

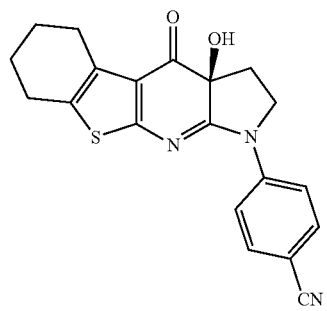

BPN-0027236

(S)-4-(3a-Hydroxy-4-oxo-2,3,3a,4,5,6,7,8-octahydro-1H-benzo[4,5]thieno[2,3-b]pyrrolo[3,2-e]pyridin-1-yl)benzonitrile was prepared as a yellow-brown solid according to Synthetic Scheme 3: $^1$H NMR (500 MHz, DMSO-d$_6$) δ 8.18-8.16 (m, 2H), 7.92-7.90 (m, 2H), 6.96 (s, 1H), 4.16-4.08 (m, 2H), 2.24-2.21 (m, 2H), 1.84-1.65 (m, 7H); ESI MS m/z 364 [C$_{20}$H$_{17}$N$_3$O$_2$S+H]$^+$; HPLC (Method B) 95.4% (AUC), t$_R$=10.52 min; Chiral HPLC (Chiralpak AD, Method A) 55.9% (AUC), t$_R$=19.88 min.

Preparation of (S)-2-Chloro-4-(4a-hydroxy-2,3-dimethyl-4-oxo-4,4a,5,6-tetrahydro-7H-pyrrolo[2,3-b]thieno[3,2-e]pyridin-7-yl)benzonitrile Preparation of (S)-2-Chloro-4-(4a-hydroxy-2-methyl-4-oxo-4,4a,5,6-tetrahydro-7H-pyrrolo[2,3-b]thieno[3,2-e]pyridin-7-yl)benzonitrile

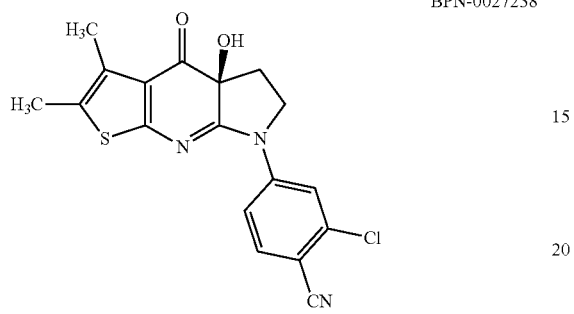

(S)-2-Chloro-4-(4a-hydroxy-2,3-dimethyl-4-oxo-4,4a,5,6-tetrahydro-7H-pyrrolo[2,3-b]thieno[3,2-e]pyridin-7-yl)benzonitrile was prepared as an orange solid according to Synthetic Scheme 3: mp=275-276° C.; $^1$H NMR (500 MHz, DMSO-d$_6$) δ 8.38 (d, J=2.2 Hz, 1H), 8.13 (dd, J=8.8, 2.2 Hz, 1H), 8.02 (d, J=8.8 Hz, 1H), 7.01 (s, 1H), 4.13-4.10 (m, 2H), 2.26 (s, 3H), 2.14-2.22 (m, 5H); ESI MS m/z 372 [C$_{18}$H$_{14}$ClN$_3$O$_2$S+H]$^+$; HPLC (Method B) 96.7% (AUC), t$_R$=10.69 min; Chiral HPLC (Chiralpak AD, Method A) 90.8% (AUC), t$_R$=20.01 min.

(S)-2-Chloro-4-(4a-hydroxy-2-methyl-4-oxo-4,4a,5,6-tetrahydro-7H-pyrrolo[2,3-b]thieno[3,2-e]pyridin-7-yl)benzonitrile was prepared as an orange solid according to Synthetic Scheme 3: $^1$H NMR (500 MHz, DMSO-d$_6$) δ 8.37 (d, J=2.2 Hz, 1H), 8.15 (dd, J=8.8, 2.2 Hz, 1H), 8.02 (d, J=8.8 Hz, 1H), 7.03 (s, 1H), 6.87 (d, J=1.3 Hz, 1H), 4.14-4.10 (m, 2H), 2.38 (d, J=1.2 Hz, 3H), 2.25-2.22 (m, 2H); ESI MS m/z 358 [C$_{17}$H$_{12}$ClN$_3$O$_2$S+H]$^+$; HPLC (Method C) 98.3% (AUC), t$_R$=16.02 min; Chiral HPLC (Chiralpak AD, Method A) 96.7% (AUC), t$_R$=20.06 min.

Preparation of (S)-3a-Hydroxy-1-(quinolin-6-yl)-1,2,3,3a,5,6,7,8-octahydro-4H-benzo[4,5]thieno[2,3-b]pyrrolo[3,2-e]pyridin-4-one Preparation of (S)-4a-Hydroxy-2,3-dimethyl-7-(quinolin-6-yl)-4a,5,6,7-tetrahydro-4H-pyrrolo[2,3-b]thieno[3,2-e]pyridin-4-one

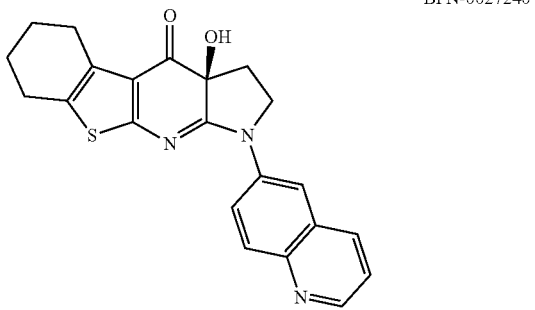

(S)-3a-Hydroxy-1-(quinolin-6-yl)-1,2,3,3a,5,6,7,8-octahydro-4H-benzo[4,5]thieno[2,3-b]pyrrolo[3,2-e]pyridin-4-one was prepared as an orange solid according to Synthetic Scheme 3: mp=245-246° C.; $^1$H NMR (500 MHz, DMSO-d$_6$) δ 8.86 (dd, J=4.2, 1.7 Hz, 1H), 8.62 (dd, J=9.3, 2.6 Hz, 1H), 8.37 (dd, J=8.3, 1.1 Hz, 1H), 8.30 (d, J=2.6 Hz, 1H), 8.09 (d, J=9.2 Hz, 1H), 7.54 (dd, J=8.3, 4.2 Hz, 1H), 6.95 (s, 1H), 4.29-4.24 (m, 1H), 4.21-4.18 (m, 1H), 2.65-2.57 (m, 4H), 2.31-2.25 (m, 2H), 1.79-1.70 (m, 4H); ESI MS m/z 390 [C$_{22}$H$_{19}$N$_3$O$_2$S+H]$^+$; HPLC (Method B) 97.8% (AUC), t$_R$=9.06 min; Chiral HPLC (Chiralpak AD, Method A) 82.3% (AUC), t$_R$=19.47 min.

(S)-4a-Hydroxy-2,3-dimethyl-7-(quinolin-6-yl)-4a,5,6,7-tetrahydro-4H-pyrrolo[2,3-b]thieno[3,2-e]pyridin-4-one was prepared as an orange-brown solid according to Synthetic Scheme 3: mp=219-224° C. $^1$H NMR (500 MHz, DMSO-d$_6$) δ 8.85 (dd, J=4.1, 1.6 Hz, 1H), 8.61 (dd, J=9.1, 2.6 Hz, 1H), 8.37 (d, J=8.6 Hz, 1H), 8.30 (d, J=2.7 Hz, 1H), 8.09 (d, J=9.5 Hz, 1H), 7.54 (dd, J=8.3, 4.2 Hz, 1H), 6.94 (s, 1H), 4.28-4.23 (m, 1H), 4.21-4.18 (m, 1H), 2.25-2.23 (m, 8H); ESI MS m/z 364 [C$_{20}$H$_{17}$N$_3$O$_2$S+H]$^+$; HPLC (Method C) 95.8% (AUC), t$_R$=12.69 min; Chiral HPLC (Chiralpak AD, Method A) 89.5% (AUC), t$_R$=19.48 min.

Preparation of (S)-6-(3a-Hydroxy-6-methyl-4-oxo-2,3,3a,4-tetrahydro-1H-pyrrolo[2,3-b]quinolin-1-yl)quinoline-2-carbonitrile

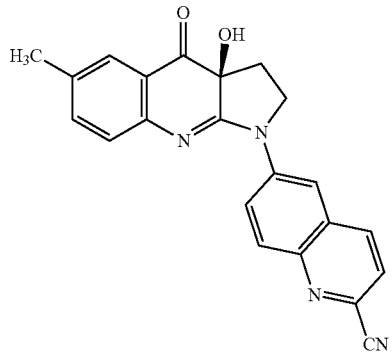

BPN-0027393

(S)-6-(3a-Hydroxy-6-methyl-4-oxo-2,3,3a,4-tetrahydro-1H-pyrrolo[2,3-b]quinolin-1-yl)quinoline-2-carbonitrile was prepared as a yellow-orange solid according to Synthetic Scheme 6: mp=271-273° C.; $^1$H NMR (500 MHz, DMSO-$d_6$) δ 9.01 (dd, J=9.4, 2.5 Hz, 1H), 8.64-8.60 (m, 2H), 8.19 (d, J=9.4 Hz, 1H), 8.01 (d, J=8.4 Hz, 1H), 7.58 (d, J=1.3 Hz, 1H), 7.45 (dd, J=8.0, 2.1 Hz, 1H), 7.29 (d, J=8.0 Hz, 1H), 6.96 (s, 1H), 4.19-4.16 (m, 2H), 2.35-2.31 (m, 5H); ESI MS m/z 369 $[C_{22}H_{16}N_4O_2+H]^+$; HPLC (Method C) 99.0% (AUC), $t_R$=13.28 min; Chiral HPLC (Chiralpak AD, Method A) 96.3% (AUC), $t_R$=22.01 min.

Preparation of (S)-1-(Benzo[c][1,2,5]thiadiazol-5-yl)-3a-hydroxy-6-methyl-1,2,3,3a-tetrahydro-4H-pyrrolo[2,3-b]quinolin-4-one

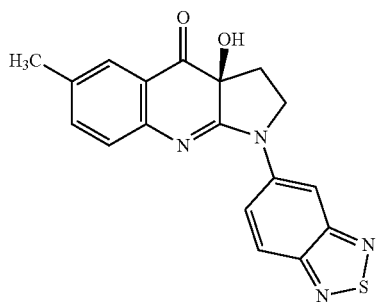

BPN-0027394

(S)-1-(Benzo[c][1,2,5]thiadiazol-5-yl)-3a-hydroxy-6-methyl-1,2,3,3a-tetrahydro-4H-pyrrolo[2,3-b]quinolin-4-one was prepared as an orange-yellow solid according to Synthetic Scheme 6: mp=231-232° C.; $^1$H NMR (500 MHz, DMSO-$d_6$) δ 8.80 (dd, J=9.7, 2.2 Hz, 1H), 8.60 (d, J=2.1 Hz, 1H), 8.13 (d, J=9.6 Hz, 1H), 7.58 (d, J=1.7 Hz, 1H), 7.43 (dd, J=8.2, 1.9 Hz, 1H), 7.23 (d, J=8.0 Hz, 1H), 6.95 (s, 1H), 4.23-4.13 (m, 2H), 2.34-2.29 (m, 5H); ESI MS m/z 351 $[C_{18}H_{14}N_4O_2S+H]^+$; HPLC (Method C) 98.8% (AUC), $t_R$=12.54 min; Chiral HPLC (Chiralpak AD, Method A) >99% (AUC), $t_R$=18.44 min.

Preparation of (S)-3a-Hydroxy-6-methyl-1-(thieno[2,3-b]pyridin-5-yl)-1,2,3,3a-tetrahydro-4H-pyrrolo[2,3-b]quinolin-4-one

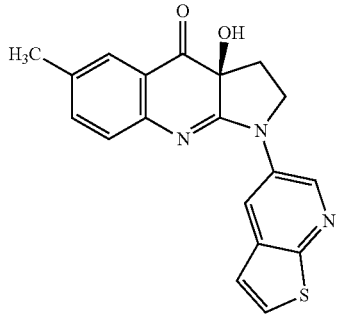

BPN-0027410

(S)-3a-Hydroxy-6-methyl-1-(thieno[2,3-b]pyridin-5-yl)-1,2,3,3a-tetrahydro-4H-pyrrolo[2,3-b]quinolin-4-one was prepared as a yellow solid according to Synthetic Scheme 6: mp=208-210° C.; $^1$H NMR (500 MHz, DMSO-$d_6$) δ 9.33 (d, J=2.5 Hz, 1H), 8.94 (d, J=2.5 Hz, 1H), 7.93 (d, J=5.9 Hz, 1H), 7.56 (d, J=1.7 Hz, 1H), 7.50 (d, J=5.9 Hz, 1H), 7.41 (dd, J=8.1, 2.1 Hz, 1H), 7.18 (d, J=8.1 Hz, 1H), 6.91 (s, 1H), 4.20-4.15 (m, 1H), 4.09-4.06 (m, 1H), 2.34-2.26 (m, 5H); ESI MS m/z 350 $[C_{19}H_{15}N_3O_2S+H]^+$; UPLC (Method A) 97.9% (AUC), $t_R$=2.96 min; Chiral HPLC (Chiralpak AD, Method A) 96.8% (AUC), $t_R$=19.56 min.

Preparation of (S)-3a-Hydroxy-6-methyl-1-(2-methylbenzo[d]thiazol-5-yl)-1,2,3,3a-tetrahydro-4H-pyrrolo[2,3-b]quinolin-4-one

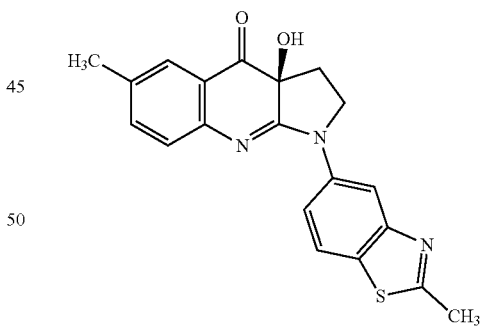

BPN-0027411

(S)-3a-Hydroxy-6-methyl-1-(2-methylbenzo[d]thiazol-5-yl)-1,2,3,3a-tetrahydro-4H-pyrrolo[2,3-b]quinolin-4-one was prepared as a yellow solid according to Synthetic Scheme 6: mp=258-259° C.; $^1$H NMR (500 MHz, DMSO-$d_6$) δ 8.71 (d, J=2.1 Hz, 1H), 8.12 (dd, J=8.9, 2.2 Hz, 1H), 8.04 (d, J=8.8 Hz, 1H), 7.55 (d, J=1.3 Hz, 1H), 7.39 (dd, J=8.2, 1.9 Hz, 1H), 7.16 (d, J=8.1 Hz, 1H), 6.87 (s, 1H), 4.18-4.13 (m, 1H), 4.06-4.03 (m, 1H), 2.81 (s, 3H), 2.31-2.26 (m, 5H); ESI MS m/z 364 $[C_{20}H_{17}N_3O_2S+H]^+$; UPLC (Method A) >99% (AUC), $t_R$=3.00 min; Chiral HPLC (Chiralpak AD, Method A) 74.7% (AUC), $t_R$=21.78 min.

Preparation of (S)-1-(3,4-Dihydro-2H-benzo[b][1,4]oxazin-7-yl)-3a-hydroxy-6-methyl-1,2,3,3a-tetrahydro-4H-pyrrolo[2,3-b]quinolin-4-one

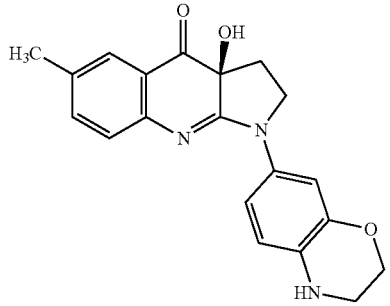

BPN-0027412

(S)-1-(3,4-Dihydro-2H-benzo[b][1,4]oxazin-7-yl)-3a-hydroxy-6-methyl-1,2,3,3a-tetrahydro-4H-pyrrolo[2,3-b]quinolin-4-one was prepared as an orange solid according to Synthetic Scheme 4: mp=207-208° C.; $^1$H NMR (500 MHz, DMSO-$d_6$) δ 7.53 (d, J=2.4 Hz, 1H), 7.48 (d, J=1.6 Hz, 1H), 7.32 (dd, J=8.1, 2.0 Hz, 1H), 7.21 (dd, J=8.7, 2.5 Hz, 1H), 7.02 (d, J=8.1 Hz, 1H), 6.71 (s, 1H), 6.58 (d, J=8.6 Hz, 1H), 5.73 (s, 1H), 4.15-4.13 (m, 2H), 3.99-3.94 (m, 1H), 3.85-3.81 (m, 1H), 2.28 (s, 3H), 2.21-2.18 (m, 2H), 2H obscured by solvent peak; ESI MS m/z 350 $[C_{20}H_{19}N_3O_3+H]^+$; UPLC (Method A) 96.6% (AUC), $t_R$=2.96 min; Chiral HPLC (Chiralpak AD, Method A) >99% (AUC), $t_R$=23.12 min.

Preparation of (S)-1-([1,2,4]Triazolo[1,5-a]pyridin-7-yl)-3a-hydroxy-6-methyl-1,2,3,3a-tetrahydro-4H-pyrrolo[2,3-b]quinolin-4-one

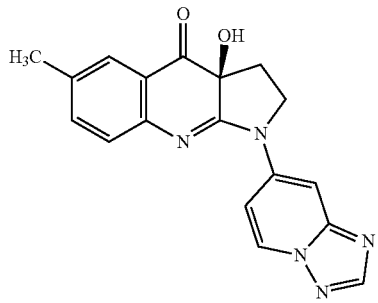

BNP-0027441

(S)-1-([1,2,4]Triazolo[1,5-a]pyridin-7-yl)-3a-hydroxy-6-methyl-1,2,3,3a-tetrahydro-4H-pyrrolo[2,3-b]quinolin-4-one was prepared as a yellow solid according to Synthetic Scheme 6: mp=260-261° C.; $^1$H NMR (500 MHz, DMSO-$d_6$) δ 8.95 (d, J=7.7 Hz, 1H), 8.43 (s, 1H), 8.35 (d, J=2.2 Hz, 1H), 8.29 (dd, J=7.6, 2.4 Hz, 1H), 7.59 (d, J=1.6 Hz, 1H), 7.45 (dd, J=8.3, 2.0 Hz, 1H), 7.25 (d, J=8.0 Hz, 1H), 6.97 (s, 1H), 4.15-4.10 (m, 2H), 2.35-2.27 (m, 5H); ESI MS m/z 334 $[C_{18}H_{15}N_5O_2+H]^+$; UPLC (Method A) 98.0% (AUC), $t_R$=2.85 min; Chiral HPLC (Chiralpak AD, Method A) 64.4% (AUC), $t_R$=20.26 min.

Preparation of (S)-1-(2-Aminoquinolin-6-yl)-3a-hydroxy-6-methyl-1,2,3,3a-tetrahydro-4H-pyrrolo[2,3-b]quinolin-4-one

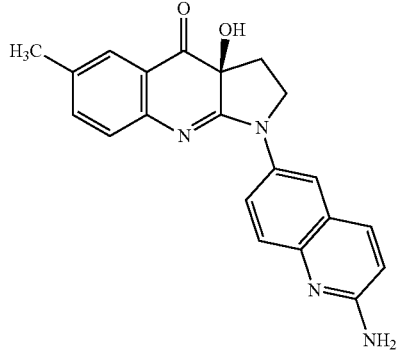

BPN-0027494

(S)-1-(2-Aminoquinolin-6-yl)-3a-hydroxy-6-methyl-1,2,3,3a-tetrahydro-4H-pyrrolo[2,3-b]quinolin-4-one was prepared as a yellow-orange solid according to Synthetic Scheme 6: mp=261-262° C.; $^1$H NMR (500 MHz, DMSO-$d_6$) δ 8.36 (dd, J=9.1, 2.6 Hz, 1H), 8.14 (d, J=2.5 Hz, 1H), 7.90 (d, J=8.9 Hz, 1H), 7.53 (d, J=2.0 Hz, 1H), 7.49 (d, J=9.2 Hz, 1H), 7.37 (dd, J=8.5, 1.8 Hz, 1H), 7.13 (d, J=8.1 Hz, 1H), 6.82 (s, 1H), 6.78 (d, J=8.9 Hz, 1H), 6.38 (s, 2H), 4.15-4.10 (m, 1H), 4.04-4.01 (m, 1H), 2.30-2.27 (m, 5H); ESI MS m/z 359 $[C_{21}H_{18}N_4O_2+H]^+$; UPLC (Method A) >99% (AUC), $t_R$=2.42 min.

Preparation of (S)-3-Chloro-5-(3a-hydroxy-6-methyl-4-oxo-2,3,3a,4-tetrahydro-1H-pyrrolo[2,3-b]quinolin-1-yl)picolinonitrile

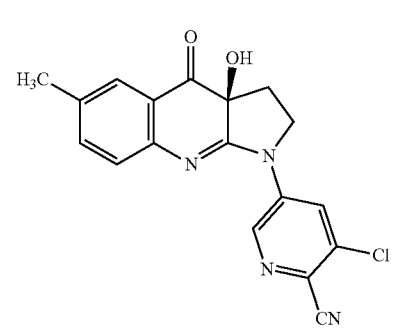

BPN-0028646

(S)-3-Chloro-5-(3a-hydroxy-6-methyl-4-oxo-2,3,3a,4-tetrahydro-1H-pyrrolo[2,3-b]quinolin-1-yl)picolinonitrile was prepared as a yellow solid according to Synthetic Scheme 6: mp=243-245° C.; $^1$H NMR (500 MHz, DMSO-$d_6$) δ 9.42 (d, J=2.3 Hz, 1H), 9.01 (d, J=2.3 Hz, 1H), 7.60 (d, J=1.5 Hz, 1H), 7.46 (ddd, J=8.0, 2.2, 0.7 Hz, 1H), 7.28 (d, J=8.1 Hz, 1H), 7.02 (s, 1H), 4.14-4.04 (m, 2H), 2.34-2.29 (m, 5H); ESI MS m/z 352 $[C_{18}H_{13}ClN_4O_2+H]^+$; UPLC (Method A) >99% (AUC), $t_R$=4.64 min; Chiral HPLC (Chiralpak AD, Method A) >99% (AUC), $t_R$=17.22 min.

Preparation of (S)-1-(3-Aminoquinolin-6-yl)-3a-hydroxy-6-methyl-1,2,3,3a-tetrahydro-4H-pyrrolo[2,3-b]quinolin-4-one

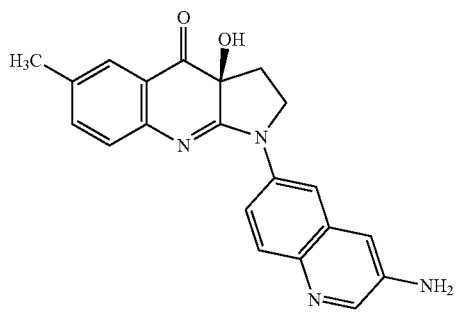

BPN-0028652

(S)-1-(3-Aminoquinolin-6-yl)-3a-hydroxy-6-methyl-1,2,3,3a-tetrahydro-4H-pyrrolo[2,3-b]quinolin-4-one was prepared as a yellow solid according to Synthetic Scheme 6: mp=243-244° C.; $^1$H NMR (500 MHz, DMSO-d$_6$) δ 8.36 (d, J=2.7 Hz, 1H), 8.28 (dd, J=9.2, 2.5 Hz, 1H), 8.08 (d, J=2.5 Hz, 1H), 7.79 (d, J=9.2 Hz, 1H), 7.55 (d, J=1.8 Hz, 1H), 7.39 (dd, J=8.1, 2.2 Hz, 1H), 7.16 (d, J=8.1 Hz, 1H), 7.12 (d, J=2.6 Hz, 1H), 6.85 (s, 1H), 5.66 (s, 2H), 4.17-4.12 (m, 1H), 4.09-4.05 (m, 1H), 2.31-2.28 (m, 5H); ESI MS m/z 358 [C$_{21}$H$_{18}$N$_4$O$_2$+H]$^+$; UPLC (Method A) >99% (AUC), t$_R$=2.44 min; Chiral HPLC (Chiralpak AD, Method A) >99% (AUC), t$_R$=21.10 min.

Preparation of (S)-1-(5,6-Dimethylpyridin-3-yl)-3a-hydroxy-6,7-dimethyl-1,2,3,3a-tetrahydro-4H-pyrrolo[2,3-b]quinolin-4-one

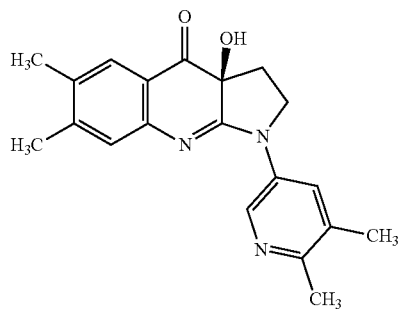

BPN-0028694

(S)-1-(5,6-Dimethylpyridin-3-yl)-3a-hydroxy-6,7-dimethyl-1,2,3,3a-tetrahydro-4H-pyrrolo[2,3-b]quinolin-4-one was prepared as a yellow solid according to Synthetic Scheme 6: mp=250-251° C.; $^1$H NMR (500 MHz, DMSO-d$_6$) δ 8.96 (d, J=2.5 Hz, 1H), 8.23 (d, J=2.3 Hz, 1H), 7.48 (s, 1H), 7.05 (s, 1H), 6.79 (s, 1H), 4.05-4.00 (m, 1H), 3.99-3.93 (m, 1H), 2.42 (s, 3H), 2.30 (s, 3H), 2.27-2.22 (m, 8H); ESI MS m/z 336 [C$_{20}$H$_{21}$N$_3$O$_2$+H]$^+$; UPLC (Method A) 98.4% (AUC), t$_R$=3.01 min; Chiral HPLC (Chiralpak AD, Method A) 82.0% (AUC), t$_R$=15.59 min.

Preparation of (S)-1-(2,3-Dihydro-1H-pyrido[2,3-b][1,4]oxazin-7-yl)-3a-hydroxy-6,7-dimethyl-1,2,3,3a-tetrahydro-4H-pyrrolo[2,3-b]quinolin-4-one

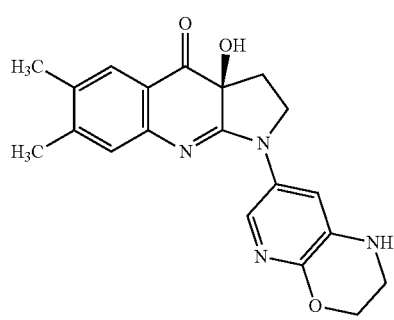

BPN-0028734

(S)-1-(2,3-Dihydro-1H-pyrido[2,3-b][1,4]oxazin-7-yl)-3a-hydroxy-6,7-dimethyl-1,2,3,3a-tetrahydro-4H-pyrrolo[2,3-b]quinolin-4-one was prepared as a red-orange solid according to Synthetic Scheme 4: mp=225-230° C.; $^1$H NMR (500 MHz, DMSO-d$_6$) δ 7.86 (d, J=2.4 Hz, 1H), 7.82 (d, J=2.4 Hz, 1H), 7.46 (s, 1H), 6.99 (s, 1H), 6.73 (s, 1H), 6.23 (s, 1H), 4.25 (t, J=4.5 Hz, 2H), 3.98-3.94 (m, 1H), 3.87-3.84 (m, 1H), 2.26-2.21 (m, 10H); ESI MS m/z 365 [C$_{20}$H$_{20}$N$_4$O$_3$+H]$^+$; UPLC (Method A) 98.3% (AUC), t$_R$=2.72 min; Chiral HPLC (Chiralpak AD, Method A) 86.1% (AUC), t$_R$=18.80 min.

Preparation of (S)-3a-Hydroxy-6,7-dimethyl-1-(1,2,3,5-tetrahydrobenzo[e][1,4]oxazepin-7-yl)-1,2,3,3a-tetrahydro-4H-pyrrolo[2,3-b]quinolin-4-one

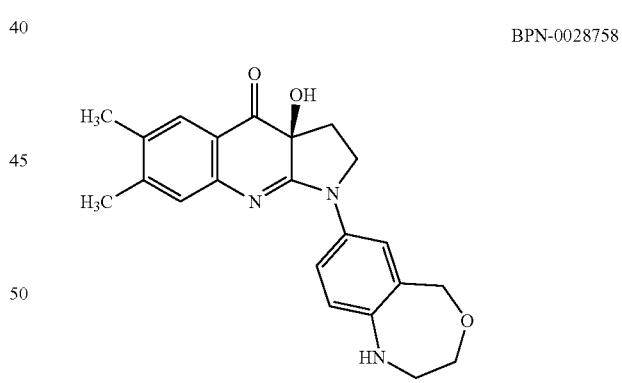

BPN-0028758

(S)-3a-Hydroxy-6,7-dimethyl-1-(1,2,3,5-tetrahydrobenzo[e][1,4]oxazepin-7-yl)-1,2,3,3a-tetrahydro-4H-pyrrolo[2,3-b]quinolin-4-one was prepared as an orange solid according to Synthetic Scheme 4: $^1$H NMR (500 MHz, DMSO-d$_6$) δ 7.78 (dd, J=8.6, 2.6 Hz, 1H), 7.74 (d, J=2.6 Hz, 1H), 7.45 (s, 1H), 6.99 (s, 1H), 6.93 (d, J=8.6 Hz, 1H), 6.68 (s, 1H), 5.68 (apparent t, J=3.7 Hz, 1H), 4.50 (s, 2H), 4.02-3.97 (m, 1H), 3.89-3.85 (m, 1H), 3.72-3.70 (m, 2H), 3.02-2.99 (m, 2H), 2.25 (s, 3H), 2.22-2.18 (m, 5H); ESI MS m/z 378 [C$_{22}$H$_{23}$N$_3$O$_3$+H]$^+$; UPLC (Method A) 96.3% (AUC), t$_R$=2.97 min; Chiral HPLC (Chiralpak AD, Method A) 91.0% (AUC), t$_R$=23.89 min.

Preparation of (S)-1-(3,4-Dihydro-2H-benzo[b][1,4]oxazin-6-yl)-3a-hydroxy-6,7-dimethyl-1,2,3,3a-tetrahydro-4H-pyrrolo[2,3-b]quinolin-4-one

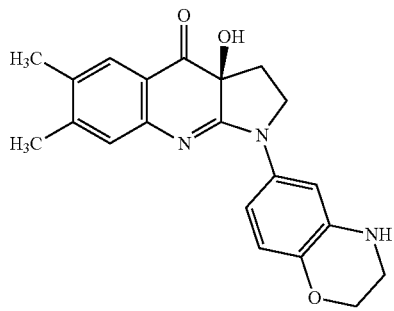

BPN-0028790

(S)-1-(3,4-Dihydro-2H-benzo[b][1,4]oxazin-6-yl)-3a-hydroxy-6,7-dimethyl-1,2,3,3a-tetrahydro-4H-pyrrolo[2,3-b]quinolin-4-one was prepared as a yellow-orange solid according to Synthetic Scheme 4: mp=200-203° C.; $^1$H NMR (500 MHz, DMSO-d$_6$) δ 7.44 (s, 1H), 7.35 (d, J=2.6 Hz, 1H), 7.03 (dd, J=8.7, 2.7 Hz, 1H), 6.97 (s, 1H), 6.67-6.64 (m, 1H), 5.88 (s, 1H), 4.12-4.10 (m, 2H), 3.98-3.93 (m, 1H), 3.83-3.79 (m, 1H), 2.25 (s, 3H), 2.20-2.14 (m, 5H), 3H obscured by solvent peak; ESI MS m/z 364 [C$_{21}$H$_{21}$N$_3$O$_3$+H]$^+$; UPLC (Method A) >99% (AUC), t$_R$=3.14 min; Chiral HPLC (Chiralpak AD, Method A) >99% (AUC), t$_R$=20.43 min.

Preparation of (S)-1-(5-Chloro-6-methoxypyridin-3-yl)-3a-hydroxy-6,7-dimethyl-1,2,3,3a-tetrahydro-4H-pyrrolo[2,3-b]quinolin-4-one

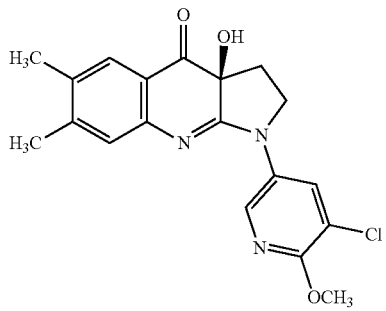

BPN-0028820

(S)-1-(5-Chloro-6-methoxypyridin-3-yl)-3a-hydroxy-6,7-dimethyl-1,2,3,3a-tetrahydro-4H-pyrrolo[2,3-b]quinolin-4-one was prepared as a yellow solid according to Synthetic Scheme 6: $^1$H NMR (500 MHz, DMSO-d$_6$) δ 8.85 (d, J=2.5 Hz, 1H), 8.70 (d, J=2.56 Hz, 1H), 7.49 (s, 1H), 7.05 (s, 1H), 6.82 (s, 1H), 4.05-4.02 (m, 1H), 3.97-3.96 (m, 4H), 2.27 (s, 3H), 2.26-2.24 (m, 2H), 2.22 (s, 3H); ESI MS m/z 372 [C$_{19}$H$_{18}$ClN$_3$O$_3$+H]$^+$; UPLC (Method A) 98.2% (AUC), t$_R$=3.42 min; Chiral HPLC (Chiralpak AD, Method A) 85.2% (AUC), t$_R$=13.81 min.

Preparation of (S)-4a-Hydroxy-2-methyl-7-(2-methylquinolin-6-yl)-4a,5,6,7-tetrahydro-4H-pyrrolo[2,3-b]thieno[3,2-e]pyridin-4-one

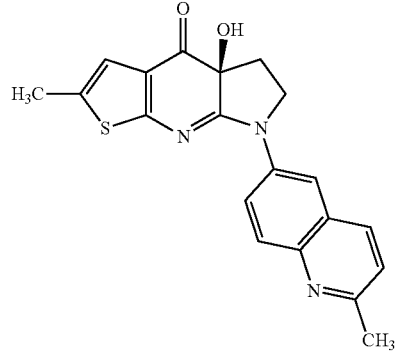

BPN-0028898

(S)-4a-Hydroxy-2-methyl-7-(2-methylquinolin-6-yl)-4a,5,6,7-tetrahydro-4H-pyrrolo[2,3-b]thieno[3,2-e]pyridin-4-one was prepared as a red solid according to Synthetic Scheme 3: mp=247-249° C.; $^1$H NMR (500 MHz, DMSO-d$_6$) δ 8.53 (d, J=10.5 Hz, 1H), 8.26-8.24 (m, 2H), 7.99 (d, J=9.5 Hz, 1H), 7.43 (d, J=9.1 Hz, 1H), 6.95 (s, 1H), 6.82 (s, 1H), 4.27-4.24 (m, 1H), 4.19-3.17 (m, 1H), 2.66 (s, 3H), 2.29-2.28 (m, 2H), 3H obscured by solvent peak; ESI MS m/z 364 [C$_{20}$H$_{17}$N$_3$O$_2$S+H]$^+$; UPLC (Method A) 97.5% (AUC), t$_R$=2.80 min; Chiral HPLC (Chiralpak AD, Method A) >99% (AUC), t$_R$=18.84 min.

Preparation of (S)-1-(2-Aminoquinolin-6-yl)-3a-hydroxy-6,7-dimethyl-1,2,3,3a-tetrahydro-4H-pyrrolo[2,3-b]quinolin-4-one

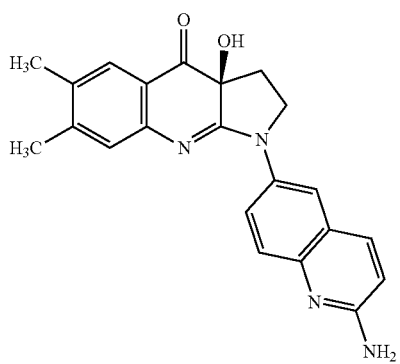

BPN-0028899

(S)-1-(2-Aminoquinolin-6-yl)-3a-hydroxy-6,7-dimethyl-1,2,3,3a-tetrahydro-4H-pyrrolo[2,3-b]quinolin-4-one was prepared as a yellow solid according to Synthetic Scheme 6: mp=282-283° C.; $^1$H NMR (500 MHz, DMSO-d$_6$) δ 8.38 (dd, J=9.1, 2.5 Hz, 1H), 8.13 (d, J=2.5 Hz, 1H), 7.91 (d, J=9.1 Hz, 1H), 7.50-7.48 (m, 2H), 7.05 (s, 1H), 6.79-6.76 (m, 2H), 6.37 (s, 2H), 4.15-4.09 (m, 1H), 4.04-4.00 (m, 1H), 2.27-2.25 (m, 5H), 2.22 (s, 3H); ESI MS m/z 373 [C$_{22}$H$_{20}$N$_4$O$_2$+H]$^+$; UPLC (Method A) >99% (AUC), t$_R$=2.58 min; Chiral HPLC (Chiralpak AD, Method A) 86.1% (AUC), t$_R$=23.54 min.

Preparation of (S)-3a-Hydroxy-6,7-dimethyl-1-(5,6, 7,8-tetrahydronaphthalen-2-yl)-1,2,3,3a-tetrahydro-4H-pyrrolo[2,3-b]quinolin-4-one

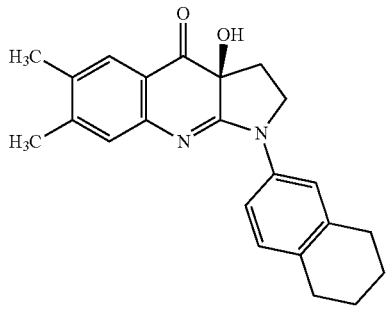

BPN-0028923

(S)-3a-Hydroxy-6,7-dimethyl-1-(5,6,7,8-tetrahydronaphthalen-2-yl)-1,2,3,3a-tetrahydro-4H-pyrrolo[2,3-b]quinolin-4-one was prepared as a yellow solid according to Synthetic Scheme 6: mp=211-212° C.; $^1$H NMR (500 MHz, DMSO-$d_6$) δ 7.84-7.82 (m, 1H), 7.64-7.63 (m, 1H), 7.46 (s, 1H), 7.08 (d, J=8.5 Hz, 1H), 6.99 (s, 1H), 6.71 (s, 1H), 4.03-3.98 (m, 1H), 3.91-3.88 (m, 1H), 2.77-2.74 (m, 2H), 2.72-2.69 (m, 2H), 2.26 (s, 3H), 2.22-2.19 (m, 5H), 1.76-1.74 (m, 4H); ESI MS m/z 361 $[C_{23}H_{24}N_2O_2+H]^+$; UPLC (Method A) 96.8% (AUC), $t_R$=3.88 min; Chiral HPLC (Chiralpak AD, Method A) >99% (AUC), $t_R$=13.95 min.

Preparation of (S)-1-(Chroman-7-yl)-3a-hydroxy-6, 7-dimethyl-1,2,3,3a-tetrahydro-4H-pyrrolo[2,3-b] quinolin-4-one

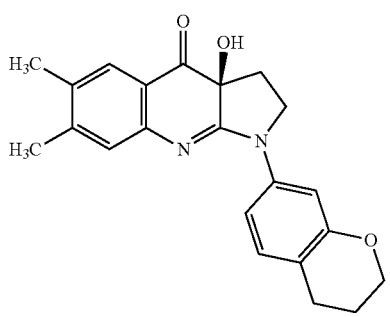

BPN-0028924

(S)-1-(Chroman-7-yl)-3a-hydroxy-6,7-dimethyl-1,2,3,3a-tetrahydro-4H-pyrrolo[2,3-b]quinolin-4-one was prepared as a yellow solid according to Synthetic Scheme 6: mp=219-221° C.; $^1$H NMR (500 MHz, DMSO-$d_6$) δ 7.63 (d, J=2.3 Hz, 1H), 7.47 (s, 1H), 7.41 (dd, J=8.4, 2.3 Hz, 1H), 7.07 (d, J=8.4 Hz, 1H), 7.02 (s, 1H), 6.72 (s, 1H), 4.15-4.13 (m, 2H), 4.01-3.95 (m, 1H), 3.90-3.87 (m, 1H), 2.74-2.71 (m, 2H), 2.27 (s, 3H), 2.21-2.18 (m, 5H), 1.95-1.90 (m, 2H); ESI MS m/z 363 $[C_{22}H_{22}N_2O_3+H]^+$; UPLC (Method A) >99% (AUC), $t_R$=3.46 min; Chiral HPLC (Chiralpak AD, Method A) 88.0% (AUC), $t_R$=19.01 min.

Preparation of (S)-3a-Hydroxy-6,7-dimethyl-1-(1,2, 3,4-tetrahydroquinolin-7-yl)-1,2,3,3a-tetrahydro-4H-pyrrolo[2,3-b]quinolin-4-one

BPN-0028925

(S)-3a-Hydroxy-6,7-dimethyl-1-(1,2,3,4-tetrahydroquinolin-7-yl)-1,2,3,3a-tetrahydro-4H-pyrrolo[2,3-b]quinolin-4-one was prepared as a yellow solid according to Synthetic Scheme 6: mp=220-221° C.; $^1$H NMR (500 MHz, DMSO-$d_6$) δ 7.45 (s, 1H), 7.19 (d, J=2.2 Hz, 1H), 7.02 (dd, J=8.2, 2.3 Hz, 1H), 6.99 (s, 1H), 6.83 (d, J=8.2 Hz, 1H), 6.68 (s, 1H), 5.73 (s, 1H), 3.97-3.92 (m, 1H), 3.83-3.80 (m, 1H), 3.19-3.17 (m, 2H), 2.65-2.63 (m, 2H), 2.25 (s, 3H), 2.20-2.16 (m, 5H), 1.82-1.77 (m, 2H); ESI MS m/z 362 $[C_{22}H_{23}N_3O_2+H]^+$; UPLC (Method A) 98.26% (AUC), $t_R$=3.07 min; Chiral HPLC (Chiralpak AD, Method A) 99.0% (AUC), $t_R$=20.30 min.

Preparation of (S)-3a-Hydroxy-1-phenyl-6-(trifluoromethyl)-3,3a-dihydro-1H-pyrrolo[2,3-b]quinolin-4 (2H)-one

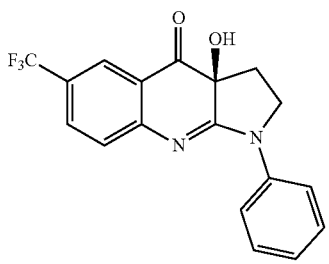

BPN-0025110

(S)-3a-Hydroxy-1-phenyl-6-(trifluoromethyl)-3,3a-dihydro-1H-pyrrolo[2,3-b]quinolin-4(2H)-one was prepared as a yellow solid according to Synthetic Scheme 2: mp=222-223° C.; $^1$H NMR (500 MHz, DMSO-$d_6$) δ 8.06 (dd, J=8.5, 1.0 Hz, 2H), 7.93 (d, J=2.5 Hz, 1H), 7.84 (dd, J=8.5, 2.5 Hz, 1H), 7.46 (apparent dt, J=7.0, 2.0 Hz, 2H), 7.36 (d, J=8.5 Hz, 1H), 7.21 (apparent t, J=7.0 Hz, 1H), 7.04 (s, 1H), 4.20-4.14 (m, 1H), 4.02 (apparent t, J=9.0 Hz, 1H), 2.43-2.36 (m, 1H), 2.28 (dd, J=13.5, 6.0 Hz, 1H); ESI MS m/z 347 $[C_{18}H_{13}F_3N_2O_2+H]^+$; Chiral HPLC (Chiralpak AD, Method A) >99% (AUC), $t_R$=10.74 min.

Preparation of (S)-3a-Hydroxy-3,3,6-trimethyl-1-phenyl-3,3a-dihydro-1H-pyrrolo[2,3-b]quinolin-4(2H)-one

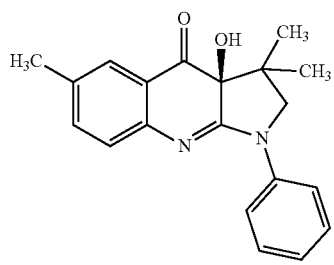

BPN-0026282

(S)-3a-Hydroxy-3,3,6-trimethyl-1-phenyl-3,3a-dihydro-1H-pyrrolo[2,3-b]quinolin-4(2H)-one was prepared as a yellow solid according to Synthetic Scheme 3: mp=177-178° C.; $^1$H NMR (500 MHz, DMSO-$d_6$) δ 8.03 (dd, J=8.5, 1.0 Hz, 2H), 7.56 (d, J=2.0 Hz, 1H), 7.43-7.39 (m, 3H), 7.15-7.12 (m, 2H), 6.88 (s, 1H), 3.85 (d, J=9.5 Hz, 1H), 3.54 (d, J=9.5 Hz, 1H), 2.30 (s, 3H), 1.40 (s, 3H), 1.00 (s, 3H); ESI MS m/z 321 $[C_{20}H_{20}N_2O_2+H]^+$; HPLC (Method C) >99% (AUC), $t_R$=13.15 min; Chiral HPLC (Chiralpak AD, Method A) 87.5% (AUC), $t_R$=10.04 min.

Preparation of (S)-6-Fluoro-3a-hydroxy-7-methyl-1-phenyl-3,3a-dihydro-1H-pyrrolo[2,3-b]quinolin-4(2H)-one

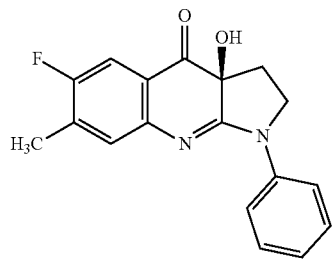

BPN-0026387

(S)-6-Fluoro-3a-hydroxy-7-methyl-1-phenyl-3,3a-dihydro-1H-pyrrolo[2,3-b]quinolin-4(2H)-one was prepared as an orange solid according to Synthetic Scheme 2: mp=211-213° C.; $^1$H NMR (500 MHz, DMSO-$d_6$) δ 8.07 (dd, J=8.5, 1.0 Hz, 2H), 7.43 (apparent dt, J=7.5, 2.0 Hz, 2H), 7.36 (d, J=9.5 Hz, 1H), 7.18-7.14 (m, 2H), 6.87 (s, 1H), 4.10-4.05 (m, 1H), 3.98-2.95 (m, 1H), 2.29-2.25 (m, 5H); ESI MS m/z 311 $[C_{18}H_{15}FN_2O_2+H]^+$; HPLC (Method C) 95.0% (AUC), $t_R$=11.66 min; Chiral HPLC (Chiralpak AD, Method A) 98.2% (AUC), $t_R$=17.81 min.

Preparation of (S)-3a-Hydroxy-1-phenyl-3,3a,5,6,7,8-hexahydro-1H-benzo[4,5]thieno[2,3-b]pyrrolo[3,2-e]pyridin-4(2H)-one

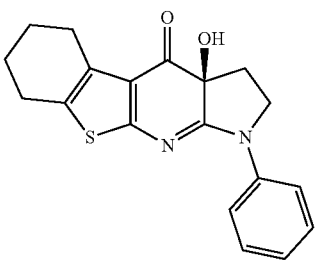

BPN-0027043

(S)-3a-Hydroxy-1-phenyl-3,3a,5,6,7,8-hexahydro-1H-benzo[4,5]thieno[2,3-b]pyrrolo[3,2-e]pyridin-4(2H)-one was prepared as a yellow solid according to Synthetic Scheme 2: mp=259-261° C.; $^1$H NMR (500 MHz, DMSO-$d_6$) δ 7.93 (br d, J=7.5 Hz, 2H), 7.45 (br s, 2H), 7.19 (br s, 1H), 6.85 (s, 1H), 4.14 (br s, 1H), 4.04-4.03 (br m, 1H), 2.74-2.59 (m, 4H), 2.21 (br s, 2H), 1.76 (br s, 4H); ESI MS m/z 339 $[C_{19}H_{18}N_2O_2S+H]^+$; HPLC (Method C) >99% (AUC), $t_R$=15.91 min; Chiral HPLC (Chiralpak AD, Method A) 89.1% (AUC), $t_R$=18.50 min.

Preparation of (S)-3a-Hydroxy-6-methyl-1-(2-methylquinolin-6-yl)-3,3a-dihydro-1H-pyrrolo[2,3-b]quinolin-4(2H)-one

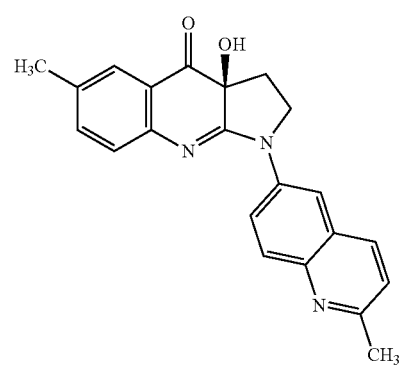

BPN-0027289

(S)-3a-Hydroxy-6-methyl-1-(2-methylquinolin-6-yl)-3,3a-dihydro-1H-pyrrolo[2,3-b]quinolin-4(2H)-one was prepared as a yellow solid according to Synthetic Scheme 3: mp=237-239° C. decomposed; $^1$H NMR (500 MHz, DMSO-$d_6$) δ 8.70 (dd, J=9.0, 2.5 Hz, 1H), 8.42 (d, J=2.5 Hz, 1H), 8.24 (d, J=8.5 Hz, 1H), 7.96 (d, J=8.5 Hz, 1H), 7.56 (d, J=1.5 Hz, 1H), 7.43-7.40 (m, 2H), 7.21 (d, J=8.0 Hz, 1H), 6.89 (s, 1H), 4.20-4.15 (m, 1H), 4.13-4.09 (m, 1H), 2.65 (s, 3H), 2.37-2.30 (m, 5H); ESI MS m/z 358 $[C_{22}H_{19}N_3O_2+H]^+$; HPLC (Method C) 97.3% (AUC), $t_R$=11.08 min; Chiral HPLC (Chiralpak AD, Method A) 95.8% (AUC), $t_R$=17.12 min.

Preparation of (S)-3a-Hydroxy-6-methyl-1-(quinoxalin-6-yl)-3,3a-dihydro-1H-pyrrolo[2,3-b]quinolin-4(2H)-one

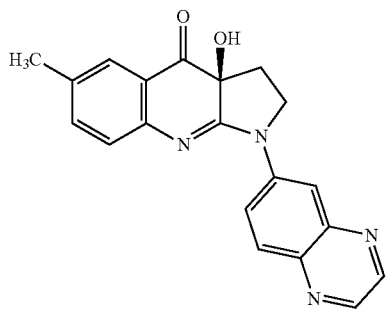

BPN-0027330

(S)-3a-Hydroxy-6-methyl-1-(quinoxalin-6-yl)-3,3a-dihydro-1H-pyrrolo[2,3-b]quinolin-4(2H)-one was prepared as a yellow solid according to Synthetic Scheme 3: mp=151-153° C. decomposed; $^1$H NMR (500 MHz, DMSO-$d_6$) δ 8.93 (d, J=1.5 Hz, 1H), 8.86 (d, J=2.0 Hz, 1H), 8.83 (dd, J=9.5, 2.5 Hz, 1H), 8.68 (d, J=2.5 Hz, 1H), 8.14 (d, J=9.0 Hz, 1H), 7.59 (d, J=2.0 Hz, 1H), 7.44 (dd, J=8.5, 2.0 Hz, 1H), 7.24 (d, J=8.0 Hz, 1H), 6.95 (s, 1H), 4.24-4.17 (m, 2H), 2.38-2.31 (m, 5H); ESI MS m/z 345 $[C_{20}H_{16}N_4O_2+H]^+$; HPLC (Method C) >99% (AUC), $t_R$=12.39 min; Chiral HPLC (Chiralpak AD, Method A) >99% (AUC), $t_R$=20.90 min.

Preparation of (S)-3a-Hydroxy-6,7-dimethyl-1-(2-methylquinolin-6-yl)-3,3a-dihydro-1H-pyrrolo[2,3-b]quinolin-4(2H)-one

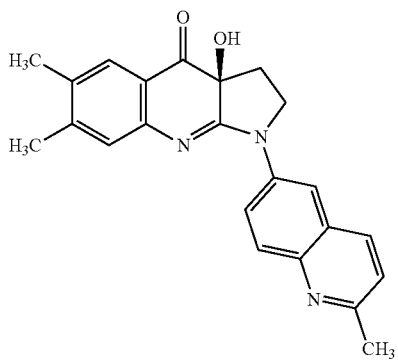

BPN-0027490

(S)-3a-Hydroxy-6,7-dimethyl-1-(2-methylquinolin-6-yl)-3,3a-dihydro-1H-pyrrolo[2,3-b]quinolin-4(2H)-one was prepared as a yellow solid according to Synthetic Scheme 3: mp=254-255° C. decomposed; $^1$H NMR (500 MHz, DMSO-$d_6$) δ 8.73 (dd, J=15.5, 4.0 Hz, 1H), 8.40 (d, J=4.0 Hz, 1H), 8.25 (d, J=14.0 Hz, 1H), 7.96 (d, J=15.0 Hz, 1H), 7.51 (s, 1H), 7.42 (d, J=14.5 Hz, 1H), 7.12 (s, 1H), 6.86 (s, 1H), 4.20-4.10 (m, 2H), 2.65 (s, 3H), 2.29-2.24 (m, 8H); ESI MS m/z 372 $[C_{23}H_{21}N_3O_2+H]^+$; UPLC (Method A) >99% (AUC), $t_R$=2.65 min; Chiral HPLC (Chiralpak AD, Method A) 97.0% (AUC), $t_R$=16.10 min.

Preparation of (S)-2-Ethyl-7a-hydroxy-5-(quinolin-6-yl)-7,7a-dihydro-5H-pyrrolo[2,3-b]thieno[2,3-e]pyridin-8(6H)-one

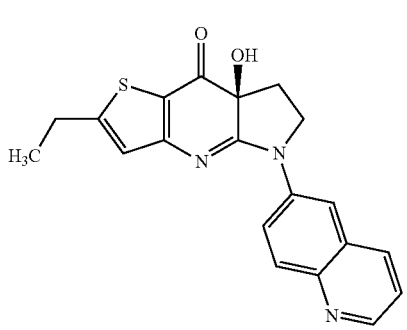

BPN-0028625

(S)-2-Ethyl-7a-hydroxy-5-(quinolin-6-yl)-7,7a-dihydro-5H-pyrrolo[2,3-b]thieno[2,3-e]pyridin-8(6H)-one was prepared as a yellow solid according to Synthetic Scheme 3: $^1$H NMR (500 MHz, DMSO-$d_6$) δ 8.85 (dd, J=4.0, 1.5 Hz, 1H), 8.68 (dd, J=9.5, 2.5 Hz, 1H), 8.39 (d, J=2.5 Hz, 1H), 8.36 (d, J=8.0 Hz, 1H), 8.07 (d, J=9.0 Hz, 1H), 7.55 (dd, J=8.0, 4.0 Hz, 1H), 6.97 (s, 1H), 6.93 (s, 1H), 4.27-4.24 (m, 1H), 4.19-4.15 (m, 1H), 2.85 (q, J=7.5 Hz, 2H), 2.35-2.26 (m, 2H), 1.28 (t, J=7.5 Hz, 3H); ESI MS m/z 364 $[C_{20}H_{17}N_3O_2S+H]^+$; UPLC (Method A) 92.2% (AUC), $t_R$=2.85 min; Chiral HPLC (Chiralpak AD, Method A) 46.3% (AUC), $t_R$=18.69 min.

Preparation of (S)-3a-Hydroxy-5,7-dimethyl-1-(quinolin-6-yl)-3,3a-dihydro-1H-pyrrolo[2,3-b]quinolin-4(2H)-one

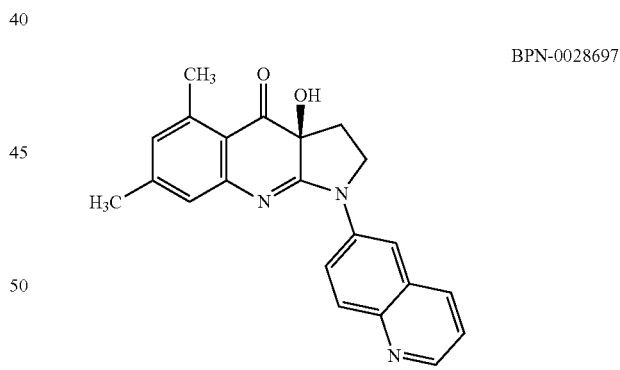

BPN-0028697

(S)-3a-Hydroxy-5,7-dimethyl-1-(quinolin-6-yl)-3,3a-dihydro-1H-pyrrolo[2,3-b]quinolin-4(2H)-one was prepared as a yellow-brown solid according to Synthetic Scheme 3: mp=242-245° C. decomposed; $^1$H NMR (500 MHz, DMSO-$d_6$) δ 8.83 (dd, J=7.0, 3.0 Hz, 1H), 8.78 (d, J=15.5, 4.0 Hz, 1H), 8.46 (d, J=4.5 Hz, 1H), 8.37 (d, J=11.5 Hz, 1H), 8.06 (d, J=15.5 Hz, 1H), 7.53 (dd, J=13.5, 7.0 Hz, 1H), 7.02 (s, 1H), 6.84 (s, 1H), 6.78 (s, 1H), 4.19-4.10 (m, 2H), 2.38-2.22 (m, 5H), 3 protons obscured by solvent; ESI MS m/z 358 $[C_{22}H_{19}N_3O_2+H]^+$; UPLC (Method A) 96.8% (AUC), $t_R$=2.76 min; Chiral HPLC (Chiralpak AD, Method A) 94.2% (AUC), $t_R$=16.59 min.

Preparation of (S)-1-(2-Ethylquinolin-6-yl)-3a-hydroxy-6,7-dimethyl-3,3a-dihydro-1H-pyrrolo[2,3-b]quinolin-4(2H)-one

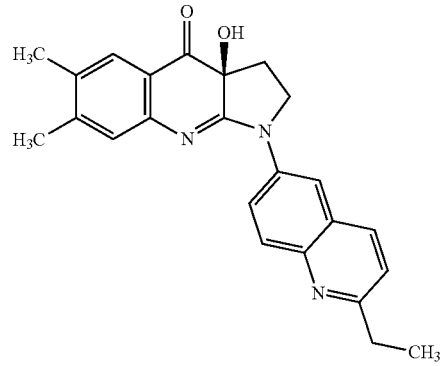

BPN-0028867

(S)-1-(2-Ethylquinolin-6-yl)-3a-hydroxy-6,7-dimethyl-3,3a-dihydro-1H-pyrrolo[2,3-b]quinolin-4(2H)-one was prepared as a yellow solid according to Synthetic Scheme 6: mp=241-242° C.; $^1$H NMR (500 MHz, DMSO-$d_6$) δ 8.73 (dd, J=9.0, 2.5 Hz, 1H), 8.40 (d, J=3.0 Hz, 1H), 8.26 (d, J=8.5 Hz, 1H), 7.97 (d, J=9.0 Hz, 1H), 7.51 (s, 1H), 7.45 (d, J=8.5 Hz, 1H), 7.14 (s, 1H), 6.84 (s, 1H), 4.19-4.08 (m, 2H), 2.93 (q, J=7.5 Hz, 2H), 2.32-2.30 (m, 5H), 2.24 (s, 3H), 1.33 (t, J=7.5 Hz, 3H); ESI MS m/z 386 $[C_{24}H_{23}N_3O_2+H]^+$; UPLC (Method A) 99.0% (AUC), $t_R$=2.86 min; Chiral HPLC (Chiralpak AD, Method A) 88.2% (AUC), $t_R$=16.96 min.

Preparation of (S)-1-(2,3-Dimethylquinolin-6-yl)-3a-hydroxy-6,7-dimethyl-3,3a-dihydro-1H-pyrrolo[2,3-b]quinolin-4(2H)-one

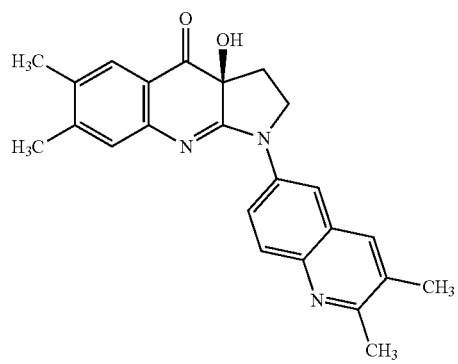

BPN-0028868

(S)-1-(2,3-Dimethylquinolin-6-yl)-3a-hydroxy-6,7-dimethyl-3,3a-dihydro-1H-pyrrolo[2,3-b]quinolin-4(2H)-one was prepared as a yellow solid according to Synthetic Scheme 6: mp=253-254° C.; $^1$H NMR (500 MHz, DMSO-$d_6$) δ 8.57 (dd, J=9.5, 2.5 Hz, 1H), 8.39 (d, J=2.5 Hz, 1H), 8.04 (s, 1H), 7.92 (d, J=9.5 Hz, 1H), 7.51 (s, 1H), 7.13 (s, 1H), 6.82 (s, 1H), 4.18-4.13 (m, 1H), 4.11-4.07 (m, 1H), 2.61 (s, 3H), 2.44 (s, 3H), 2.31-2.28 (m, 5H), 2.24 (s, 3H); ESI MS m/z 386 $[C_{24}H_{23}N_3O_2+H]^+$; UPLC (Method A) >99% (AUC), $t_R$=2.78 min; Chiral HPLC (Chiralpak AD, Method A) 88.5% (AUC), $t_R$=17.13 min.

Preparation of (S)-1-(3-((Dimethylamino)methyl)quinolin-6-yl)-3a-hydroxy-6,7-dimethyl-1,2,3,3a-tetrahydro-4H-pyrrolo[2,3-b]quinolin-4-one

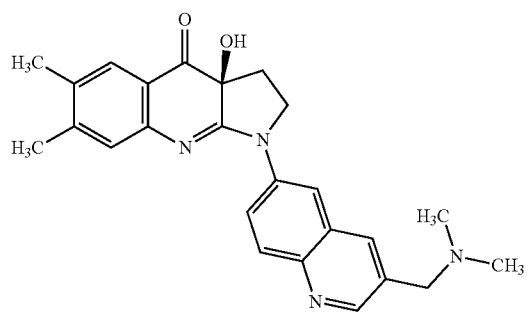

BPN-0028866

(S)-1-(3-((Dimethylamino)methyl)quinolin-6-yl)-3a-hydroxy-6,7-dimethyl-1,2,3,3a-tetrahydro-4H-pyrrolo[2,3-b]quinolin-4-one was prepared as an orange solid according to Synthetic Scheme 6: $^1$H NMR (300 MHz, DMSO-$d_6$) δ 8.76 (dd, J=9.6, 2.1 Hz, 1H), 8.42 (d, J=2.4 Hz, 1H), 8.33-8.30 (m, 1H), 8.01 (d, J=9.3 Hz, 1H), 7.61 (d, J=8.7 Hz, 1H), 7.51 (s, 1H), 7.14 (s, 1H), 6.86 (s, 1H), 4.16-4.10 (m, 2H), 3.68 (s, 2H), 2.51-2.24 (m, 14H); ESI MS m/z 415 $[C_{25}H_{26}N_4O_2+H]^+$; UPLC (Method A) 96.0% (AUC), $t_R$=2.64 min; Chiral HPLC (Chiralpak AD, Method A) 82.8% (AUC), $t_R$=17.32 min.

Preparation of (S)-1-(2-((Dimethylamino)methyl)quinolin-6-yl)-3a-hydroxy-6,7-dimethyl-1,2,3,3a-tetrahydro-4H-pyrrolo[2,3-b]quinolin-4-one

BPN-0028897

(S)-1-(3-((Dimethylamino)methyl)quinolin-6-yl)-3a-hydroxy-6,7-dimethyl-1,2,3,3a-tetrahydro-4H-pyrrolo[2,3-b]quinolin-4-one was prepared as an orange solid according to Synthetic Scheme 6: $^1$H NMR (300 MHz, DMSO-$d_6$) δ 8.76 (dd, J=9.0, 2.4 Hz, 1H), 8.43-8.41 (m, 1H), 8.33-8.30 (m, 1H), 8.01 (d, J=9.0 Hz, 1H), 7.61 (d, J=8.4 Hz, 1H), 7.51 (s, 1H), 7.14 (s, 1H), 6.86 (s, 1H), 4.16-4.10 (m, 2H), 3.69 (s, 2H), 2.35-2.23 (m, 14H); ESI MS m/z 415 $[C_{25}H_{26}N_4O_2+H]^+$; UPLC (Method A) 98.8% (AUC), $t_R$=2.77 min; Chiral HPLC (Chiralpak AD, Method A) 52.4% (AUC), $t_R$=17.67 min.

Preparation of (S)-1-(Benzofuran-5-yl)-3a-hydroxy-6-methyl-1,2,3,3a-tetrahydro-4H-pyrrolo[2,3-b]quinolin-4-one

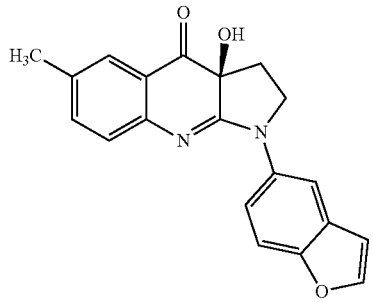

BPN-0026283

(S)-1-(Benzofuran-5-yl)-3a-hydroxy-6-methyl-1,2,3,3a-tetrahydro-4H-pyrrolo[2,3-b]quinolin-4-one was prepared as a yellow solid according to Synthetic Scheme 3: mp=213-214° C.; $^1$H NMR (300 MHz, DMSO-$d_6$) δ 8.29 (d, J=2.1 Hz, 1H), 8.06 (d, J=2.1 Hz, 1H), 8.03 (d, J=2.4 Hz, 1H), 7.65 (d, J=9.0 Hz, 1H), 7.53 (d, J=1.5 Hz, 1H), 7.36 (dd, J=8.4, 1.5 Hz, 1H), 7.10 (d, J=8.4 Hz, 1H), 7.02 (dd, J=2.1, 0.9 Hz, 1H), 6.85 (s, 1H), 4.19-4.10 (m, 1H), 4.02-3.96 (m, 1H), 2.30 (s, 3H), 2.29-2.27 (m, 2H); ESI MS m/z 333 $[C_{20}H_{16}N_2O_3+H]^+$; HPLC (Method B) 97.8% (AUC), $t_R$=9.42 min; Chiral HPLC (Chiralpak AD, Method A) 96.7% (AUC), $t_R$=17.19 min.

Preparation of (S)-4-(3a-Hydroxy-6-methyl-4-oxo-2,3,3a,4-tetrahydro-1H-pyrrolo[2,3-b]quinolin-1-yl)-2-methylbenzonitrile

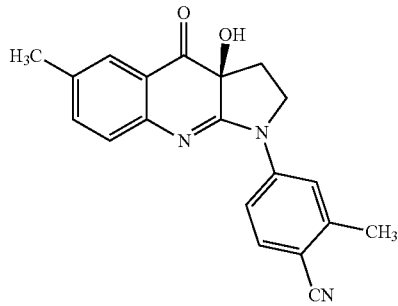

BPN-0026324

(S)-4-(3a-Hydroxy-6-methyl-4-oxo-2,3,3a,4-tetrahydro-1H-pyrrolo[2,3-b]quinolin-1-yl)-2-methylbenzonitrile was prepared as a yellow solid according to Synthetic Scheme 3: mp=229-231° C.; $^1$H NMR (500 MHz, DMSO-$d_6$) δ 8.27 (dd, J=9.0, 2.5 Hz, 1H), 8.11 (d, J=2.0 Hz, 1H), 7.79 (d, J=4.0 Hz, 1H), 7.56 (d, J=1.5 Hz, 1H), 7.42 (dd, J=8.0, 1.5 Hz, 1H), 7.21 (d, J=8.0 Hz, 1H), 6.90 (s, 1H), 4.04-4.01 (m, 2H), 2.53 (s, 3H), 2.32 (s, 3H), 2.28-2.26 (m, 2H); ESI MS m/z 332 $[C_{20}H_{17}N_3O_2+H]^+$; HPLC (Method B) 98.4% (AUC), $t_R$=9.26 min; Chiral HPLC (Chiralpak AD, Method A) 98.9% (AUC), $t_R$=17.48 min.

Preparation of (S)-3a-Hydroxy-1-(4-methoxyphenyl)-6-(trifluoromethyl)-1,2,3,3a-tetrahydro-4H-pyrrolo[2,3-b]quinolin-4-one

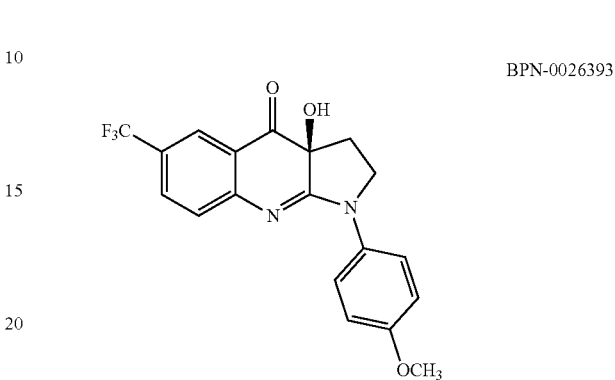

BPN-0026393

(S)-3a-Hydroxy-1-(4-methoxyphenyl)-6-(trifluoromethyl)-1,2,3,3a-tetrahydro-4H-pyrrolo[2,3-b]quinolin-4-one was prepared as a yellow solid according to Synthetic Scheme 3: mp=216-220° C.; $^1$H NMR (500 MHz, DMSO-$d_6$) δ 7.93 (dd, J=7.0, 2.5 Hz, 2H), 7.90 (d, J=2.0 Hz, 1H), 7.81 (dd, J=8.5, 2.5 Hz, 1H), 7.29 (d, J=8.0 Hz, 1H), 7.03 (dd, J=7.0, 2.0 Hz, 2H), 6.99 (s, 1H), 4.17-4.12 (m, 1H), 3.98-3.94 (m, 1H), 3.79 (s, 3H), 2.42-2.35 (m, 1H), 2.28-2.25 (m, 1H); ESI MS m/z 377 $[C_{19}H_{15}F_3N_2O_3+H]^+$; HPLC (Method D) 98.6% (AUC), $t_R$=9.55 min; Chiral HPLC (Chiralpak AD, Method A) >99% (AUC), $t_R$=14.30 min.

Preparation of (S)-2-Chloro-4-(3a-hydroxy-6-methyl-4-oxo-2,3,3a,4-tetrahydro-1H-pyrrolo[2,3-b]quinolin-1-yl)benzonitrile

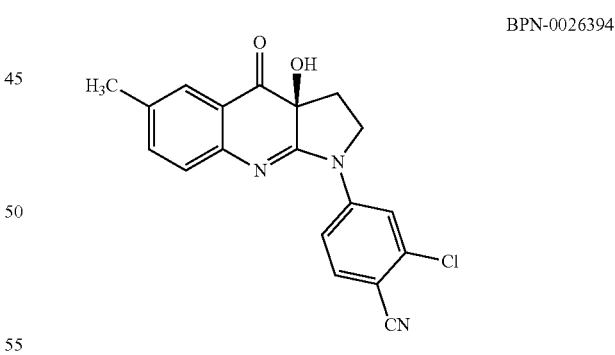

BPN-0026394

(S)-2-Chloro-4-(3a-hydroxy-6-methyl-4-oxo-2,3,3a,4-tetrahydro-1H-pyrrolo[2,3-b]quinolin-1-yl)benzonitrile was prepared as a yellow solid according to Synthetic Scheme 4: mp=215-220° C.; $^1$H NMR (300 MHz, DMSO-$d_6$) δ 8.65 (d, J=2.1 Hz, 1H), 8.19 (dd, J=9.0, 2.1 Hz, 1H), 8.01 (d, J=9.0 Hz, 1H), 7.58 (s, 1H), 7.46 (d, J=8.4 Hz, 1H), 7.23 (d, J=8.1 Hz, 1H), 6.99 (s, 1H), 4.05-4.02 (m, 2H), 2.33 (s, 3H), 2.27 (apparent s, 2H); ESI MS m/z 352 $[C_{19}H_{14}ClN_3O_2+H]^+$; HPLC (Method B) >99% (AUC), $t_R$=10.49 min; Chiral HPLC (Chiralpak AD, Method A) >99% (AUC), $t_R$=18.14 min.

Preparation of (S)-3a-Hydroxy-1-(2-methylthiazol-5-yl)-6-(trifluoromethyl)-1,2,3,3a-tetrahydro-4H-pyrrolo[2,3-b]quinolin-4-one

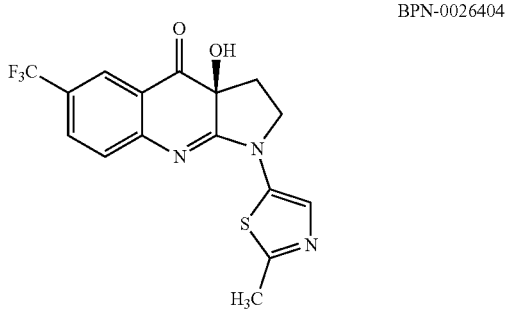 [SMILES: Cc1ncc(N2CC[C@@]3(O)C(=O)c4cc(C(F)(F)F)ccc4N=C23)s1]

BPN-0026404

(S)-3a-Hydroxy-1-(2-methylthiazol-5-yl)-6-(trifluoromethyl)-1,2,3,3a-tetrahydro-4H-pyrrolo[2,3-b]quinolin-4-one was prepared as a yellow-orange solid according to Synthetic Scheme 4: mp=233-235° C.; $^1$H NMR (500 MHz, DMSO-$d_6$) δ 7.93 (d, J=2.5 Hz, 1H), 7.88 (dd, J=8.5, 2.5 Hz, 1H), 7.56 (s, 1H), 7.39 (d, J=8.0 Hz, 1H), 7.11 (s, 1H), 4.14-4.09 (m, 1H), 4.07-4.03 (m, 1H), 2.62 (s, 3H), 2.56-2.52 (m, 1H), 2.37-2.31 (m, 1H); ESI MS m/z 368 $[C_{16}H_{12}F_3N_3O_2S+H]^+$; HPLC (Method B) >99% (AUC), $t_R$=10.32 min; Chiral HPLC (Chiralpak AD, Method A) >99% (AUC), $t_R$=13.78 min.

Preparation of (S)-3a-Hydroxy-1-(1-methyl-1H-pyrazol-4-yl)-6-(trifluoromethyl)-1,2,3,3a-tetrahydro-4H-pyrrolo[2,3-b]quinolin-4-one

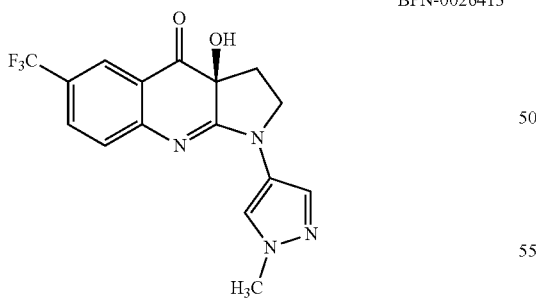

BPN-0026413

(S)-3a-Hydroxy-1-(1-methyl-1H-pyrazol-4-yl)-6-(trifluoromethyl)-1,2,3,3a-tetrahydro-4H-pyrrolo[2,3-b]quinolin-4-one was prepared as a yellow-brown solid according to Synthetic Scheme 4: $^1$H NMR (500 MHz, DMSO-$d_6$) δ 8.32 (s, 1H), 7.90-7.89 (m, 2H), 7.82 (dd, J=8.5, 2.0 Hz, 1H), 7.37 (d, J=8.5 Hz, 1H), 6.96 (s, 1H), 4.01-3.96 (m, 1H), 3.91-3.87 (m, 4H), 2.47-2.40 (m, 1H), 2.30-2.26 (m, 1H); ESI MS m/z 351 $[C_{16}H_{13}F_3N_4O_2+H]^+$; Chiral HPLC (Chiralpak AD, Method A) 49.5% (AUC), $t_R$=15.24 min.

Preparation of (S)-4-(6-Chloro-3a-hydroxy-4-oxo-2,3,3a,4-tetrahydro-1H-pyrrolo[2,3-b]quinolin-1-yl)-2-methylbenzonitrile

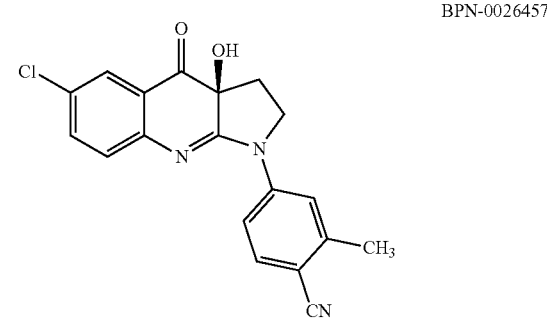 [SMILES: Cc1cc(N2CC[C@@]3(O)C(=O)c4cc(Cl)ccc4N=C23)ccc1C#N]

BPN-0026457

(S)-4-(6-Chloro-3a-hydroxy-4-oxo-2,3,3a,4-tetrahydro-1H-pyrrolo[2,3-b]quinolin-1-yl)-2-methylbenzonitrile was prepared as an orange solid according to Synthetic Scheme 3: mp=236-239° C.; $^1$H NMR (500 MHz, DMSO-$d_6$) δ 8.24 (dd, J=9.0, 2.0 Hz, 1H), 8.12 (s, 1H), 7.81 (d, J=9.0 Hz, 1H), 7.68 (d, J=3.0 Hz, 1H), 7.62 (dd, J=8.5, 2.5 Hz, 1H), 7.33 (d, J=8.5 Hz, 1H), 7.03 (s, 1H), 4.11-4.02 (m, 2H), 2.53 (s, 3H), 2.29-2.25 (m, 2H); ESI MS m/z 352 $[C_{19}H_{14}ClN_3O_2+H]^+$; HPLC (Method D) >99% (AUC), $t_R$=10.20 min; Chiral HPLC (Chiralpak AD, Method A) 96.5% (AUC), $t_R$=16.89 min.

Preparation of (S)-1-(Benzofuran-6-yl)-3a-hydroxy-6-(trifluoromethyl)-1,2,3,3a-tetrahydro-4H-pyrrolo[2,3-b]quinolin-4-one

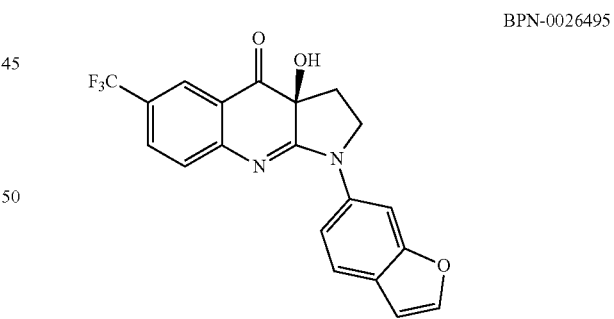

BPN-0026495

(S)-1-(Benzofuran-6-yl)-3a-hydroxy-6-(trifluoromethyl)-1,2,3,3a-tetrahydro-4H-pyrrolo[2,3-b]quinolin-4-one was prepared as a yellow solid according to Synthetic Scheme 3: mp=232-234° C.; $^1$H NMR (300 MHz, DMSO-$d_6$) δ 8.49 (s, 1H), 8.03 (d, J=2.1 Hz, 1H), 7.94 (s, 1H), 7.91-7.84 (m, 2H), 7.72 (d, J=8.7 Hz, 1H), 7.39 (d, J=8.4 Hz, 1H), 7.08 (s, 1H), 6.98 (dd, J=2.1, 0.9 Hz, 1H), 4.27-4.21 (m, 1H), 4.11-4.05 (m, 1H), 2.34-2.27 (m, 2H); ESI MS m/z 387 $[C_{20}H_{13}F_3N_2O_3+H]^+$; HPLC (Method E) >99% (AUC), $t_R$=9.56 min; Chiral HPLC (Chiralpak AD, Method A) >99% (AUC), $t_R$=14.72 min.

Preparation of (S)-3a-Hydroxy-1-(2-methoxypyridin-4-yl)-6-(trifluoromethyl)-1,2,3,3a-tetrahydro-4H-pyrrolo[2,3-b]quinolin-4-one

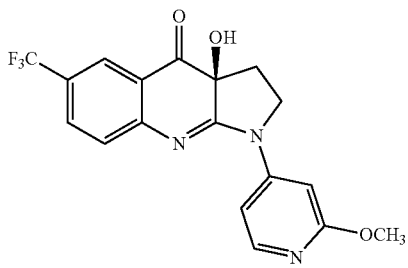

BPN-0026533

(S)-3a-Hydroxy-1-(2-methoxypyridin-4-yl)-6-(trifluoromethyl)-1,2,3,3a-tetrahydro-4H-pyrrolo[2,3-b]quinolin-4-one was prepared as a yellow solid according to Synthetic Scheme 4: $^1$H NMR (500 MHz, DMSO-$d_6$) δ 8.17 (d, J=6.0 Hz, 1H), 7.96 (s, 1H), 7.92 (dd, J=8.0, 2.5 Hz, 1H), 7.75 (dd, J=6.0, 2.0 Hz, 1H), 7.58 (d, J=2.0 Hz, 1H), 7.49 (d, J=8.5 Hz, 1H), 7.11 (s, 1H), 4.08-4.05 (m, 2H), 3.88 (s, 3H), 2.44-2.37 (m, 1H), 2.30-2.25 (m, 1H); ESI MS m/z 378 [$C_{18}H_{14}F_3N_3O_3$+H]$^+$; HPLC (Method B) 93.3% (AUC), $t_R$=9.81 min; Chiral HPLC (Chiralpak AD, Method A) 47.7% (AUC), $t_R$=12.01 min.

Preparation of (S)-1-(4-Chlorophenyl)-3a-hydroxy-6-(trifluoromethyl)-1,2,3,3a-tetrahydro-4H-pyrrolo[2,3-b]quinolin-4-one

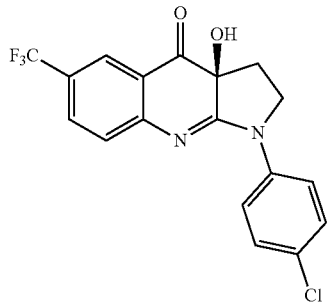

BPN-0026544

(S)-1-(4-Chlorophenyl)-3a-hydroxy-6-(trifluoromethyl)-1,2,3,3a-tetrahydro-4H-pyrrolo[2,3-b]quinolin-4-one was prepared as a yellow-brown solid according to Synthetic Scheme 3: mp=204-207° C.; $^1$H NMR (500 MHz, DMSO-$d_6$) δ 8.12 (dd, J=7.0, 2.5 Hz, 2H), 7.93 (d, J=2.0 Hz, 1H), 7.86 (dd, J=8.5, 2.5 Hz, 1H), 7.52 (dd, J=7.0, 2.0 Hz, 2H), 7.37 (d, J=8.5 Hz, 1H), 7.05 (s, 1H), 4.17-4.12 (m, 1H), 4.03-3.99 (m, 1H), 2.46-2.39 (m, 1H), 2.30-2.26 (m, 1H); ESI MS m/z 381 [$C_{18}H_{12}ClF_3N_2O_2$+H]$^+$; HPLC (Method B) 97.9% (AUC), $t_R$=10.34 min; Chiral HPLC (Chiralpak AD, Method A) 93.0% (AUC), $t_R$=12.86 min.

Preparation of (S)-6-Fluoro-3a-hydroxy-7-methyl-1-(p-tolyl)-1,2,3,3a-tetrahydro-4H-pyrrolo[2,3-b]quinolin-4-one

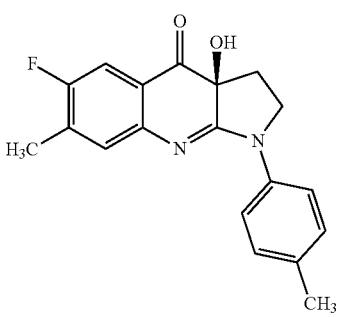

BPN-0026579

(S)-6-Fluoro-3a-hydroxy-7-methyl-1-(p-tolyl)-1,2,3,3a-tetrahydro-4H-pyrrolo[2,3-b]quinolin-4-one was prepared as a yellow solid according to Synthetic Scheme 3: mp=217-220° C.; $^1$H NMR (500 MHz, DMSO-$d_6$) δ 7.94 (d, J=8.5 Hz, 2H), 7.35 (d, J=9.0 Hz, 1H), 7.23 (d, J=8.5 Hz, 2H), 7.14 (d, J=7.0 Hz, 1H), 6.85 (s, 1H), 4.08-4.03 (m, 1H), 3.94-3.91 (m, 1H), 2.31 (s, 3H), 2.28 (s, 3H), 2.26-2.24 (m, 2H); ESI MS m/z 325 [$C_{19}H_{17}FN_2O_2$+H]$^+$; HPLC (Method C) 95.9% (AUC), $t_R$=12.90 min; Chiral HPLC (Chiralpak AD, Method A) 98.5% (AUC), $t_R$=13.82 min.

Preparation of (S)-6-Fluoro-3a-hydroxy-1-(4-methoxyphenyl)-7-methyl-1,2,3,3a-tetrahydro-4H-pyrrolo[2,3-b]quinolin-4-one

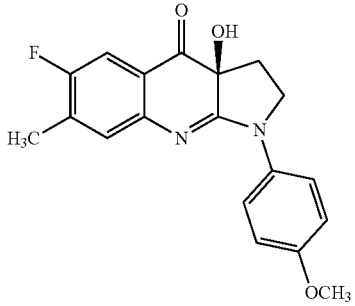

BPN-0026605

(S)-6-Fluoro-3a-hydroxy-1-(4-methoxyphenyl)-7-methyl-1,2,3,3a-tetrahydro-4H-pyrrolo[2,3-b]quinolin-4-one was prepared as a yellow solid according to Synthetic Scheme 3: mp=220-222° C.; $^1$H NMR (300 MHz, DMSO-$d_6$) δ 7.96 (d, J=9.0 Hz, 2H), 7.35 (d, J=9.6 Hz, 1H), 7.11 (d, J=6.9 Hz, 1H), 7.00 (d, J=9.0 Hz, 2H), 6.85 (s, 1H), 4.10-4.01 (m, 1H), 3.93-3.88 (m, 1H), 3.77 (s, 3H), 2.27 (s, 3H), 2.23 (apparent s, 2H); ESI MS m/z 341 [$C_{19}H_{17}FN_2O_3$+H]$^+$; HPLC (Method B) >99% (AUC), $t_R$=8.57 min; Chiral HPLC (Chiralpak AD, Method A) >99% (AUC), $t_R$=16.69 min.

Preparation of (S)-1-(3-Chloro-4-methylphenyl)-6-fluoro-3a-hydroxy-7-methyl-1,2,3,3a-tetrahydro-4H-pyrrolo[2,3-b]quinolin-4-one

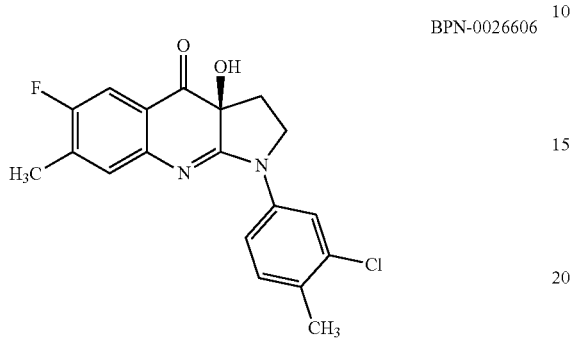

BPN-0026606

(S)-1-(3-Chloro-4-methylphenyl)-6-fluoro-3a-hydroxy-7-methyl-1,2,3,3a-tetrahydro-4H-pyrrolo[2,3-b]quinolin-4-one was prepared as a yellow solid according to Synthetic Scheme 3: mp=213-215° C.; $^1$H NMR (300 MHz, DMSO-$d_6$) δ 8.37 (d, J=2.4 Hz, 1H), 7.81 (dd, J=8.4, 2.4 Hz, 1H), 7.39 (dd, J=8.1, 2.4 Hz, 2H), 7.18 (d, J=7.2 Hz, 1H), 6.92 (s, 1H), 4.09-3.92 (m, 2H), 2.33 (s, 3H), 2.30 (s, 3H), 2.27-2.24 (m, 2H); ESI MS m/z 359 $[C_{19}H_{16}ClFN_2O_2+H]^+$; HPLC (Method B) >99% (AUC), $t_R$=9.59 min; Chiral HPLC (Chiralpak AD, Method A) 98.6% (AUC), $t_R$=12.35 min.

Preparation of (S)-4-(6-Fluoro-3a-hydroxy-7-methyl-4-oxo-2,3,3a,4-tetrahydro-1H-pyrrolo[2,3-b]quinolin-1-yl)-2-methylbenzonitrile

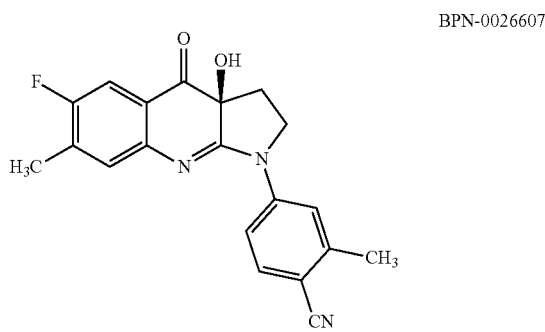

BPN-0026607

(S)-4-(6-Fluoro-3a-hydroxy-7-methyl-4-oxo-2,3,3a,4-tetrahydro-1H-pyrrolo[2,3-b]quinolin-1-yl)-2-methylbenzonitrile was prepared as a yellow solid according to Synthetic Scheme 3: mp=229-231° C.; $^1$H NMR (300 MHz, DMSO-$d_6$) δ 8.25 (dd, J=8.4, 1.8 Hz, 1H), 8.11 (d, J=2.1 Hz, 1H), 7.80 (d, J=8.7 Hz, 1H), 7.41 (d, J=9.3 Hz, 1H), 7.28 (d, J=6.9 Hz, 1H), 6.97 (s, 1H), 4.07-4.02 (m, 2H), 2.53 (s, 3H), 2.31 (s, 3H), 2.27 (apparent s, 2H); ESI MS m/z 350 $[C_{20}H_{16}FN_3O_2+H]^+$; HPLC (Method B) 97.8% (AUC), $t_R$=9.58 min; Chiral HPLC (Chiralpak AD, Method A) 96.1% (AUC), $t_R$=16.29 min.

Preparation of provide (S)-4-(3a-Hydroxy-4-oxo-6-(trifluoromethyl)-2,3,3a,4-tetrahydro-1H-pyrrolo[2,3-b]quinolin-1-yl)benzonitrile

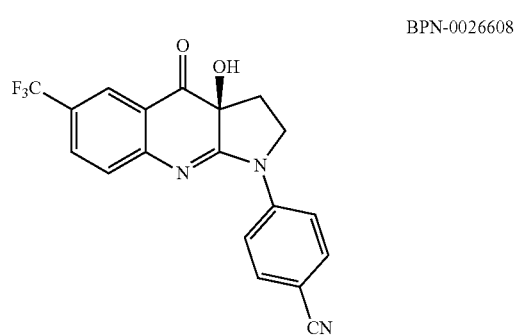 [SMILES: N#Cc1ccc(N2CC[C@@]3(O)C(=O)c4cc(C(F)(F)F)ccc4N=C23)cc1]

BPN-0026608

(S)-4-(3a-Hydroxy-4-oxo-6-(trifluoromethyl)-2,3,3a,4-tetrahydro-1H-pyrrolo[2,3-b]quinolin-1-yl)benzonitrile was prepared as a yellow solid according to Synthetic Scheme 3: mp=233-235° C.; $^1$H NMR (500 MHz, DMSO-$d_6$) δ 8.33 (dd, J=7.0, 2.0 Hz, 2H), 7.96 (d, J=2.0 Hz, 1H), 7.93-7.90 (m, 3H), 7.46 (d, J=8.5 Hz, 1H), 7.12 (s, 1H), 4.18-4.13 (m, 1H), 4.10-4.06 (m, 1H), 2.44-2.39 (m, 1H), 2.32-2.28 (m, 1H); ESI MS m/z 372 $[C_{19}H_{12}F_3N_3O_2+H]^+$; HPLC (Method B) >99% (AUC), $t_R$=10.66 min; Chiral HPLC (Chiralpak AD, Method A) 95.3% (AUC), $t_R$=16.42 min.

Preparation of (S)-6-Fluoro-3a-hydroxy-1-(3-methoxyphenyl)-7-methyl-1,2,3,3a-tetrahydro-4H-pyrrolo[2,3-b]quinolin-4-one

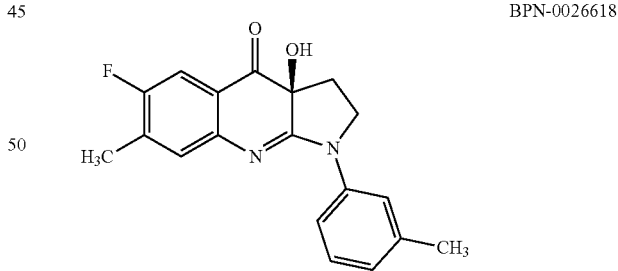

BPN-0026618

(S)-6-Fluoro-3a-hydroxy-1-(3-methoxyphenyl)-7-methyl-1,2,3,3a-tetrahydro-4H-pyrrolo[2,3-b]quinolin-4-one was prepared as a yellow solid according to Synthetic Scheme 3: mp=182-183° C.; $^1$H NMR (500 MHz, DMSO-$d_6$) δ 7.96 (t, J=2.0 Hz, 1H), 7.47 (dd, J=8.0, 1.5 Hz, 1H), 7.37 (d, J=9.0 Hz, 1H), 7.32 (t, J=8.0 Hz, 1H), 7.18 (d, J=6.5 Hz, 1H), 6.87 (s, 1H), 6.74 (dd, J=8.0, 2.0 Hz, 1H), 4.08-4.03 (m, 1H), 3.98-3.95 (m, 1H), 3.80 (s, 3H), 2.29 (s, 3H), 2.28-2.24 (m, 2H); ESI MS m/z 341 $[C_{19}H_{17}FN_2O_3+H]^+$; HPLC (Method B) >99% (AUC), $t_R$=8.53 min; Chiral HPLC (Chiralpak AD, Method A) >99% (AUC), $t_R$=14.78 min.

Preparation of (S)-1-(Benzofuran-6-yl)-6-fluoro-3a-hydroxy-7-methyl-1,2,3,3a-tetrahydro-4H-pyrrolo[2,3-b]quinolin-4-one

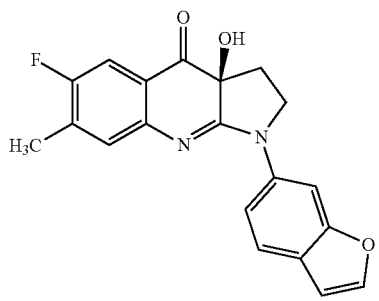

BPN-0026619

(S)-1-(Benzofuran-6-yl)-6-fluoro-3a-hydroxy-7-methyl-1,2,3,3a-tetrahydro-4H-pyrrolo[2,3-b]quinolin-4-one was prepared as a brown-orange solid according to Synthetic Scheme 3: mp=211-214° C.; $^1$H NMR (500 MHz, DMSO-$d_6$) δ 8.54 (s, 1H), 7.99 (d, J=2.0 Hz, 1H), 7.87 (dd, J=8.5, 2.0 Hz, 1H), 7.68 (d, J=8.5 Hz, 1H), 7.38 (d, J=9.0 Hz, 1H), 7.22 (d, J=6.5 Hz, 1H), 6.95 (dd, J=2.0, 1.0 Hz, 1H), 6.90 (s, 1H), 4.18-4.13 (m, 1H), 4.05-4.02 (m, 1H), 2.30-2.26 (m, 5H); ESI MS m/z 351 $[C_{20}H_{15}FN_2O_3+H]^+$; HPLC (Method B) >99% (AUC), $t_R$=8.89 min; Chiral HPLC (Chiralpak AD, Method A) >99% (AUC), $t_R$=17.52 min.

Preparation of (S)-6-Fluoro-3a-hydroxy-7-methyl-1-(m-tolyl)-1,2,3,3a-tetrahydro-4H-pyrrolo[2,3-b]quinolin-4-one

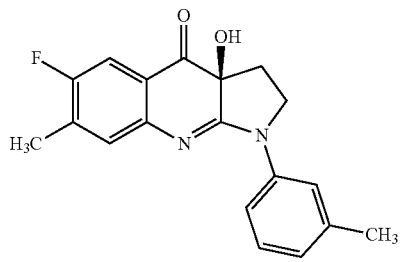

BPN-0026620

(S)-6-Fluoro-3a-hydroxy-7-methyl-1-(m-tolyl)-1,2,3,3a-tetrahydro-4H-pyrrolo[2,3-b]quinolin-4-one was prepared as a yellow solid according to Synthetic Scheme 3: mp=201-203° C.; $^1$H NMR (500 MHz, DMSO-$d_6$) δ 7.92 (d, J=6.0 Hz, 1H), 7.83 (s, 1H), 7.36 (d, J=9.0 Hz, 1H), 7.30 (t, J=8.0 Hz, 1H), 7.16 (d, J=6.5 Hz, 1H), 6.98 (d, J=7.0 Hz, 1H), 6.86 (s, 1H), 4.08-4.03 (m, 1H), 3.97-3.93 (m, 1H), 2.36 (s, 3H), 2.28 (apparent d, J=1.0 Hz, 3H), 2.27-2.24 (m, 2H); ESI MS m/z 325 $[C_{19}H_{17}FN_2O_2+H]^+$; HPLC (Method B) >99% (AUC), $t_R$=8.80 min; Chiral HPLC (Chiralpak AD, Method A) >99% (AUC), $t_R$=12.23 min.

Preparation of (S)-4-(6-Fluoro-3a-hydroxy-7-methyl-4-oxo-2,3,3a,4-tetrahydro-1H-pyrrolo[2,3-b]quinolin-1-yl)benzonitrile

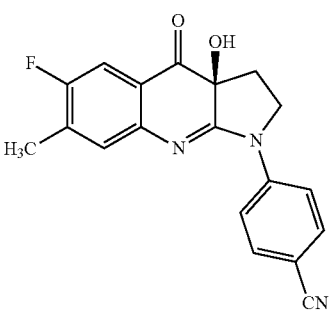

BPN-0026638

(S)-4-(6-Fluoro-3a-hydroxy-7-methyl-4-oxo-2,3,3a,4-tetrahydro-1H-pyrrolo[2,3-b]quinolin-1-yl)benzonitrile was prepared as a yellow solid according to Synthetic Scheme 4: $^1$H NMR (500 MHz, DMSO-$d_6$) δ 8.31 (d, J=9.0 Hz, 2H), 7.88 (d, J=9.0 Hz, 2H), 7.42 (d, J=9.0 Hz, 1H), 7.27 (d, J=6.5 Hz, 1H), 6.98 (broad s, 1H), 4.07-4.03 (m, 2H), 2.31-2.27 (m, 5H); ESI MS m/z 336 $[C_{19}H_{14}FN_3O_2+H]^+$; HPLC (Method B) >99% (AUC), $t_R$=8.24 min; Chiral SFC (Chiralcel OJ-H, Method B) >99% (AUC), $t_R$=5.29 min.

Preparation of (S)-6,7-Dichloro-3a-hydroxy-1-phenyl-1,2,3,3a-tetrahydro-4H-pyrrolo[2,3-b]quinolin-4-one

BPN-0026643

(S)-6,7-Dichloro-3a-hydroxy-1-phenyl-1,2,3,3a-tetrahydro-4H-pyrrolo[2,3-b]quinolin-4-one was prepared as a yellow solid according to Synthetic Scheme 3: mp=202-204° C.; $^1$H NMR (300 MHz, DMSO-$d_6$) δ 8.05 (dd, J=8.7, 1.2 Hz, 2H), 7.81 (s, 1H), 7.47-7.42 (m, 3H), 7.20 (t, J=7.5 Hz, 1H), 7.04 (s, 1H), 4.18-4.10 (m, 1H), 4.02-3.96 (m, 1H), 2.42-2.32 (m, 1H), 2.28-2.22 (m, 1H); ESI MS m/z 347 $[C_{17}H_{12}Cl_2N_2O_2+H]^+$; HPLC (Method B) 97.4% (AUC), $t_R$=9.10 min; Chiral HPLC (Chiralpak AD, Method A) >99% (AUC), $t_R$=12.93 min.

Preparation of (S)-3a-Hydroxy-6-methyl-1-phenyl-7-(trifluoromethyl)-1,2,3,3a-tetrahydro-4H-pyrrolo[2,3-b]quinolin-4-one

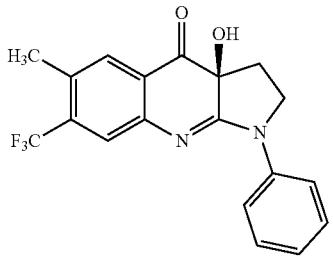

BPN-0026648

(S)-3a-Hydroxy-6-methyl-1-phenyl-7-(trifluoromethyl)-1,2,3,3a-tetrahydro-4H-pyrrolo[2,3-b]quinolin-4-one was prepared as a yellow solid according to Synthetic Scheme 3: mp=205-209° C.; $^1$H NMR (300 MHz, DMSO-d$_6$) δ 8.08 (d, J=7.8 Hz, 2H), 7.73 (s, 1H), 7.48-7.43 (m, 3H), 7.18 (t, J=7.5 Hz, 1H), 6.99 (s, 1H), 4.13-4.08 (m, 1H), 4.03-3.96 (m, 1H), 2.43 (s, 3H), 2.38-2.29 (m, 2H); ESI MS m/z 361 [C$_{19}$H$_{15}$F$_3$N$_2$O$_2$+H]$^+$; HPLC (Method B) 98.3% (AUC), t$_R$=9.29 min; Chiral SFC (Chiralcel OJ, Method A) 91.3% (AUC), t$_R$=4.16 min.

Preparation of (S)-6-Fluoro-3a-hydroxy-7-methyl-1-(2-methylthiazol-5-yl)-1,2,3,3a-tetrahydro-4H-pyrrolo[2,3-b]quinolin-4-one

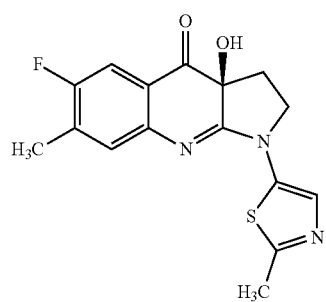

BPN-0026667

(S)-6-Fluoro-3a-hydroxy-7-methyl-1-(2-methylthiazol-5-yl)-1,2,3,3a-tetrahydro-4H-pyrrolo[2,3-b]quinolin-4-one was prepared as a yellow solid according to Synthetic Scheme 4: $^1$H NMR (500 MHz, DMSO-d$_6$) δ 7.47 (s, 1H), 7.38 (d, J=9.0 Hz, 1H), 7.18 (d, J=6.5 Hz, 1H), 6.97 (s, 1H), 4.07-3.92 (m, 2H), 2.60 (s, 3H), 2.44-2.41 (m, 1H), 2.31-2.28 (m, 4H); ESI MS m/z 332 [C$_{16}$H$_{14}$FN$_3$O$_2$S+H]$^+$; HPLC (Method B) >99% (AUC), t$_R$=9.16 min; Chiral HPLC (Chiralpak AD, Method A) 98.6% (AUC), t$_R$=13.72 min.

Preparation of (S)-6-Fluoro-3a-hydroxy-7-methyl-1-(2-methylbenzofuran-5-yl)-1,2,3,3a-tetrahydro-4H-pyrrolo[2,3-b]quinolin-4-one

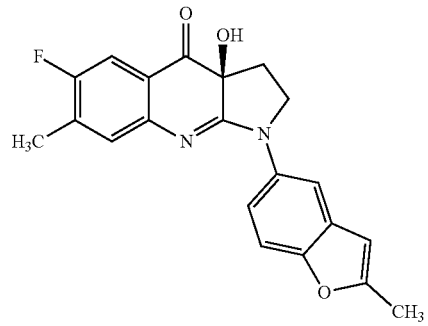

BPN-0026726

(S)-6-Fluoro-3a-hydroxy-7-methyl-1-(2-methylbenzofuran-5-yl)-1,2,3,3a-tetrahydro-4H-pyrrolo[2,3-b]quinolin-4-one was prepared as a yellow solid according to Synthetic Scheme 4: mp=203-205° C.; $^1$H NMR (500 MHz, DMSO-d$_6$) δ 8.12 (d, J=2.5 Hz, 1H), 7.91 (dd, J=9.0, 2.5 Hz, 1H), 7.52 (d, J=9.0 Hz, 1H), 7.36 (d, J=9.5 Hz, 1H), 7.13 (d, J=7.0 Hz, 1H), 6.86 (s, 1H), 6.62 (s, 1H), 4.17-4.12 (m, 1H), 3.99-3.95 (m, 1H), 2.46 (apparent d, J=1.0 Hz, 3H), 2.28-2.26 (m, 5H); ESI MS m/z 365 [C$_{21}$H$_{17}$FN$_2$O$_3$+H]$^+$; HPLC (Method B) >99% (AUC), t$_R$=9.12 min; Chiral HPLC (Chiralpak AD, Method A) 95.8% (AUC), t$_R$=15.34 min.

Preparation of (S)-6-Fluoro-3a-hydroxy-1-(2-methoxypyridin-4-yl)-7-methyl-1,2,3,3a-tetrahydro-4H-pyrrolo[2,3-b]quinolin-4-one

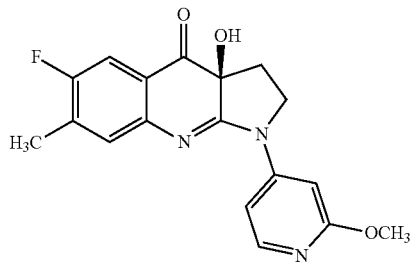

BPN-0026745

(S)-6-Fluoro-3a-hydroxy-1-(2-methoxypyridin-4-yl)-7-methyl-1,2,3,3a-tetrahydro-4H-pyrrolo[2,3-b]quinolin-4-one was prepared as a yellow solid according to Synthetic Scheme 4: mp=211-215° C.; $^1$H NMR (500 MHz, DMSO-d$_6$) δ 8.13 (d, J=6.0 Hz, 1H), 7.68 (dd, J=6.0, 2.0 Hz, 1H), 7.59 (d, J=2.0 Hz, 1H), 7.41 (d, J=9.0 Hz, 1H), 7.29 (d, J=7.0 Hz, 1H), 6.96 (s, 1H), 4.00-3.97 (m, 2H), 3.87 (s, 3H), 2.36 (s, 3H), 2.31-2.23 (m, 2H); ESI MS m/z 342 [C$_{18}$H$_{16}$FN$_3$O$_3$+H]$^+$; HPLC (Method B) >99% (AUC), t$_R$=8.95 min; Chiral HPLC (Chiralpak AD, Method A) 97.7% (AUC), t$_R$=14.01 min.

Preparation of (S)-6-Fluoro-3a-hydroxy-7-methyl-1-(1-methyl-1H-pyrazol-4-yl)-1,2,3,3a-tetrahydro-4H-pyrrolo[2,3-b]quinolin-4-one

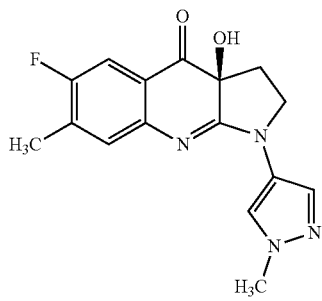

BPN-0026746

(S)-6-Fluoro-3a-hydroxy-7-methyl-1-(1-methyl-1H-pyrazol-4-yl)-1,2,3,3a-tetrahydro-4H-pyrrolo[2,3-b]quinolin-4-one was prepared as a yellow solid according to Synthetic Scheme 4: mp=234-238° C.; $^1$H NMR (500 MHz, DMSO-d$_6$) δ 8.25 (s, 1H), 7.83 (s, 1H), 7.32 (d, J=9.5 Hz, 1H), 7.15 (d, J=7.0 Hz, 1H), 6.80 (s, 1H), 3.92-3.91 (m, 1H), 3.87 (s, 3H), 3.83-3.81 (m, 1H), 2.36-2.35 (m, 1H), 2.31 (s, 3H), 2.28-2.25 (m, 1H); ESI MS m/z 315 [C$_{16}$H$_{15}$FN$_4$O$_2$+H]$^+$; HPLC (Method B) >99% (AUC), t$_R$=7.31 min; Chiral HPLC (Chiralpak AD, Method A) 98.3% (AUC), t$_R$=16.79 min.

Preparation of (S)-6-Fluoro-3a-hydroxy-7-methyl-1-(thiophen-2-yl)-1,2,3,3a-tetrahydro-4H-pyrrolo[2,3-b]quinolin-4-one

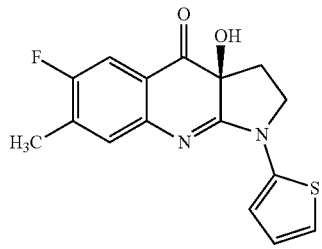

BPN-0026748

(S)-6-Fluoro-3a-hydroxy-7-methyl-1-(thiophen-2-yl)-1,2,3,3a-tetrahydro-4H-pyrrolo[2,3-b]quinolin-4-one was prepared as a red-orange solid according to Synthetic Scheme 4: mp=210-215° C.; $^1$H NMR (500 MHz, DMSO-d$_6$) δ 7.37 (d, J=9.5 Hz, 1H), 7.18-7.15 (m, 2H), 6.96 (dd, J=5.5, 4.0 Hz, 1H), 6.94 (s, 1H), 6.85 (dd, J=4.0, 1.5 Hz, 1H), 4.09-3.99 (m, 2H), 2.44-2.37 (m, 1H), 2.30-2.27 (m, 4H); ESI MS m/z 317 [C$_{16}$H$_{13}$FN$_2$O$_2$S+H]$^+$; HPLC (Method B) >99% (AUC), t$_R$=8.89 min; Chiral HPLC (Chiralpak AD, Method A) 96.7% (AUC), t$_R$=15.19 min.

Preparation of (S)-3a-Hydroxy-1-phenyl-1,2,3,3a-tetrahydro-4H-benzo[4,5]thieno[2,3-b]pyrrolo[3,2-e]pyridin-4-one

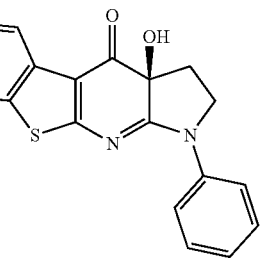

BPN-0026785

(S)-3a-Hydroxy-1-phenyl-1,2,3,3a-tetrahydro-4H-benzo[4,5]thieno[2,3-b]pyrrolo[3,2-e]pyridin-4-one was prepared as a yellow solid according to Synthetic Scheme 3: mp=247-248° C.; $^1$H NMR (500 MHz, DMSO-d$_6$) δ 8.19 (d, J=7.5 Hz, 1H), 7.96 (dd, J=8.5, 7.5 Hz, 2H), 7.84 (d, J=7.5 Hz, 1H), 7.52-7.49 (m, 2H), 7.42-7.39 (m, 1H), 7.29-7.25 (m, 2H), 7.06 (s, 1H), 4.30-4.25 (m, 1H), 4.12 (apparent t, J=7.5 Hz, 1H), 2.36-2.30 (m, 2H); ESI MS m/z 335 [C$_{19}$H$_{14}$N$_2$O$_2$S+H]$^+$; HPLC (Method B) >99% (AUC), t$_R$=10.70 min; Chiral HPLC (Chiralpak AD, Method A) >99% (AUC), t$_R$=21.14 min.

Preparation of (S)-1-(3-Chloro-4-methylphenyl)-3a-hydroxy-6-methyl-7-(trifluoromethyl)-1,2,3,3a-tetrahydro-4H-pyrrolo[2,3-b]quinolin-4-one

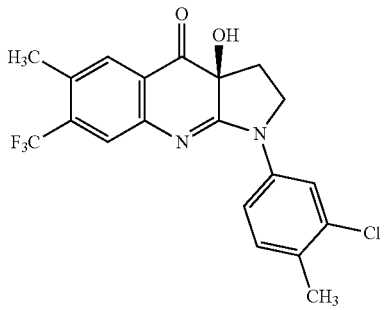

BPN-0026786

(S)-1-(3-Chloro-4-methylphenyl)-3a-hydroxy-6-methyl-7-(trifluoromethyl)-1,2,3,3a-tetrahydro-4H-pyrrolo[2,3-b]quinolin-4-one was prepared as an orange solid according to Synthetic Scheme 3: mp=212-217° C.; $^1$H NMR (300 MHz, DMSO-d$_6$) δ 8.28 (d, J=2.4 Hz, 1H), 7.89 (dd, J=8.4, 2.1 Hz, 1H), 7.74 (s, 1H), 7.41 (t, J=4.8 Hz, 2H), 7.01 (s, 1H), 4.13-3.95 (m, 2H), 2.44 (s, 3H), 2.34 (s, 3H), 2.28-2.26 (m, 2H); ESI MS m/z 409 [C$_{20}$H$_{16}$ClF$_3$N$_2$O$_2$+H]$^+$; HPLC (Method B) >99% (AUC), t$_R$=10.44 min; Chiral HPLC (Chiralpak AD, Method A) >99% (AUC), t$_R$=9.82 min.

Preparation of (S)-3a-Hydroxy-6-methyl-1-(p-tolyl)-7-(trifluoromethyl)-1,2,3,3a-tetrahydro-4H-pyrrolo[2,3-b]quinolin-4-one

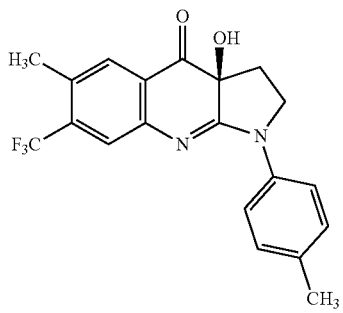

BPN-0026819

(S)-3a-Hydroxy-6-methyl-1-(p-tolyl)-7-(trifluoromethyl)-1,2,3,3a-tetrahydro-4H-pyrrolo[2,3-b]quinolin-4-one was prepared as an orange-yellow solid according to Synthetic Scheme 3: mp=202-205° C.; $^1$H NMR (500 MHz, DMSO-$d_6$) δ 7.93 (d, J=8.5 Hz, 2H), 7.71 (s, 1H), 7.39 (s, 1H), 7.25 (d, J=8.5 Hz, 2H), 6.94 (s, 1H), 4.12-4.07 (m, 1H), 3.96 (apparent t, J=7.5 Hz, 1H) 2.42 (s, 3H), 2.36-2.34 (m, 1H), 2.32 (s, 3H), 2.27-2.23 (m, 1H); ESI MS m/z 375 $[C_{20}H_{17}F_3N_2O_2+H]^+$; HPLC (Method C) >99% (AUC), $t_R$=14.19 min; Chiral HPLC (Chiralpak AD, Method A) >99% (AUC), $t_R$=10.94 min.

Preparation of (S)-3a-Hydroxy-6-methyl-1-(m-tolyl)-7-(trifluoromethyl)-1,2,3,3a-tetrahydro-4H-pyrrolo[2,3-b]quinolin-4-one

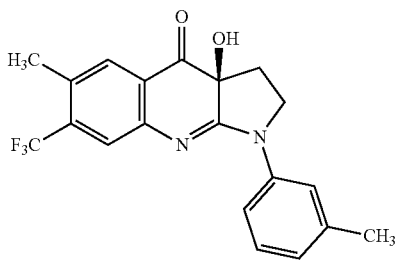

BPN-0026847

(S)-3a-Hydroxy-6-methyl-1-(m-tolyl)-7-(trifluoromethyl)-1,2,3,3a-tetrahydro-4H-pyrrolo[2,3-b]quinolin-4-one was prepared as a yellow solid according to Synthetic Scheme 3: mp=181-185° C.; $^1$H NMR (300 MHz, DMSO-$d_6$) δ 7.95 (d, J=8.4 Hz, 1H), 7.80 (s, 1H), 7.73 (s, 1H), 7.42 (s, 1H), 7.33 (t, J=7.8 Hz, 1H), 7.00 (d, J=7.5 Hz, 1H), 6.98 (s, 1H), 4.15-4.06 (m, 1H), 3.98 (apparent t, J=9.0 Hz, 1H), 2.43 (s, 3H), 2.37 (s, 3H), 2.30-2.22 (m, 2H); ESI MS m/z 375 $[C_{20}H_{17}F_3N_2O_2+H]^+$; HPLC (Method B) >99% (AUC), $t_R$=9.63 min; Chiral HPLC (Chiralpak AD, Method A) >99% (AUC), $t_R$=9.40 min.

Preparation of (S)-3a-Hydroxy-1-(4-methoxyphenyl)-6-methyl-7-(trifluoromethyl)-1,2,3,3a-tetrahydro-4H-pyrrolo[2,3-b]quinolin-4-one

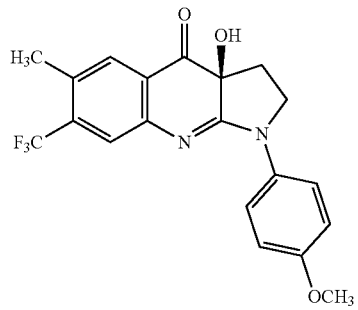

BPN-0026849

(S)-3a-Hydroxy-1-(4-methoxyphenyl)-6-methyl-7-(trifluoromethyl)-1,2,3,3a-tetrahydro-4H-pyrrolo[2,3-b]quinolin-4-one was prepared as a yellow solid according to Synthetic Scheme 3: mp=185-188° C.; $^1$H NMR (500 MHz, DMSO-$d_6$) δ 7.95 (dd, J=7.0, 2.5 Hz, 2H), 7.70 (s, 1H), 7.36 (s, 1H), 7.01 (dd, J=7.0, 2.0 Hz, 2H), 6.93 (s, 1H), 4.10-4.08 (m, 1H), 3.94 (apparent t, J=9.0 Hz, 1H), 3.78 (s, 3H), 2.42 (s, 3H), 2.36-2.33 (m, 1H), 2.27-2.23 (m, 1H); ESI MS m/z 391 $[C_{20}H_{17}F_3N_2O_3+H]^+$; HPLC (Method B) >99% (AUC), $t_R$=9.83 min; Chiral HPLC (Chiralpak AD, Method A) >99% (AUC), $t_R$=13.62 min.

Preparation of (S)-5-(3-Chloro-4-methylphenyl)-7a-hydroxy-2-methyl-5,6,7,7a-tetrahydro-8H-pyrrolo[2,3-b]thieno[2,3-e]pyridin-8-one

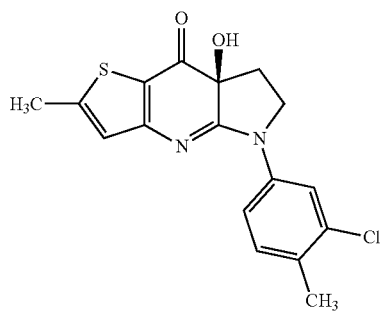

BPN-0026882

(S)-5-(3-Chloro-4-methylphenyl)-7a-hydroxy-2-methyl-5,6,7,7a-tetrahydro-8H-pyrrolo[2,3-b]thieno[2,3-e]pyridin-8-one was prepared as a yellow solid according to Synthetic Scheme 3: mp=210-212° C.; $^1$H NMR (500 MHz, DMSO-$d_6$) δ 8.25 (apparent d, J=2.0 Hz, 1H), 7.75 (dd, J=8.0, 2.0 Hz, 1H), 7.40 (d, J=8.5 Hz, 1H), 6.90 (s, 1H), 6.84 (s, 1H), 4.11-4.09 (m, 1H), 3.99 (apparent t, J=9.5 Hz, 1H), 2.33 (s, 3H), 2.24-2.18 (m, 2H), 3H obscured by solvent peak; ESI MS m/z 347 $[C_{17}H_{15}ClN_2O_2S+H]^+$; HPLC (Method B) >99% (AUC), $t_R$=9.74 min; Chiral HPLC (Chiralpak AD, Method A) >99% (AUC), $t_R$=16.62 min.

Preparation of (S)-3a-Hydroxy-1-(2-methoxypyridin-4-yl)-6-methyl-7-(trifluoromethyl)-1,2,3,3a-tetrahydro-4H-pyrrolo[2,3-b]quinolin-4-one

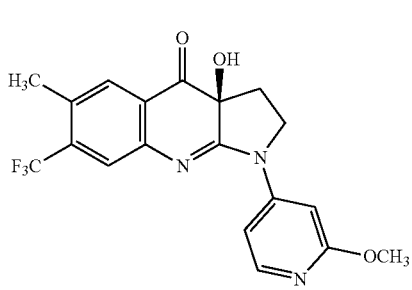

BPN-0027037

(S)-3a-Hydroxy-1-(2-methoxypyridin-4-yl)-6-methyl-7-(trifluoromethyl)-1,2,3,3a-tetrahydro-4H-pyrrolo[2,3-b]quinolin-4-one was prepared as a yellow solid according to Synthetic Scheme 4: $^1$H NMR (500 MHz, DMSO-d$_6$) δ 8.15 (d, J=6.0 Hz, 1H), 7.80-7.77 (m, 2H), 7.53-7.51 (m, 2H), 7.05 (s, 1H), 4.03-4.01 (m, 2H), 3.87 (s, 3H), 2.46 (s, 3H), 2.28-2.23 (m, 2H); ESI MS m/z 392 [C$_{19}$H$_{16}$F$_3$N$_3$O$_3$+H]$^+$; HPLC (Method B) >99% (AUC), t$_R$=11.12 min; Chiral HPLC (Chiralpak AD, Method A) 69.1% (AUC), t$_R$=11.35 min.

Preparation of (S)-4-(3a-Hydroxy-6-methyl-4-oxo-7-(trifluoromethyl)-2,3,3a,4-tetrahydro-1H-pyrrolo[2,3-b]quinolin-1-yl)benzonitrile

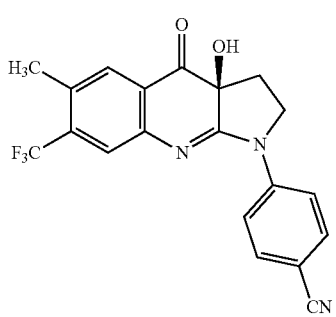

BPN-0027071

(S)-4-(3a-Hydroxy-6-methyl-4-oxo-7-(trifluoromethyl)-2,3,3a,4-tetrahydro-1H-pyrrolo[2,3-b]quinolin-1-yl)benzonitrile was prepared as a yellow solid according to Synthetic Scheme 6: mp=225-228° C.; $^1$H NMR (500 MHz, DMSO-d$_6$) δ 8.33 (d, J=9.0 Hz, 2H), 7.89 (d, J=9.0 Hz, 2H), 7.77 (s, 1H), 7.53 (s, 1H), 7.05 (s, 1H), 4.11-4.06 (m, 2H), 2.45 (s, 3H), 2.43-2.38 (m, 1H), 2.30-2.27 (m, 1H); ESI MS m/z 386 [C$_{20}$H$_{14}$F$_3$N$_3$O$_2$+H]$^+$; HPLC (Method C) >99% (AUC), t$_R$=15.95 min; Chiral HPLC (Chiralpak AD, Method A) 45.6% (AUC), t$_R$=16.30 min.

Preparation of (S)-4-(7a-Hydroxy-2-methyl-8-oxo-6,7,7a,8-tetrahydro-5H-pyrrolo[2,3-b]thieno[2,3-e]pyridin-5-yl)-2-methylbenzonitrile

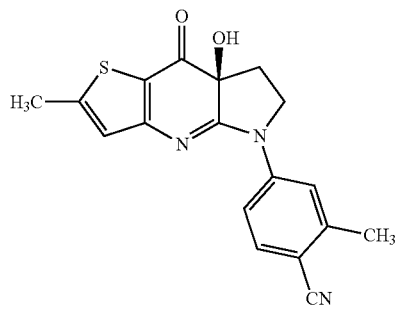

BPN-0027072

(S)-4-(7a-Hydroxy-2-methyl-8-oxo-6,7,7a,8-tetrahydro-5H-pyrrolo[2,3-b]thieno[2,3-e]pyridin-5-yl)-2-methylbenzonitrile was prepared as a yellow-brown solid according to Synthetic Scheme 3: mp=223-224° C.; $^1$H NMR (500 MHz, DMSO-d$_6$) δ 8.19 (dd, J=8.5, 2.5 Hz, 1H), 8.02 (d, J=2.0 Hz, 1H), 7.81 (d, J=8.5 Hz, 1H), 6.97 (s, 1H), 6.90 (apparent d, J=1.0 Hz, 1H), 4.12-4.05 (m, 2H), 2.52 (s, 3H), 2.49 (s, 3H), 2.27-2.22 (m, 2H); ESI MS m/z 338 [C$_{18}$H$_{15}$N$_3$O$_2$S+H]$^+$; HPLC (Method B) >99% (AUC), t$_R$=8.67 min; Chiral HPLC (Chiralpak AD, Method A) 96.3% (AUC), t$_R$=19.63 min.

Preparation of (S)-5-(3-Bromophenyl)-7a-hydroxy-2-methyl-5,6,7,7a-tetrahydro-8H-pyrrolo[2,3-b]thieno[2,3-e]pyridin-8-one

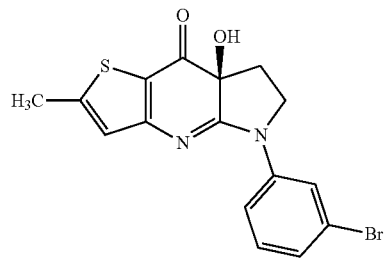

BPN-0027074

(S)-5-(3-Bromophenyl)-7a-hydroxy-2-methyl-5,6,7,7a-tetrahydro-8H-pyrrolo[2,3-b]thieno[2,3-e]pyridin-8-one was prepared as a yellow-orange solid according to Synthetic Scheme 3: mp=193-197° C.; $^1$H NMR (300 MHz, DMSO-d$_6$) δ 8.42 (s, 1H), 7.90 (dd, J=7.2, 4.8 Hz, 1H), 7.43-7.38 (m, 2H), 6.94 (s, 1H), 6.90 (apparent d, J=0.9 Hz, 1H), 4.16-3.98 (m, 2H), 2.27-2.14 (m, 2H), 3H obscured by solvent peak; ESI MS m/z 377 [C$_{16}$H$_{13}$BrN$_2$O$_2$S+H]$^+$; HPLC (Method B) 97.4% (AUC), t$_R$=8.27 min; Chiral HPLC (Chiralpak AD, Method A) >99% (AUC), t$_R$=16.25 min.

Preparation of (S)-1-(4-Chlorophenyl)-3a-hydroxy-6-methyl-7-(trifluoromethyl)-1,2,3,3a-tetrahydro-4H-pyrrolo[2,3-b]quinolin-4-one

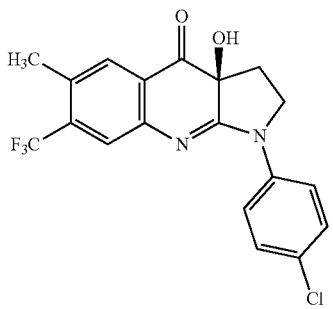
BPN-0027080

(S)-1-(4-Chlorophenyl)-3a-hydroxy-6-methyl-7-(trifluoromethyl)-1,2,3,3a-tetrahydro-4H-pyrrolo[2,3-b]quinolin-4-one was prepared as a yellow solid according to Synthetic Scheme 3: mp=223-226° C.; $^1$H NMR (500 MHz, DMSO-$d_6$) δ 8.13 (apparent dt, J=9.0, 3.5 Hz, 2H), 7.34 (s, 1H), 7.50 (apparent dt, J=9.0, 3.5 Hz, 2H), 7.44 (s, 1H), 6.99 (s, 1H), 4.11-4.07 (m, 1H), 3.99 (apparent t, J=9.5 Hz, 1H), 2.43 (s, 3H), 2.40-2.34 (m, 1H), 2.28-2.24 (m, 1H); ESI MS m/z 395 $[C_{19}H_{14}ClF_3N_2O_2+H]^+$; HPLC (Method C) >99% (AUC), $t_R$=15.90 min; Chiral HPLC (Chiralpak AD, Method A) >99% (AUC), $t_R$=12.18 min.

Preparation of (S)-1-(Benzofuran-6-yl)-3a-hydroxy-6-methyl-7-(trifluoromethyl)-1,2,3,3a-tetrahydro-4H-pyrrolo[2,3-b]quinolin-4-one

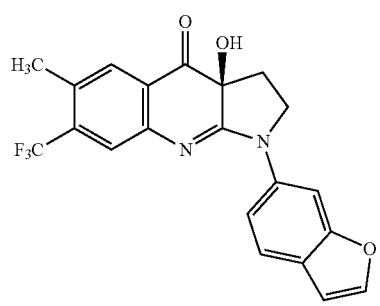
BPN-0027108

(S)-1-(Benzofuran-6-yl)-3a-hydroxy-6-methyl-7-(trifluoromethyl)-1,2,3,3a-tetrahydro-4H-pyrrolo[2,3-b]quinolin-4-one was prepared as a bright orange solid according to Synthetic Scheme 3: mp=206-209° C.; $^1$H NMR (500 MHz, DMSO-$d_6$) δ 8.47 (s, 1H), 8.01 (d, J=2.5 Hz, 1H), 7.92 (dd, J=8.5, 2.0 Hz, 1H), 7.74 (s, 1H), 7.70 (d, J=8.5 Hz, 1H), 7.45 (s, 1H), 6.99 (s, 1H), 6.97 (apparent dd, J=2.0, 1.0 Hz, 1H), 4.22-4.17 (m, 1H), 4.06 (apparent t, J=9.0 Hz, 1H), 2.43 (s, 3H), 2.41-2.38 (m, 1H), 2.30-2.27 (m, 1H); ESI MS m/z 401 $[C_{21}H_{15}F_3N_2O_3+H]^+$; HPLC (Method B) >99% (AUC), $t_R$=8.96 min; Chiral HPLC (Chiralpak AD, Method A) >99% (AUC), $t_R$=14.11 min.

Preparation of (S)-3a-Hydroxy-6,7-dimethyl-1-(2-methylbenzo[d]oxazol-5-yl)-1,2,3,3a-tetrahydro-4H-pyrrolo[2,3-b]quinolin-4-one

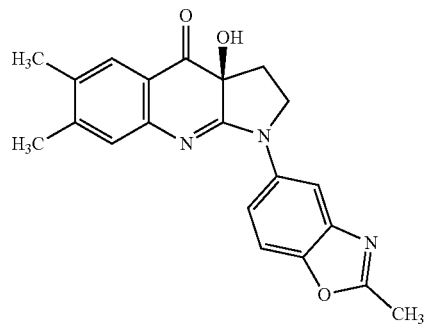
BPN-0027118

(S)-3a-Hydroxy-6,7-dimethyl-1-(2-methylbenzo[d]oxazol-5-yl)-1,2,3,3a-tetrahydro-4H-pyrrolo[2,3-b]quinolin-4-one was prepared as a yellow solid according to Synthetic Scheme 4: $^1$H NMR (500 MHz, DMSO-$d_6$) δ 8.44 (apparent d, J=2.0 Hz, 1H), 8.01 (dd, J=9.0, 2.5 Hz, 1H), 7.68 (d, J=9.0 Hz, 1H), 7.49 (s, 1H), 7.05 (s, 1H), 6.78 (s, 1H), 4.16-4.11 (m, 1H), 4.05-3.98 (m, 1H), 2.62 (s, 3H), 2.27-2.26 (m, 5H), 2.22 (s, 3H); ESI MS m/z 362 $[C_{21}H_{19}N_3O_3+H]^+$; HPLC (Method B) >99% (AUC), $t_R$=7.83 min; Chiral HPLC (Chiralpak AD, Method A) 84.2% (AUC), $t_R$=23.32 min.

Preparation of (S)-2-Chloro-4-(7a-hydroxy-2-methyl-8-oxo-6,7,7a,8-tetrahydro-5H-pyrrolo[2,3-b]thieno[2,3-e]pyridin-5-yl)benzonitrile

BPN-0027162

(S)-2-Chloro-4-(7a-hydroxy-2-methyl-8-oxo-6,7,7a,8-tetrahydro-5H-pyrrolo[2,3-b]thieno[2,3-e]pyridin-5-yl)benzonitrile was prepared as a yellow solid according to Synthetic Scheme 3: mp=247-250° C.; $^1$H NMR (500 MHz, DMSO-$d_6$) δ 8.55 (apparent d, J=2.0 Hz, 1H), 8.13 (dd, J=9.0, 2.0 Hz, 1H), 8.01 (d, J=9.0 Hz, 1H), 7.04 (s, 1H), 6.95 (apparent d, J=1.0 Hz, 1H), 4.14-4.08 (m, 2H), 2.52 (s, 3H), 2.29-2.19 (m, 2H); ESI MS m/z 358 $[C_{17}H_{12}ClN_3O_2S+H]^+$; HPLC (Method B) >99% (AUC), $t_R$=9.82 min; Chiral HPLC (Chiralpak AD, Method A) 77.2% (AUC), $t_R$=20.56 min.

Preparation of (S)-7a-Hydroxy-2-methyl-5-(quinolin-6-yl)-5,6,7,7a-tetrahydro-8H-pyrrolo[2,3-b]thieno[2,3-e]pyridin-8-one

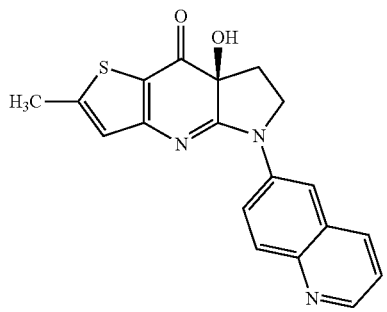

BPN-0027181

(S)-7a-Hydroxy-2-methyl-5-(quinolin-6-yl)-5,6,7,7a-tetrahydro-8H-pyrrolo[2,3-b]thieno[2,3-e]pyridin-8-one was prepared as a yellow solid according to Synthetic Scheme 3: mp=247-249° C.; $^1$H NMR (500 MHz, DMSO-d$_6$) δ 8.86 (dd, J=4.5, 2.0 Hz, 1H), 8.67 (dd, J=9.0, 2.5 Hz, 1H), 8.38 (d, J=2.0 Hz, 1H), 8.36 (d, J=7.0 Hz, 1H), 8.07 (d, J=9.5 Hz, 1H), 7.55 (dd, J=8.0, 4.0 Hz, 1H), 6.97 (s, 1H), 6.88 (apparent d, J=0.5 Hz, 1H), 4.29-4.24 (m, 1H), 4.17 (apparent t, J=7.5 Hz, 1H), 2.52 (s, 3H), 2.32-2.27 (m, 2H); ESI MS m/z 350 [C$_{19}$H$_{15}$N$_3$O$_2$S+H]$^+$; HPLC (Method B) >99% (AUC), t$_R$=7.18 min; Chiral HPLC (Chiralpak AD, Method A) 97.5% (AUC), t$_R$=21.48 min.

Preparation of (S)-1-(Benzo[d]thiazol-6-yl)-6-fluoro-3a-hydroxy-7-methyl-1,2,3,3a-tetrahydro-4H-pyrrolo[2,3-b]quinolin-4-one

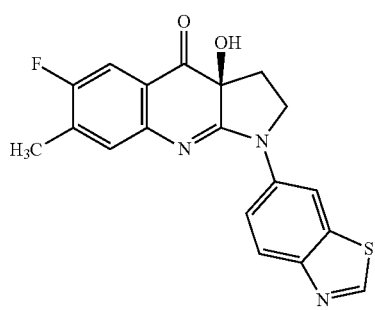

BPN-0027196

(S)-1-(Benzo[d]thiazol-6-yl)-6-fluoro-3a-hydroxy-7-methyl-1,2,3,3a-tetrahydro-4H-pyrrolo[2,3-b]quinolin-4-one was prepared as a yellow solid according to Synthetic Scheme 6: mp=130-133° C.; $^1$H NMR (500 MHz, DMSO-d$_6$) δ 9.33 (s, 1H), 8.90 (d, J=2.5 Hz, 1H), 8.32 (dd, J=9.0, 2.0 Hz, 1H), 8.12 (d, J=9.0 Hz, 1H), 7.39 (d, J=9.0 Hz, 1H), 7.26 (d, J=6.5 Hz, 1H), 6.93 (s, 1H), 4.20-4.14 (m, 1H), 4.07 (apparent t, J=8.0 Hz, 1H), 2.34-2.27 (m, 5H); ESI MS m/z 368 [C$_{19}$H$_{14}$FN$_3$O$_2$S+H]$^+$; HPLC (Method C) >99% (AUC), t$_R$=12.76 min; Chiral HPLC (Chiralpak AD, Method A) 75.2% (AUC), t$_R$=20.73 min.

Preparation of (S)-6-Fluoro-3a-hydroxy-7-methyl-1-(quinolin-6-yl)-3,3a-dihydro-1H-pyrrolo[2,3-b]quinolin-4(2H)-one

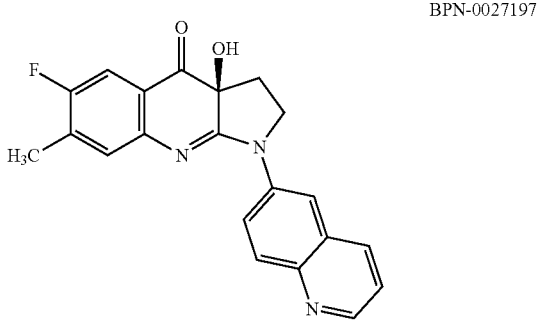 [SMILES: Cc1cc2c(cc1F)C(=O)[C@]1(O)CCN(c3ccc4ncccc4c3)C1=N2]

BPN-0027197

(S)-6-Fluoro-3a-hydroxy-7-methyl-1-(quinolin-6-yl)-3,3a-dihydro-1H-pyrrolo[2,3-b]quinolin-4(2H)-one was prepared as a yellow solid according to Synthetic Scheme 6: $^1$H NMR (500 MHz, DMSO-d$_6$) δ 8.84 (dd, J=4.5, 2.0 Hz, 1H), 8.76 (dd, J=9.0, 2.5 Hz, 1H), 8.46 (d, J=2.5 Hz, 1H), 8.37 (d, J=8.5 Hz, 1H), 8.06 (d, J=9.0 Hz, 1H), 7.54 (dd, J=8.5, 4.5 Hz, 1H), 7.41 (d, J=9.5 Hz, 1H), 7.28 (d, J=6.5 Hz, 1H), 6.96 (s, 1H), 4.21-4.14 (m, 2H), 2.37-2.31 (m, 5H); ESI MS m/z 362 [C$_{21}$H$_{16}$FN$_3$O$_2$+H]$^+$; HPLC (Method C) >99% (AUC), t$_R$=12.21 min; Chiral HPLC (Chiralpak AD, Method A) 58.8% (AUC), t$_R$=19.16 min.

Preparation of (S)-6-Fluoro-3a-hydroxy-7-methyl-1-(2-methylbenzo[d]oxazol-5-yl)-1,2,3,3a-tetrahydro-4H-pyrrolo[2,3-b]quinolin-4-one

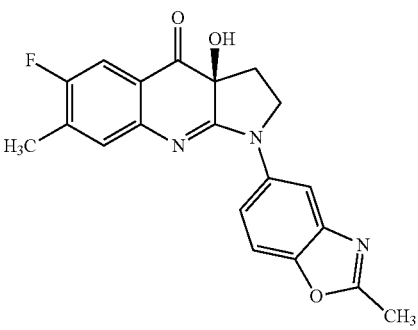

BPN-0027198

(S)-6-Fluoro-3a-hydroxy-7-methyl-1-(2-methylbenzo[d]oxazol-5-yl)-1,2,3,3a-tetrahydro-4H-pyrrolo[2,3-b]quinolin-4-one was prepared as a yellow solid according to Synthetic Scheme 4: $^1$H NMR (500 MHz, DMSO-d$_6$) δ 8.42 (d, J=2.0 Hz, 1H), 7.99 (dd, J=9.0, 2.0 Hz, 1H), 7.69 (d, J=9.0 Hz, 1H), 7.37 (d, J=9.0 Hz, 1H), 7.18 (d, J=7.5 Hz, 1H), 6.89 (s, 1H), 4.16-4.13 (m, 1H), 4.01 (apparent t, J=7.5 Hz, 1H), 2.63 (s, 3H), 2.31-2.26 (m, 5H); ESI MS m/z 366 [C$_{20}$H$_{16}$FN$_3$O$_3$+H]$^+$; HPLC (Method C) >99% (AUC), t$_R$=12.02 min; Chiral HPLC (Chiralpak AD, Method A) 72.8% (AUC), t$_R$=20.60 min.

Preparation of (S)-3a-Hydroxy-1-(quinolin-6-yl)-6-(trifluoromethyl)-1,2,3,3a-tetrahydro-4H-pyrrolo[2,3-b]quinolin-4-one

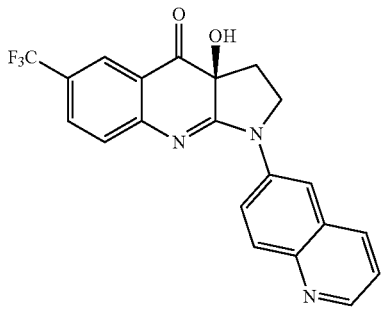

BPN-0027218

(S)-3a-Hydroxy-1-(quinolin-6-yl)-6-(trifluoromethyl)-1,2,3,3a-tetrahydro-4H-pyrrolo[2,3-b]quinolin-4-one was prepared as a yellow solid according to Synthetic Scheme 6: mp=258-260° C.; $^1$H NMR (300 MHz, DMSO-d$_6$) δ 8.87 (dd, J=3.9, 2.4 Hz, 1H), 8.73 (dd, J=9.0, 2.7 Hz, 1H), 8.51 (s, 1H), 8.41 (d, J=6.9 Hz, 1H), 8.10 (d, J=9.3 Hz, 1H), 7.96 (s, 1H), 7.91 (d, J=8.4 Hz, 1H), 7.56 (dd, J=8.4, 4.5 Hz, 1H), 7.47 (d, J=8.7 Hz, 1H), 7.13 (s, 1H), 4.30-4.16 (m, 2H), 2.74-2.63 (m, 1H), 2.17-1.98 (m, 1H); ESI MS m/z 398 [C$_{21}$H$_{14}$F$_3$N$_3$O$_2$+H]$^+$; HPLC (Method C) >99% (AUC), t$_R$=13.48 min; Chiral HPLC (Chiralpak AD, Method A) 49.1% (AUC), t$_R$=16.74 min.

Preparation of (S)-1-(Benzo[d]thiazol-6-yl)-3a-hydroxy-6-(trifluoromethyl)-1,2,3,3a-tetrahydro-4H-pyrrolo[2,3-b]quinolin-4-one

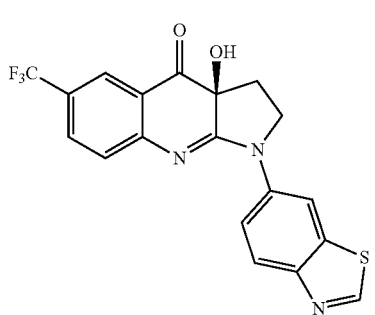

BPN-0027219

(S)-1-(Benzo[d]thiazol-6-yl)-3a-hydroxy-6-(trifluoromethyl)-1,2,3,3a-tetrahydro-4H-pyrrolo[2,3-b]quinolin-4-one was prepared as a yellow solid according to Synthetic Scheme 6: $^1$H NMR (500 MHz, DMSO-d$_6$) δ 9.37 (s, 1H), 8.87 (d, J=2.5 Hz, 1H), 8.32 (dd, J=9.0, 2.5 Hz, 1H), 8.15 (d, J=9.0 Hz, 1H), 7.94 (d, J=2.0 Hz, 1H), 7.87 (dd, J=8.5, 2.5 Hz, 1H), 7.44 (d, J=8.5 Hz, 1H), 7.09 (s, 1H), 4.28-4.23 (m, 1H), 4.12 (apparent t, J=9.5 Hz, 1H), 2.34-2.31 (m, 2H); ESI MS m/z 404 [C$_{19}$H$_{12}$F$_3$N$_3$O$_2$S+H]$^+$; HPLC (Method C) >99% (AUC), t$_R$=13.22 min; Chiral HPLC (Chiralpak AD, Method A) 50.0% (AUC), t$_R$=16.78 min.

Preparation of (S)-3a-Hydroxy-6,7-dimethyl-1-(quinazolin-6-yl)-1,2,3,3a-tetrahydro-4H-pyrrolo[2,3-b]quinolin-4-one

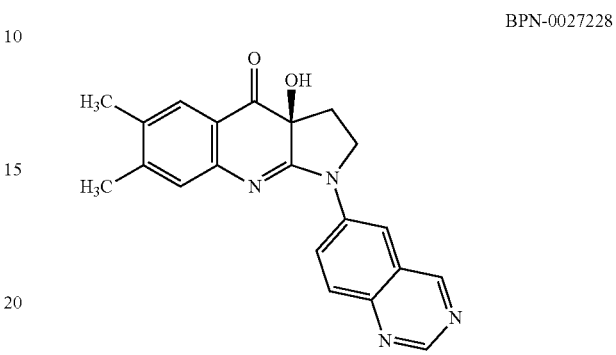

BPN-0027228

(S)-3a-Hydroxy-6,7-dimethyl-1-(quinazolin-6-yl)-1,2,3,3a-tetrahydro-4H-pyrrolo[2,3-b]quinolin-4-one was prepared as a yellow solid according to Synthetic Scheme 6: mp=275-276° C.; $^1$H NMR (500 MHz, DMSO-d$_6$) δ 9.61 (s, 1H), 9.23 (s, 1H), 9.04 (dd, J=9.0, 2.5 Hz, 1H), 8.65 (d, J=2.5 Hz, 1H), 8.08 (d, J=9.5 Hz, 1H), 7.53 (s, 1H), 7.19 (s, 1H), 6.89 (s, 1H), 4.23-4.13 (m, 2H), 2.34-2.32 (m, 2H), 2.31 (s, 3H), 2.25 (s, 3H); ESI MS m/z 359 [C$_{21}$H$_{18}$N$_4$O$_2$+H]$^+$; HPLC (Method C) >99% (AUC), t$_R$=11.18 min; Chiral HPLC (Chiralpak AD, Method A) 70.8% (AUC), t$_R$=20.49 min.

Preparation of (S)-3a-Hydroxy-1-(3-methylisoxazol-5-yl)-6-(trifluoromethyl)-1,2,3,3a-tetrahydro-4H-pyrrolo[2,3-b]quinolin-4-one

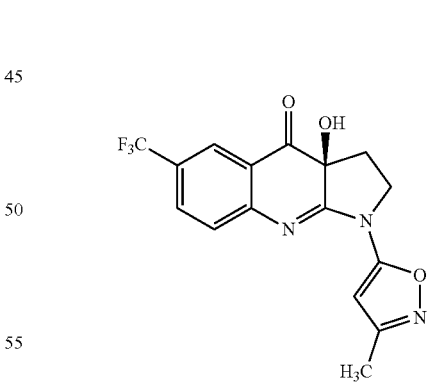

BPN-0027237

(S)-3a-Hydroxy-1-(3-methylisoxazol-5-yl)-6-(trifluoromethyl)-1,2,3,3a-tetrahydro-4H-pyrrolo[2,3-b]quinolin-4-one was prepared as a yellow solid according to Synthetic Scheme 6: $^1$H NMR (500 MHz, DMSO-d$_6$) δ 7.97-7.94 (m, 2H), 7.52 (d, J=8.0 Hz, 1H), 7.18 (s, 1H), 7.00 (s, 1H), 4.17-4.07 (m, 2H), 2.32-2.29 (m, 2H), 2.27 (s, 3H); ESI MS m/z 352 [C$_{16}$H$_{12}$F$_3$N$_3$O$_3$+H]$^+$; HPLC (Method F) 98.2% (AUC), t$_R$=15.70 min; Chiral HPLC (Chiralpak AD, Method B) 59.1% (AUC), t$_R$=12.14 min.

Preparation of (S)-1-(Cinnolin-6-yl)-3a-hydroxy-6,7-dimethyl-1,2,3,3a-tetrahydro-4H-pyrrolo[2,3-b]quinolin-4-one

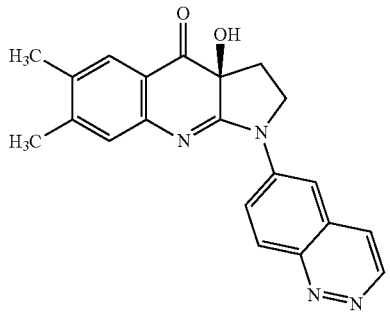

BPN-0027241

(S)-1-(Cinnolin-6-yl)-3a-hydroxy-6,7-dimethyl-1,2,3,3a-tetrahydro-4H-pyrrolo[2,3-b]quinolin-4-one was prepared as a yellow solid according to Synthetic Scheme 6: mp=274-276° C.; $^1$H NMR (500 MHz, DMSO-d$_6$) δ 9.28 (d, J=6.0 Hz, 1H), 9.03 (dd, J=9.5, 2.5 Hz, 1H), 8.49 (dd, J=5.0, 2.5 Hz, 2H), 8.17 (d, J=6.0 Hz, 1H), 7.55 (s, 1H), 7.22 (s, 1H), 6.92 (s, 1H), 4.19-4.16 (m, 2H), 2.36-2.32 (m, 5H), 2.26 (s, 3H); ESI MS m/z 359 [C$_{21}$H$_{18}$N$_4$O$_2$+H]$^+$; HPLC (Method C) >99% (AUC), t$_R$=12.43 min; Chiral HPLC (Chiralpak AD, Method A) 54.2% (AUC), t$_R$=16.90 min.

Preparation of (S)-3a-Hydroxy-1-(2-methoxyquinolin-6-yl)-6,7-dimethyl-1,2,3,3a-tetrahydro-4H-pyrrolo[2,3-b]quinolin-4-one

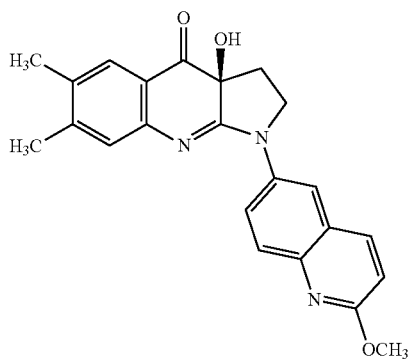

BPN-0027250

(S)-3a-Hydroxy-1-(2-methoxyquinolin-6-yl)-6,7-dimethyl-1,2,3,3a-tetrahydro-4H-pyrrolo[2,3-b]quinolin-4-one was prepared as a yellow solid according to Synthetic Scheme 6: mp=233-237° C.; $^1$H NMR (500 MHz, DMSO-d$_6$) δ 8.65 (dd, J=9.5, 2.5 Hz, 1H), 8.38 (d, J=2.5 Hz, 1H), 8.25 (d, J=9.0 Hz, 1H), 7.83 (d, J=9.5 Hz, 1H), 7.50 (s, 1H), 7.11 (s, 1H), 7.04 (d, J=9.0 Hz, 1H), 6.81 (s, 1H), 4.18-4.13 (m, 1H), 4.09-4.04 (m, 1H), 3.99 (s, 3H), 2.31-2.29 (m, 5H), 2.23 (s, 3H); ESI MS m/z 388 [C$_{23}$H$_{21}$N$_3$O$_3$+H]$^+$; HPLC (Method C) 95.9% (AUC), t$_R$=14.47 min; Chiral HPLC (Chiralpak AD, Method A) 78.1% (AUC), t$_R$=18.25 min.

Preparation of (S)-3a-Hydroxy-1-(2-methoxyquinolin-6-yl)-6-methyl-1,2,3,3a-tetrahydro-4H-pyrrolo[2,3-b]quinolin-4-one

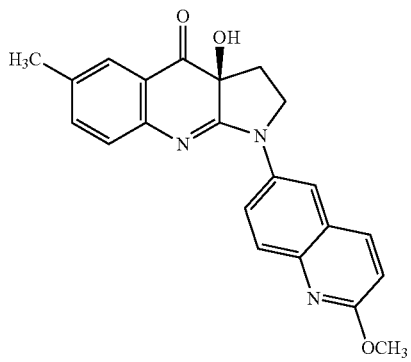

BPN-0027255

(S)-3a-Hydroxy-1-(2-methoxyquinolin-6-yl)-6-methyl-1,2,3,3a-tetrahydro-4H-pyrrolo[2,3-b]quinolin-4-one was prepared as a yellow solid according to Synthetic Scheme 6: mp=230-234° C.; $^1$H NMR (500 MHz, DMSO-d$_6$) δ 8.62 (dd, J=9.0, 2.5 Hz, 1H), 8.40 (d, J=2.5 Hz, 1H), 8.25 (d, J=8.5 Hz, 1H), 7.83 (d, J=9.0 Hz, 1H), 7.55 (d, J=1.5 Hz, 1H), 7.40 (dd, J=8.5, 2.5 Hz, 1H), 7.19 (d, J=8.0 Hz, 1H), 7.04 (d, J=9.0 Hz, 1H), 6.87 (s, 1H), 4.19-4.14 (m, 1H), 4.10-4.07 (m, 1H), 3.99 (s, 3H), 2.32-2.30 (m, 5H); ESI MS m/z 374 [C$_{22}$H$_{19}$N$_3$O$_3$+H]$^+$; HPLC (Method C) >99% (AUC), t$_R$=13.28 min; Chiral HPLC (Chiralpak AD, Method A) 71.5% (AUC), t$_R$=17.22 min.

Preparation of (S)-3a-Hydroxy-6-methyl-1-(3-methylisoxazol-5-yl)-7-(trifluoromethyl)-1,2,3,3a-tetrahydro-4H-pyrrolo[2,3-b]quinolin-4-one

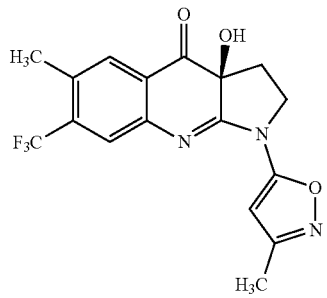

BPN-0027346

(S)-3a-Hydroxy-6-methyl-1-(3-methylisoxazol-5-yl)-7-(trifluoromethyl)-1,2,3,3a-tetrahydro-4H-pyrrolo[2,3-b]quinolin-4-one was prepared as a yellow solid according to Synthetic Scheme 6: $^1$H NMR (500 MHz, DMSO-d$_6$) δ 7.78 (s, 1H), 7.59 (s, 1H), 7.12 (s, 1H), 6.69 (s, 1H), 4.15-4.11 (m, 1H), 4.09-4.03 (m, 1H), 2.46 (s, 3H), 2.30-2.28 (m, 2H), 2.26 (s, 3H); ESI MS m/z 366 [C$_{17}$H$_{14}$F$_3$N$_3$O$_3$+H]$^+$; HPLC (Method C) 98.3% (AUC), t$_R$=18.85 min; Chiral HPLC (Chiralpak AD, Method A) 49.5% (AUC), t$_R$=15.32 min.

Preparation of (S)-3a-Hydroxy-6-methyl-1-(3-methylbenzo[d]isoxazol-6-yl)-1,2,3,3a-tetrahydro-4H-pyrrolo[2,3-b]quinolin-4-one

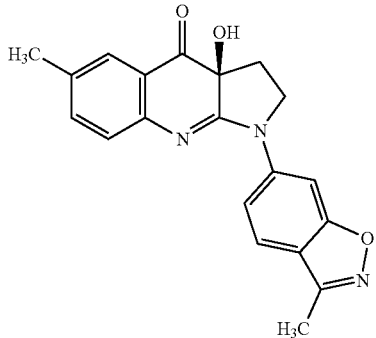

BPN-0027374

(S)-3a-Hydroxy-6-methyl-1-(3-methylbenzo[d]isoxazol-6-yl)-1,2,3,3a-tetrahydro-4H-pyrrolo[2,3-b]quinolin-4-one was prepared as a yellow solid according to Synthetic Scheme 6: mp=249-251° C.; $^1$H NMR (500 MHz, DMSO-$d_6$) δ 8.62 (d, J=1.5 Hz, 1H), 8.08 (dd, J=9.0, 2.0 Hz, 1H), 7.86 (d, J=9.0 Hz, 1H), 7.57 (d, J=1.5 Hz, 1H), 7.42 (dd, J=8.0, 1.5 Hz, 1H), 7.23 (d, J=8.0 Hz, 1H), 6.91 (s, 1H), 4.17-4.02 (m, 2H), 2.55 (s, 3H), 2.33 (s, 3H), 2.31-2.29 (m, 2H); ESI MS m/z 348 $[C_{20}H_{17}N_3O_3+H]^+$; HPLC (Method C) >99% (AUC), $t_R$=12.92 min; Chiral HPLC (Chiralpak AD, Method A) 68.8% (AUC), $t_R$=19.68 min.

Preparation of (S)-3a-Hydroxy-6-methyl-1-(pyrazolo[1,5-a]pyridin-5-yl)-1,2,3,3a-tetrahydro-4H-pyrrolo[2,3-b]quinolin-4-one

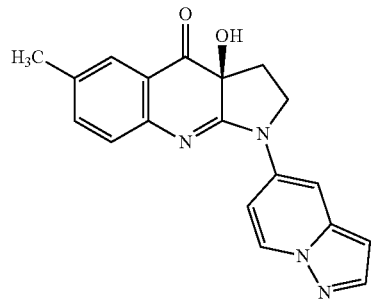

BPN-0027396

(S)-3a-Hydroxy-6-methyl-1-(pyrazolo[1,5-a]pyridin-5-yl)-1,2,3,3a-tetrahydro-4H-pyrrolo[2,3-b]quinolin-4-one was prepared as a yellow solid according to Synthetic Scheme 6: mp=242-243° C.; $^1$H NMR (500 MHz, DMSO-$d_6$) δ 8.69 (d, J=8.0 Hz, 1H), 8.16 (d, J=2.5 Hz, 1H), 8.00 (dd, J=8.0, 2.5 Hz, 1H), 7.96 (d, J=2.0 Hz, 1H), 7.56 (d, J=2.0 Hz, 1H), 7.42 (dd, J=8.5, 2.0 Hz, 1H), 7.21 (d, J=8.0 Hz, 1H), 6.91 (s, 1H), 6.56 (dd, J=2.0, 0.5 Hz, 1H), 4.18-4.13 (m, 1H), 4.09-4.05 (m, 2H), 2.36 (s, 3H), 2.30-2.28 (m, 2H); ESI MS m/z 333 $[C_{19}H_{16}N_4O_2+H]^+$; UPLC (Method A) 95.5% (AUC), $t_R$=2.80 min; Chiral HPLC (Chiralpak AD, Method A) 74.1% (AUC), $t_R$=21.26 min.

Preparation of (S)-3a-Hydroxy-1-(imidazo[1,5-a]pyridin-6-yl)-6-methyl-1,2,3,3a-tetrahydro-4H-pyrrolo[2,3-b]quinolin-4-one

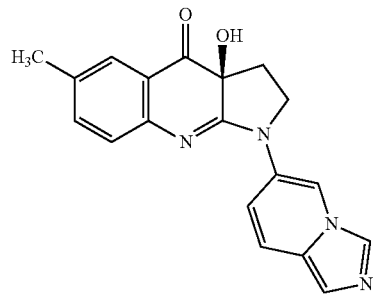

BPN-0027406

(S)-3a-Hydroxy-1-(imidazo[1,5-a]pyridin-6-yl)-6-methyl-1,2,3,3a-tetrahydro-4H-pyrrolo[2,3-b]quinolin-4-one was prepared as a yellow solid according to Synthetic Scheme 6: mp=215-219° C. dec.; $^1$H NMR (500 MHz, DMSO-$d_6$) δ 9.26 (s, 1H), 8.45 (s, 1H), 7.62 (d, J=10.0 Hz, 1H), 7.54-7.50 (m, 2H), 7.40 (d, J=8.0 Hz, 1H), 7.37 (s, 1H), 7.18 (d, J=8.0 Hz, 1H), 6.87 (s, 1H), 4.08-4.02 (m, 1H), 3.96 (apparent t, J=8.0 Hz, 1H), 2.31 (s, 3H), 2.28-2.25 (m, 2H); ESI MS m/z 333 $[C_{19}H_{16}N_4O_2+H]^+$; UPLC (Method A) >99% (AUC), $t_R$=2.40 min; Chiral HPLC (Chiralpak AD, Method A) 84.0% (AUC), $t_R$=20.09 min.

Preparation of (S)-3a-Hydroxy-6-methyl-1-(thieno[3,2-b]pyridin-2-yl)-1,2,3,3a-tetrahydro-4H-pyrrolo[2,3-b]quinolin-4-one

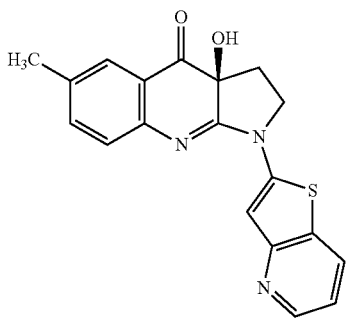

BPN-0027468

(S)-3a-Hydroxy-6-methyl-1-(thieno[3,2-b]pyridin-2-yl)-1,2,3,3a-tetrahydro-4H-pyrrolo[2,3-b]quinolin-4-one was prepared as an orange solid according to Synthetic Scheme 6: mp=260-262° C.; $^1$H NMR (300 MHz, DMSO-$d_6$) δ 8.57 (d, J=3.3 Hz, 1H), 8.36 (d, J=7.5 Hz, 1H), 7.58 (s, 1H), 7.45 (d, J=7.8 Hz, 1H), 7.25-7.20 (m, 2H), 7.16 (s, 1H), 7.05 (s, 1H), 4.17-4.15 (m, 2H), 2.38-2.28 (m, 5H); ESI MS m/z 350 $[C_{19}H_{15}N_3O_2S+H]^+$; UPLC (Method A) >99% (AUC), $t_R$=3.30 min; Chiral HPLC (Chiralpak AD, Method A) 62.6% (AUC), $t_R$=17.28 min.

Preparation of (S)-3a-Hydroxy-6-methyl-1-(thieno[2,3-b]pyridin-2-yl)-1,2,3,3a-tetrahydro-4H-pyrrolo[2,3-b]quinolin-4-one

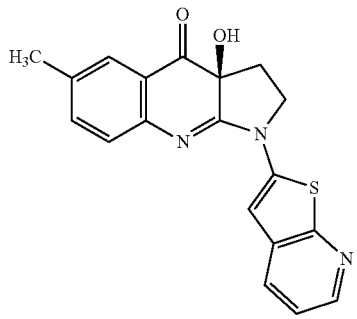

BPN-0027469

(S)-3a-Hydroxy-6-methyl-1-(thieno[2,3-b]pyridin-2-yl)-1,2,3,3a-tetrahydro-4H-pyrrolo[2,3-b]quinolin-4-one was prepared as a yellow solid according to Synthetic Scheme 6: mp=255-257° C.; $^1$H NMR (300 MHz, DMSO-$d_6$) δ 8.42 (dd, J=4.5, 1.5 Hz, 1H), 8.08 (dd, J=8.1, 1.5 Hz, 1H), 7.57 (s, 1H), 7.45 (d, J=7.8 Hz, 1H), 7.39 (dd, J=7.8, 4.5 Hz, 1H), 7.25 (d, J=7.8 Hz, 1H), 7.02 (d, J=7.8 Hz, 2H), 4.14-4.06 (m, 2H), 2.36-2.33 (m, 5H); ESI MS m/z 350 $[C_{19}H_{15}N_3O_2S+H]^+$; UPLC (Method A) >99% (AUC), $t_R$=3.71 min; Chiral HPLC (Chiralpak AD, Method A) 61.0% (AUC), $t_R$=19.64 min.

Preparation of (S)-3a-Hydroxy-6,7-dimethyl-1-(pyrazolo[1,5-a]pyridin-5-yl)-1,2,3,3a-tetrahydro-4H-pyrrolo[2,3-b]quinolin-4-one

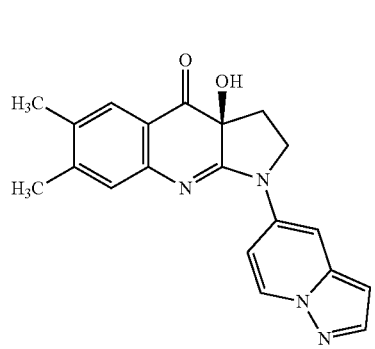

BPN-0027488

(S)-3a-Hydroxy-6,7-dimethyl-1-(pyrazolo[1,5-a]pyridin-5-yl)-1,2,3,3a-tetrahydro-4H-pyrrolo[2,3-b]quinolin-4-one was prepared as a yellow solid according to Synthetic Scheme 6: mp=261-264° C.; $^1$H NMR (300 MHz, DMSO-$d_6$) δ 8.70 (d, J=7.8 Hz, 1H), 8.17 (d, J=2.1 Hz, 1H), 8.01 (dd, J=7.5, 2.1 Hz, 1H), 7.97 (d, J=2.1 Hz, 1H), 7.52 (s, 1H), 7.13 (s, 1H), 6.88 (s, 1H), 6.56 (d, J=2.1 Hz, 1H), 4.08-3.99 (m, 2H), 2.29 (s, 3H), 2.26 (apparent s, 2H), 2.24 (s, 3H); ESI MS m/z 347 $[C_{20}H_{18}N_4O_2+H]^+$; UPLC (Method A) 98.7% (AUC), $t_R$=3.02 min; Chiral HPLC (Chiralpak AD, Method A) 67.3% (AUC), $t_R$=18.70 min.

Preparation of (S)-3a-Hydroxy-6,7-dimethyl-1-(thieno[2,3-b]pyridin-5-yl)-1,2,3,3a-tetrahydro-4H-pyrrolo[2,3-b]quinolin-4-one

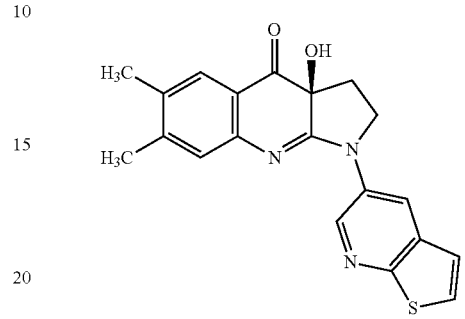

BPN-0027489

(S)-3a-Hydroxy-6,7-dimethyl-1-(thieno[2,3-b]pyridin-5-yl)-1,2,3,3a-tetrahydro-4H-pyrrolo[2,3-b]quinolin-4-one was prepared as a yellow solid according to Synthetic Scheme 6: mp=237-241° C.; $^1$H NMR (300 MHz, DMSO-$d_6$) δ 9.32 (d, J=2.1 Hz, 1H), 8.97 (d, J=2.1 Hz, 1H), 7.94 (d, J=6.0 Hz, 1H), 7.50 (d, J=5.7 Hz, 2H), 7.11 (s, 1H), 6.88 (s, 1H), 4.21-4.07 (m, 2H), 2.32-2.28 (m, 5H), 2.23 (s, 3H); ESI MS m/z 364 $[C_{20}H_{17}N_3O_2S+H]^+$; UPLC (Method A) >99% (AUC), $t_R$=3.16 min; Chiral HPLC (Chiralpak AD, Method A) 85.0% (AUC), $t_R$=18.22 min.

Preparation of (S)-3a-Hydroxy-6,7-dimethyl-1-(2-methylbenzo[d]thiazol-5-yl)-1,2,3,3a-tetrahydro-4H-pyrrolo[2,3-b]quinolin-4-one

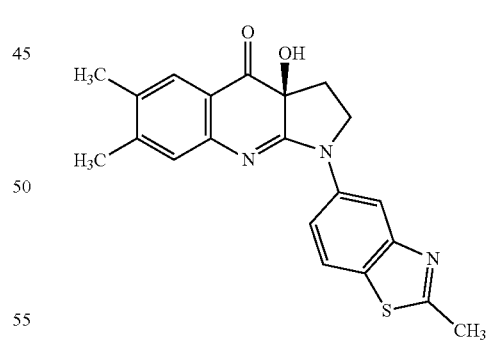

BPN-0027491

(S)-3a-Hydroxy-6,7-dimethyl-1-(2-methylbenzo[d]thiazol-5-yl)-1,2,3,3a-tetrahydro-4H-pyrrolo[2,3-b]quinolin-4-one was prepared as a yellow solid according to Synthetic Scheme 6: mp=233-235° C.; $^1$H NMR (300 MHz, DMSO-$d_6$) δ 8.75 (d, J=2.1 Hz, 1H), 8.12 (dd, J=9.0, 2.1 Hz, 1H), 8.04 (d, J=9.0 Hz, 1H), 7.50 (s, 1H), 7.10 (s, 1H), 6.83 (s, 1H), 4.19-4.02 (m, 2H), 2.82 (s, 3H), 2.29 (apparent s, 5H), 2.23 (s, 3H); ESI MS m/z 378 $[C_{21}H_{19}N_3O_2S+H]^+$; UPLC (Method A) 96.9% (AUC), $t_R$=3.19 min; Chiral HPLC (Chiralpak AD, Method A) 84.9% (AUC), $t_R$=21.69 min.

Preparation of (S)-6-(3a-Hydroxy-6,7-dimethyl-4-oxo-2,3,3a,4-tetrahydro-1H-pyrrolo[2,3-b]quinolin-1-yl)quinoline-2-carbonitrile

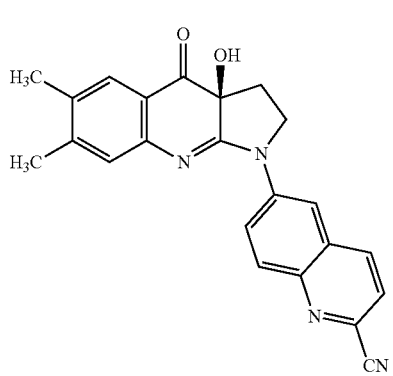

BPN-0027492

(S)-6-(3a-Hydroxy-6,7-dimethyl-4-oxo-2,3,3a,4-tetrahydro-1H-pyrrolo[2,3-b]quinolin-1-yl)quinoline-2-carbonitrile was prepared as a yellow-orange solid according to Synthetic Scheme 6: mp=272-274° C.; $^1$H NMR (300 MHz, DMSO-$d_6$) δ 9.04 (dd, J=9.6, 2.4 Hz, 1H), 8.63 (d, J=8.4 Hz, 1H), 8.58 (d, J=2.4 Hz, 1H), 8.19 (d, J=9.3 Hz, 1H), 8.02 (d, J=8.7 Hz, 1H), 7.54 (s, 1H), 7.21 (s, 1H), 6.93 (s, 1H), 4.18-4.14 (m, 2H), 2.33-2.31 (m, 5H), 2.25 (s, 3H); ESI MS m/z 383 $[C_{23}H_{18}N_4O_2+H]^+$; UPLC (Method A) >99% (AUC), $t_R$=3.46 min; Chiral HPLC (Chiralpak AD, Method A) 89.5% (AUC), $t_R$=21.66 min.

Preparation of (S)-1-(Benzo[d][1,2,3]thiadiazol-6-yl)-3a-hydroxy-6,7-dimethyl-1,2,3,3a-tetrahydro-4H-pyrrolo[2,3-b]quinolin-4-one

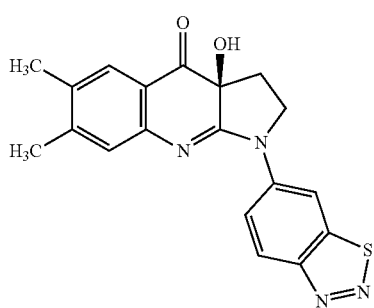

BPN-0028550

(S)-1-(Benzo[d][1,2,3]thiadiazol-6-yl)-3a-hydroxy-6,7-dimethyl-1,2,3,3a-tetrahydro-4H-pyrrolo[2,3-b]quinolin-4-one was prepared as a yellow solid according to Synthetic Scheme 6: $^1$H NMR (300 MHz, DMSO-$d_6$) δ 9.10 (d, J=1.8 Hz, 1H), 8.74-8.64 (m, 2H), 7.54 (s, 1H), 7.22 (s, 1H), 6.93 (s, 1H), 4.18-4.13 (m, 2H), 2.31 (apparent s, 5H), 2.25 (s, 3H); ESI MS m/z 365 $[C_{19}H_{16}N_4O_2S+H]^+$; UPLC (Method A) 96.2% (AUC), $t_R$=3.36 min; Chiral HPLC (Chiralpak AD, Method A) 50.7% (AUC), $t_R$=18.41 min.

Preparation of (S)-1-(3,4-Dihydro-2H-benzo[b][1,4]oxazin-7-yl)-3a-hydroxy-6,7-dimethyl-1,2,3,3a-tetrahydro-4H-pyrrolo[2,3-b]quinolin-4-one

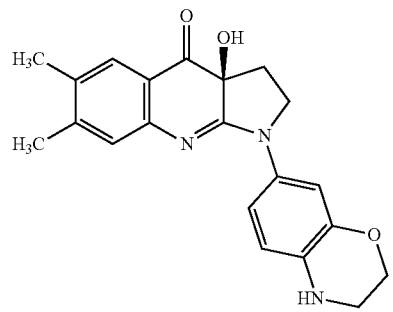

BPN-0028552

(S)-1-(3,4-Dihydro-2H-benzo[b][1,4]oxazin-7-yl)-3a-hydroxy-6,7-dimethyl-1,2,3,3a-tetrahydro-4H-pyrrolo[2,3-b]quinolin-4-one was prepared as a red-orange solid according to Synthetic Scheme 4: $^1$H NMR (300 MHz, DMSO-$d_6$) δ 7.57 (d, J=2.4 Hz, 1H), 7.44 (s, 1H), 7.21 (dd, J=8.4, 2.7 Hz, 1H), 6.96 (s, 1H), 6.62 (s, 1H), 6.58 (d, J=8.7 Hz, 1H), 5.73 (s, 1H), 4.14-4.13 (m, 2H), 3.99-3.79 (m, 2H), 3.30 (apparent s, 2H), 2.26 (s, 3H), 2.25-2.20 (m, 5H); ESI MS m/z 364 $[C_{21}H_{21}N_3O_3+H]^+$; UPLC (Method A) 96.7% (AUC), $t_R$=3.16 min; Chiral HPLC (Chiralpak AD, Method A) 71.1% (AUC), $t_R$=23.14 min.

Preparation of (S)-3a-Hydroxy-6,7-dimethyl-1-(2-methylpyridin-4-yl)-1,2,3,3a-tetrahydro-4H-pyrrolo[2,3-b]quinolin-4-one

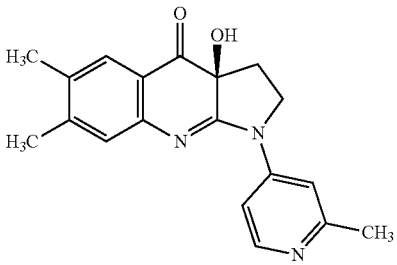

BPN-0028616

(S)-3a-Hydroxy-6,7-dimethyl-1-(2-methylpyridin-4-yl)-1,2,3,3a-tetrahydro-4H-pyrrolo[2,3-b]quinolin-4-one was prepared as a yellow solid according to Synthetic Scheme 6: mp=265-267° C.; $^1$H NMR (300 MHz, DMSO-$d_6$) δ 8.38 (d, J=6.0 Hz, 1H), 8.03 (dd, J=6.0, 2.4 Hz, 1H), 7.85 (d, J=2.1 Hz, 1H), 7.52 (s, 1H), 7.16 (s, 1H), 6.87 (s, 1H), 4.04-3.94 (m, 2H), 2.30 (s, 3H), 2.28-2.24 (m, 1H), 2.21 (apparent s, 4H), 3H obscured by solvent peak; ESI MS m/z 322 $[C_{19}H_{19}N_3O_2+H]^+$; UPLC (Method A) 95.1% (AUC), $t_R$=3.17 min; Chiral HPLC (Chiralpak AD, Method A) 50.8% (AUC), $t_R$=14.81 min.

Preparation of (S)-3a-Hydroxy-1-(6-methoxypyridin-3-yl)-6,7-dimethyl-1,2,3,3a-tetrahydro-4H-pyrrolo[2,3-b]quinolin-4-one

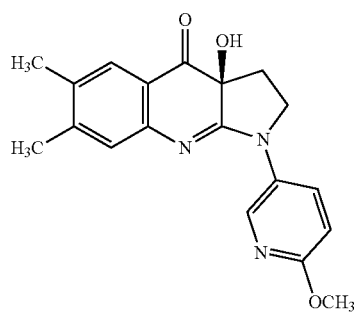

BPN-0028648

(S)-3a-Hydroxy-1-(6-methoxypyridin-3-yl)-6,7-dimethyl-1,2,3,3a-tetrahydro-4H-pyrrolo[2,3-b]quinolin-4-one was prepared as a yellow solid according to Synthetic Scheme 6: mp=213-216° C.; $^1$H NMR (300 MHz, DMSO-$d_6$) δ 8.74 (d, J=3.0 Hz, 1H), 8.53 (dd, J=9.0, 2.7 Hz, 1H), 7.48 (s, 1H), 7.02 (s, 1H), 6.91 (d, J=9.3 Hz, 1H), 6.80 (s, 1H), 4.09-3.91 (m, 2H), 3.87 (s, 3H), 2.28-2.26 (m, 5H), 2.21 (s, 3H); ESI MS m/z 338 $[C_{19}H_{19}N_3O_3+H]^+$; UPLC (Method A) >99% (AUC), $t_R$=2.97 min; Chiral HPLC (Chiralpak AD, Method A) 82.7% (AUC), $t_R$=15.44 min.

Preparation of (S)-1-(5-Chloro-6-(hydroxymethyl)pyridin-3-yl)-3a-hydroxy-6,7-dimethyl-1,2,3,3a-tetrahydro-4H-pyrrolo[2,3-b]quinolin-4-one

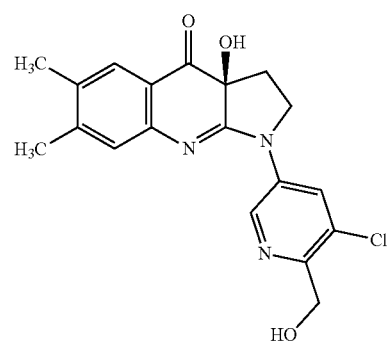

BPN-0028649

(S)-1-(5-Chloro-6-(hydroxymethyl)pyridin-3-yl)-3a-hydroxy-6,7-dimethyl-1,2,3,3a-tetrahydro-4H-pyrrolo[2,3-b]quinolin-4-one was prepared as a yellow solid according to Synthetic Scheme 6: mp=242-245° C.; $^1$H NMR (300 MHz, DMSO-$d_6$) δ 9.10 (d, J=2.1 Hz, 1H), 8.83 (d, J=2.4 Hz, 1H), 7.52 (s, 1H), 7.10 (s, 1H), 6.89 (s, 1H), 5.24 (t, J=6.0 Hz, 1H), 4.64 (apparent t, J=5.7 Hz, 2H), 4.12-4.03 (m, 2H), 2.30-2.27 (m, 5H), 2.23 (s, 3H); ESI MS m/z 372 $[C_{19}H_{18}ClN_3O_3+H]^+$; UPLC (Method A) >99% (AUC), $t_R$=2.98 min; Chiral HPLC (Chiralpak AD, Method A) 62.9% (AUC), $t_R$=17.17 min.

Preparation of (S)-3a-Hydroxy-6,7-dimethyl-1-(2-(methylamino)pyridin-4-yl)-1,2,3,3a-tetrahydro-4H-pyrrolo[2,3-b]pyrrolo[2,3-b]quinolin-4-one

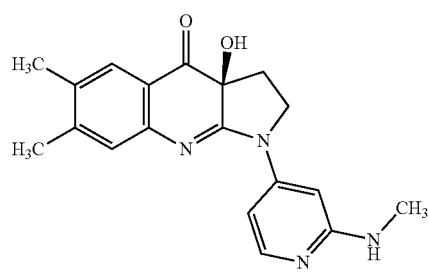

BPN-0028650

(S)-3a-Hydroxy-6,7-dimethyl-1-(2-(methylamino)pyridin-4-yl)-1,2,3,3a-tetrahydro-4H-pyrrolo[2,3-b]quinolin-4-one was prepared as a yellow solid according to Synthetic Scheme 6: $^1$H NMR (300 MHz, DMSO-$d_6$) δ 7.93 (d, J=6.0 Hz, 1H), 7.51 (s, 1H), 7.29 (s, 1H), 7.22 (d, J=5.7 Hz, 1H), 7.11 (s, 1H), 6.83 (s, 1H), 6.61-6.40 (m, 1H), 3.92 (apparent t, J=6.0 Hz, 2H), 2.79 (d, J=4.8 Hz, 3H), 2.29 (s, 3H), 2.24-2.18 (m, 5H); ESI MS m/z 337 $[C_{19}H_{20}N_4O_2+H]^+$; UPLC (Method A) 95.5% (AUC), $t_R$=3.22 min; Chiral HPLC (Chiralpak AD, Method A) 70.0% (AUC), $t_R$=18.22 min.

Preparation of (S)-3a-Hydroxy-1-(6-methoxy-5-methylpyridin-3-yl)-6,7-dimethyl-1,2,3,3a-tetrahydro-4H-pyrrolo[2,3-b]quinolin-4-one

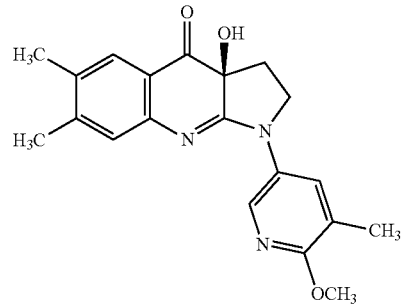

BPN-0028731

(S)-3a-Hydroxy-1-(6-methoxy-5-methylpyridin-3-yl)-6,7-dimethyl-1,2,3,3a-tetrahydro-4H-pyrrolo[2,3-b]quinolin-4-one was prepared as a yellow solid according to Synthetic Scheme 6: mp=195-199° C.; $^1$H NMR (300 MHz, DMSO-$d_6$) δ 8.65 (d, J=2.4 Hz, 1H), 8.29 (s, 1H), 7.47 (s, 1H), 7.03 (s, 1H), 6.78 (s, 1H), 4.07-3.93 (m, 2H), 3.89 (s, 3H), 2.26 (apparent s, 5H), 2.21 (s, 6H); ESI MS m/z 352 $[C_{20}H_{21}N_3O_3+H]^+$; UPLC (Method A) >99% (AUC), $t_R$=3.26 min; Chiral HPLC (Chiralpak AD, Method A) 81.1% (AUC), $t_R$=13.45 min.

Preparation of (S)-3a-Hydroxy-1-(6-(hydroxymethyl)-5-methylpyridin-3-yl)-6,7-dimethyl-1,2,3,3a-tetrahydro-4H-pyrrolo[2,3-b]quinolin-4-one

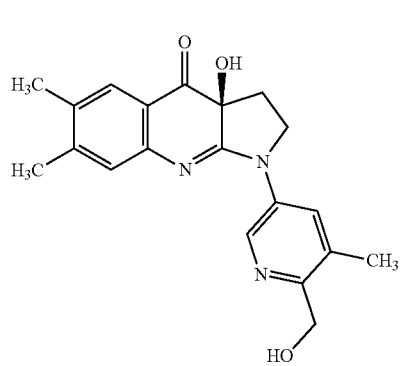

BPN-0028733

(S)-3a-Hydroxy-1-(6-(hydroxymethyl)-5-methylpyridin-3-yl)-6,7-dimethyl-1,2,3,3a-tetrahydro-4H-pyrrolo[2,3-b]quinolin-4-one was prepared as a yellow solid according to Synthetic Scheme 6: mp=218-222° C.; $^1$H NMR (300 MHz, DMSO-$d_6$) δ 9.07 (d, J=2.7 Hz, 1H), 8.28 (s, 1H), 7.50 (s, 1H), 7.07 (s, 1H), 6.83 (s, 1H), 5.02 (t, J=5.4 Hz, 1H), 4.57 (d, J=5.4 Hz, 2H), 4.09-3.98 (m, 2H), 2.39 (s, 3H), 2.28 (apparent s, 5H), 2.23 (s, 3H); ESI MS m/z 352 [$C_{20}H_{21}N_3O_3$+H]$^+$; UPLC (Method A) 98.3% (AUC), $t_R$=2.89 min; Chiral HPLC (Chiralpak AD, Method A) 74.8% (AUC), $t_R$=18.63 min.

Preparation of (S)-5-(3a-Hydroxy-6,7-dimethyl-4-oxo-2,3,3a,4-tetrahydro-1H-pyrrolo[2,3-b]quinolin-1-yl)-3-methylpicolinonitrile

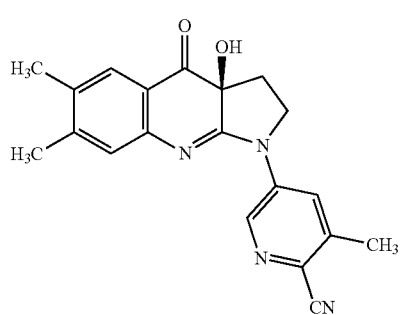

BPN-0028760

(S)-5-(3a-Hydroxy-6,7-dimethyl-4-oxo-2,3,3a,4-tetrahydro-1H-pyrrolo[2,3-b]quinolin-1-yl)-3-methylpicolinonitrile was prepared as a yellow solid according to Synthetic Scheme 6: mp=249-253° C.; $^1$H NMR (300 MHz, DMSO-$d_6$) δ 9.41 (d, J=2.4 Hz, 1H), 8.58 (d, J=2.1 Hz, 1H), 7.54 (s, 1H), 7.19 (s, 1H), 6.94 (s, 1H), 4.05 (apparent t, J=6.3 Hz, 2H), 2.34 (s, 3H), 2.30-2.27 (m, 5H), 2.25 (s, 3H); ESI MS m/z 347 [$C_{20}H_{18}N_4O_2$+H]$^+$; UPLC (Method A) 95.0% (AUC), $t_R$=3.91 min; Chiral HPLC (Chiralpak AD, Method A) 40.3% (AUC), $t_R$=17.33 min.

Preparation of (S)-7a-Hydroxy-2-methyl-5-(2-methylquinolin-6-yl)-5,6,7,7a-tetrahydro-8H-pyrrolo[2,3-b]thieno[2,3-e]pyridin-8-one

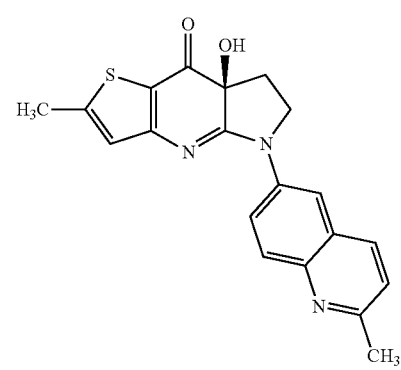

BPN-0028863

(S)-7a-Hydroxy-2-methyl-5-(2-methylquinolin-6-yl)-5,6,7,7a-tetrahydro-8H-pyrrolo[2,3-b]thieno[2,3-e]pyridin-8-one was prepared as an orange solid according to Synthetic Scheme 3: mp=244-247° C.; $^1$H NMR (300 MHz, DMSO-$d_6$) δ 8.61 (dd, J=9.3, 2.7 Hz, 1H), 8.33 (d, J=2.7 Hz, 1H), 8.24 (d, J=8.4 Hz, 1H), 7.97 (d, J=9.3 Hz, 1H), 7.44 (d, J=8.4 Hz, 1H), 6.97 (s, 1H), 6.88 (d, J=1.2 Hz, 1H), 4.29-4.12 (m, 2H), 2.66 (s, 3H), 2.36-2.25 (m, 2H), 3H obscured by solvent peak; ESI MS m/z 364 [$C_{20}H_{17}N_3O_2S$+H]$^+$; UPLC (Method A) 98.8% (AUC), $t_R$=2.47 min; Chiral HPLC (Chiralpak AD, Method A) 91.2% (AUC), $t_R$=19.24 min.

Preparation of (S)-1-(2-Ethylpyridin-4-yl)-3a-hydroxy-6,7-dimethyl-1,2,3,3a-tetrahydro-4H-pyrrolo[2,3-b]quinolin-4-one

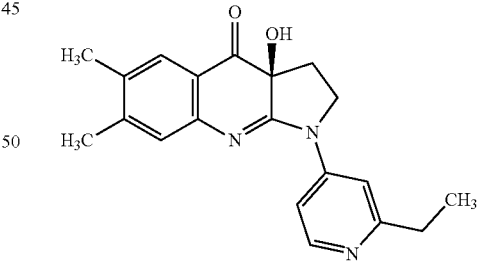

BPN-0028864

(S)-1-(2-Ethylpyridin-4-yl)-3a-hydroxy-6,7-dimethyl-1,2,3,3a-tetrahydro-4H-pyrrolo[2,3-b]quinolin-4-one was prepared as a yellow solid according to Synthetic Scheme 6: mp=269-270° C.; $^1$H NMR (300 MHz, DMSO-$d_6$) δ 8.41 (d, J=5.7 Hz, 1H), 7.99 (dd, J=5.7, 2.4 Hz, 1H), 7.91 (d, J=1.8 Hz, 1H), 7.52 (s, 1H), 7.15 (s, 1H), 6.87 (s, 1H), 4.04-3.95 (m, 2H), 2.76 (q, J=7.5 Hz, 2H), 2.30 (s, 3H), 2.28-2.24 (m, 5H), 1.26 (t, J=7.5 Hz, 3H); ESI MS m/z 336 [$C_{20}H_{21}N_3O_2$+H]$^+$; UPLC (Method A) >99% (AUC), $t_R$=3.31 min; Chiral HPLC (Chiralpak AD, Method A) 65.4% (AUC), $t_R$=13.92 min.

Preparation of (S)-1-(2-Ethylbenzo[d]thiazol-5-yl)-3a-hydroxy-6,7-dimethyl-1,2,3,3a-tetrahydro-4H-pyrrolo[2,3-b]quinolin-4-one

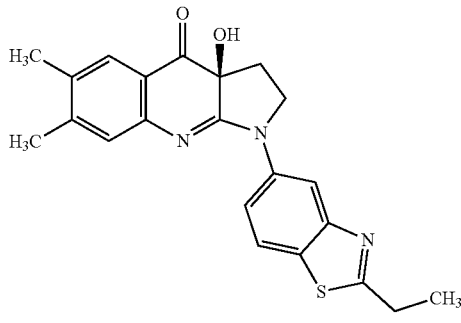

BPN-0028918

(S)-1-(2-Ethylbenzo[d]thiazol-5-yl)-3a-hydroxy-6,7-dimethyl-1,2,3,3a-tetrahydro-4H-pyrrolo[2,3-b]quinolin-4-one was prepared as a yellow solid according to Synthetic Scheme 6: mp=232-235° C.; $^1$H NMR (300 MHz, DMSO-$d_6$) δ 8.73 (d, J=2.1 Hz, 1H), 8.16 (dd, J=9.0, 2.4 Hz, 1H), 8.06 (d, J=8.7 Hz, 1H), 7.50 (s, 1H), 7.10 (s, 1H), 6.83 (s, 1H), 4.19-4.02 (m, 2H), 3.15 (q, J=7.2 Hz, 2H), 2.29 (m, 5H), 2.23 (s, 3H), 1.40 (t, J=7.5 Hz, 3H); ESI MS m/z 392 [$C_{22}H_{21}N_3O_2S+H$]$^+$; UPLC (Method A) >99% (AUC), $t_R$=3.45 min; Chiral HPLC (Chiralpak AD, Method A) 97.2% (AUC), $t_R$=22.48 min.

Preparation of (S)-3a-Hydroxy-1-(2-isopropylbenzo[d]thiazol-5-yl)-6,7-dimethyl-1,2,3,3a-tetrahydro-4H-pyrrolo[2,3-b]quinolin-4-one

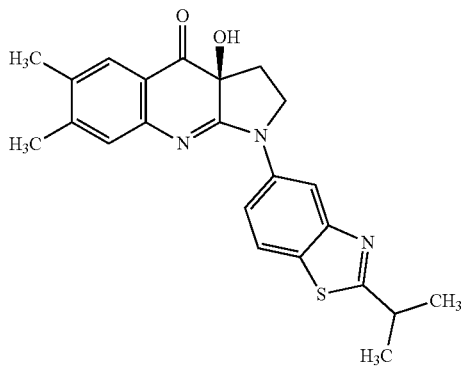

BPN-0028919

(S)-3a-Hydroxy-1-(2-isopropylbenzo[d]thiazol-5-yl)-6,7-dimethyl-1,2,3,3a-tetrahydro-4H-pyrrolo[2,3-b]quinolin-4-one was prepared as a yellow solid according to Synthetic Scheme 6: $^1$H NMR (300 MHz, DMSO-$d_6$) δ 8.71 (d, J=2.1 Hz, 1H), 8.20 (dd, J=8.7, 2.1 Hz, 1H), 8.07 (d, J=8.7 Hz, 1H), 7.50 (s, 1H), 7.10 (s, 1H), 6.83 (s, 1H), 4.16-4.02 (m, 2H), 3.50-3.38 (m, 1H), 2.29 (m, 5H), 2.23 (s, 3H), 1.44 (s, 3H), 1.42 (s, 3H); ESI MS m/z 406 [$C_{23}H_{23}N_3O_2S+H$]$^+$; UPLC (Method A) >99% (AUC), $t_R$=3.72 min; Chiral HPLC (Chiralpak AD, Method A) 95.4% (AUC), $t_R$=20.82 min.

Preparation of (S)-3a-Hydroxy-6,7-dimethyl-1-(5,6,7,8-tetrahydroquinolin-3-yl)-1,2,3,3a-tetrahydro-4H-pyrrolo[2,3-b]quinolin-4-one

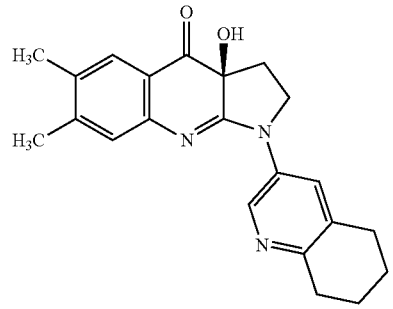

BPN-0028920

(S)-3a-Hydroxy-6,7-dimethyl-1-(5,6,7,8-tetrahydroquinolin-3-yl)-1,2,3,3a-tetrahydro-4H-pyrrolo[2,3-b]quinolin-4-one was prepared as a yellow solid according to Synthetic Scheme 6: mp=243-248° C.; $^1$H NMR (300 MHz, DMSO-$d_6$) δ 9.00 (d, J=2.7 Hz, 1H), 8.13 (d, J=2.4 Hz, 1H), 7.49 (s, 1H), 7.03 (s, 1H), 6.81 (s, 1H), 4.06-3.91 (m, 2H), 2.82-2.78 (m, 4H), 2.33 (s, 5H), 2.22 (s, 3H), 1.84-1.76 (m, 4H); ESI MS m/z 362 [$C_{22}H_{23}N_3O_2+H$]$^+$; UPLC (Method A) >99% (AUC), $t_R$=3.23 min; Chiral HPLC (Chiralpak AD, Method A) 97.5% (AUC), $t_R$=15.36 min.

Preparation of (S)-1-(2,3-Dihydrobenzo[b][1,4]dioxin-6-yl)-3a-hydroxy-6,7-dimethyl-1,2,3,3a-tetrahydro-4H-pyrrolo[2,3-b]quinolin-4-one

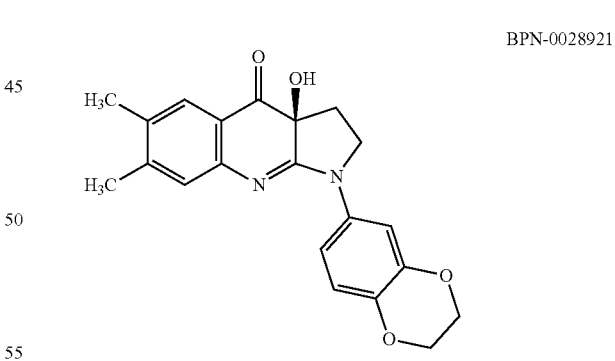

BPN-0028921

(S)-1-(2,3-Dihydrobenzo[b][1,4]dioxin-6-yl)-3a-hydroxy-6,7-dimethyl-1,2,3,3a-tetrahydro-4H-pyrrolo[2,3-b]quinolin-4-one was prepared as a yellow-orange solid according to Synthetic Scheme 6: mp=213-217° C.; $^1$H NMR (300 MHz, DMSO-$d_6$) δ 7.80 (d, J=2.7 Hz, 1H), 7.46 (s, 1H), 7.39 (dd, J=9.0, 2.7 Hz, 1H), 7.00 (s, 1H), 6.89 (d, J=9.0 Hz, 1H), 6.74 (s, 1H), 4.27-4.26 (m, 4H), 4.00-3.85 (m, 2H), 2.28 (s, 5H), 2.21 (s, 3H); ESI MS m/z 365 [$C_{21}H_{20}N_2O_4+H$]$^+$; UPLC (Method A) >99% (AUC), $t_R$=3.26 min; Chiral HPLC (Chiralpak AD, Method A) 95.9% (AUC), $t_R$=22.57 min.

Preparation of (S)-1-(3,4-Dihydro-2H-benzo[b][1,4]thiazin-6-yl)-3a-hydroxy-6,7-dimethyl-1,2,3,3a-tetrahydro-4H-pyrrolo[2,3-b]quinolin-4-one

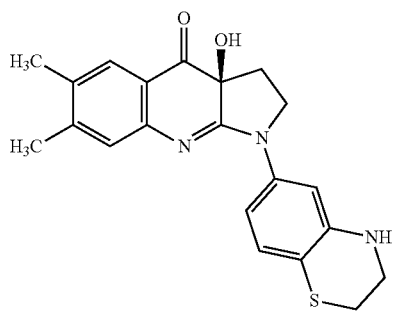

BPN-0028922

(S)-1-(3,4-Dihydro-2H-benzo[b][1,4]thiazin-6-yl)-3a-hydroxy-6,7-dimethyl-1,2,3,3a-tetrahydro-4H-pyrrolo[2,3-b]quinolin-4-one was prepared as an orange solid according to Synthetic Scheme 6: $^1$H NMR (300 MHz, DMSO-$d_6$) δ 7.46 (s, 1H), 7.36 (d, J=2.4 Hz, 1H), 7.12 (dd, J=8.4, 2.1 Hz, 1H), 7.02 (s, 1H), 6.86 (d, J=8.4 Hz, 1H), 6.72 (s, 1H), 6.18 (s, 1H), 3.95-3.82 (m, 2H), 3.53-3.46 (m, 2H), 2.99-2.96 (m, 2H), 2.27 (s, 3H), 2.21 (s, 5H); ESI MS m/z 380 $[C_{21}H_{21}N_3O_2S+H]^+$; UPLC (Method A) 98.5% (AUC), $t_R$=3.50 min; Chiral HPLC (Chiralpak AD, Method A) 95.3% (AUC), $t_R$=22.99 min.

Preparation of (S)-3a-Hydroxy-1-(2-methoxypyridin-4-yl)-6-methyl-3,3a-dihydro-1H-pyrrolo[2,3-b]quinolin-4(2H)-one

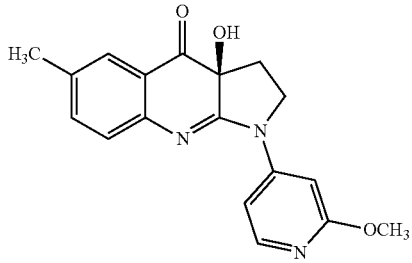

BPN-0025919

(S)-3a-Hydroxy-1-(2-methoxypyridin-4-yl)-6-methyl-3,3a-dihydro-1H-pyrrolo[2,3-b]quinolin-4(2H)-one was prepared as a yellow solid according to Synthetic Scheme 4: mp=229-230° C.; $^1$H NMR (500 MHz, CDCl$_3$) δ 8.14 (d, J=6.0 Hz, 1H), 7.70 (d, J=1.6 Hz, 1H), 7.62 (dd, J=6.0, 1.9 Hz, 1H), 7.42-7.39 (m, 2H), 7.30 (d, J=8.1 Hz, 1H), 4.13-4.08 (m, 1H), 3.98-3.92 (m, 4H), 2.50 (dd, J=14.0, 5.9 Hz, 1H), 2.36-2.27 (m, 4H), OH proton is missing; ESI MS m/z 324 $[C_{18}H_{17}N_3O_3+H]^+$; HPLC (Method C) 95.0% (AUC), $t_R$=12.46 min; Chiral HPLC (Chiralpak AD, Method A) 48.1% (AUC), $t_R$=15.26 min.

Preparation of (S)-1-(Benzo[b]thiophen-6-yl)-3a-hydroxy-6-methyl-3,3a-dihydro-1H-pyrrolo[2,3-b]quinolin-4(2H)-one

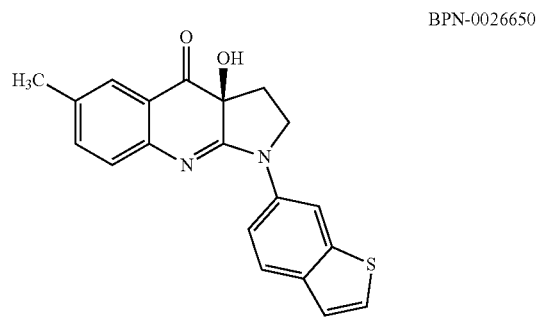 [SMILES: Cc1ccc2c(c1)C(=O)[C@]1(O)CCN(c3ccc4ccsc4c3)C1=N2]

BPN-0026650

(S)-1-(Benzo[b]thiophen-6-yl)-3a-hydroxy-6-methyl-3,3a-dihydro-1H-pyrrolo[2,3-b]quinolin-4(2H)-one was prepared as a yellow solid according to Synthetic Scheme 5: mp=217-218° C.; $^1$H NMR (500 MHz, DMSO-$d_6$) δ 8.74 (d, J=1.9 Hz, 1H), 8.16 (dd, J=8.8, 2.1 Hz, 1H), 7.91 (d, J=8.8 Hz, 1H), 7.70 (d, J=5.5 Hz, 1H), 7.54 (d, J=1.3 Hz, 1H), 7.44-7.43 (m, 1H), 7.39-7.37 (m, 1H), 7.17 (d, J=8.0 Hz, 1H), 6.85 (s, 1H), 4.17-4.12 (m, 1H), 4.07-4.03 (m, 1H), 2.31-2.28 (m, 5H); ESI MS m/z 349 $[C_{20}H_{16}N_2O_2S+H]^+$; HPLC (Method C) >99% (AUC), $t_R$=12.99 min; Chiral HPLC (Chiralpak AD, Method A) >99% (AUC), $t_R$=17.48 min.

Preparation of (S)-1-(Benzo[b]thiophen-5-yl)-3a-hydroxy-6-methyl-3,3a-dihydro-1H-pyrrolo[2,3-b]quinolin-4(2H)-one

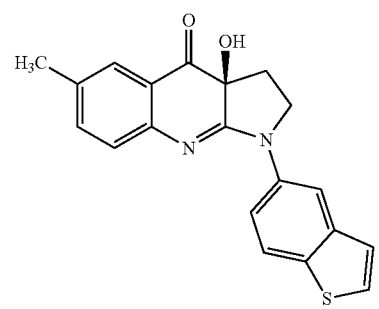

BPN-0026651

(S)-1-(Benzo[b]thiophen-5-yl)-3a-hydroxy-6-methyl-3,3a-dihydro-1H-pyrrolo[2,3-b]quinolin-4(2H)-one was prepared as an orange solid according to Synthetic Scheme 5: mp=215-216° C.; $^1$H NMR (500 MHz, DMSO-$d_6$) δ 8.50 (d, J=2.1 Hz, 1H), 8.20 (dd, J=8.9, 2.1 Hz, 1H), 8.03 (d, J=8.9 Hz, 1H), 7.80 (d, J=5.4 Hz, 1H), 7.54 (d, J=1.5 Hz, 1H), 7.49 (d, J=5.4 Hz, 1H), 7.38 (d, J=8.1, 1.8 Hz, 1H), 7.14 (d, J=8.1 Hz, 1H), 6.85 (s, 1H), 4.18-4.12 (m, 1H), 4.05-4.02 (m, 1H), 2.32-2.29 (m, 5H); ESI MS m/z 349 $[C_{20}H_{16}N_2O_2S+H]^+$; HPLC (Method C) >99% (AUC), $t_R$=13.35 min; Chiral HPLC (Chiralpak AD, Method A) 96.3% (AUC), $t_R$=21.69 min.

Preparation of (S)-1-(Benzo[d]thiazol-5-yl)-3a-hydroxy-6-methyl-3,3a-dihydro-1H-pyrrolo[2,3-b]quinolin-4(2H)-one

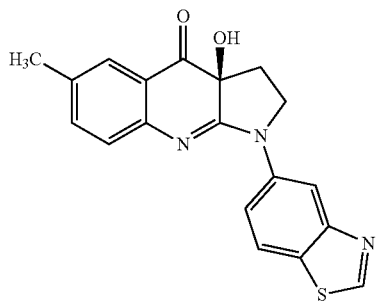

BPN-0026669

(S)-1-(Benzo[d]thiazol-5-yl)-3a-hydroxy-6-methyl-3,3a-dihydro-1H-pyrrolo[2,3-b]quinolin-4(2H)-one was prepared as an orange-yellow solid according to Synthetic Scheme 4: mp=224-225° C.; $^1$H NMR (500 MHz, DMSO-$d_6$) δ 9.42 (s, 1H), 8.83 (d, J=2.1 Hz, 1H), 8.28 (dd, J=8.9, 2.2 Hz, 1H), 8.19 (d, J=8.9 Hz, 1H), 7.55 (d, J=1.6 Hz, 1H), 7.41-7.39 (m, 1H), 7.17 (d, J=8.1 Hz, 1H), 6.89 (s, 1H), 4.20-4.15 (m, 1H), 4.10-4.06 (m, 1H), 2.34-2.27 (m, 5H); ESI MS m/z 350 [$C_{19}H_{15}N_3O_2S$+H]$^+$; HPLC (Method C) >99% (AUC), $t_R$=11.40 min; Chiral HPLC (Chiralpak AD, Method A) >99% (AUC), $t_R$=26.92 min.

Preparation of (S)-3a-Hydroxy-6,7-dimethyl-1-(2-methylbenzofuran-5-yl)-3,3a-dihydro-1H-pyrrolo[2,3-b]quinolin-4(2H)-one

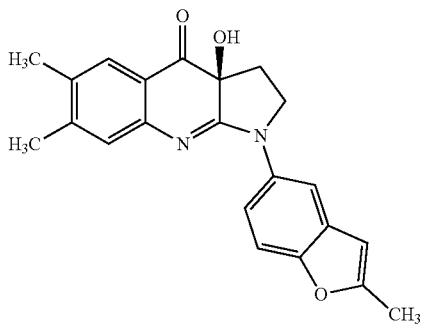

BPN-0026852

(S)-3a-Hydroxy-6,7-dimethyl-1-(2-methylbenzofuran-5-yl)-3,3a-dihydro-1H-pyrrolo[2,3-b]quinolin-4(2H)-one was prepared as a yellow solid according to Synthetic Scheme 5: mp=191-192° C.; $^1$H NMR (500 MHz, DMSO-$d_6$) δ 8.14 (d, J=2.3 Hz, 1H), 7.94 (dd, J=9.0, 2.3 Hz, 1H), 7.52 (d, J=9.0 Hz, 1H), 7.47 (s, 1H), 7.01 (s, 1H), 6.74 (s, 1H), 6.62 (apparent t, J=0.9 Hz, 1H), 4.14-4.09 (m, 1H), 3.98-3.94 (m, 1H), 2.46 (d, J=0.8 Hz, 3H), 2.26-2.25 (m, 5H), 2.21 (s, 3H); ESI MS m/z 361 [$C_{22}H_{20}N_2O_3$+H]$^+$; HPLC (Method A) 96.6% (AUC), $t_R$=13.64 min; Chiral HPLC (Chiralpak AD, Method A) 81.8% (AUC), $t_R$=17.48 min.

Preparation of (S)-1-(Benzo[d]thiazol-6-yl)-3a-hydroxy-6-methyl-3,3a-dihydro-1H-pyrrolo[2,3-b]quinolin-4(2H)-one

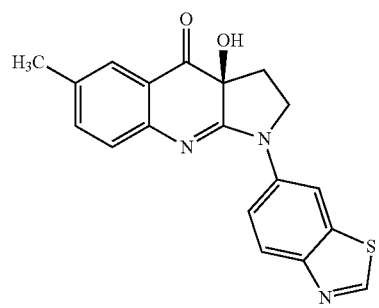

BPN-0027036

(S)-1-(Benzo[d]thiazol-6-yl)-3a-hydroxy-6-methyl-3,3a-dihydro-1H-pyrrolo[2,3-b]quinolin-4(2H)-one was prepared as a yellow solid according to Synthetic Scheme 6: mp=225-226° C.; $^1$H NMR (500 MHz, DMSO-$d_6$) δ 9.32 (s, 1H), 8.88 (d, J=2.2 Hz, 1H), 8.35 (dd, J=9.0, 2.3 Hz, 1H), 8.12 (d, J=9.0 Hz, 1H), 7.55 (d, J=1.7 Hz, 1H), 7.40 (dd, J=8.2, 2.1 Hz, 1H), 7.20 (d, J=8.1 Hz, 1H), 6.88 (s, 1H), 4.18-4.13 (m, 1H), 4.08-4.04 (m, 1H), 2.33-2.29 (m, 5H); ESI MS m/z 350 [$C_{19}H_{15}N_3O_2S$+H]$^+$; HPLC (Method C) 97.0% (AUC), $t_R$=11.57 min; Chiral HPLC (Chiralpak AD, Method A) >99% (AUC), $t_R$=23.11 min.

Preparation of (S)-4a-Hydroxy-1-methyl-7-phenyl-4a,5,6,7-tetrahydropyrazolo[3,4-b]pyrrolo[3,2-e]pyridin-4(1H)-one

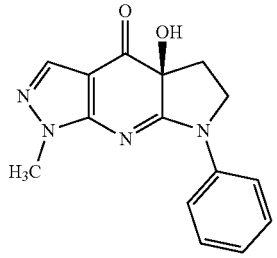

BPN-0027159

(S)-4a-Hydroxy-1-methyl-7-phenyl-4a,5,6,7-tetrahydropyrazolo[3,4-b]pyrrolo[3,2-e]pyridin-4(1H)-one was prepared as a yellow solid according to Synthetic Scheme 2: mp=244-245° C.; $^1$H NMR (500 MHz, DMSO-$d_6$) δ 8.01 (d, J=7.9 Hz, 2H), 7.72 (s, 1H), 7.49-7.46 (m, 2H), 7.23 (apparent t, J=7.4 Hz, 1H), 6.84 (s, 1H), 4.22-4.17 (m, 1H), 4.07-4.04 (m, 1H), 3.73 (s, 3H), 2.26-2.14 (m, 2H); ESI MS m/z 283 [$C_{15}H_{14}N_4O_2$+H]$^+$; HPLC (Method C) >99% (AUC), $t_R$=12.99 min; Chiral HPLC (Chiralpak AD, Method A) >99% (AUC), $t_R$=22.19 min.

Preparation of (S)-1-(3-Chloro-4-(hydroxymethyl)phenyl)-3a-hydroxy-6-methyl-3,3a-dihydro-1H-pyrrolo[2,3-b]quinolin-4(2H)-one

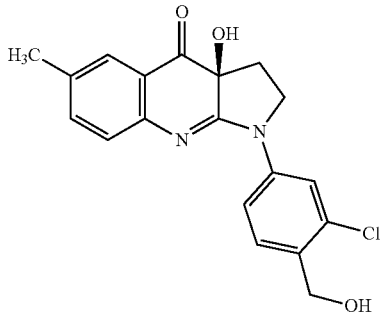

BPN-0027163

(S)-1-(3-Chloro-4-(hydroxymethyl)phenyl)-3a-hydroxy-6-methyl-3,3a-dihydro-1H-pyrrolo[2,3-b]quinolin-4(2H)-one was prepared as a yellow solid according to Synthetic Scheme 6: mp=199-200° C.; $^1$H NMR (500 MHz, DMSO-$d_6$) δ 8.40 (d, J=2.3 Hz, 1H), 7.88 (dd, J=8.6, 2.3 Hz, 1H), 7.56-7.54 (m, 2H), 7.40-7.38 (m, 1H), 7.13 (d, J=8.1 Hz, 1H), 6.85 (s, 1H), 5.34 (apparent t, J=5.6 Hz, 1H), 4.56 (d, J=5.6 Hz, 2H), 4.06-4.01 (m, 1H), 3.99-3.95 (m, 1H), 2.31 (s, 3H), 2.29-2.24 (m, 2H); ESI MS m/z 357 $[C_{19}H_{17}ClN_2O_3+H]^+$; HPLC (Method C) 98.9% (AUC), $t_R$=11.91 min; Chiral HPLC (Chiralpak AD, Method A) 92.4% (AUC), $t_R$=20.92 min.

Preparation of (S)-3a-Hydroxy-6,7-dimethyl-1-(2-methylbenzo[d]oxazol-6-yl)-3,3a-dihydro-1H-pyrrolo[2,3-b]quinolin-4(2H)-one

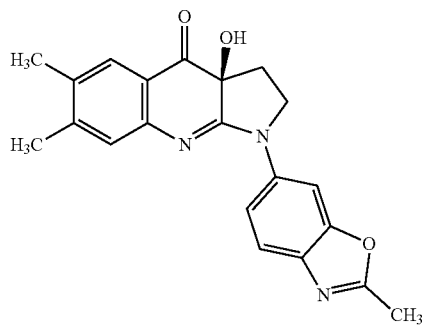

BPN-0027213

(S)-3a-Hydroxy-6,7-dimethyl-1-(2-methylbenzo[d]oxazol-6-yl)-3,3a-dihydro-1H-pyrrolo[2,3-b]quinolin-4(2H)-one was prepared as a yellow solid according to Synthetic Scheme 6: mp=205-209° C.; $^1$H NMR (500 MHz, DMSO-$d_6$) δ 8.66 (d, J=2.0 Hz, 1H), 7.90 (dd, J=8.8, 2.1 Hz, 1H), 7.67 (d, J=8.7 Hz, 1H), 7.50 (s, 1H), 7.09 (s, 1H), 6.80 (s, 1H), 4.14-4.09 (m, 1H), 4.04-3.99 (m, 1H), 2.62 (s, 3H), 2.28-2.25 (m, 5H), 2.23 (s, 3H); ESI MS m/z 362 $[C_{21}H_{19}N_3O_3+H]^+$; HPLC (Method C) 90.8% (AUC), $t_R$=12.58 min; Chiral HPLC (Chiralpak AD, Method A) 79.2% (AUC), $t_R$=18.93 min.

Preparation of (S)-3a-Hydroxy-1-(2-(hydroxymethyl)quinolin-6-yl)-6-methyl-3,3a-dihydro-1H-pyrrolo[2,3-b]quinolin-4(2H)-one

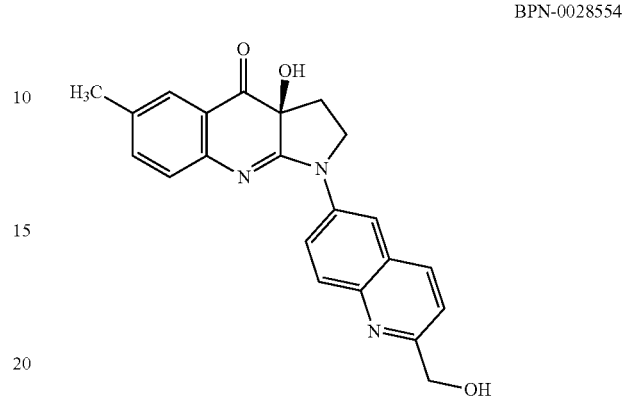

BPN-0028554

(S)-3a-Hydroxy-1-(2-(hydroxymethyl)quinolin-6-yl)-6-methyl-3,3a-dihydro-1H-pyrrolo[2,3-b]quinolin-4(2H)-one was prepared as a yellow solid according to Synthetic Scheme 6: mp=223-224° C.; $^1$H NMR (300 MHz, DMSO-$d_6$) δ 8.75 (dd, J=9.3, 2.6 Hz, 1H), 8.46 (d, J=2.4 Hz, 1H), 8.36 (d, J=8.5 Hz, 1H), 8.00 (d, J=9.3 Hz, 1H), 7.66 (d, J=8.5 Hz, 1H), 7.56 (d, J=2.1 Hz, 1H), 7.43-7.40 (m, 1H), 7.22 (d, J=8.1 Hz, 1H), 6.91 (s, 1H), 5.55 (apparent t, J=5.9 Hz, 1H), 4.72 (d, J=5.9 Hz, 2H), 4.19-4.12 (m, 2H), 2.36-2.27 (m, 5H); ESI MS m/z 374 $[C_{22}H_{19}N_3O_3+H]^+$; UPLC (Method A) 97.9% (AUC), $t_R$=2.47 min; Chiral HPLC (Chiralpak AD, Method A) 91.6% (AUC), $t_R$=19.66 min.

Preparation of (S)-3a-Hydroxy-1-(2-(hydroxymethyl)benzofuran-5-yl)-6,7-dimethyl-3,3a-dihydro-1H-pyrrolo[2,3-b]quinolin-4(2H)-one

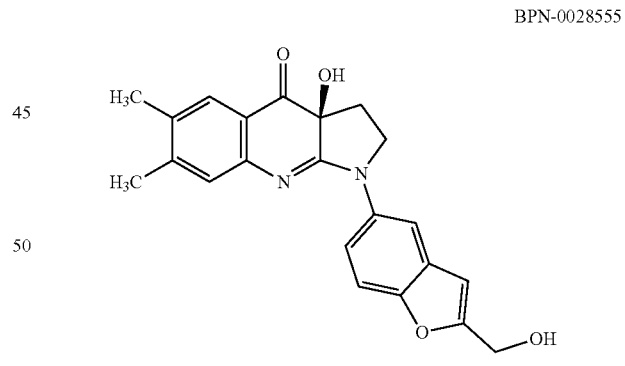

BPN-0028555

(S)-3a-Hydroxy-1-(2-(hydroxymethyl)benzofuran-5-yl)-6,7-dimethyl-3,3a-dihydro-1H-pyrrolo[2,3-b]quinolin-4(2H)-one was prepared as a yellow-orange solid according to Synthetic Scheme 6: mp=210-211° C.; $^1$H NMR (300 MHz, DMSO-$d_6$) δ 8.21 (d, J=2.2 Hz, 1H), 8.03 (dd, J=9.0, 2.3 Hz, 1H), 7.58 (d, J=9.0 Hz, 1H), 7.48 (s, 1H), 7.03 (s, 1H), 6.80 (d, J=0.7 Hz, 1H), 6.78 (s, 1H), 5.52-5.48 (m, 1H), 4.58 (d, J=5.7 Hz, 2H), 4.17-4.09 (m, 1H), 4.00-3.94 (m, 1H), 2.26-2.22 (m, 8H); ESI MS m/z 377 $[C_{22}H_{20}N_2O_4+H]^+$; UPLC (Method A) 97.4% (AUC), $t_R$=3.05 min; Chiral HPLC (Chiralpak AD, Method A) 64.2% (AUC), $t_R$=24.05 min.

All patents and publications referred to herein are incorporated by reference herein to the same extent as if each individual publication was specifically and individually indicated to be incorporated by reference in its entirety.

DOCUMENTS CITED

1. Childress, A. R.; Mozley, P. D.; McElgin, W.; Fitzgerald, J.; Reivich, M.; O'Brien, C. P., Limbic activation during cue-induced cocaine craving. *The American journal of psychiatry* 1999, 156 (1), 11-8.
2. Si, J.; Ge, Y.; Zhuang, S.; Gong, R., Inhibiting nonmuscle myosin II impedes inflammatory infiltration and ameliorates progressive renal disease. *Lab Invest* 2010, 90 (3), 448-58.
3. Doller, A.; Badawi, A.; Schmid, T.; Brauss, T.; Pleli, T.; zu Heringdorf, D. M.; Piiper, A.; Pfeilschifter, J.; Eberhardt, W., The cytoskeletal inhibitors latrunculin A and blebbistatin exert antitumorigenic properties in human hepatocellular carcinoma cells by interfering with intracellular HuR trafficking. *Exp Cell Res* 2015, 330 (1), 66-80.
4. Duxbury, M. S.; Ashley, S. W.; Whang, E. E., Inhibition of pancreatic adenocarcinoma cellular invasiveness by blebbistatin: a novel myosin II inhibitor. *Biochem Biophys Res Commun* 2004, 313 (4), 992-7.
5. Derycke, L.; Stove, C.; Vercoutter-Edouart, A. S.; De Wever, O.; Dolle, L.; Colpaert, N.; Depypere, H.; Michalski, J. C.; Bracke, M., The role of non-muscle myosin IIA in aggregation and invasion of human MCF-7 breast cancer cells. *Int J Dev Biol* 2011, 55 (7-9), 835-40.
6. Poincloux, R.; Collin, O.; Lizarraga, F.; Romao, M.; Debray, M.; Piel, M.; Chavrier, P., Contractility of the cell rear drives invasion of breast tumor cells in 3D Matrigel. *Proc Natl Acad Sci USA* 2011, 108 (5), 1943-8.
7. Tomii, S.; Akashi, T.; Ando, N.; Tamura, T.; Sakurai, A.; Terada, A.; Furukawa, A.; Suzuki, Y.; Kayamori, K.; Sakamoto, K.; Ishibashi, H.; Eishi, Y., Cortical Actin Alteration at the Matrix-Side Cytoplasm in Lung Adenocarcinoma Cells and Its Significance in Invasion. *Pathobiology* 2017, 84 (4), 171-183.
8. Beadle, C.; Assanah, M. C.; Monzo, P.; Vallee, R.; Rosenfeld, S. S.; Canoll, P., The role of myosin II in glioma invasion of the brain. *Mol Biol Cell* 2008, 19 (8), 3357-68.
9. Ivkovic, S.; Beadle, C.; Noticewala, S.; Massey, S. C.; Swanson, K. R.; Toro, L. N.; Bresnick, A. R.; Canoll, P.; Rosenfeld, S. S., Direct inhibition of myosin II effectively blocks glioma invasion in the presence of multiple motogens. *Mol Biol Cell* 2012, 23 (4), 533-42.
10. Wigton, E. J.; Thompson, S. B.; Long, R. A.; Jacobelli, J., Myosin-IIA regulates leukemia engraftment and brain infiltration in a mouse model of acute lymphoblastic leukemia. *J Leukoc Biol* 2016, 100 (1), 143-53.
11. Picariello, H.; Kenchappa, R.; Rai, V.; Crish, J.; Dovas, A.; Pogoda, K.; McMahon, M.; Bell, E.; Chandrasekharan, U.; Luu, A.; West, R.; Lammerding, J.; Canoll, P.; Odde, D.; Janmey, P.; Egelhoff, T.; Rosenfeld, S. S., Myosin IIA Suppresses Glioblastoma Development In a Mechanically-Sensitive Manner. *Proceedings of the National Academy of Sciences of the United States of America* 2019, (submitted).
12. Chen, P.; Yin, J.; Guo, Y. M.; Xiao, H.; Wang, X. H.; DiSanto, M. E.; Zhang, X. H., The expression and functional activities of smooth muscle myosin and non-muscle myosin isoforms in rat prostate. *J Cell Mol Med* 2018, 22 (1), 576-588.
13. Zhai, K.; Tang, Y.; Zhang, Y.; Li, F.; Wang, Y.; Cao, Z.; Yu, J.; Kou, J.; Yu, B., NMMHC IIA inhibition impedes tissue factor expression and venous thrombosis via Akt/GSK3beta-NF-kappaB signalling pathways in the endothelium. *Thromb Haemost* 2015, 114 (1), 173-85.
14. Zhang, Y.; Li, L.; Zhao, Y.; Han, H.; Hu, Y.; Liang, D.; Yu, B.; Kou, J., The Myosin II Inhibitor, Blebbistatin, Ameliorates FeCl3-induced Arterial Thrombosis via the GSK3beta-NF-kappaB Pathway. *Int J Biol Sci* 2017, 13 (5), 630-639.
15. Feghhi, S.; Tooley, W. W.; Sniadecki, N. J., Nonmuscle Myosin IIA Regulates Platelet Contractile Forces Through Rho Kinase and Myosin Light-Chain Kinase. *J Biomech Eng* 2016, 138 (10).
16. Wang, Y.; Xu, Y.; Liu, Q.; Zhang, Y.; Gao, Z.; Yin, M.; Jiang, N.; Cao, G.; Yu, B.; Cao, Z.; Kou, J., Myosin IIA-related Actomyosin Contractility Mediates Oxidative Stress-induced Neuronal Apoptosis. *Front Mol Neurosci* 2017, 10, 75.
17. Wang, J. F.; Zarbin, M. A.; Sugino, I.; Whitehead, I.; Townes-Anderson, E., RhoA Signaling and Synaptic Damage Occur within Hours in a Live Pig Model of Retinal Detachment. *Investigative Ophthalmology & Visual Science* 2016, 57 (12).
18. Southern, B. D.; Grove, L. M.; Rahaman, S. O.; Abraham, S.; Scheraga, R. G.; Niese, K. A.; Sun, H.; Herzog, E. L.; Liu, F.; Tschumperlin, D. J.; Egelhoff, T. T.; Rosenfeld, S. S.; Olman, M. A., Matrix-driven Myosin II Mediates the Pro-fibrotic Fibroblast Phenotype. *J Biol Chem* 2016, 291 (12), 6083-95.
19. Liu, Z.; van Grunsven, L. A.; Van Rossen, E.; Schroyen, B.; Timmermans, J. P.; Geerts, A.; Reynaert, H., Blebbistatin inhibits contraction and accelerates migration in mouse hepatic stellate cells. *Br J Pharmacol* 2010, 159 (2), 304-15.
20. Atluri, K.; De Jesus, A. M.; Chinnathambi, S.; Brouillette, M. J.; Martin, J. A.; Salem, A. K.; Sander, E. A., Blebbistatin-Loaded Poly(D,L-lactide-co-glycolide) Particles For Treating Arthrofibrosis. *Acs Biomaterials Science & Engineering* 2016, 2 (7), 1097-1107.
21. Bond, J. E.; Bergeron, A.; Thurlow, P.; Selim, M. A.; Bowers, E. V.; Kuang, A.; Levinson, H., Angiotensin-II mediates nonmuscle myosin II activation and expression and contributes to human keloid disease progression. *Mol Med* 2011, 17 (11-12), 1196-203.
22. Bond, J. E.; Ho, T. Q.; Selim, M. A.; Hunter, C. L.; Bowers, E. V.; Levinson, H., Temporal spatial expression and function of non-muscle myosin II isoforms IIA and IIB in scar remodeling. *Lab Invest* 2011, 91 (4), 499-508.
23. Arora, P. D.; Wang, Y.; Bresnick, A.; Janmey, P. A.; McCulloch, C. A., Flightless I interacts with NMMIIA to promote cell extension formation, which enables collagen remodeling. *Mol Biol Cell* 2015, 26 (12), 2279-97.
24. Kubo, T.; Yamaguchi, A.; Iwata, N.; Yamashita, T., The therapeutic effects of Rho-ROCK inhibitors on CNS disorders. *Ther Clin Risk Manag* 2008, 4 (3), 605-15.
25. Yoshimoto, T.; Fujita, T.; Kajiya, M.; Ouhara, K.; Matsuda, S.; Komatsuzawa, H.; Shiba, H.; Kurihara, H., *Aggregatibacter actinomycetemcomitans* outer membrane protein 29 (Omp29) induces TGF-beta-regulated apoptosis signal in human gingival epithelial cells via fibronectin/integrinbeta1/FAK cascade. *Cell Microbiol* 2016, 18 (12), 1723-1738.
26. Zhang, M.; Rao, P. V., Blebbistatin, a novel inhibitor of myosin II ATPase activity, increases aqueous humor outflow facility in perfused enucleated porcine eyes. *Invest Ophthalmol Vis Sci* 2005, 46 (11), 4130-8.

27. Epstein, D. L.; Rowlette, L. L.; Roberts, B. C., Actomyosin drug effects and aqueous outflow function. *Invest Ophthalmol Vis Sci* 1999, 40 (1), 74-81.
28. Jiang, L.; Hu, J.; Feng, J.; Han, D.; Yang, C., Substrate stiffness of endothelial cells directs LFA-1/ICAM-1 interaction: A physical trigger of immune-related diseases? *Clin Hemorheol Microcirc* 2016, 61 (4), 633-43.
29. Antoine, T. E.; Shukla, D., Inhibition of myosin light chain kinase can be targeted for the development of new therapies against herpes simplex virus type-1 infection. *Antivir Ther* 2014, 19 (1), 15-29.
30. Arii, J.; Goto, H.; Suenaga, T.; Oyama, M.; Kozuka-Hata, H.; Imai, T.; Minowa, A.; Akashi, H.; Arase, H.; Kawaoka, Y.; Kawaguchi, Y., Non-muscle myosin IIA is a functional entry receptor for herpes simplex virus-1. *Nature* 2010, 467 (7317), 859-62.
31. Kumakura, M.; Kawaguchi, A.; Nagata, K., Actin-myosin network is required for proper assembly of influenza virus particles. *Virology* 2015, 476, 141-150.
32. Sun, Y.; Qi, Y.; Liu, C.; Gao, W.; Chen, P.; Fu, L.; Peng, B.; Wang, H.; Jing, Z.; Zhong, G.; Li, W., Nonmuscle myosin heavy chain IIA is a critical factor contributing to the efficiency of early infection of severe fever with thrombocytopenia syndrome virus. *J Virol* 2014, 88 (1), 237-48.
33. Cymerys, J.; Slonska, A.; Skwarska, J.; Banbura, M. W., Function of myosin during entry and egress of equid herpesvirus type 1 in primary murine neurons. *Acta Virol* 2016, 60 (4), 410-416.
34. Michael, S. K.; Surks, H. K.; Wang, Y.; Zhu, Y.; Blanton, R.; Jamnongjit, M.; Aronovitz, M.; Baur, W.; Ohtani, K.; Wilkerson, M. K.; Bonev, A. D.; Nelson, M. T.; Karas, R. H.; Mendelsohn, M. E., High blood pressure arising from a defect in vascular function. *Proc Natl Acad Sci USA* 2008, 105 (18), 6702-7.
35. Xiao, J. W.; Zhu, X. Y.; Wang, Q. G.; Zhang, D. Z.; Cui, C. S.; Zhang, P.; Chen, H. Y.; Meng, L. L., Acute effects of Rho-kinase inhibitor fasudil on pulmonary arterial hypertension in patients with congenital heart defects. *Circ J* 2015, 79 (6), 1342-8.
36. Sirigu, S.; Hartman, J. J.; Planelles-Herrero, V. J.; Ropars, V.; Clancy, S.; Wang, X.; Chuang, G.; Qian, X.; Lu, P. P.; Barrett, E.; Rudolph, K.; Royer, C.; Morgan, B. P.; Stura, E. A.; Malik, F. I.; Houdusse, A. M., Highly selective inhibition of myosin motors provides the basis of potential therapeutic application. *Proc Natl Acad Sci USA* 2016, 113 (47), E7448-E7455.
37. Brozovich, F. V.; Nicholson, C. J.; Degen, C. V.; Gao, Y. Z.; Aggarwal, M.; Morgan, K. G., Mechanisms of Vascular Smooth Muscle Contraction and the Basis for Pharmacologic Treatment of Smooth Muscle Disorders. *Pharmacol Rev* 2016, 68 (2), 476-532.
38. Zhang, X. H.; Aydin, M.; Kuppam, D.; Melman, A.; Disanto, M. E., In vitro and in vivo relaxation of corpus cavernosum smooth muscle by the selective myosin II inhibitor, blebbistatin. *J Sex Med* 2009, 6 (10), 2661-71.
39. Zhang, X.; Kuppam, D. S.; Melman, A.; DiSanto, M. E., In vitro and in vivo relaxation of urinary bladder smooth muscle by the selective myosin II inhibitor, blebbistatin. *BJU Int* 2011, 107 (2), 310-7.
40. Kampourakis, T.; Zhang, X.; Sun, Y. B.; Irving, M., Omecamtiv mercabil and blebbistatin modulate cardiac contractility by perturbing the regulatory state of the myosin filament. *J Physiol* 2018, 596 (1), 31-46.
41. Maher, C.; Underwood, M.; Buchbinder, R., Non-specific low back pain. *Lancet* 2017, 389 (10070), 736-747.
42. Hirayama, J.; Yamagata, M.; Ogata, S.; Shimizu, K.; Ikeda, Y.; Takahashi, K., Relationship between low-back pain, muscle spasm and pressure pain thresholds in patients with lumbar disc herniation. *Eur Spine J* 2006, 15 (1), 41-7.
43. Foley, P. L.; Vesterinen, H. M.; Laird, B. J.; Sena, E. S.; Colvin, L. A.; Chandran, S.; MacLeod, M. R.; Fallon, M. T., Prevalence and natural history of pain in adults with multiple sclerosis: systematic review and meta-analysis. *Pain* 2013, 154 (5), 632-42.
44. Mameniskiene, R.; Wolf, P., Epilepsia partialis continua: A review. *Seizure* 2017, 44, 74-80.
45. Espay, A. J.; Schmithorst, V. J.; Szaflarski, J. P., Chronic isolated hemifacial spasm as a manifestation of epilepsia partialis continua. *Epilepsy Behav* 2008, 12 (2), 332-6.
46. Pacik, P. T., Understanding and treating vaginismus: a multimodal approach. *Int Urogynecol J* 2014, 25 (12), 1613-20.
47. Ochala, J.; Sun, Y. B., Novel myosin-based therapies for congenital cardiac and skeletal myopathies. *J Med Genet* 2016, 53 (10), 651-4.
48. Mohamed, R. M. P.; Kumar, J.; Yap, E.; Mohamed, I. N.; Sidi, H.; Adam, R. L.; Das, S., Try to Remember: Interplay between Memory and Substance Use Disorder. *Current Drug Targets* 2019, 20 (2), 158-165.
49. Soeter, M.; Kindt, M., An Abrupt Transformation of Phobic Behavior After a Post-Retrieval Amnesic Agent. *Biol Psychiatry* 2015, 78 (12), 880-6.
50. Brunet, A.; Saumier, D.; Liu, A.; Streiner, D. L.; Tremblay, J.; Pitman, R. K., Reduction of PTSD Symptoms With Pre-Reactivation Propranolol Therapy: A Randomized Controlled Trial. *Am J Psychiatry* 2018, 175 (5), 427-433.
51. Young, E. J.; Blouin, A. M.; Briggs, S. B.; Sillivan, S. E.; Lin, L.; Cameron, M. D.; Rumbaugh, G.; Miller, C. A., Nonmuscle myosin IIB as a therapeutic target for the prevention of relapse to methamphetamine use. *Molecular Psychiatry* 2016, 21 (5), 615-623.
52. Young, E. J.; Briggs, S. B.; Rumbaugh, G.; Miller, C. A., Nonmuscle myosin II inhibition disrupts methamphetamine-associated memory in females and adolescents. *Neurobiol Learn Mem* 2017, 139, 109-116.
53. Grant, J. E.; Chamberlain, S. R., Expanding the definition of addiction: DSM-5 vs. ICD-11. *CNS Spectr* 2016, 21 (4), 300-3.
54. Kasai, H.; Fukuda, M.; Watanabe, S.; Hayashi-Takagi, A.; Noguchi, J., Structural dynamics of dendritic spines in memory and cognition. *Trends in neurosciences* 2010, 33 (3), 121-9.
55. Lai, C. S. W.; Franke, T. F.; Gan, W.-B., Opposite effects of fear conditioning and extinction on dendritic spine remodelling. *Nature* 2012, 483 (7387), 87-91.
56. Yang, G.; Pan, F.; Gan, W.-B., Stably maintained dendritic spines are associated with lifelong memories. *Nature* 2009, 462 (7275), 920-924.
57. Kasai, H.; Matsuzaki, M.; Noguchi, J.; Yasumatsu, N.; Nakahara, H., Structure-stability-function relationships of dendritic spines. *Trends in Neurosciences* 2003, 26 (7), 360-368.
58. Smart, F. M.; Halpain, S., Regulation of dendritic spine stability. *Hippocampus* 2000, 10 (5), 542-554.
59. Rex, C. S.; Gavin, C. F.; Rubio, M. D.; Kramar, E. A.; Chen, L. Y.; Jia, Y.; Huganir, R. L.; Muzyczka, N.; Gall, C. M.; Miller, C. A.; Lynch, G.; Rumbaugh, G., Myosin IIb regulates actin dynamics during synaptic plasticity and memory formation. *Neuron* 2010, 67 (4), 603-17.

60. Mantzur, L.; Joels, G.; Lamprecht, R., Actin polymerization in lateral amygdala is essential for fear memory formation. *Neurobiology of learning and memory* 2009, 91 (1), 85-8.

61. Rehberg, K.; Bergado-Acosta, J. R.; Koch, J. C.; Stork, O., Disruption of fear memory consolidation and reconsolidation by actin filament arrest in the basolateral amygdala. *Neurobiology of learning and memory* 2010, 94 (2), 117-26.

62. Fischer, A.; Sananbenesi, F.; Schrick, C.; Spiess, J.; Radulovic, J., Distinct roles of hippocampal de novo protein synthesis and actin rearrangement in extinction of contextual fear. *The Journal of neuroscience: the official journal of the Society for Neuroscience* 2004, 24 (8), 1962-6.

63. Gavin, C. F.; Rubio, M. D.; Young, E.; Miller, C.; Rumbaugh, G., Myosin II motor activity in the lateral amygdala is required for fear memory consolidation. *Learn Mem* 2012, 19 (1), 9-14.

64. Star, E. N.; Kwiatkowski, D. J.; Murthy, V. N., Rapid turnover of actin in dendritic spines and its regulation by activity. *Nature neuroscience* 2002, 5 (3), 239-46.

65. Young, E. J.; Aceti, M.; Griggs, E. M.; Fuchs, R. A.; Zigmond, Z.; Rumbaugh, G.; Miller, C. A., Selective, retrieval-independent disruption of methamphetamine-associated memory by actin depolymerization. *Biological psychiatry* 2014, 75 (2), 96-104.

66. Krucker, T.; Siggins, G. R.; Halpain, S., Dynamic actin filaments are required for stable long-term potentiation (LTP) in area CA1 of the hippocampus. *Proc. Nat. Acad. Sci.* 2000, 97 (12), 6856-6861.

67. Honkura, N.; Matsuzaki, M.; Noguchi, J.; Ellis-Davies, G. C.; Kasai, H., The subspine organization of actin fibers regulates the structure and plasticity of dendritic spines. *Neuron* 2008, 57 (5), 719-29.

68. Kaech, S.; Fischer, M.; Doll, T.; Matus, A., Isoform specificity in the relationship of actin to dendritic spines. *J Neurosci* 1997, 17 (24), 9565-72.

69. Kramar, E. A., Integrin-driven actin polymerization consolidates long-term potentiation. *Proc. Nat. Acad. Sci.* 2006, 103 (14), 5579-5584.

70. Straight, A. F.; Cheung, A.; Limouze, J.; Chen, I.; Westwood, N. J.; Sellers, J. R.; Mitchison, T. J., Dissecting temporal and spatial control of cytokinesis with a myosin II Inhibitor. *Science* 2003, 299 (5613), 1743-7.

71. Kovacs, M.; Toth, J.; Hetenyi, C.; Malnasi-Csizmadia, A.; Sellers, J. R., Mechanism of blebbistatin inhibition of myosin II. *The Journal of biological chemistry* 2004, 279 (34), 35557-63.

72. Limouze, J.; Straight, A. F.; Mitchison, T.; Sellers, J. R., Specificity of blebbistatin, an inhibitor of myosin II. *Journal of muscle research and cell motility* 2004, 25 (4-5), 337-41.

73. Sakamoto, T.; Limouze, J.; Combs, C. A.; Straight, A. F.; Sellers, J. R., Blebbistatin, a myosin II inhibitor, is photoinactivated by blue light. *Biochemistry* 2005, 44 (2), 584-8.

74. Young, E. J.; Blouin, A. M.; Briggs, S. B.; Sillivan, S. E.; Lin, L.; Cameron, M. D.; Rumbaugh, G.; Miller, C. A., Nonmuscle myosin IIB as a therapeutic target for the prevention of relapse to methamphetamine use. *Molecular psychiatry* 2015.

75. Briggs, S. B.; Blouin, A. M.; Young, E. J.; Rumbaugh, G.; Miller, C. A., Memory disrupting effects of nonmuscle myosin II inhibition depend on the class of abused drug and brain region. *Learn Mem* 2017, 24 (2), 70-75.

76. Briggs, S. B.; Hafenbreidel, M.; Young, E. J.; Rumbaugh, G.; Miller, C. A., The role of nonmuscle myosin II in polydrug memories and memory reconsolidation. *Learn Mem* 2018, 25 (9), 391-398.

77. Allingham, J. S.; Smith, R.; Rayment, I., The structural basis of blebbistatin inhibition and specificity for myosin II. *Nat. Struct. Mol. Biol.* 2005, 12 (4), 378-379.

78. Lucas-Lopez, C.; Allingham, J. S.; Lebl, T.; Lawson, C. P.; Brenk, R.; Sellers, J. R.; Rayment, I.; Westwood, N. J., The small molecule tool (S)-(−)-blebbistatin: novel insights of relevance to myosin inhibitor design. *Org. Biomol. Chem.* 2008, 6 (12), 2076-2084.

79. Eddinger, T. J.; Meer, D. P.; Miner, A. S.; Meehl, J.; Rovner, A. S.; Ratz, P. H., Potent inhibition of arterial smooth muscle tonic contractions by the selective myosin II inhibitor, blebbistatin. *J. Pharmacol. Exp. Ther.* 2007, 320 (2), 865-870.

80. Borlak, J.; Zwadlo, C., The Myosin ATPase Inhibitor 2,3-Butanedione monoxime Dictates Transcriptional Activation of Ion Channels and $Ca^{2+}$-Handling Proteins. *Mol. Pharmacol.* 2004, 66 (3), 708-717.

81. Cheung, A.; Dantzig, J. A.; Hollingworth, S.; Baylor, S. M.; Goldman, Y. E.; Mitchison, T. J.; Straight, A. F., A small-molecule inhibitor of skeletal muscle myosin II. *Nature Cell Biol.* 2002, 4 (83-88).

82. Lucas-Lopez, C.; Patterson, S.; Blum, T.; Straight, A. F.; Toth, J.; Slawin, A. M. Z.; Mitchison, T. J.; Sellers, J. R.; Westwood, N. J., Absolute Stereochemical Assignment and Fluorescence Tuning of the Small Molecule Tool, (−)-Blebbistatin. *Eur. J. Org. Chem.* 2005, 1736-1740.

83. Kepiro, M.; Varkuti, B. H.; Vegner, L.; Voros, G.; Hegyi, G.; Varga, M.; Malnasi-Csizmadia, A., para-Nitroblebbistatin, the Non-Cytotoxic and Photostable Myosin II Inhibitor. *Angew. Chem. Int. Ed. Engl.* 2014, 53(31), 8211-8215.

84. Kepiro, M.; Varkuti, B. H.; Bodor, A.; Hegyi, G.; Drahos, L.; Kovacs, M.; Malnasi-Csizmadia, A., Azidoblebbistatin, a photoreactive myosin inhibitor. *Proc. Nat. Acad. Sci.* 2012, 109 (24), 9402-9407.

85. Kovacs, M.; Toth, J.; Hetenyi, C.; Malnasi-Csizmadia, A.; Sellers, J. R., Mechanism of blebbistatin inhibition of myosin II. *J. Biol. Chem.* 2004, 279 (34), 35557-35563.

86. Zhang, X.; Kuppam, D. S. R.; Melman, A.; DiSanto, M. E., In vitro and in vivo relaxation of urinary bladder smooth muscle by the selective myosin II inhibitor, blebbistatin. *BJUI* 2010, 107, 310-317.

87. Zhang, X. H.; Aydin, M.; Kuppam, D.; Melman, A.; Disanto, M. E., In vitro and in vivo relaxation of corpus cavernosum smooth muscle by the selective myosin II inhibitor, blebbistatin. *J. Sex Med.* 2009, 6 (10), 2661-2671.

88. Limouze, J.; Straight, A. F.; Mitchison, T.; Sellers, J. R., Specificity of blebbistatin, an inhibitor of myosin II. *J. Muscle Res. Cell Motil.* 2004, 25 (4-5), 337-341.

89. Ponsaerts, R.; D'Hondt, C.; Bultynck, G.; Srinivas, S. P.; Vereecke, J.; Himpens, B., The myosin II ATPase inhibitor blebbistatin prevents thrombin-induced inhibition of intercellular calcium wave propagation in corneal endothelial cells. *Invest. Ophthalmol. Vis. Sci.* 2008, 49 (11), 4816-4827.

90. Zhang, M.; Rao, P. V., Blebbistatin, a novel inhibitor of myosin II ATPase activity, increases aqueous humor outflow facility in perfused enucleated porcine eyes. *Invest. Ophthalmol. Vis. Sci.* 2005, 46 (11), 4130-4138.

91. Villanueva, J.; Torres, V.; Torregrosa-Hetland, C. J.; Garcia-Martinez, V.; Lopez-Font, I.; Viniegra, S.; Gutierrez, L. M., F-actin-myosin II inhibitors affect chromaffin granule plasma membrane distance and fusion kinetics by retraction of the cytoskeletal cortex. *J. Mol. Neurosci.* 2012, 48 (2), 328-338.

92. Yumoto, M.; Watanabe, M., Blebbistatin, a myosin II inhibitor, suppresses Ca(2+)-induced and "sensitized"-contraction of skinned tracheal muscles from guinea pig. *J. Smooth Muscle Res.* 2013, 49, 89-98.

93. Watanabe, M.; Yumoto, M.; Tanaka, H.; Wang, H. H.; Katayama, T.; Yoshiyama, S.; Black, J.; Thatcher, S. E.; Kohama, K., Blebbistatin, a myosin II inhibitor, suppresses contraction and disrupts contractile filaments organization of skinned taenia cecum from guinea pig. *Am. J. Physiol. Cell Physiol.* 2010, 298 (5), C1118-26.

94. Bond, J. E.; Ho, T. Q.; Selim, M. A.; Hunter, C. L.; Bowers, E. V.; Levinson, H., Temporal spatial expression and function of non-muscle myosin II isoforms IIA and IIB in scar remodeling. *Lab. Invest.* 2011, 91 (4), 499-508.

All patents and publications referred to herein are incorporated by reference herein to the same extent as if each individual publication was specifically and individually indicated to be incorporated by reference in its entirety.

We claim:

1. A compound of formula (IIa) or (IIb)

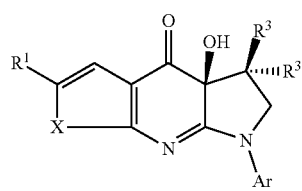
(IIa)

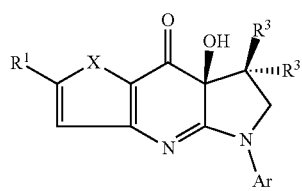
(IIb)

wherein
X is a group of formula

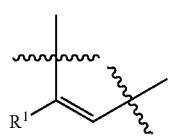

wherein wavy lines indicate points of bonding;
$R^1$ is independently at each occurrence H, (C1-C4)alkyl, $CF_3$, nitro, or halo;
Ar is a monocyclic aryl, a monocyclic heteroaryl, or a bicyclic heteroaryl substituted with 1, 2 or 3 $R^2$, or a bicyclic aryl substituted with 0, 1, 2 or 3 $R^2$; wherein
when Ar is a monocyclic aryl, then $R^2$ is independently at each occurrence hydroxymethyl, $R_2NCH_2$ wherein R is H or alkyl, or nitro; and
when Ar is a bicyclic aryl or heteroaryl or a monocyclic heteroaryl, then $R^2$ is independently at each occurrence (C1-C4)alkyl, (C1-C4)alkoxyl), (C1-C4)alkoxycarbonyl, (C1-C4)haloalkyl, hydroxymethyl, $R_2NCH_2$ wherein R is H or alkyl, cyano, nitro, halo, or $CF_3$;
$R^3$ is independently at each occurrence H or $CH_3$;
provided that the compound is not any of the formulae

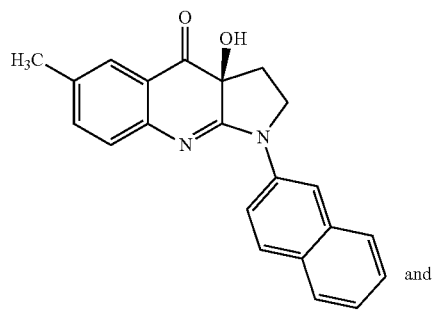
BPN-0025915 and

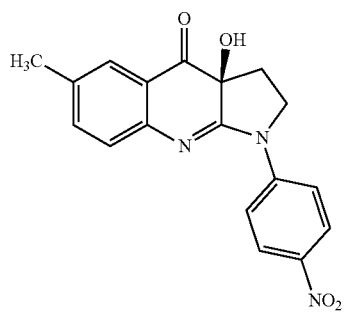
BPN-0025001 or a pharmaceutically acceptable salt thereof.

2. The compound of claim 1 wherein at least one $R^1$ group of formula (IIa) or (IIb) is methyl, halo or $CF_3$.

3. The compound of claim 1 wherein Ar is a group of formula

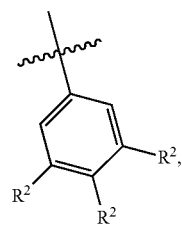

wherein a wavy line indicates a point of bonding.

4. The compound of claim 1 wherein Ar is a pyrazolyl, thiophenyl, isoquinolinyl, benzoxazolyl, quinazolinyl, isoxazolyl, cinnolinyl, quinoxalinyl, benzisoxazolyl, benzothiadiazolyl, pyrazolopyridinyl, imidazopyridinyl, thieopyridinyl, dihydrobenzoxazinyl, triazolopyridinyl, dihydropyridoxazinyl, tetrahydrobenzoxazepinyl, dihydrobenzodioxinyl, dihydrobenzothiazinyl, tetrahydroquinolinyl, tetrahydronaphthyl, or chromanyl ring system, any of which is substituted with 1, 2, or 3 $R^2$.

5. A compound or pharmaceutically acceptable salt thereof, of any one of the formulae:

| | |
|---|---|
| BPN-0027181 | 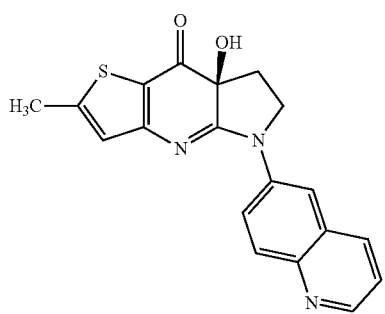 [SMILES: Cc1cc2c(s1)C(=O)[C@]1(O)CCN(c3ccc4ncccc4c3)C1=N2] |
| BPN-0028898 | 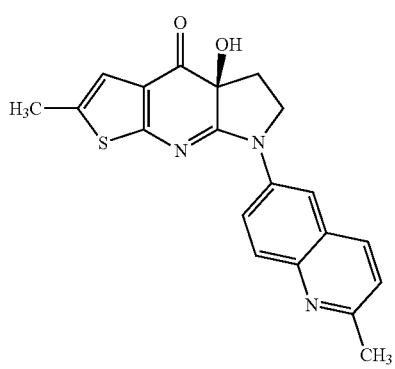 [SMILES: Cc1ccc2cc(N3CC[C@@]4(O)C(=O)c5cc(C)sc5N=C34)ccc2n1] |
| BPN-0028863 | 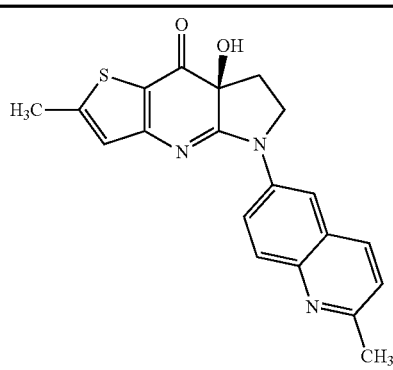 |
| BPN-0027216 | 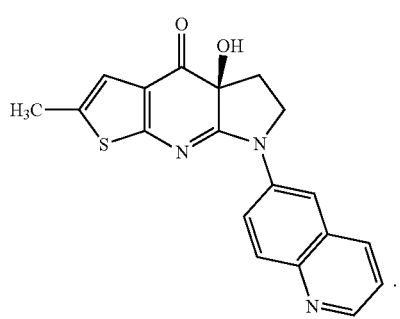 [SMILES: Cc1cc2c(s1)N=C1N(c3ccc4ncccc4c3)CC[C@@]1(O)C2=O] |
* * * * *